(12) United States Patent
Sadelain et al.

(10) Patent No.: US 12,404,316 B2
(45) Date of Patent: Sep. 2, 2025

(54) TRANSGENIC T CELL AND CHIMERIC ANTIGEN RECEPTOR T CELL COMPOSITIONS AND RELATED METHODS

(71) Applicant: Memorial Sloan Kettering Cancer Center, New York, NY (US)

(72) Inventors: Michel W. J. Sadelain, New York, NY (US); Justin Gabriel Andre Francois Eyquem, New York, NY (US); Jorge Mansilla-Soto, Forest Hills, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 752 days.

(21) Appl. No.: 17/824,650

(22) Filed: May 25, 2022

(65) Prior Publication Data
US 2022/0411753 A1   Dec. 29, 2022

Related U.S. Application Data

(62) Division of application No. 16/091,494, filed as application No. PCT/US2017/027601 on Apr. 14, 2017, now Pat. No. 11,377,637.

(60) Provisional application No. 62/462,243, filed on Feb. 22, 2017, provisional application No. 62/461,677, filed on Feb. 21, 2017, provisional application No. 62/323,675, filed on Apr. 16, 2016, provisional application No. 62/323,623, filed on Apr. 15, 2016.

(51) Int. Cl.
| | | |
|---|---|---|
| C07K 14/725 | (2006.01) | |
| A61K 40/11 | (2025.01) | |
| A61K 40/31 | (2025.01) | |
| A61K 40/42 | (2025.01) | |
| A61K 40/50 | (2025.01) | |
| C12N 5/0783 | (2010.01) | |
| C12N 9/22 | (2006.01) | |
| C12N 15/63 | (2006.01) | |
| C12N 15/86 | (2006.01) | |

(52) U.S. Cl.
CPC .......... *C07K 14/7051* (2013.01); *A61K 40/11* (2025.01); *A61K 40/31* (2025.01); *A61K 40/4211* (2025.01); *C12N 5/0636* (2013.01); *C12N 9/22* (2013.01); *C12N 15/63* (2013.01); *C12N 15/86* (2013.01); *A61K 40/50* (2025.01); *A61K 2239/31* (2023.05); *A61K 2239/38* (2023.05); *A61K 2239/48* (2023.05); *C12N 2510/00* (2013.01); *C12N 2830/001* (2013.01)

(58) Field of Classification Search
None
See application file for complete search history.

(56) References Cited

U.S. PATENT DOCUMENTS

| | | |
|---|---|---|
| 4,956,778 A | 9/1990 | Naito |
| 5,091,513 A | 2/1992 | Huston et al. |
| 5,132,405 A | 7/1992 | Huston et al. |
| 5,399,346 A | 3/1995 | Anderson et al. |
| 7,446,190 B2 | 11/2008 | Sadelain et al. |
| 8,697,359 B1 | 4/2014 | Zhang |
| 8,802,374 B2 | 8/2014 | Jensen |
| 8,945,868 B2 | 2/2015 | Collingwood et al. |
| 9,181,527 B2 | 11/2015 | Sentman |
| 9,273,283 B2 | 3/2016 | Sentman |
| 9,587,020 B2 | 3/2017 | Wu et al. |
| 9,663,763 B2 | 5/2017 | Sentman |
| 9,821,011 B1 | 11/2017 | Sentman |
| 9,822,340 B1 | 11/2017 | Sentman |
| 9,937,207 B2 | 4/2018 | Gregory et al. |
| 9,938,497 B2 | 4/2018 | Sentman |
| 9,969,975 B1 | 5/2018 | Jantz et al. |
| 10,286,007 B2 | 5/2019 | Galetto et al. |
| 10,287,606 B2 | 5/2019 | Valamehr et al. |
| 10,450,585 B2 | 10/2019 | Lee et al. |
| 10,858,628 B2 | 12/2020 | Valamehr et al. |
| 11,377,637 B2 | 7/2022 | Sadelain et al. |
| 2003/0093818 A1 | 5/2003 | Belmont et al. |
| 2005/0196754 A1 | 9/2005 | Drmanac et al. |
| 2010/0273213 A1 | 10/2010 | Mineno et al. |
| 2011/0059056 A1 | 3/2011 | Grawunder et al. |

(Continued)

FOREIGN PATENT DOCUMENTS

| | | |
|---|---|---|
| CA | 2945393 A1 | 10/2015 |
| EP | 1321477 B1 | 10/2004 |

(Continued)

OTHER PUBLICATIONS

U.S. Appl. No. 62/008,359, filed Jun. 5, 2014, Sangamo Biosciences, Inc.

(Continued)

*Primary Examiner* — Amy E Juedes
(74) *Attorney, Agent, or Firm* — Jones Day

(57) ABSTRACT

The invention provides a T cell wherein one or more therapeutic transgenes is integrated at a within the genome of the cell such that expression of the transgene is under control of an endogenous promoter of the T cell. The invention additional provides methods of making and using such cells to treat a subject with T cell therapy. The invention also provides a T cell wherein a recombinant nucleic acid sequence encoding a chimeric antigen receptor (CAR) is integrated at a first site within the genome of the cell such that the CAR is expressed by the cell at the surface of the cell, and wherein integration of the nucleic acid encoding the CAR at the first site reduces or prevents expression of a functional T cell receptor (TCR) complex at the surface of the cell. The invention additional provides methods of making and using such cells to treat a subject with CAR therapy.

15 Claims, 89 Drawing Sheets

Figure 1A:
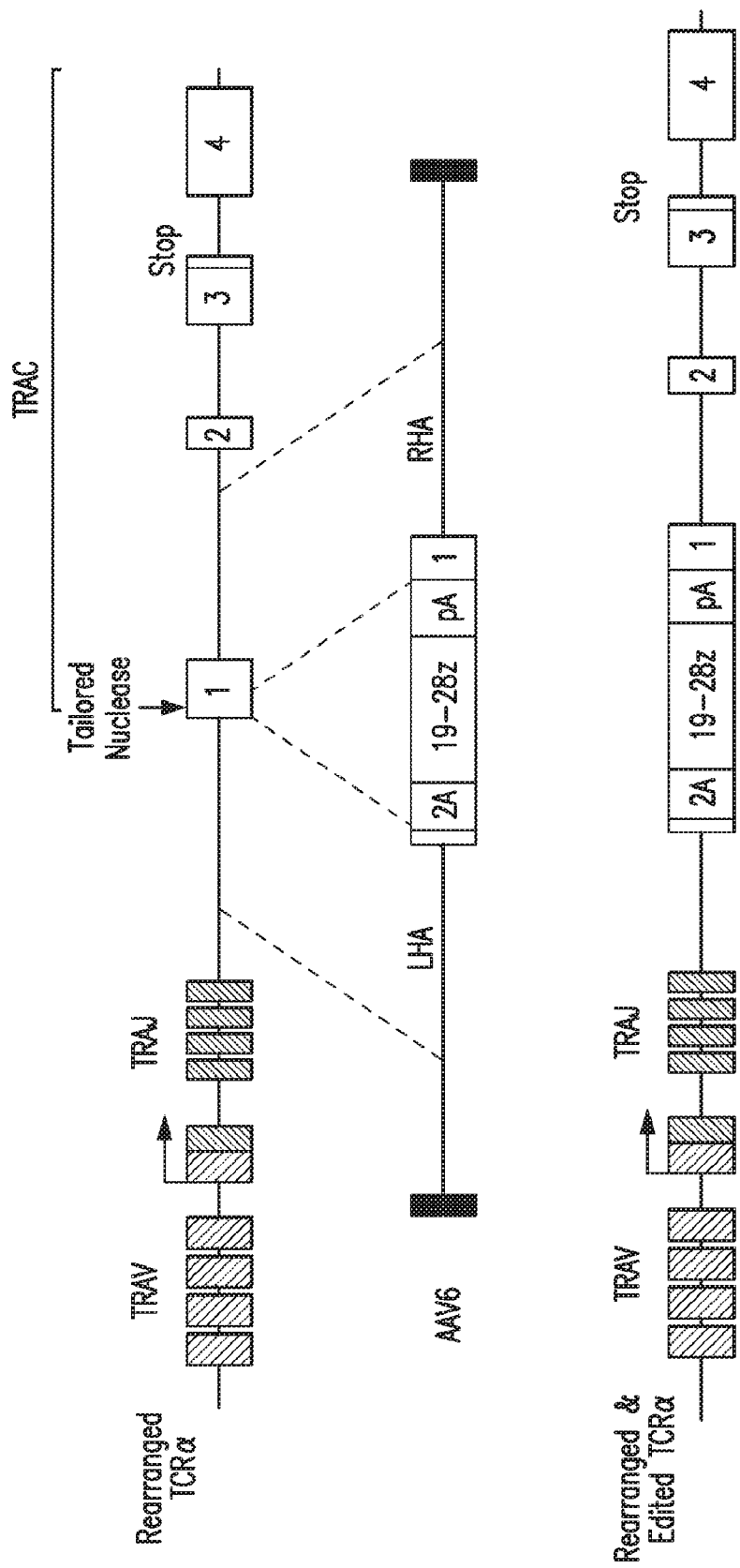

Specification includes a Sequence Listing.

(56) References Cited

U.S. PATENT DOCUMENTS

| | | |
|---|---|---|
| 2011/0158957 A1 | 6/2011 | Bonini et al. |
| 2011/0213288 A1 | 9/2011 | Choi et al. |
| 2012/0321667 A1 | 12/2012 | Sentman |
| 2013/0280222 A1 | 10/2013 | Kay et al. |
| 2014/0068797 A1 | 3/2014 | Doudna et al. |
| 2014/0271581 A1 | 9/2014 | Hyde et al. |
| 2015/0368342 A1 | 12/2015 | Wu et al. |
| 2015/0376650 A1 | 12/2015 | Auerbach et al. |
| 2016/0009813 A1 | 1/2016 | Themeli et al. |
| 2016/0081314 A1 | 3/2016 | Thurston et al. |
| 2016/0184362 A1 | 6/2016 | Duchateau et al. |
| 2016/0272999 A1 | 9/2016 | Duchateau et al. |
| 2017/0130200 A1 | 5/2017 | Moriarity et al. |
| 2017/0143765 A1 | 5/2017 | Wu et al. |
| 2017/0198306 A1 | 7/2017 | Valton et al. |
| 2017/0211099 A1 | 7/2017 | Auerbach et al. |
| 2017/0224735 A1 | 8/2017 | Hyde et al. |
| 2017/0240918 A1 | 8/2017 | Ortiz et al. |
| 2017/0296678 A1 | 10/2017 | Frost et al. |

FOREIGN PATENT DOCUMENTS

| | | |
|---|---|---|
| EP | 3004337 B1 | 8/2017 |
| EP | 2956175 B1 | 10/2017 |
| JP | 2012510812 A | 5/2012 |
| WO | WO 2005026718 A1 | 3/2005 |
| WO | WO 2010065123 A1 | 6/2010 |
| WO | WO 2011011767 A1 | 1/2011 |
| WO | WO 2011059836 A2 | 5/2011 |
| WO | WO 2013026833 A1 | 2/2013 |
| WO | WO 2013176915 A1 | 11/2013 |
| WO | WO 2014059173 A2 | 4/2014 |
| WO | WO 2014127261 A1 | 8/2014 |
| WO | WO 2014165707 A2 | 10/2014 |
| WO | WO 2014172584 A1 | 10/2014 |
| WO | WO 2014186469 A2 | 11/2014 |
| WO | WO 2014191128 A1 | 12/2014 |
| WO | WO 2015140347 A1 | 9/2015 |
| WO | WO 2015164740 A1 | 10/2015 |
| WO | WO 2015172147 A1 | 11/2015 |
| WO | WO 2015188056 A1 | 12/2015 |
| WO | WO 2015188109 A1 | 12/2015 |
| WO | WO 2016044745 A1 | 3/2016 |
| WO | WO 2016081924 A1 | 5/2016 |
| WO | WO 2016160721 A1 | 10/2016 |
| WO | WO 2016166268 A1 | 10/2016 |
| WO | WO 2017011519 A1 | 1/2017 |
| WO | WO 2017062439 A1 | 4/2017 |
| WO | WO 2017062451 A1 | 4/2017 |
| WO | WO 2017078807 A1 | 5/2017 |
| WO | WO 2017079673 A1 | 5/2017 |
| WO | WO 2017087723 A1 | 5/2017 |
| WO | WO 2017156484 A1 | 9/2017 |
| WO | WO 2017165245 A2 | 9/2017 |
| WO | WO 2017177137 A1 | 10/2017 |
| WO | WO 2017180989 A2 | 10/2017 |

OTHER PUBLICATIONS

U.S. Appl. No. 62/237,394, filed May 20, 2015, Precision Biosciences, Inc.
U.S. Appl. No. 62/297,426, filed Feb. 19, 2016, Precision Biosciences, Inc.
U.S. Appl. No. 62/307,245, filed Mar. 11, 2016, Bluebird Bio, Inc.
U.S. Appl. No. 62/322,604, filed Apr. 14, 2016, Bluebird Bio, Inc.
Abate-Daga et al., "A novel chimeric antigen receptor against prostate stem cell antigen mediates tumor destruction in a humanized mouse model of pancreatic cancer," Hum. Gene Ther., 25:1003-1012 (2014).
Adusumilli et al., "Regional delivery of mesothelin-targeted CAR T cell therapy generates potent and long-lasting CD4-dependent tumor immunity," Sci. Transl. Med., 6(261):261ra151 (2014).
Afkarian et al., "T-bet is a STAT1-induced regulator of IL-12R expression in naïve CD4+ T cells," Nat. Immunol., 3(6):549-557 (2002).
Agarwal et al., "Scaffold attachment region-mediated enhancement of retroviral vector expression in primary T cells," J. Virol., 72:3720-3728 (1998).
Ahmad et al., "scFv antibody: principles and clinical application," Clin. Dev. Immunol., 2012: ID980250 (2012).
Ahmed et al., "HER2-specific T cells target primary glioblastoma stem cells and induce regression of autologous experimental tumors," Clin. Cancer Res., 16:474-485 (2010).
Ahmed et al., "Human Epidermal Growth Factor Receptor 2 (HER2)-Specific Chimeric Antigen Receptor-Modified T Cells for the Immunotherapy of HER2-Positive Sarcoma," J Clin. Oncol., 33:1688-1696 (2015).
Ahmed et al., "Immunotherapy for osteosarcoma: genetic modification of T cells overcomes low levels of tumor antigen expression," Mol. Ther., 17:1779-1787 (2009).
Ahmed et al., "Regression of experimental medulloblastoma following transfer of HER2-specific T cells," Cancer Res., 67:5957-5964 (2007).
Allison et al., "Affinity and dose of TCR engagement yield proportional enhancer and gene activity in CD4+ T cells," Elife, 5:e10134 (2016).
Anderson et al., "T-bet, a Th1 transcription factor regulates the expression of Tim-3," Eur. J. Immunol., 40(3):859-866 (2010).
Anderson, "Prospects for human gene therapy," Science, 226:401-409 (1984).
Andrake et al., "Retroviral Integrase: Then and Now," Annu. Rev. Virol., 2(1):241-264 (2015).
Arakawa et al., "Targeting of T cells to CEA-expressing tumor cells by chimeric immune receptors with a highly specific single-chain anti-CEA activity," Anticancer Res., 22:4285-4289 (2002).
Argani et al., "Mesothelin is overexpressed in the vast majority of ductal adenocarcinomas of the pancreas: identification of a new pancreatic cancer marker by serial analysis of gene expression (SAGE).," Clin. Cancer Res., 7(12):3862-3868 (2001).
Assenmacher et al., Cytometric Cytokine Secretion Assay, in Analyzing T Cell Responses: How to Analyze Cellular Immune Responses Against Tumor Associated Antigens, Nagorsen et al., eds., Springer, The Netherlands, Ch. 10, pp. 183-195 (2005).
Baba et al., "Mesothelin expression correlates with prolonged patient survival in gastric cancer," J Surg. Oncol., 105:195-199 (2012).
Bacher et al., "Antigen-specific expansion of human regulatory T cells as a major tolerance mechanism against mucosal fungi," Mucosal. Immunol., 7:916-928 (2014).
Bakhtiari et al., "Anti-MUC1 nanobody can redirect T-body cytotoxic effector function," Hybridoma, 28:85-92 (2009).
Barber et al., "Chimeric NKG2D expressing T cells eliminate immunosuppression and activate immunity within the ovarian tumor microenvironment," J Immunol., 183:6939-6947 (2009).
Bayoglu et al., "Prognostic value of mesothelin expression in patients with triple negative and HER2-positive breast cancers," Biomed. Pharmacother., 70:190-195 (2015).
Beard et al., "Multiple chimeric antigen receptors successfully target chondroitin sulfate proteoglycan 4 in several different cancer histologies and cancer stem cells," J Immunother. Cancer, 2:25 (2014).
Beatty, "Engineered chimeric antigen receptor-expressing T cells for the treatment of pancreatic ductal adenocarcinoma," Oncoimmunology, 3:e28327 (2014).
Best et al., "Transcriptional insights into the CD8(+) T cell response to infection and memory T cell formation," Nat. Immunol., 14(4):404-412 (2013).
Blackburn et al., "Coregulation of CD8+ T cell exhaustion by multiple inhibitory receptors during chronic viral infection," Natl. Immunol., 10(1):29-37 (2009).
Bluestone et al., "T cells in the control of organ-specific autoimmunity," J. Clin. Invest., 125:2250-2260 (2015).
Bluestone et al., "Type 1 diabetes immunotherapy using polyclonal regulatory T cells," Sci. Transl. Med., 7(315):315ra189 (2015).

(56) References Cited

OTHER PUBLICATIONS

Brentjens et al., "CD19-targeted T cells rapidly induce molecular remissions in adults with chemotherapy-refractory acute lymphoblastic leukemia," Sci. Transl. Med., 5(177):177ra38 (2013).
Brentjens et al., "Eradication of systemic B-cell tumors by genetically targeted human T lymphocytes co-stimulated by CD80 and interleukin-15," Nature Medicine, 9:279-286 (2003).
Brentjens et al., "Genetically targeted T cells eradicate systemic acute lymphoblastic leukemia xenografts," Clin. Cancer Res., 13:5426-5435 (2007).
Brown et al., "Bioactivity and Safety of IL13Rα2-Redirected Chimeric Antigen Receptor CD8+ T Cells in Patients with Recurrent Glioblastoma," Clin. Cancer Res., 21(18):4062-4072 (2015).
Brusko et al., "Human Antigen-Specific Regulatory T Cells Generated by T Cell Receptor Gene Transfer," PLoS One, 5(7):e11726 (2010).
Bunos et al., "Automated isolation of primary antigen-specific T cells from donor lymphocyte concentrates: results of a feasibility exercise," Vox Sanguinis, 109:387-393 (2015).
Burga et al., "Liver myeloid-derived suppressor cells expand in response to liver metastases in mice and inhibit the anti-tumor efficacy of anti-CEA CAR-T," Cancer Immunol. Immunother., 64(7):817-829 (2015).
Burns et al., "A high molecular weight melanoma-associated antigen-specific chimeric antigen receptor redirects lymphocytes to target human melanomas," Cancer Res., 70:3027-3033 (2010).
Call et al., "The organizing principle in the formation of the T cell receptor-CD3 complex," Cell, 111(7):967-979 (2002).
Call et al., "The T cell receptor: critical role of the membrane environment in receptor assembly and function," Annu. Rev. Immunol., 23:101-125 (2005).
Cao et al., "Expression of mesothelin, fascin, and prostate stem cell antigen in primary ovarian mucinous tumors and their utility in differentiating primary ovarian mucinous tumors from metastatic pancreatic mucinous carcinomas in the ovary," Int. J Gynecol. Pathol., 24:67-72 (2005).
Capecchi et al., "Gene targeting in mice: functional analysis of the mammalian genome for the twenty-first century," Nat. Rev. Genet., 6:507-512 (2005).
Carpenito et al., "Control of large, established tumor xenografts with genetically retargeted human T cells containing CD28 and CD137 domains," Proc. Natl. Acad. Sci. U.SA., 106:3360-3365 (2009).
Chames et al., "Therapeutic antibodies: successes, limitations and hopes for the future," Br. J. Pharmacol., 157:220-233 (2009).
Chang et al., "Emerging concepts of T cell metabolism as a target of immunotherapy," Nat. Immunol., 17:364-368 (2016).
Chang et al., "Transgene-enforced co-stimulation of CD4+ T cells leads to enhanced and sustained anti-tumor effector functioning," Cytotherapy, 9:771-784 (2007).
Chekmasova et al., "Adoptive T cell immunotherapy strategies for the treatment of patients with ovarian cancer," Discov. Med., 9:62-70 (2010).
Chen et al., "Direct expansion of human allospecific FoxP3+CD4+ regulatory T cells with allogeneic B cells for therapeutic application," J. Immunol., 183:4094-4102 (2009).
Chen et al., "Molecular mechanisms of T cell co-stimulation and co-inhibition," Nat. Rev. Immunol., 13(4):227-242 (2013).
Chen, "Mesothelin expression in thymic epithelial tumors (TETs)," J Clin. Oncol., 32:503s, abstract 7607 (2014).
Cheung et al., "Anti-idiotypic antibody facilitates scFv chimeric immune receptor gene transduction and clonal expansion of human lymphocytes for tumor therapy," Hybrid Hybridomics, 22:209-218 (2003).
Chinnasamy et al., "Local delivery of interleukin-12 using T cells targeting VEGF receptor-2 eradicates multiple vascularized tumors in mice," Clin. Cancer Res., 18:1672-1683 (2012).
Chinnasamy et al., "Simultaneous targeting of tumor antigens and the tumor vasculature using T lymphocyte transfer synergize to induce regression of established tumors in mice," Cancer Res., 73:3371-3380 (2013).
Chmielewski et al., "T cells redirected by a CD3ζ chimeric antigen receptor can establish self-antigen-specific tumour protection in the long term," Gene Ther., 20:177-186 (2013).
Chmielewski et al., "T cells that target carcinoembryonic antigen eradicate orthotopic pancreatic carcinomas without inducing auto-immune colitis in mice.," Gastroenterology, 143:1095-1107 (2012).
Choi et al., "Intracerebral delivery of a third generation EGFRvIII-specific chimeric antigen receptor is efficacious against human glioma," J Clin. Neurosci., 21:189-190 (2014).
Chow et al., "T cells redirected to EphA2 for the immunotherapy of glioblastoma," Mol. Ther., 21:629-637 (2013).
Chuvpilo et al., "Multiple closely-linked NFAT/octamer and HMG I(Y) binding sites are part of the interleukin-4 promoter," Nucleic Acids Res., 21(24):5694-5704 (1993).
Cooper et al., "Enhanced antilymphoma efficacy of CD19-redirected influenza MP1-specific CTLs by cotransfer of T cells modified to present influenza MP1," Blood, 105(4):1622-1631 (2005).
Cornetta et al., "Gene transfer into primates and prospects for gene therapy in humans," Prog. Nucleic Acid Res. Mol. Biol., 36:311-322 (1989).
Corthay et al., "Evaluation of the percentage of peripheral T cells with two different T cell receptor alpha-chains and of their potential role in autoimmunity," J. Autoimmun., 16(4):423-429 (2001).
Dainty et al., "Overexpression of folate binding protein and mesothelin are associated with uterine serous carcinoma," Gynecol. Oncol., 105:563-570 (2007).
Darcy et al., "Expression in cytotoxic T lymphocytes of a single-chain anti-carcinoembryonic antigen antibody. Redirected Fas ligand-mediated lysis of colon carcinoma," Eur J Immunol., 28:1663-1672 (1998).
Darcy et al., "Redirected perforin-dependent lysis of colon carcinoma by ex vivo genetically engineered CTL," J Immunol., 164:3705-3712 (2000).
Davies et al., "Flexible targeting of ErbB dimers that drive tumorigenesis by using genetically engineered T cells," Mol. Med., 18:565-576 (2012).
Davila et al., "How do CARs work?: Early insights from recent clinical studies targeting CD19," Oncoimmunol. 1(9):1577-1583 (2012).
De Vree et al., "Targeted sequencing by proximity ligation for comprehensive variant detection and local haplotyping," Nat. Biotechnol., 32(10):1019-1025 (2014).
Deng et al., "Adoptive T-cell therapy of prostate cancer targeting the cancer stem cell antigen EpCAM," BMC Immunol., 16:1 (2015).
Deniger et al., "Sleeping Beauty Transposition of Chimeric Antigen Receptors Targeting Receptor Tyrosine Kinase-Like Orphan Receptor-1 (ROR1) into Diverse Memory T-Cell Populations," PLoS One, 10:e0128151 (2015).
Dennis et al., "Markers of adenocarcinoma characteristic of the site of origin: development of a diagnostic algorithm," Clin. Cancer Res., 11:3766-3772 (2005).
Drapkin et al., "Expression of candidate tumor markers in ovarian carcinoma and benign ovary: evidence for a link between epithelial phenotype and neoplasia" Hum. Pathol., 35:1014-1021 (2004).
Duong et al., "Enhancing the specificity of T-cell cultures for adoptive immunotherapy of cancer," Immunotherapy, 3:33-48 (2011).
Dupont et al., "Artificial antigen-presenting cells transduced with telomerase efficiently expand epitope-specific, human leukocyte antigen-restricted cytotoxic T cells," Cancer Res., 65(12):5417-5427 (2005).
Eglitis et al., "Retroviral vectors for introduction of genes into mammalian cells," BioTechniques, 6:608-614 (1988).
Einama et al., "Luminal membrane expression of mesothelin is a prominent poor prognostic factor for gastric cancer," Br. J Cancer, 107:137-142 (2012).
Ellis, "Silencing and variegation of gammaretrovirus and lentivirus vectors," Hum. Gene Ther., 316(11):1241-1246 (2005).

(56) References Cited

OTHER PUBLICATIONS

Emtage et al., "Second-generation anti-carcinoembryonic antigen designer T cells resist activation-induced cell death, proliferate on tumor contact, secrete cytokines, and exhibit superior antitumor activity in vivo: a preclinical evaluation," Clin. Cancer Res., 14:8112-8122 (2008).
Eyquem et al., "One Step Generation of Universal CAR T Cells," Mol. Ther., 24(Supp 1):S109 (2016) (Published online Apr. 22, 2016, accessable online at American Society of Gene & Cell Therapy (ASGCT) Apr. 18, 2016, ASGCT 19th Annual Meeting, May 4-7, 2016, Washington DC).
Eyquem et al., "Targeting a CAR to the TRAC locus with CRISPR/Cas9 enhances tumour rejection," Nature, 543(7643):113-117 (2017).
Fantini et al., "Cutting edge: TGF-beta induces a regulatory phenotype in CD4+CD25-T cells through Foxp3 induction and down-regulation of Smad7," J. Immunol., 172(9):5149-5153 (2004).
Finney et al., "Chimeric receptors providing both primary and costimulatory signaling in T cells from a single gene product," J. Immunol., 161:2791-2797 (1998).
Frank et al., "Mesothelin expression in pancreatic mucinous cysts.," Am. J Clin. Pathol., 142:313-319 (2014).
Friedman, "Progress toward human gene therapy," Science, 244:1275-1281 (1989).
Frierson et al., "Large-scale molecular and tissue microarray analysis of mesothelin expression in common human carcinomas," Hum. Pathol., 34(6):605-609 (2003).
Frigault et al., "Identification of chimeric antigen receptors that mediate constitutive or inducible proliferation of T cells," Cancer Immunol Res., 3(4):356-367 (2015).
Gade et al., "Targeted elimination of prostate cancer by genetically directed human T lymphocytes," Cancer Res., 65:9080-9088 (2005).
Gaj et al., "ZFN, TALEN, and CRISPR/Cas-based methods for genome engineering," Trends Biotechnol., 31(7):397-405 (2013).
Gallardo et al., "The internal ribosomal entry site of the encephalomyocarditis virus enables reliable coexpression of two transgenes in human primary T lymphocytes," Gene Ther., 4(10):1115-1119 (1997).
Galloway et al., "The use of the monoclonal antibody mesothelin in the diagnosis of malignant mesothelioma in pleural biopsies," Histopathology, 48:767-769 (2006).
Gao et al., "Development of T cells redirected to glypican-3 for the treatment of hepatocellular carcinoma," Clin. Cancer Res., 20:6418-6428 (2014).
Gattinoni et al., "A human memory T cell subset with stem cell-like properties," Nat. Med., 17(10):1290-1297 (2011).
Geldres et al., "T lymphocytes redirected against the chondroitin sulfate proteoglycan-4 control the growth of multiple solid tumors both in vitro and in vivo," Clin. Cancer Res., 20:962-971 (2014).
GenBank Accession No. NP_000607.1, "T-cell surface glycoprotein CD4 isoform 1 precursor [*Homo sapiens*]," (Apr. 23, 2016).
GenBank Accession No. NP_001139345.1, "T-cell surface glycoprotein CD8 alpha chain isoform 1 precursor [*Homo sapiens*]," (Mar. 15, 2015).
GenBank Accession No. NP_001181943.1, "T-cell surface glycoprotein CD4 isoform 2 [*Homo sapiens*]," (Mar. 15, 2015).
GenBank Accession No. NP_001181944.1, "T-cell surface glycoprotein CD4 isoform 3 [*Homo sapiens*]," (Mar. 15, 2015).
GenBank Accession No. NP_001181945.1, "T-cell surface glycoprotein CD4 isoform 3 [*Homo sapiens*]," (Mar. 15, 2015).
GenBank Accession No. NP_001181946.1, "T-cell surface glycoprotein CD4 isoform 3 [*Homo sapiens*]," (Mar. 15, 2015).
GenBank Accession No. NP_001552.2, "tumor necrosis factor receptor superfamily member 9 precursor [*Homo sapiens*]," (Sep. 1, 2016).
GenBank Accession No. NP_003318.1, "tumor necrosis factor receptor superfamily member 4 precursor [*Homo sapiens*]," (Sep. 1, 2016).
GenBank Accession No. NP_006130.1, "T-cell-specific surface glycoprotein CD28 isoform 1 precursor [*Homo sapiens*]," (Mar. 15, 2015).
GenBank Accession No. NP_036224.1, "inducible T-cell costimulator precursor [*Homo sapiens*]," (May 30, 2016).
GenBank Accession No. NP_055081.1, "hematopoietic cell signal transducer isoform 1 precursor [*Homo sapiens*]," (Mar. 15, 2015).
GenBank Accession No. NP_932170.1, "T-cell surface glycoprotein CD3 zeta chain isoform 1 precursor [*Homo sapiens*]," (Mar. 15, 2015).
GenBank Accession No. NP_955592.1, "p46 IN [Moloney murine leukemia virus]," (Feb. 10, 2015).
GenBank Accession No. P10747.1, "T-cell-specific surface glycoprotein CD28," (Jul. 6, 2016).
GenBank Accession No. P41273.1, "Tumor necrosis factor ligand superfamily member 9," (Jul. 6, 2016).
GenBank Accession No. P43489.1, "Tumor necrosis factor receptor superfamily member 4," (Jul. 6, 2016).
Gersbach et al., "Targeted plasmid integration into the human genome by an engineered zinc-finger recombinase," Nucl. Acids Res., 39:7868-7878 (2011).
Gierasch, "Signal sequences," Biochem., 28:923-930 (1989).
Gilham et al., "Primary polyclonal human T lymphocytes targeted to carcino-embryonic antigens and neural cell adhesion molecule tumor antigens by CD3zeta-based chimeric immune receptors," J Immunother., 25:139-151 (2002).
Gong et al., "Cancer patient T cells genetically targeted to prostate-specific membrane antigen specifically lyse prostate cancer cells and release cytokines in response to prostate-specific membrane antigen," Neoplasia, 1:123-127 (1999).
Guedan et al., "ICOS-based chimeric antigen receptors program bipolar TH17/THI cells," Blood, 124:1070-1080 (2014).
Guillonneau et al., "CD8+ regulatory T cells in solid organ transplantation," Curr. Opin. Organ Transplant., 15:751-756 (2010).
Gyobu et al., "Generation and targeting of human tumor-specific Tc1 and Th1 cells transduced with a lentivirus containing a chimeric immunoglobulin T-cell receptor," Cancer Res., 64:1490-1495 (2004).
Haney et al., "Isolation of viable antigen-specific CD8+ T cells based on membrane-bound tumor necrosis factor (TNF)-α expression," J. Immunol. Methods, 369:33-41 (2011).
Hassan et al., "Localization of mesothelin in epithelial ovarian cancer," Appl. Immunohistochem. Mol. Morphol. 13:243-247 (2005).
Hassan et al., "Mesothelin is overexpressed in pancreaticobiliary adenocarcinomas but not in normal pancreas and chronic pancreatitis," Am. J. Clin. Pathol., 124:838-845 (2005).
Haynes et al., "Fas-ligand-mediated lysis of erbB-2-expressing tumour cells by redirected cytotoxic T lymphocytes," Cancer Immunol. Immunother., 47:278-286 (1999).
Haynes et al., "Rejection of syngeneic colon carcinoma by CTLs expressing single-chain antibody receptors codelivering CD28 costimulation," J Immunol., 169:5780-5786 (2002).
Haynes et al., 2001, "Redirecting Mouse CTL Against Colon Carcinoma: Superior Signaling Efficacy of Single-Chain Variable Domain Chimeras Containing TCR-zeta vs Fc Epsilon RI-gamma," J. Immunol., 166:182-187.
Hegde et al., "Combinational targeting offsets antigen escape and enhances effector functions of adoptively transferred T cells in glioblastoma," Mol. Ther., 21:2087-2101 (2013).
Hillerdal et al., "Systemic treatment with CAR-engineered T cells against PSCA delays subcutaneous tumor growth and prolongs survival of mice," BMC Cancer, 14:30 (2014).
Hollyman et al., "Manufacturing validation of biologically functional T cells targeted to CD19 antigen for autologous adoptive cell therapy," J. Immunother., 32:169-180 (2009).
Hombach et al., "A chimeric receptor that selectively targets membrane-bound carcinoembryonic antigen (mCEA) in the presence of soluble CEA," Gene Ther., 6:300-304 (1999).
Hombach et al., "T cell targeting of TAG72+ tumor cells by a chimeric receptor with antibody-like specificity for a carbohydrate epitope," Gastroenterology, 113:1163-1170 (1997).
Honey et al., "Understanding why T-cell receptors remain single," Nat. Rev. Immunol., 5:95 (2005).
Hong et al., "Diverse solid tumors expressing a restricted epitope of L1-CAM can be targeted by chimeric antigen receptor redirected T lymphocytes," J Immunother., 37:93-104 (2014).

(56) References Cited

OTHER PUBLICATIONS

Huang et al., "Genetically modified T cells targeting interleukin-11 receptor α-chain kill human osteosarcoma cells and induce the regression of established osteosarcoma lung metastases," Cancer Res., 72:271-281 (2012).
Hubbard et al., "Targeted gene editing restores regulated CD40L function in X-linked hyper-IgM syndrome," Blood, 127(21):2513-2522 (2016).
Hudecek et al., "Receptor affinity and extracellular domain modifications affect tumor recognition by ROR1-specific chimeric antigen receptor T cells," Clin. Cancer Res., 19:3153-3164 (2013).
Huse et al., "Generation of a large combinatorial library of the immunoglobulin repertoire in phage lambda," Science, 246:1275-1281 (1989).
Huston et al., "Protein engineering of antibody binding sites: recovery of specific activity in an anti-digoxin single-chain Fv analogue produced in *Escherichia coli*," Proc. Nat. Acad. Sci. USA, 85:5879-5883 (1988).
Imai et al., "Genetic modification of T cells for cancer therapy," J. Biol. Regul. Homeost. Agents, 18(1):62-71 (2004).
Inami et al., "Secretion of N-ERC/mesothelin and expression of C-ERC/mesothelin in human pancreatic ductal carcinoma," Oncol. Rep., 20:1375-1380 (2008).
International Search Report for International Application No. PCT/US2017/027601 dated Nov. 14, 2017.
Ito et al., "ERC/mesothelin is expressed in human gastric cancer tissues and cell lines," Oncol. Rep., 31:27-33 (2014).
Iyer et al., "Role of interleukin 10 transcriptional regulation in inflammation and autoimmune disease," Crit. Rev. Immunol., 32(1):23-63 (2012).
Jain et al., "Transcriptional regulation of the IL-2 gene," Curr. Opin. Immunol., 7(3):333-342 (1995).
Jensen et al., "Design and implementation of adoptive therapy with chimeric antigen receptor-modified T cells," Immunol. Rev., 257:127-133 (2014).
Jensen et al., "Designing chimeric antigen receptors to effectively and safely target tumors," Curr. Opin. Immunol., 33:9-15 (2015).
Johnson et al., "Rational development and characterization of humanized anti-EGFR variant III chimeric antigen receptor T cells for glioblastoma," Sci. Transl. Med., 7:275ra22 (2015).
Johnson, "Gene therapy for cystic fibrosis," Chest, 107:77S-83S (1995).
Juillerat et al., "Design of chimeric antigen receptors with integrated controllable transient functions," Sci. Rep., 18950 (2016).
Kachala et al., "Mesothelin overexpression is a marker of tumor aggressiveness and is associated with reduced recurrence-free and overall survival in early-stage lung adenocarcinoma," Clin. Cancer Res., 20(4):1020-1028 (2014).
Kailayangiri et al., "The ganglioside antigen G(D2) is surface-expressed in Ewing sarcoma and allows for MHC-independent immune targeting," Br. J Cancer, 106:1123-1133 (2012).
Kaiser et al., "Towards a commercial process for the manufacture of genetically modified T cells for therapy," Cancer Gene Therapy, 22:72-78 (2015).
Kakarla et al., "Antitumor effects of chimeric receptor engineered human T cells directed to tumor stroma," Mol. Ther., 21:1611-1620 (2013).
Kanagawa et al., "Tumor vessel-injuring ability improves antitumor effect of cytotoxic T lymphocytes in adoptive immunotherapy," Cancer Gene Ther., 20:57-64 (2013).
Kandalaft et al., "A phase I clinical trial of adoptive transfer of folate receptor-alpha redirected autologous T cells for recurrent ovarian cancer," J Transl. Med., 10:157 (2012).
Katz et al., "Phase I Hepatic Immunotherapy for Metastases Study of Intra-Arterial Chimeric Antigen Receptor-Modified T-cell Therapy for CEA+ Liver Metastases," Clin. Cancer Res., 21:3149-3159 (2015).
Kawamata et al., "C-ERC/mesothelin provokes lymphatic invasion of colorectal adenocarcinoma," J Gastroenterol., 49:81-92 (2014).

Kawamata et al., "Intracellular localization of mesothelin predicts patient prognosis of extrahepatic bile duct cancer," Int. J Oncol., 41:2109-2118 (2012).
Kershaw et al., "A phase I study on adoptive immunotherapy using gene-modified T cells for ovarian cancer," Clin. Cancer Res., 12:6106-6115 (2006).
Kershaw et al., "Gene-engineered T cells as a superior adjuvant therapy for metastatic cancer," J. Immunol., 173:2143-2150 (2004).
Kim et al., "The basis for TCR-mediated regulation of the IL-2 receptor alpha chain gene: role of widely separated regulatory elements," EMBO J, 21(12):3051-3059 (2002).
Kobayashi et al., "A chimeric antigen receptor for TRAIL-receptor 1 induces apoptosis in various types of tumor cells," Biochem. Biophys. Res. Commun. 453:798-803 (2014).
Koenen et al., "CD27/CFSE-Based Ex Vivo Selection of Highly Suppressive Alloantigen-Specific Human Regulatory T Cells," J. Immunol., 174:7573-7583 (2005).
Koneru et al., "IL-12 secreting tumor-targeted chimeric antigen receptor T cells eradicate ovarian tumors in vivo," Oncoimmunology, 4:e994446 (2015).
Kong et al., "Suppression of human glioma xenografts with second-generation IL13R-specific chimeric antigen receptor-modified T cells," Clin. Cancer Res., 18:5949-5960 (2012).
Krause et al., "Antigen-dependent CD28 signaling selectively enhances survival and proliferation in genetically modified activated human primary T lymphocytes," J Exp. Med., 188:619-626 (1998).
Krebs et al., "T cells redirected to interleukin-13Rα2 with interleukin-13 mutein—chimeric antigen receptors have anti-glioma activity but also recognize interleukin-13Rα1," Cytotherapy, 16:1121-1131 (2014).
Krishnamurthy et al., "Genetic Engineering of T Cells to Target HERV-K, an Ancient Retrovirus on Melanoma," Clin. Cancer Res., 21:3241-3251 (2015).
Kushitani et al., "Immunohistochemical marker panels for distinguishing between epithelioid mesothelioma and lung adenocarcinomam," Pathol. Int., 57:190-199 (2007).
Lamers et al., "Immune responses to transgene and retroviral vector in patients treated with ex vivo-engineered T cells," Blood, 117(1):72-82 (2011).
Lamers et al., "Treatment of metastatic renal cell carcinoma with CAIX CAR-engineered T cells: clinical evaluation and management of on-target toxicity," Mol Ther., 21:904-912 (2013).
Lan et al., "Induced Foxp3+ regulatory T cells: a potential new weapon to treat autoimmune and inflammatory diseases?," J. Mol. Cell. Biol., 4:22-28 (2012).
Lanitis et al., "Primary human ovarian epithelial cancer cells broadly express HER2 at immunologically-detectable levels," PLoS One, 7:e49829 (2012).
Lanitis et al., "Redirected antitumor activity of primary human lymphocytes transduced with a fully human anti-mesothelin chimeric receptor," Mol. Ther., 20:633-643 (2012).
Latouche et al., "Induction of human cytotoxic T lymphocytes by artificial antigen-presenting cells," Nat. Biotechnol., 18:405-409 (2000).
Lazovic et al., "Imaging immune response in vivo: cytolytic action of genetically altered T cells directed to glioblastoma multiforme" Clin. Cancer Res., 14:3832-3839 (2008).
Le Gal La Salle et al., "An adenovirus vector for gene transfer into neurons and glia in the brain," Science, 259:988-990 (1993).
Lee et al., "A distal cis-regulatory element, CNS-9, controls NFAT1 and IRF4-mediated IL-10 gene activation in T helper cells," Mol. Immunol., 46(4):613-621 (2009).
Lee et al., "In vivo inhibition of human CD19 targeted effector T cells by natural T regulatory cells in a xenotransplant murine model of B cell malignancy," Cancer Res., 71:2871-2881 (2011).
Li et al., "Genetically engineered T cells expressing a HER2-specific chimeric receptor mediate antigen-specific tumor regression," Cancer Gene Ther., 15:382-392 (2008).
Li et al., "Mesothelin expression is associated with poor outcomes in breast cancer," Breast Cancer Res. Treat., 147:675-684 (2014).
Liebig et al., "Forced expression of deltaN-TCF-1B in colon cancer derived cell lines is accompanied by the induction of CEACAM5/6 and mesothelin," Cancer Lett., 223:159-167 (2005).

(56) References Cited

OTHER PUBLICATIONS

Lim et al., "CCR5: no longer a "good for nothing" gene—chemokine control of West Nile virus infection," Trends Immunol., 27(7):308-312 (2006).
Liu et al., "CD127 expression inversely correlates with FoxP3 and suppressive function of human CD4+ T reg cells," J. Exp. Med., 203:1701-1711 (2006).
Liu et al., "On the dynamics of TCR:CD3 complex cell surface expression and downmodulation," Immunity, 13(5):665-675 (2000).
Lo et al., "Anti-GD3 chimeric sFv-CD28/T-cell receptor zeta designer T cells for treatment of metastatic melanoma and other neuroectodermal tumors," Clin. Cancer Res., 16:2769-2780 (2010).
Lombardo et al., "Site-specific integration and tailoring of cassette design for sustainable gene transfer," Nat. Methods, 8(10):861-869 (2011).
Louis et al., "Antitumor activity and long-term fate of chimeric antigen receptor-positive T cells in patients with neuroblastoma," Blood, 118:6050-6056 (2011).
Luria, 1987, "Promoter and enhancer elements in the rearranged alpha chain gene of the human T cell receptor", EMBO J, 6(11):3307-3312.
Ma et al., "Anti-prostate specific membrane antigen designer T cells for prostate cancer therapy," Prostate, 61:12-25 (2004).
Ma et al., "Serine Is an Essential Metabolite for Effector T Cell Expansion," Cell Metab., 25(2):345-357 (2017).
Macdonald et al., "Alloantigen-specific regulatory T cells generated with a chimeric antigen receptor," J. Clin. Invest., 126:1413-1424 (2016).
Macian, "NFAT proteins: key regulators of T-cell development and function," Nat. Rev. Immunol., 5(6):472-484 (2005).
Macleod et al., "Antigen-based immunotherapy (AIT) for autoimmune and allergic disease," Curr. Opin. Pharmacol., 23:11-16 (2015).
Macleod et al., "Integration of a CD19 CAR into the TCR Alpha Chain Locus Streamlines Production of Allogeneic Gene-Edited CAR T Cells," Mol. Ther., 25(4):949-961 (2017).
Maher et al., "Human T-lymphocyte cytotoxicity and proliferation directed by a single chimeric TCRzeta /CD28 receptor," Nat. Biotechnol., 20:70-75 (2002).
Mahnke et al., "The who's who of T-cell differentiation: human memory T-cell subsets," Eur. J. Immunol., 43(11):2797-2809 (2013).
Maliar et al., "Redirected T cells that target pancreatic adenocarcinoma antigens eliminate tumors and metastases in mice," Gastroenterology, 143:1375-1384 (2012).
Mcguinness et al., "Anti-tumor activity of human T cells expressing the CC49-zeta chimeric immune receptor," Hum Gene Ther., 10:165-173 (1999).
Mcnamee et al., "Hypoxia and hypoxia-inducible factors as regulators of T cell development, differentiation, and function," Immunol. Res., 55(1-3):58-70 (2013).
Mehta et al., "NFATc2 and T-bet contribute to T-helper-cell-subset-specific regulation of IL-21 expression," Proc. Natl. Acad. Sci. USA, 102(6):2016-2021 (2005).
Miao et al., "EGFRvIII-specific chimeric antigen receptor T cells migrate to and kill tumor deposits infiltrating the brain parenchyma in an invasive xenograft model of glioblastoma," PLoS One, 9:e94281 (2014).
Miettinen et al., "Expression of calretinin, thrombomodulin, keratin 5, and mesothelin in lung carcinomas of different types: an immunohistochemical analysis of 596 tumors in comparison with epithelioid mesotheliomas of the pleura," Am. J Surg. Pathol., 27:150-158 (2003).
Miller et al., "Improved Retroviral Vectors for Gene Transfer and Expression," Biotechniques, 7:980-990 (1989).
Miller et al., "The journey from discoveries in fundamental immunology to cancer immunotherapy," Cancer Cell, 27(4):439-449 (2015).
Miller, "Retrovirus packaging cells," Hum. Gene Ther., 1(1):5-14 (1990).
Miyara et al., "TREG-cell therapies for autoimmune rheumatic diseases," Nat. Rev. Rheumatol., 10:543-551 (2014).
Moen, "Directions in gene therapy," Blood Cells, 17:407-416 (1991).
Montes et al., "Optimum in vitro expansion of human antigen-specific CD8 T cells for adoptive transfer therapy," Clin. Exp. Immunol. 142:292-302 (2005).
Moon et al., "Multifactorial T-cell hypofunction that is reversible can limit the efficacy of chimeric antigen receptor-transduced human T cells in solid tumors," Clin. Cancer Res., 20(16):4262-4273 (2014).
Morgan et al., "Cancer regression in patients after transfer of genetically engineered lymphocytes," Science, 314(5796):126-129 (2006).
Morgan et al., "Recognition of glioma stem cells by genetically modified T cells targeting EGFRVIII and development of adoptive cell therapy for glioma," Hum. Gene Ther., 23:1043-1053 (2012).
Morgenroth et al., "Targeting of tumor cells expressing the prostate stem cell antigen (PSCA) using genetically engineered T-cells," Prostate, 67:1121-1131 (2007).
Moritz et al., "Cytotoxic T lymphocytes with a grafted recognition specificity for ERBB2-expressing tumor cells," Proc. Natl. Acad. Sci. U.S.A., 91:4318-4322 (1994).
Movassagh et al., "Retrovirus-mediated gene transfer into T cells: 95% transduction efficiency without further in vitro selection," Hum. Gene Ther., 11:1189-1200 (2000).
Neeson et al., "Ex vivo culture of chimeric antigen receptor T cells generates functional CD8+ T cells with effector and central memory-like phenotype" Gene Ther., 17:1105-1116 (2010).
Nolan et al., "Bypassing immunization: optimized design of "designer T cells" against carcinoembryonic antigen (CEA)-expressing tumors, and lack of suppression by soluble CEA," Clin Cancer Res., 5:3928-3941 (1999).
Nomura et al., "Mesothelin expression is a prognostic factor in cholangiocellular carcinoma," Int. Surg., 98:164-169 (2013).
Noyan et al., "Isolation of human antigen-specific regulatory T cells with high suppressive function," Eur. J. Immunol., 44:2592-2602 (2014).
Obulhasim et al., "Mesothelin gene expression and promoter methylation/hypomethylation in gynecological tumors," Eur. J Gynaecol. Oncol., 31:63-71 (2010).
Oestreich et al., "NFATc1 regulates PD-1 expression upon T cell activation," J. Immunol., 181(7):4832-4839 (2008).
Ohno et al., "Expression of miR-17-92 enhances anti-tumor activity of T-cells transduced with the anti-EGFRvIII chimeric antigen receptor in mice bearing human GBM xenografts," J Immunother. Cancer, 1:21 (2013).
Ohno et al., "Retrovirally engineered T-cell-based immunotherapy targeting type III variant epidermal growth factor receptor, a glioma-associated antigen," Cancer Sci., 101:2518-2524 (2010).
Ordonez et al., "Diagnostic utility of immunohistochemistry in distinguishing between epithelioid pleural mesotheliomas and breast carcinomas: a comparative study," Hum. Pathol., 45:1529-1540 (2014).
Ordonez, "Application of mesothelin immunostaining in tumor diagnosis," Am. J Surg. Pathol., 27:1418-1428 (2003).
Ordonez, "The diagnostic utility of immunohistochemistry in distinguishing between epithelioid mesotheliomas and squamous carcinomas of the lung: a comparative study," Mod. Pathol., 19:417-428 (2006).
Ordonez, "The diagnostic utility of immunohistochemistry in distinguishing between mesothelioma and renal cell carcinoma: a comparative study," Hum. Pathol., 35:697-710 (2004).
Ordonez, "The immunohistochemical diagnosis of mesothelioma: a comparative study of epithelioid mesothelioma and lung adenocarcinoma," Am. J Surg. Pathol., 27:1031-1051 (2003).
Ordonez, "Value of mesothelin immunostaining in the diagnosis of mesothelioma," Mod. Pathol., 16:192-197 (2003).
Osborn et al., "Evaluation of TCR Gene Editing Achieved by TALENs, CRISPR/Cas9, and megaTAL Nucleases," Mol. Ther., 24(3):570-581 (2016).

(56) References Cited

OTHER PUBLICATIONS

Pan et al., "Expression of calretinin and other mesothelioma-related markers in thymic carcinoma and thymoma," Hum. Pathol., 34:1155-1162 (2003).
Panelli et al., "A tumor-infiltrating lymphocyte from a melanoma metastasis with decreased expression of melanoma differentiation antigens recognizes MAGE-12," J. Immunol., 164(8):4382-4392 (2000).
Panelli et al., "Expansion of tumor-T cell pairs from fine needle aspirates of melanoma metastases," J. Immunol., 164:495-504 (2000).
Papa et al., "Clinical Evaluation of ErbB-Targeted CAR T-Cells, Following Intracavity Delivery in Patients with ErbB-Expressing Solid Tumors," Methods Mol. Biol., 1317:365-382 (2015).
Papanicolaou et al., "Rapid expansion of cytomegalovirus-specific cytotoxic T lymphocytes by artificial antigen-presenting cells expressing a single HLA allele," Blood, 102(7):2498-2505 (2003).
Parente-Pereira et al., "Use of retroviral-mediated gene transfer to deliver and test function of chimeric antigen receptors in human T-cells," J. Biol. Methods, 1(2):e7 (2014).
Parinyanitikul et al., "Mesothelin expression and survival outcomes in triple receptor negative breast cancer," Clin. Breast Cancer, 13(5): doi:10.1016/j.clbc.2013.05.001 (2013).
Park et al., "Adoptive transfer of chimeric antigen receptor re-directed cytolytic T lymphocyte clones in patients with neuroblastoma," Mol. Ther., 15:825-833 (2007).
Parker et al., "Expansion and characterization of T cells transduced with a chimeric receptor against ovarian cancer," Hum. Gene Ther., 11:2377-2387 (2000).
Patel et al., "T-cell killing of heterogenous tumor or viral targets with bispecific chimeric immune receptors," Cancer Gene Ther. 7:1127-1134 (2000).
Petrausch et al., "Re-directed T cells for the treatment of fibroblast activation protein (FAP)-positive malignant pleural mesothelioma (FAPME-1)," BMC Cancer, 12:615 (2012).
Pinthus et al., "Immuno-gene therapy of established prostate tumors using chimeric receptor-redirected human lymphocytes," Cancer Res., 63:2470-2476 (2003).
Poirot et al., "Multiplex Genome-Edited T-cell Manufacturing Platform for "Off-the-Shelf" Adoptive T-cell Immunotherapies," Cancer Res., 75(18):3853-3864 (2015).
Pollok et al., "Costimulation of transduced T lymphocytes via T cell receptor-CD3 complex and CD28 leads to increased transcription of integrated retrovirus," Hum. Gene Ther., 10:2221-2236 (1999).
Ponomarev et al., "Imaging TCR-dependent NFAT-mediated T-cell activation with positron emission tomography in vivo," Neoplasia, 3(6):480-488 (2001).
Provasi et al., "Editing T cell specificity towards leukemia by zinc finger nucleases and lentiviral gene transfer," Nat. Med., 18(5):807-815 (2012).
Pu et al., "Utility of WT-1, p63, MOC31, mesothelin, and cytokeratin (K903 and CK5/6) immunostains in differentiating adenocarcinoma, squamous cell carcinoma, and malignant mesothelioma in effusions," Diagn. Cytopathol., 36:20-25 (2008).
Pule et al., "Virus-specific T cells engineered to coexpress tumor-specific receptors: persistence and antitumor activity in individuals with neuroblastoma," Nat. Med., 14:1264-1270 (2008).
Putnam et al., "Clinical grade manufacturing of human alloantigen-reactive regulatory T cells for use in transplantation," Am. J. Transplant., 13(11):3010-3020 (2013).
Putnam et al., "Expansion of Human Regulatory T-Cells From Patients With Type 1 Diabetes," Diabetes, 58:652-662 (2009).
Quinn et al., "T cell activation modulates retrovirus-mediated gene expression," Hum. Gene Ther., 9:1457-1467 (1998).
Rader, "DARTs take aim at BiTEs," Blood, 117(17):4403-4404 (2011).
Rainusso et al., "Immunotherapy targeting HER2 with genetically modified T cells eliminates tumor-initiating cells in osteosarcoma," Cancer Gene Ther., 19:212-217 (2012).
Rettig et al., "Transduction and selection of human T cells with novel CD34/thymidine kinase chimeric suicide genes for the treatment of graft-versus-host disease," Mol. Ther., 8:29-41 (2003).
Riese et al., "Enhanced effector responses in activated CD8+ T cells deficient in diacylglycerol kinases," Cancer Res., 73:3566-3577 (2013).
Riley et al., "Human T regulatory cell therapy: take a billion or so and call me in the morning," Immunity, 30:656-665 (2009).
Riviere et al., "Effects of retroviral vector design on expression of human adenosine deaminase in murine bone marrow transplant recipients engrafted with genetically modified cells," Proc. Natl. Acad. Sci. USA, 92:6733-6737 (1995).
Riviere et al., "Hematopoietic stem cell engineering at a crossroads," Blood, 119(5):1107-1116 (2012).
Rizk et al., "Tissue and serum mesothelin are potential markers of neoplastic progression in Barrett's associated esophageal adenocarcinoma," Cancer Epidemiol. Biomarkers Prev., 21(3):482-486 (2012).
Roe et al., "Mesothelin-related predictive and prognostic factors in malignant mesothelioma: a nested case-control study," Lung Cancer, 61:235-243 (2008).
Rosen et al., "Potential markers that complement expression of CA125 in epithelial ovarian cancer," Gynecol. Oncol. 99:267-277 (2005).
Rosenberg et al., "Gene transfer into humans—immunotherapy of patients with advanced melanoma, using tumor-infiltrating lymphocytes modified by retroviral gene transduction," N. Engl. J. Med., 323:570-578 (1990).
Rossig et al., "Targeting of G(D2)-positive tumor cells by human T lymphocytes engineered to express chimeric T-cell receptor genes," Int. J Cancer, 94:228-236 (2001).
Roybal et al., "Engineering T Cells with Customized Therapeutic Response Programs Using Synthetic Notch Receptors," Cell, 167(2):419-432 (2016).
Sabatos-Peyton et al., "Antigen-specific immunotherapy of autoimmune and allergic diseases," Curr. Opin. Immunol., 22(5):609-615 (2010).
Sadelain et al., "Efficient retroviral-mediated gene transfer into murine primary lymphocytes," 8th International Congress of Immunology, Budapest, Hungary, Aug. 23-28, 1992, W-88:542, Absract 34.
Sadelain et al., "Targeting Tumours with Genetically Enhanced T Lymphocytes," Nat. Rev. Cancer, 3:35-45 (2003).
Sadelain et al., "The basic principles of chimeric antigen receptor design," Cancer Discov., 3(4):388-398 (2013).
Sadelain et al., "The promise and potential pitfalls of chimeric antigen receptors," Curr. Opin. Immunol., 21(2):215-223 (2009).
Sadelain, "CAR therapy: the CD19 paradigm," J. Clin. Invest., 125(9):3392-3400 (2015).
Sage et al., "PD-1 controls Lymph Node and Blood T Follicular Regulatory Cells," Nat. Immunol., 14(2):152-161 (2013).
Sakuma et al., "Homologous Recombination-Independent Large Gene Cassette Knock-in in CHO Cells Using TALEN and MMEJ-Directed Donor Plasmids," Int. J. Mol. Sci., 16(10):23849-23866 (2015).
Sampson et al., "EGFRVIII mCAR-modified T-cell therapy cures mice with established intracerebral glioma and generates host immunity against tumor-antigen loss," Clin. Cancer Res., 20:972-984 (2014).
Sanchez et al., "Combining T-cell immunotherapy and anti-androgen therapy for prostate cancer," Prostate Cancer Prostatic Dis., 16:123-131 (2013).
Sather et al., "Efficient modification of CCR5 in primary human hematopoietic cells using a megaTAL nuclease and AAV donor template," Sci. Transl. Med., 7(307):307ra156 (2015).
Scales et al., "An antimesothelin-monomethyl auristatin e conjugate with potent antitumor activity in ovarian, pancreatic, and mesothelioma models," Mol. Cancer Ther., 13:2630-2640 (2014).
Schietinger et al., "Tolerance and exhaustion: defining mechanisms of T cell dysfunction," Trends Immunol., 35(2):51-60 (2014).
Schirrmann et al., "Human natural killer cell line modified with a chimeric immunoglobulin T-cell receptor gene leads to tumor growth inhibition in vivo," Cancer Gene Ther., 9:390-398 (2002).

(56) References Cited

OTHER PUBLICATIONS

Schmidt et al., "Eradication of melanomas by targeted elimination of a minor subset of tumor cells," Proc. Natl. Acad. Sci. U.S.A., 108:2474-2479 (2011).
Scholler et al., "Decade-Long Safety and Function of Retroviral-Modified Chimeric Antigen Receptor T-cells," Sci. Transl. Med., 4:132ra53 (2012).
Schroder et al., "HIV-1 integration in the human genome favors active genes and local hotspots," Cell, 110(4):521-529 (2002).
Schrum et al., "Surface T-cell antigen receptor expression and availability for long-term antigenic signaling," Immunol. Rev., 196:7-24 (2003).
Schuberth et al., "Treatment of malignant pleural mesothelioma by fibroblast activation protein-specific re-directed T cells," J. Transl. Med., 11:187 (2013).
Seddiki et al., "Expression of interleukin (IL)-2 and IL-7 receptors discriminates between human regulatory and activated T cells," J. Exp. Med., 203:1693-1700 (2006).
Servais et al., "Mesothelin overexpression promotes mesothelioma cell invasion and MMP-9 secretion in an orthotopic mouse model and in epithelioid pleural mesothelioma patients," Clin. Cancer Res., 18(9):2478-2489 (2012).
Sharifzadeh et al., "Genetically engineered T cells bearing chimeric nanoconstructed receptors harboring TAG-72-specific camelid single domain antibodies as targeting agents," Cancer Lett., 334:237-244 (2013).
Sharp, "Gene Therapy," Lancet, 337:1277-1278 (1991).
Sharpe et al., "Genetically modified T cells in cancer therapy: opportunities and challenges," Dis. Model Mech., 8(4):337-350 (2015).
Shen et al., "Chimeric antigen receptor containing ICOS signaling domain mediates specific and efficient antitumor effect of T cells against EGFRvIII expressing glioma," J Hematol. Oncol., 6:33 (2013).
Shibaguchi et al., "A fully human chimeric immune receptor for retargeting T-cells to CEA-expressing tumor cells," Anticancer Res., 26:4067-4072 (2006).
Shirasu et al., "Molecular characterization of a fully human chimeric T-cell antigen receptor for tumor-associated antigen EpCAM.," J Biomed. Biotechnol., 2012:ID853879 (2012).
Singh et al., "Nature of tumor control by permanently and transiently modified GD2 chimeric antigen receptor T cells in xenograft models of neuroblastoma," Cancer Immunol. Res., 2:1059-1070 (2014).
Sommermeyer et al., "Chimeric antigen receptor-modified T cells derived from defined CD8+ and CD4+ subsets confer superior antitumor reactivity in vivo," Leukemia, 30(2):492-500 (2016).
Song et al., "A fully human chimeric antigen receptor with potent activity against cancer cells but reduced risk for off-tumor toxicity," Oncotarget, 6(25):21533-21546 (2015).
Song et al., Chimeric NKG2D CAR-expressing T cell-mediated attack of human ovarian cancer is enhanced by histone deacetylase inhibition Hum. Gene Ther., 24:295-305 (2013).
Song et al., "In vivo persistence, tumor localization, and antitumor activity of CAR-engineered T cells is enhanced by costimulatory signaling through CD137 (4-1BB)," Cancer Res., 71:4617-4627 (2011).
Sontheimer, "The Bacterial Origins of the CRISPR Genome-Editing Revolution," Hum. Gene Ther., 26(7):413-424 (2015).
Stancovski et al., "Targeting of T lymphocytes to Neu/HER2-expressing cells using chimeric single chain Fv receptors," J Immunol., 151:6577-6582 (1993).
Stastny et al., "Medulloblastomas expressing IL13Ralpha2 are targets for IL 13-zetakine+ cytolytic T cells," J Pediatr. Hematol. Oncol., 29:669-677 (2007).
Su et al., "Human CD4+CD25 high CD127 low/neg Regulatory T Cells," Methods Mol. Biol., 806:287-299 (2012).
Sun et al., "Construction and evaluation of a novel humanized HER2-specific chimeric receptor," Breast Cancer Res., 16:R61 (2014).

Swierczynski et al., "Analysis of novel tumor markers in pancreatic and biliary carcinomas using tissue microarrays," Hum. Pathol., 35:357-366 (2004).
Szymczak et al., "Development of 2A peptide-based strategies in the design of multicistronic vectors," Expert Opin. Biol. Therapy, 5(5):627-638 (2005).
Tan et al., "Mesothelin (MSLN) promoter is hypomethylated in malignant mesothelioma, but its expression is not associated with methylation status of the promoter," Hum. Pathol.,41:1330-1338 (2010).
Tang et al., "T cells expressing a LMP1-specific chimeric antigen receptor mediate antitumor effects against LMP1-positive nasopharyngeal carcinoma cells in vitro and in vivo," J Biomed. Res., 28:468-475 (2014).
Tchou et al., "Mesothelin, a novel immunotherapy target for triple negative breast cancer," Breast Cancer Res. Treat., 133:799-804 (2012).
Tey, "Adoptive T-cell therapy: adverse events and safety switches," Clin. Transl. Immunology, 3(6):e17 (2014).
Themeli et al., "Generation of tumor-targeted human T lymphocytes from induced pluripotent stem cells for cancer therapy," Nat. Biotechnol., 31(10):928-933 (2013).
Tollefson et al., "Inhibition of TRAIL-Induced Apoptosis and Forced Internalization of TRAIL Receptor 1 by Adenovirus Proteins," J. Virol., 75(19):8875-8887 (2001).
Tolstoshev et al., "Gene expression using retroviral vectors," Current Opin. Biotechnol., 1:55-61 (1990).
Torikai et al., "A foundation for universal T-cell based immunotherapy: T cells engineered to express a CD19-specific chimeric-antigen-receptor and eliminate expression of endogenous TCR," Blood, 119(24):5697-5705 (2012).
Torikai et al., "Toward eliminating HLA class I expression to generate universal cells from allogeneic donors," Blood, 122(8):1341-1349 (2013).
Tozbikian et al., "Mesothelin expression in triple negative breast carcinomas correlates significantly with basal-like phenotype, distant metastases and decreased survival," PLoS One, 9(12):e114900 (2014).
Tsai et al., "Defining and improving the genome-wide specificities of CRISPR-Cas9 nucleases," Nat. Rev. Genet., 17(5):300-312 (2016).
Ukena et al., "Isolation strategies of regulatory T cells for clinical trials: Phenotype, function, stability, and expansion capacity," Exp. HEmatol., 39:1152-1160 (2011).
Van Lent et al., "Functional human antigen-specific T cells produced in vitro using retroviral T cell receptor transfer into hematopoietic progenitors," J. Immunol., 179:4959-4968 (2007).
Vasileva et al., "Genome-editing tools for stem cell biology," Cell Death Dis., 6:e1831 (2015).
Von Heijne, "Signal sequences. The limits of variation," J. Mol. Biol., 184(1):99-105 (1985).
Von Kalle et al., "Vector integration and tumorigenesis," Hum. Gene Ther., 25(6):475-481 (2014).
Wang et al., "Clinical manufacturing of CAR T cells: foundation of a promising therapy," Mol. Ther. Oncolytics, 3:16015 (2016).
Wang et al., "Clinicopathological significance of mesothelin expression in invasive breast cancer," J Int. Med. Res., 40:909-916 (2012).
Wang et al., "Generation of Potent T-cell Immunotherapy for Cancer Using DAP12-Based, Multichain, Chimeric Immunoreceptors," Cancer Immunol. Res., 3:815-826 (2015).
Wang et al., "Genetically targeted T cells eradicate established breast cancer in syngeneic mice," Clin. Cancer Res., 15:943-950 (2009).
Wang et al., "Highly efficient homology-driven genome editing in human T cells by combining zinc-finger nuclease mRNA and AAV6 donor delivery," Nucelic Acids Res., 44(3):e30 (2016).
Wang et al., "Quantitative analysis of clinically relevant mutations occurring in lymphoid cells harboring gamma-retrovirus-encoded hsvtk suicide genes," Gene Therapy, 15:1454-1459 (2008).
Wang et al., "Specificity redirection by CAR with human VEGFR-1 affinity endows T lymphocytes with tumor-killing ability and anti-angiogenic potency," Gene Ther., 20:970-978 (2013).

(56) References Cited

OTHER PUBLICATIONS

Wang et al., "Targeting fibroblast activation protein in tumor stroma with chimeric antigen receptor T cells can inhibit tumor growth and augment host immunity without severe toxicity," Cancer Immunol. Res., 2:154-166 (2014).
Wang et al., "The transcription factor Myc controls metabolic reprogramming upon T lymphocyte activation," Immunity, 35(6):871-882 (2011).
Wanisch et al., "Integration-deficient lentiviral vectors: a slow coming of age," Mol. Ther., 17(8):1316-1332 (2009).
Ward et al., "Binding activities of a repertoire of single immunoglobulin variable domains secreted from *Escherichia coli*," Nature, 341:544-546 (1989).
Waring et al., "Cell death induced by the Fas/Fas ligand pathway and its role in pathology," Immunol. Cell Biol., 77(4):312-317 (1999).
Westwood et al., "Adoptive transfer of T cells modified with a humanized chimeric receptor gene inhibits growth of Lewis-Y-expressing tumors in mice," Proc. Natl. Acad. Sci. U.S.A., 102:19051-19056 (2005).
Westwood et al., "The Lewis-Y carbohydrate antigen is expressed by many human tumors and can serve as a target for genetically redirected T cells despite the presence of soluble antigen in serum," J Immunother., 32:292-301 (2009).
Wherry et al., "Molecular and cellular insights into T cell exhaustion," Nat. Rev. Immunol., 15(8):486-499 (2015).
Wilkie et al., "Dual targeting of ErbB2 and MUC1 in breast cancer using chimeric antigen receptors engineered to provide complementary signaling," J Clin. Immunol., 32:1059-1070 (2012).
Wilkie et al., "Retargeting of human T cells to tumor-associated MUC1: the evolution of a chimeric antigen receptor," J Immunol., 180:4901-4909 (2008).
Willemsen et al., "A phage display selected fab fragment with MHC class I-restricted specificity for MAGE-A1 allows for retargeting of primary human T lymphocytes," Gene Ther., 8:1601-1608 (2001).
Willemsen et al., "T cell retargeting with MHC class I-restricted antibodies: the CD28 costimulatory domain enhances antigen-specific cytotoxicity and cytokine production," J Immunol., 174:7853-7858 (2005).
Winter et al., "Humanized antibodies," Immunol. Today, 14:243-246 (1993).
Wolfl et al., "Antigen-specific activation and cytokine-facilitated expansion of naive, human CD8+ T cells," Nat. Protoc., 9(4):950-966 (2014).
Wright et al, "Biology and Applications of CRISPR Systems: Harnessing Nature's Toolbox for Genome Engineering," Cell, 164:29-44 (2016).
Written Opinion for International Application No. PCT/US2017/027601 dated Nov. 14, 2017.
Wu et al., "B7H6-Specific Bispecific T Cell Engagers Lead to Tumor Elimination and Host Antitumor Immunity," J Immunol., 194:5305-5311 (2015).
Wu et al., "B7H6-specific chimeric antigen receptors lead to tumor elimination and host antitumor immunity," Gene Ther., 22:675-684 (2015).
Wu et al., "DNAM-1-based chimeric antigen receptors enhance T cell effector function and exhibit in vivo efficacy against melanoma," Cancer Immunol. Immunother., 64:409-418 (2015).
Wu et al., "FOXP3 controls regulatory T cell function through cooperation with NFAT," Cell, 126(2):375-387 (2006).
Wu et al., "Remote control of therapeutic T cells through a small molecule-gated chimeric receptor," Science, 350(6258):aab4077 (2015).
Wu et al., "Transcription start regions in the human genome are favored targets for MLV integration," Science, 300(5626):1749-1751 (2003).
Yamagiwa et al., "A role for TGF-beta in the generation and expansion of CD4+CD25+ regulatory T cells from human peripheral blood," J. Immunol., 166:7282-7289 (2001).
Yant et al., "High-resolution genome-wide mapping of transposon integration in mammals," Mol. Cell Biol., 25(6):2085-2094 (2005).
Yen et al., "Diffuse mesothelin expression correlates with prolonged patient survival in ovarian serous carcinoma," Clin. Cancer Res., 12:827-831 (2006).
Yu et al., "Mesothelin as a potential therapeutic target in human cholangiocarcinoma," J Cancer, 1:141-149 (2010).
Yun et al., "Targeting of T lymphocytes to melanoma cells through chimeric anti-GD3 immunoglobulin T-cell receptors," Neoplasia, 2:449-459 (2000).
Yvon et al., "Immunotherapy of metastatic melanoma using genetically engineered GD2-specific T cells," Clin. Cancer Res., 15:5852-5860 (2009).
Zhang et al., "An NKp30-based chimeric antigen receptor promotes T cell effector functions and antitumor efficacy in vivo," J Immunol., 189:2290-2299 (2012).
Zhang et al., "Anti-melanoma activity of T cells redirected with a TCR-like chimeric antigen receptor," Sci. Rep., 4:3571 (2014).
Zhang et al., "Improving adoptive T cell therapy by targeting and controlling IL-12 expression to the tumor environment," Mol. Ther., 19(4):751-759 (2011).
Zhang et al., "Retargeting NK-92 for anti-melanoma activity by a TCR-like single-domain antibody," Immunol. Cell Biol., 91:615-624 (2013).
Zhao et al., "Herceptin-based chimeric antigen receptor with modified signaling domains leads to enhanced survival of transduced T lymphocytes and antitumor activity," J. Immunol., 183:5563-5574 (2009).
Zhao et al., "Multiple injections of electroporated autologous T cells expressing a chimeric antigen receptor mediate regression of human disseminated tumor," Cancer Res., 70:9053-9061 (2010).
Zhao et al., "Structural Design of Engineered Costimulation Determines Tumor Rejection Kinetics and Persistence of CAR T Cells," Cancer Cell, 28(4):415-428 (2015).
Zheng et al., "Generation ex vivo of TGF-beta-producing regulatory T cells from CD4+CD25—precursors," J. Immunol., 169(8):4183-4189 (2002).
Zhou et al., "TGF-beta-induced Foxp3 inhibits T(H)17 cell differentiation by antagonizing RORgammat function," Nature, 453(7192):236-240 (2008).
Ziegler et al., "The activation antigen CD69," Stem Cells, 12(5):456-465 (1994).

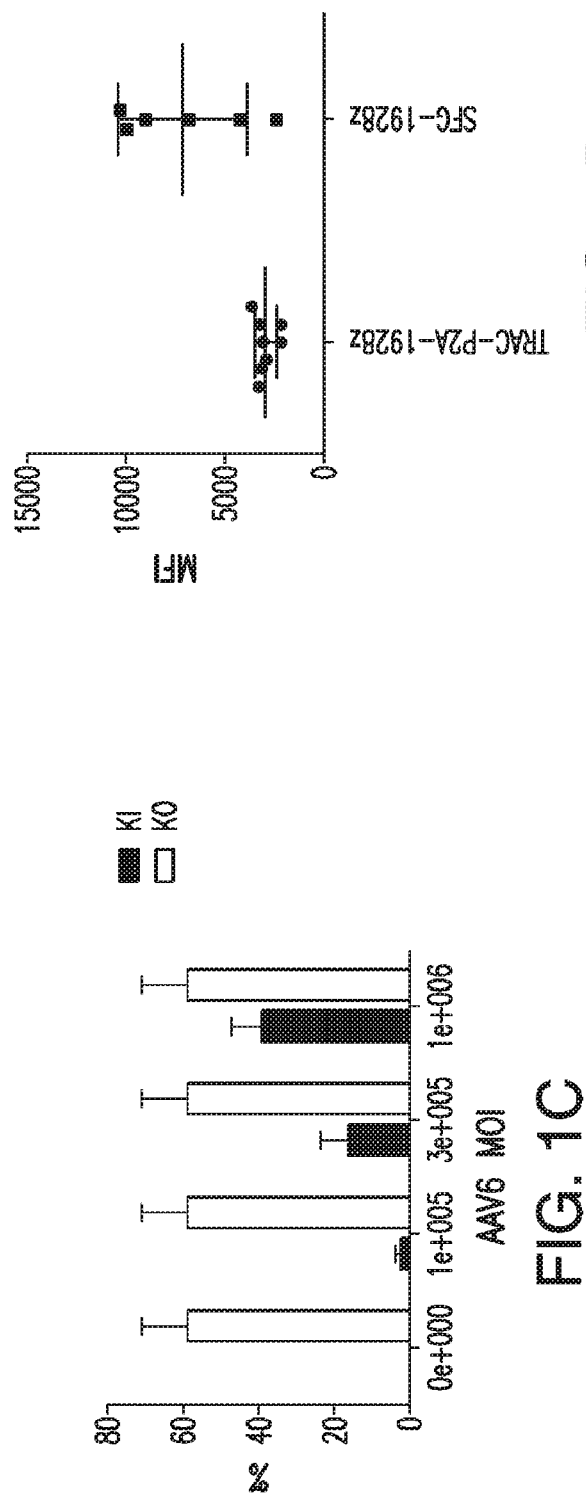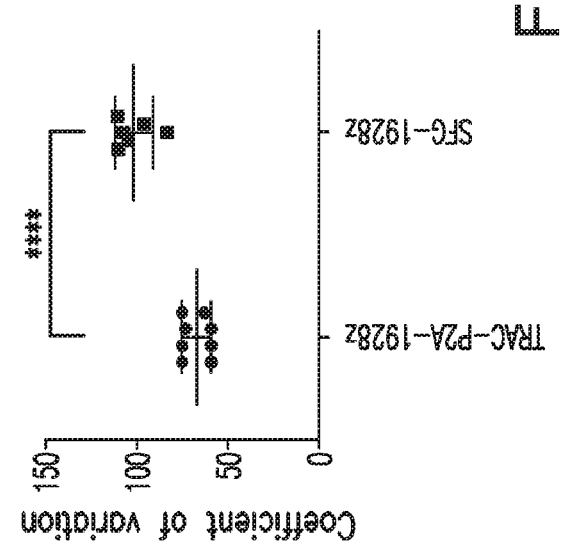

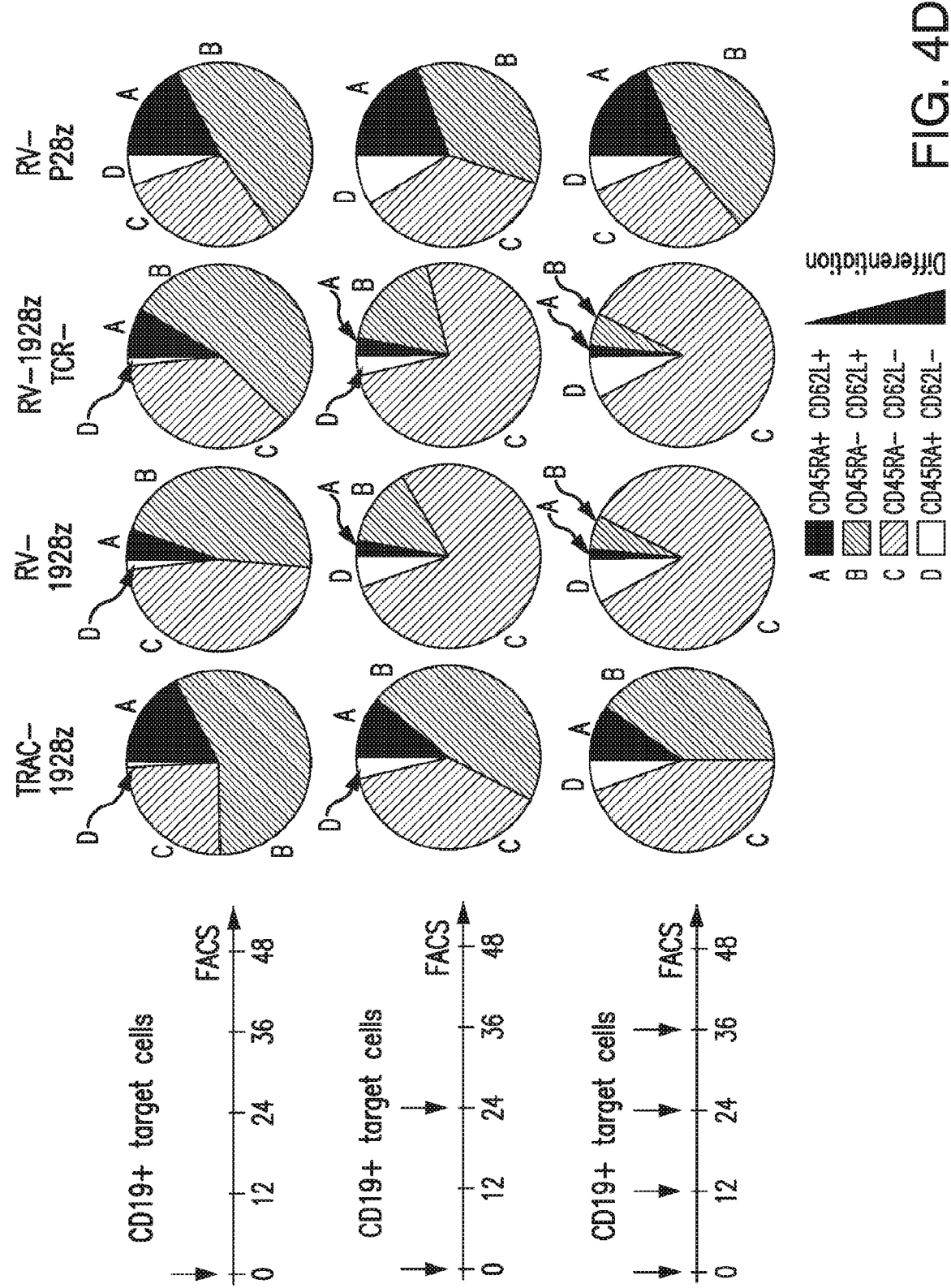

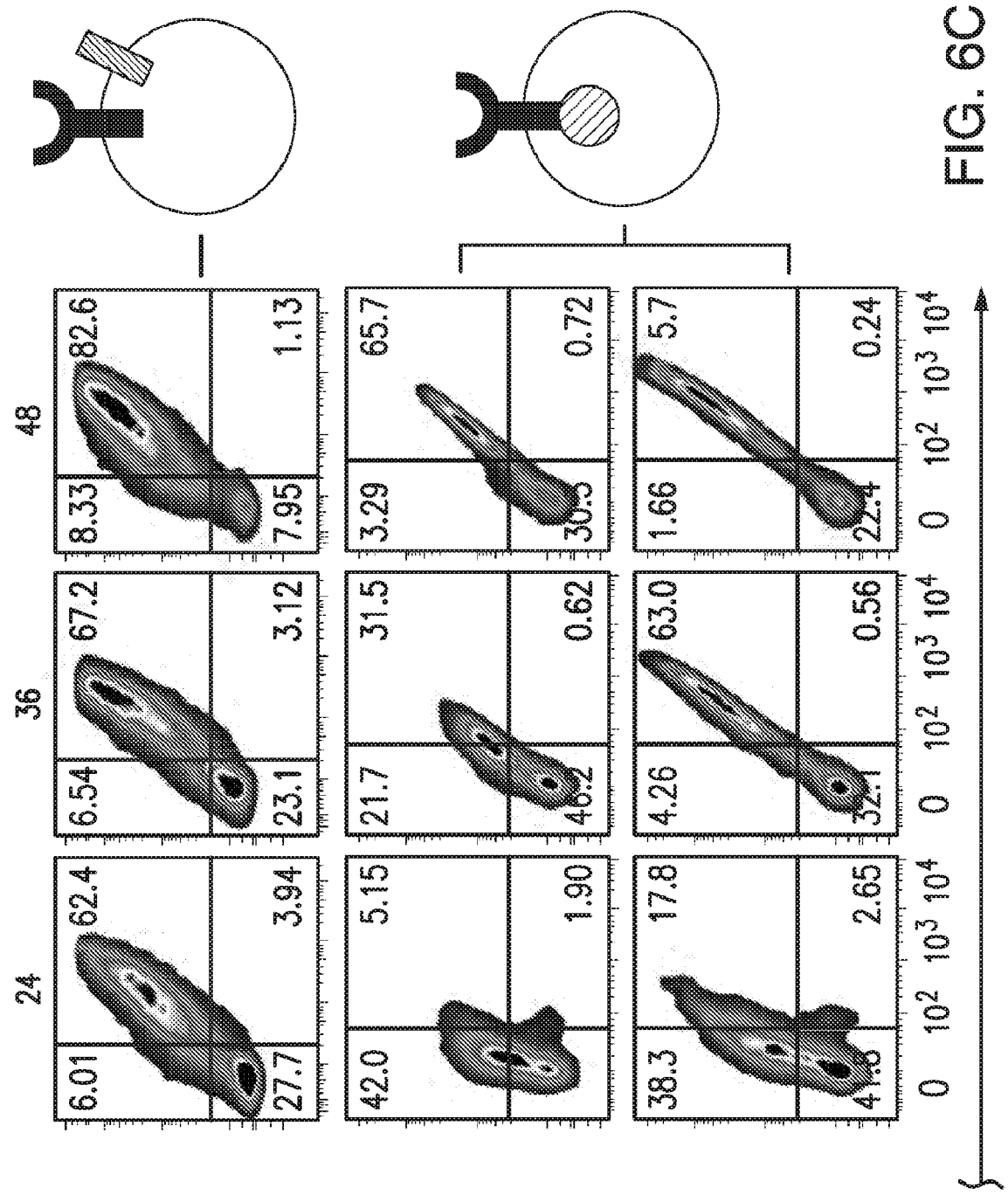

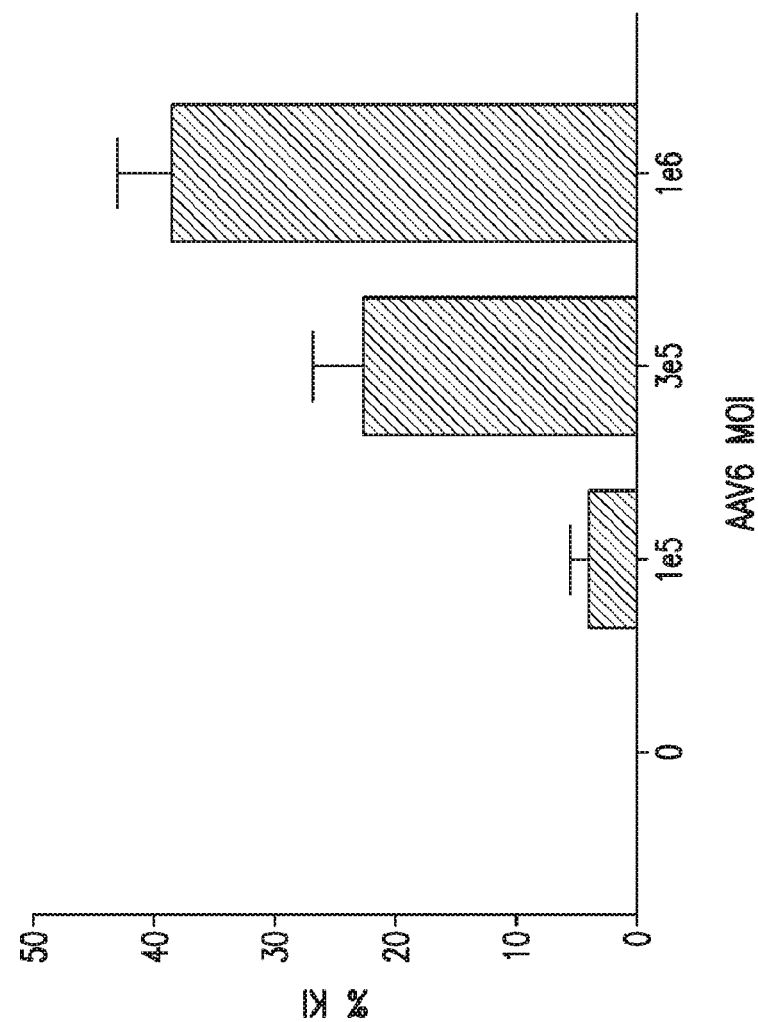
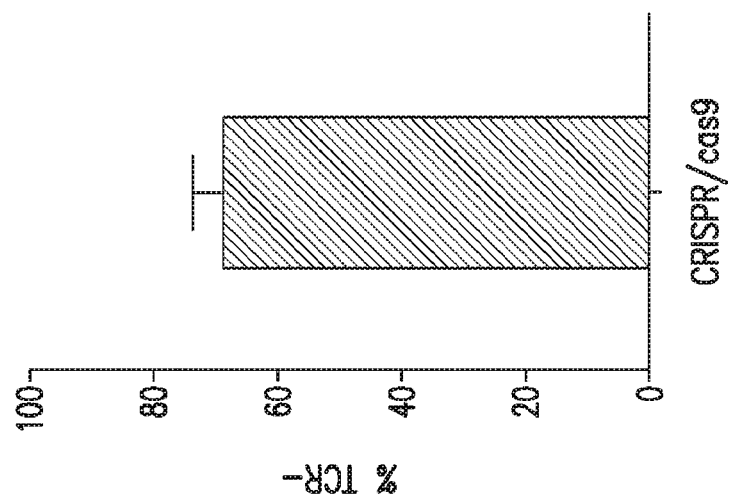

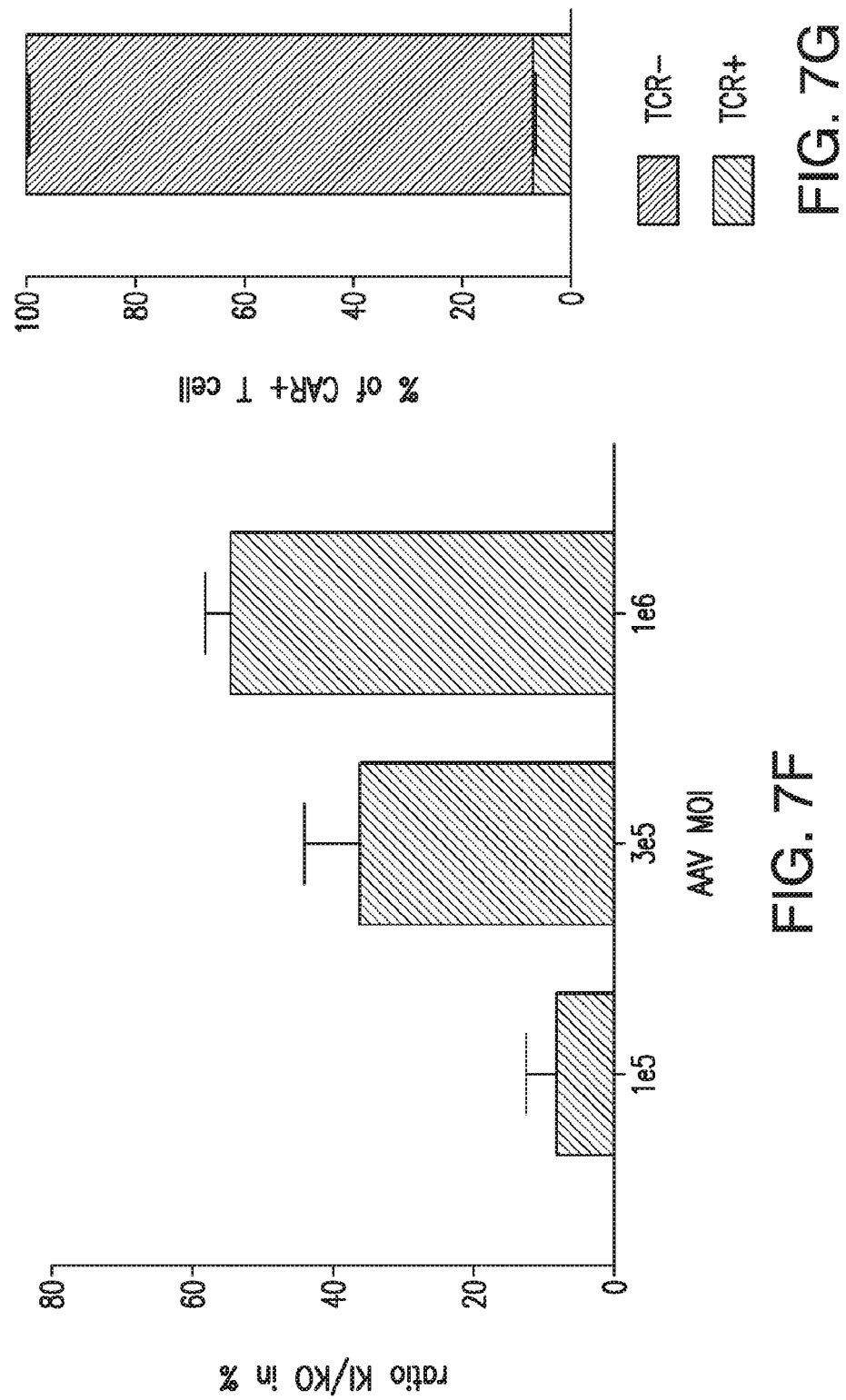

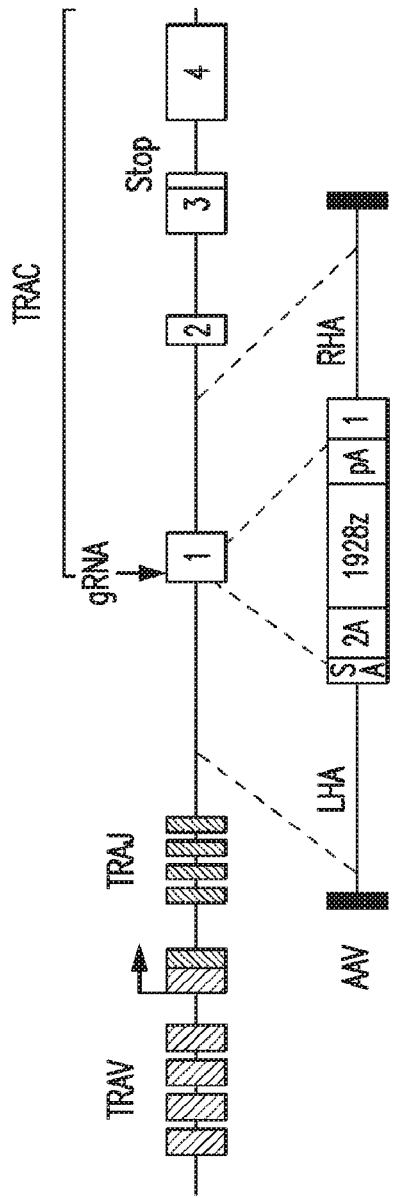
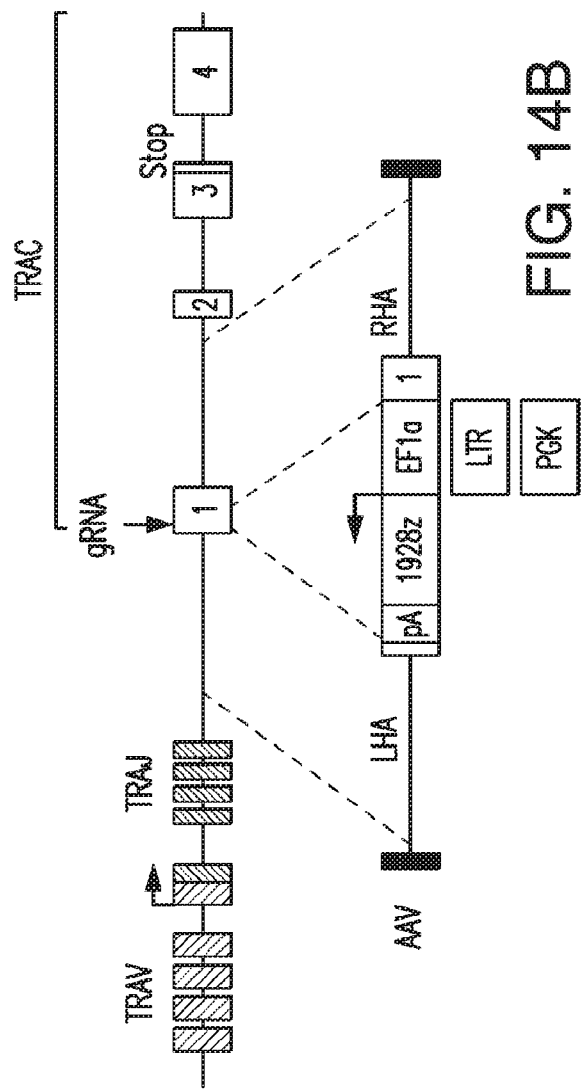
FIG. 14A
FIG. 14B

```
>wild type MLV IN sequence
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weidfteikp glygykyllv fidtfsgwie afptkketak vvtkklleei fprfgmpqvl
181 gtdngpafvs kvsqtvadll qidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124A IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiAfteikp glygykyllv fidtfsgwie afptkketak vvtkklleei fprfgmpqvl
181 gtdngpafvs kvsqtvadll qidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124E IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiEfteikp glygykyllv fidtfsgwie afptkketak vvtkklleei fprfgmpqvl
181 gtdngpafvs kvsqtvadll qidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124N IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiNfteikp glygykyllv fidtfsgwie afptkketak vvtkklleei fprfgmpqvl
181 gtdngpafvs kvsqtvadll qidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124V IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiVfteikp glygykyllv fidtfsgwie afptkketak vvtkklleei fprfgmpqvl
181 gtdngpafvs kvsqtvadll qidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D183A IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weidfteikp glygykyllv fidtfsgwie afptkketak vvtkklleei fprfgmpqvl
181 gtAngpafvs kvsqtvadll qidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap
```

FIG. 18

```
>D183N IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weidfteikp glygykyllv fidtfsgwie afptkketak vvtkklleei fprfgmpqvl
181 gtNngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124A + D183A IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiAfteikp glygykyllv fidtfsgwie afptkketak vvtkklleei fprfgmpqvl
181 gtAngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124A + D183N IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiAfteikp glygykyllv fidtfsgwie afptkketak vvtkklleei fprfgmpqvl
181 gtNngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124E + D183A IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiEfteikp glygykyllv fidtfsgwie afptkketak vvtkklleei fprfgmpqvl
181 gtAngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124E + D183N IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiEfteikp glygykyllv fidtfsgwie afptkketak vvtkklleei fprfgmpqvl
181 gtNngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124N + D183A IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiNfteikp glygykyllv fidtfsgwie afptkketak vvtkklleei fprfgmpqvl
181 gtAngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap
```

FIG. 18 continued

```
>D124N + D183N IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiNfteikp glygykyllv fidtfsqwie afptkketak vvtkklleei fprfgmpqvl
181 gtNngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124V + D183A IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiVfteikp glygykyllv fidtfsqwie afptkketak vvtkklleei fprfgmpqvl
181 gtAngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap >D124V + D183N IN
  1 ensspytseh fhytvtdikd ltklgaiydk tkkywvyqgk pvmpdqftfe lldflhqlth
 61 lsfskmkall ershspyyml nrdrtlknit etckacaqvn asksavkqgt rvrghrpgth
121 weiVfteikp glygykyllv fidtfsqwie afptkketak vvtkklleei fprfgmpqvl
181 gtNngpafvs kvsqtvadll gidwklhcay rpqssgqver mnrtiketlt kltlatgsrd
241 wvlllplaly rarntpgphg ltpyeilyga ppplvnfpdp dmtrvtnsps lqahlqalyl
301 vqhevwrpla aayqeqldrp vvphpyrvgd tvwvrrhqtk nleprwkgpy tvllttptal
361 kvdgiaawih aahvkaadpg ggpssrltwr vqrsqnplki rltreap
```

FIG. 18 continued

TRANSGENIC T CELL AND CHIMERIC ANTIGEN RECEPTOR T CELL COMPOSITIONS AND RELATED METHODS

1. CROSS-REFERENCE TO RELATED APPLICATIONS

This application is a divisional of U.S. application Ser. No. 16/091,494, national stage of International Application No. PCT/US2017/027601, filed Apr. 14, 2017, which claims the benefit of U.S. Provisional application No. 62/323,623, filed Apr. 15, 2016, U.S. Provisional application No. 62/323,675, filed Apr. 16, 2016, U.S. Provisional application No. 62/461,677, filed Feb. 21, 2017, and U.S. Provisional application No. 62/462,243, filed Feb. 22, 2017, each of which is incorporated by reference herein in its entirety.

2. REFERENCE TO SEQUENCE LISTING SUBMITTED ELECTRONICALLY

This application incorporates by reference a Sequence Listing with this application as an ASCII text file entitled "13542-076-999SL.txt" created on May 13, 2022, and having a size of 76,470 bytes.

3. FIELD

The present invention relates generally to immunotherapy, and more specifically to immunotherapy using engineered immune cells such as T cells.

4. BACKGROUND

Targeted immunotherapies rely on the use of immune cells or molecules that engage immune cells to treat a variety of diseases, including cancer, infectious and autoimmune disorders (Miller & Sadelain, *Cancer Cell.* 27(4):439-49 (2015); Sabatos-Peyton et al., *Curr. Opin. Immunol.* 22(5): 609-615 (2010); McLeod & Anderton, *Curr. Opin. Pharmacol.* 23:1-108 (2015)). Recently, the genetic modification of T cells to express chimeric antigen receptors (CARs) that target tumor antigens has allowed the successful eradication of leukemic cells in humans (Brentjens et al., *Sci. Transl. Med.* 5(177):177ra38. doi: 10.1126/scitranslmed.3005930 (2013)). In the latter approach, the complementary DNA (cDNA) encoding the CAR is delivered to T cells via integration-competent gamma-retroviruses or lentiviruses. These recombinant viral vectors require a viral integrase enzyme, which catalyzes the integration of the viral DNA into the human genome in a semi-random manner (Schroder et al., *Cell* 110(4):521-529 (2002); Wu et al., *Science* 300 (5626):1749-1751 (2003)). A third approach makes use of a DNA transposition mechanism, whose components can be delivered into the cells without the need of viral particles. In this case, a DNA transposase carries out the integration of the DNA transposon (containing the gene(s) of interest) into the human genome, also in a semi-random fashion (Yant et al., *Mol. Cell. Biol.* 25(6):2085-2094 (2005)). All the above-mentioned gene delivery methods produce a T cell population exhibiting heterogeneous CAR expression due to different genomic locations of the integrated vector. This "variegated expression" limits the number of cells with a CAR expression that is optimal for target cell interaction and for T cell activation strength. In addition, this uncontrolled DNA integration may potentially result in insertional mutagenesis, which can either activate a proto-oncogene or inactivate a tumor suppressor gene. Another limitation of these genetic modification approaches is that T cells still express their antigen receptor, known as TCR, which can still participate in antigen recognition, thus activating the CAR T cell. This potential side effect limits the use of autologous CAR T cells in patients with autoimmune disorders, or the use of allogeneic CAR T cells in any recipient, two circumstances where the T cell may attack the recipient's tissues (causing autoimmunity in the first instance and graft versus host disease (GvHD) in the latter).

The genetic modification of cells through homologous recombination permits the precise integration of exogenous DNA at chosen genomic sites (Cappechi et al., *Nat. Rev. Genet.* 6(6):507-512 (2005)). Such targeted delivery has been recently described where a promoter-containing CAR construct was targeted into the CCR5 locus in human primary T cells, which allowed the modified T cells to kill tumor cells in vitro (Sather et al., *Sci. Transl. Med.* 7(307): 307ra156. doi: 10.1126/scitranslmed.aac5530 (2015)). Though interesting, the authors did not show whether CAR expression driven by the MND promoter can be maintained constant in the CCR5 locus, and more importantly, they did not show that the level of CAR expression was optimal to eradicate tumor cells in vivo. In addition, CCR5 disruption has been linked to an increased susceptibility to West Nile virus infection (Lim et al, *Trends Immunol.* 27(7):308-312 (2006)).

Adoptive immunotherapy using chimeric antigen receptors (CARs) has shown remarkable clinical results in the treatment of leukemia and is one of the most promising new strategies to treat cancer. Current clinical protocols utilize autologous T cells that are collected by apheresis and engineered with retroviral vectors to stably express the CAR, which is responsible for the recognition of an extracellular tumor molecule, and for the activation of the engineered T cell. This approach requires patient-specific cell manufacturing, which unavoidably results in patient-to-patient variability in the final cell product. Widespread implementation of this approach will further require progress in automation and miniaturization of cell manufacturing to meet the demand for CAR T cells. Furthermore, current approaches utilize randomly integrating vectors, including gamma-retroviral, lentiviral and transposons, which all result in semi-random integration and variable expression of the CAR owing to transgene variegation. Position effects may result in heterogeneous T cell function, transgene silencing and, potentially, insertional oncogenesis. Thus, the conjunction of autologous cell sourcing and random vector integration is prone to generating cell products with variable potency.

Different tailored nucleases, including CRISPR/Cas9 system, Zinc Finger Nucleases or TAL effector nucleases (TAL-ENs), have been previously used for gene disruption in a wide range of human cells including primary T cells. In some instances, these nucleases have been used to generate so-called "universal T cells" for allogeneic administration, by disrupting T cell receptor (TCR) or HLA class I expression, but viral vectors or the sleeping beauty transposon were used to deliver the CAR cDNA, all of which result in semi-random transgene integration and its downstream consequences.

To address the negative impact that TCR expression may have on the alloreactivity of CAR T cells, a number of laboratories have designed tailored nucleases (zinc-finger nuclease, TALE nuclease, and CRISPR/Cas9 nuclease) that specifically target and cleave the 5' end of the constant region of the TCR alpha or beta chain (Provasi et al, *Nat. Med.* 18(5):807-815 (2012); Poirot et al., *Cancer Res.*

75(18):3853-3864 (2015); Osborn et al., *Mol. Ther.* 24(3): 570-581 (2016)). The cleavage at either site results in DNA modifications incorporated through the DNA repair mechanism called non-homologous end joining (NHEJ). The mutated region prevents correct splicing between the rearranged V(D)J genes with their respective constant region, thus impeding the proper assembly of the TCR complex at the cell surface. These TCR negative cells, which were disabled for causing GVHD, were then used to express CARs that were delivered with transposons or lentiviruses (Torikai et al., *Blood* 119(24):5697-5705 (2012); Poirot et al., *Cancer Res.* 75(18):3853-3864 (2015)). Though these CART cells have the advantage of not expressing a TCR that can cause GVHD, they still present the above-mentioned pitfalls due to the semi-random integration of the CAR gene (variegated expression, insertional mutagenesis).

Previously described approaches for genetically engineering a cell, such as a T cell, include the use of inducible promoters within viral vectors (e.g., NFAT promoter in a retroviral vector, or synNotch constructs), or the use of small molecules that control transcription or protein aggregation (Ponomarev et al., *Neoplasia* 3(6):480-488 (2001); Zhang et al., *Mol. Ther.* 19(4): 751-759 (2011); Roybal et al., *Cell* 167(2):419-432, e16 (2016): Wu et al., *Science* 16; 350 (6258):aab4077 (2015); Juillerat et al., *Sci. report* 18950 (2016)). These approaches are vulnerable to a number of complications and barriers, including variegated expression of randomly integrated transgenes, the necessity for intravenous drug infusion and pharmacodynamic limitations of these drugs, and immunogenicity of some of the protein components used in some of these approaches (e.g., chimeric transcription factors, immunogenic protein domains).

Chimeric antigen receptors (CARs) are synthetic receptors that redirect and reprogram T cells to mediate tumour rejection (Jensen et al., *Curr. Opin. Immunol.* 33:9-15 (2015)). The most successful CARs used to date are those targeting CD19 (Brentjens et al., *Nat. Med.* 9:279-286 (2003)), which offer the prospect of complete remissions in patients with chemorefractory/relapsed B cell malignancies (Sadelain, *J. Clin. Invest.* 125:3392-3400 (2015)). CARs are typically transduced into patient T cells using γ-retroviral (Sadelain et al., *Ninth International Immunology Congress, Budapest,* 88:34 (1992)) or other randomly integrating vectors (Wang et al., *Mol. Ther. Oncolytics* 3:16015 (2016)), which may result in clonal expansion, oncogenic transformation, variegated transgene expression and transcriptional silencing (Ellis, *Hum. Gene. Ther.* 16:1241-1246 (2005); Riviere et al., *Blood* 119:1107-1116 (2012); von Kalle et al., *Hum. Gene Ther.* 25:475-481 (2014)). Recent advances in genome editing enable efficient sequence-specific interventions in human cells (Wright et al., *Cell* 164:29-44 (2016); Tsai et al., *Nat. Rev. Genet.* 17:300-312 (2016)), including targeted gene delivery to the CCR5 and AAVS1 loci (Lombardo et al., *Nat. Methods* 8:861-869 (2011); Sather et al., *Sci. Transl. Med.* 7:307ra156 (2015)).

Thus, there exists a need for therapies to provide improved treatment using immunotherapy, such as treatment of cancer or other diseases. The present invention satisfies this need.

5. SUMMARY OF THE INVENTION

The invention is reflected by the claims presented herein and as described below. The present invention relates to T cells wherein a transgene is integrated within the genome of the T cells such that expression of the transgene is under the control of an endogenous promoter, and to methods of using such cells.

In one aspect, provided herein is a T cell wherein a transgene is integrated at a first site within the genome of the T cell such that expression of the transgene is under control of an endogenous promoter of the T cell, wherein the transgene encodes a therapeutic protein or therapeutic nucleic acid. In certain embodiments, the transgene encodes a therapeutic protein. In certain embodiments, the transgene encodes a therapeutic nucleic acid. In certain embodiments, the transgene is integrated at a single site within the genome. In certain embodiments, the transgene is integrated at two sites within the genome of the cell. In certain embodiments, the first site is an exon of the endogenous gene under control of the endogenous promoter. In a particular embodiment, the first site is within the first exon of the endogenous gene.

In certain embodiments of a T cell wherein a transgene is integrated at a first site within the genome of the T cell as described above, the endogenous promoter is constitutive. In certain embodiments, the endogenous promoter that is constitutive is selected from the group consisting of CD4 promoter, CD8a promoter, CD8b promoter, TCRa promoter, TCRb promoter, CD3d promoter, CD3g promoter, CD3e promoter, and CD3z promoter.

In certain embodiments of a T cell wherein a transgene is integrated at a first site within the genome of the T cell as described above, the endogenous promoter is active in a subset of T cells. In certain embodiments, the endogenous promoter that is active in a subset of T cells is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

In certain embodiments of a T cell wherein a transgene is integrated at a first site within the genome of the T cell as described above, the endogenous promoter is inducible.

In certain embodiments, the endogenous promoter that is inducible is induced by activation of the T cell. In certain embodiments, the endogenous promoter that is inducible is induced by binding of a chimeric antigen receptor (CAR), a chimeric co-stimulatory receptor (CCR), T cell receptor (TCR), CD28, CD27, or 4-1BB expressed by the T cell to its respective binding partner. In certain embodiments, the promoter is induced by binding of a CAR, CCR or TCR expressed by the T cell to its respective binding partner. In certain embodiments, the promoter induced by binding of a CAR, CCR or TCR expressed by the T cell to its respective binding partner is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

In certain embodiments, the endogenous promoter that is inducible is induced by binding of a ligand to an inhibitory receptor expressed by the T cell. In certain embodiments where the promoter is induced by binding of a ligand to an inhibitory receptor expressed by the T cell, the inhibitory receptor is selected from the group consisting of PD-1, CTLA4, TRAIL, LAG-3, BTLA, TIM-3, Fas, TIGIT, and 2B4. In certain embodiments where the promoter is induced by binding of a ligand to an inhibitory receptor expressed by the T cell, the promoter is selected from the group consisting of CPT1a promoter and ATGL promoter.

In certain embodiments, the endogenous promoter that is inducible is induced by binding of a cytokine to a cytokine receptor expressed by the T cell. In certain embodiments where the promoter is induced by binding of a cytokine to a cytokine receptor expressed by the T cell, the cytokine is selected from the group consisting of interleukin 2 (IL2), interleukin 7 (IL7), interleukin 15 (IL15), and interleukin 21 (IL21). In certain embodiments where the promoter is induced by binding of a cytokine to a cytokine receptor expressed by the T cell, the cytokine is selected from the group consisting of interleukin 10 (IL10) and transforming growth factor β (TGFβ). In certain embodiments where the promoter is induced by binding of a cytokine to a cytokine receptor expressed by the T cell, the promoter is selected from the group consisting of T-bet promoter, Eomes promoter, GATA3 promoter, and CD45RA promoter.

In certain embodiments, the endogenous promoter that is inducible is induced by contact of the cell with a nucleic acid. In certain embodiments where a promoter is induced by contact of the cell with a nucleic acid, the nucleic acid is selected from the group consisting of viral DNA, viral RNA, and intracellular microRNA. In certain embodiments, where the promoter is induced by contact with a nucleic acid selected from the group consisting of viral DNA, viral RNA, and intracellular microRNA, the promoter is selected from the group consisting of Type I interferon (IFN) alpha, Type I IFN beta, IRF3, IRF7, NFkB, AP-1, TNF-alpha, ILL and IL6.

In certain embodiments, the endogenous promoter that is inducible is induced by contact of the cell with a metabolite. In certain embodiments, the metabolite is selected from the group consisting of pyruvate, glutamine, and beta-hydroxybutyrate.

In certain embodiments, the endogenous promoter that is inducible is induced by a metabolic change in the cell or contact of the cell with a substance that causes a metabolic change in the cell. In a particular embodiment, the promoter induced by a metabolic change in the cell or contact of the cell with a substance that causes a metabolic change in the cell is PKM2 promoter.

In certain embodiments, the endogenous promoter that is inducible is induced by a particular ion concentration in the cell or contact of the cell with a particular ion concentration. In certain embodiments, the ion is potassium or calcium. In certain embodiments, the promoter induced by a particular ion concentration in the cell or contact of the cell with a particular ion concentration is selected from the group consisting of IL2 promoter, TNFalpha promoter, and IFN-gamma promoter.

In certain embodiments of a T cell wherein a transgene is integrated at a first site within the genome of the T cell as described above, the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

In certain embodiments, the transgene encodes a cytokine. In one embodiment, optionally the cytokine is immunostimulatory. In certain embodiments, the cytokine that is immunostimulatory is selected from the group consisting of IL2, IL12, IL15, and IL18. In another embodiment, optionally the cytokine is immunoinhibitory. In certain embodiments, the cytokine that is immunoinhibitory is selected from the group consisting of TGFBeta and IL10.

In certain embodiments, the transgene encodes an antibody. In certain embodiments, optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

In certain embodiments, the transgene encodes a CAR. In a particular embodiment, the CAR binds to a cancer antigen.

In certain embodiments of a T cell wherein a transgene is integrated at a first site within the genome of the T cell as described above, the T cell is sensitized to a target antigen.

In certain embodiments of a T cell wherein a transgene is integrated at a first site within the genome of the T cell as described above, a transgene (hereinafter "reporter transgene") encoding a reporter molecule is integrated within the genome of the T cell such that expression of the reporter transgene is under control of a promoter, preferably an endogenous promoter of the T cell.

In certain embodiments of a T cell wherein a transgene is integrated at a first site within the genome of the T cell as described above, the T cell is derived from a human. In certain embodiments of a T cell derived from a human, the T cell is a primary human T cell, a T cell derived from a CD34 hematopoietic stem cell, a T cell derived from an embryonic stem cell, or a T cell derived from an induced pluripotent stem cell.

In certain embodiments of a T cell wherein a transgene is integrated at a first site within the genome of the T cell as described above, the transgene is integrated into the first site by targeted homologous recombination. In certain embodiments, the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, Aureus, Meganuclease or a Mega-Tal.

In certain embodiments of a T cell wherein a transgene is integrated at a first site within the genome of the T cell as described above, the transgene is integrated at a plurality of sites within the genome of the T cell, and such that expression of the transgene at the plurality of sites is under the control of different endogenous promoters.

In another aspect, provided herein is a T cell wherein a first transgene is integrated at a first site within the genome of the T cell such that expression of the first transgene is under control of a first endogenous promoter of the T cell, and wherein a second transgene is integrated at a second site within the genome of the T cell, such that expression of the second transgene is under the control of a second endogenous promoter, wherein the first and second endogenous promoters are different promoters, and wherein the first transgene encodes a first therapeutic protein or first therapeutic nucleic acid, and the second transgene encodes a second therapeutic protein or second therapeutic nucleic acid, preferably wherein the first therapeutic protein or first therapeutic nucleic acid is different from the second therapeutic protein or second therapeutic nucleic nucleic, respectively. In certain embodiments, the first transgene encodes a first therapeutic protein. In certain embodiments, the first transgene encodes a first therapeutic nucleic acid. In certain embodiments, the second transgene encodes a second therapeutic protein. In certain embodiments, the second transgene encodes a second therapeutic nucleic acid.

In certain embodiments of a T cell wherein a first transgene is integrated at a first site within the genome and a second transgene is integrated at a second site within the genome of the cell, the first endogenous promoter is constitutive, and the second endogenous promoter is inducible. In certain embodiments, the constitutive promoter is selected from the group consisting of CD4 promoter, CD8a promoter, CD8b promoter, TCRa promoter, TCRb promoter, CD3d promoter, CD3g promoter, CD3e promoter, and CD3z promoter.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the first endogenous promoter and/or the second endogenous promoter is active in a subset of T cells. In certain embodiments, the first endogenous promoter and/or the second endogenous promoter is independently selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by activation of the T cell.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by binding of a chimeric antigen receptor (CAR), a chimeric co-stimulatory receptor (CCR), T cell receptor (TCR), CD28, CD27, and 4-1BB expressed by the T cell to its respective binding partner. In certain embodiments, the inducible promoter is induced by binding of a CAR, CCR or TCR expressed by the T cell to its respective binding partner. In certain embodiments where the inducible promoter is induced by binding of a CAR, CCR or TCR expressed by the T cell to its respective binding partner, the inducible promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by binding of a ligand to an inhibitory receptor expressed by the T cell. In certain embodiments, the inhibitory receptor is selected from the group consisting of PD-1, CTLA4, TRAIL, LAG-3, BTLA, TIM-3, Fas, TIGIT, and 2B4. In certain embodiments, the inducible promoter is selected from the group consisting of CPT1a promoter and ATGL promoter.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by binding of a cytokine to a cytokine receptor expressed by the T cell. In certain embodiments, the cytokine is selected from the group consisting of interleukin 2 (IL2), interleukin 7 (IL7), interleukin 15 (IL15), and interleukin 21 (IL21). In certain embodiments, the cytokine is selected from the group consisting of interleukin 10 (IL10) and transforming growth factor β (TGFβ). In certain embodiments, the inducible promoter is selected from the group consisting of T-bet promoter, Eomes promoter, GATA3 promoter, and CD45RA promoter.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by contact of the cell with a nucleic acid. In certain embodiments, the nucleic acid is selected from the group consisting of viral DNA, viral, RNA, and intracellular microRNA. In certain embodiments where the inducible promoter is induced by contact of the cell with viral DNA, viral, RNA, or intracellular microRNA, the inducible promoter is selected from the group consisting of Type I interferon (IFN) alpha, Type I IFN beta, IRF3, IRF7, NFkB, AP-1, TNF-alpha, ILL and IL6.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by contact of the cell with a metabolite. In certain embodiments, the metabolite is selected from the group consisting of pyruvate, glutamine, and beta-hydroxybutyrate.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by a metabolic change in the cell or contact of the cell with a substance that causes a metabolic change in the cell. In certain embodiments, such an inducible promoter is PKM2 promoter.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the inducible promoter is induced by a particular ion concentration in the cell or contact of the cell with a particular ion concentration. In certain embodiments, the ion is potassium or calcium. In certain embodiments where the inducible promoter is induced by a particular ion concentration in the cell or contact of the cell with a particular ion concentration, the inducible promoter is selected from the group consisting of IL2 promoter, TNFalpha promoter, and IFNgamma promoter.

In certain embodiments of a T cell wherein a first transgene is integrated at a first site within the genome and a second transgene is integrated at a second site within the genome of the cell, as described above, the first transgene and/or second transgene each encodes a molecule independently selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

In certain embodiments of a T cell wherein a first transgene is integrated at a first site within the genome and a second transgene is integrated at a second site within the genome of the cell, as described above, the first transgene and/or second transgene encodes a cytokine. In certain embodiments wherein the first and/or second transgene encodes a cytokine, the cytokine preferably is immunostimulatory. In certain embodiments where the cytokine is immunostimulatory, the cytokine is selected from the group consisting of IL2, IL12, IL15, and IL18. In certain embodiments wherein the first transgene and/or second transgene encodes a cytokine, the cytokine preferably is immunoinhibitory. In certain embodiments where the cytokine is immunoinhibitory, the cytokine is selected from the group consisting of TGFBeta and IL10.

In certain embodiments of a T cell wherein a first transgene is integrated at a first site within the genome and a second transgene is integrated at a second site within the genome of the cell, as described above, the first transgene and/or second transgene encodes an antibody. In certain embodiments, the antibody is an immunoglobulin, a Bi-specific T-cell engager (BiTE), a diabody, a dual affinity re-targeting (DART), a Fab, a F(ab'), a single chain variable fragment (scFv), and a nanobody.

In certain embodiments of a T cell wherein a first transgene is integrated at a first site within the genome and a second transgene is integrated at a second site within the genome of the cell, as described above, the first transgene and/or second transgene encodes a CAR. In a particular embodiment, the CAR binds to a cancer antigen.

In certain embodiments of a T cell wherein a first transgene is integrated at a first site within the genome and a second transgene is integrated at a second site within the genome of the cell, as described above, the T cell is sensitized to a target antigen.

In certain embodiments of a T cell wherein a first transgene is integrated at a first site within the genome and a second transgene is integrated at a second site within the genome of the cell, as described above, a transgene (hereinafter "reporter transgene") encoding a reporter molecule is integrated within the genome of the T cell such that expression of the reporter transgene is under control of a promoter, preferably an endogenous promoter of the T cell.

In certain embodiments of a T cell wherein a first transgene is integrated at a first site within the genome and a second transgene is integrated at a second site within the genome of the cell, as described above, the T cell is derived from a human. In certain embodiments of a T cell derived from a human, the T cell is a primary human T cell, a T cell derived from a CD34 hematopoietic stem cell, a T cell derived from an embryonic stem cell, or a T cell derived from an induced pluripotent stem cell.

In certain embodiments of a T cell wherein a first transgene is integrated at a first site within the genome and a second transgene is integrated at a second site within the genome of the cell, as described above, the first transgene and/or second transgene is integrated into the first site by targeted homologous recombination. In certain embodiments, the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, Aureus, Meganuclease or a Mega-Tal.

In certain embodiments of a T cell wherein a first transgene is integrated at a first site within the genome and a second transgene is integrated at a second site within the genome of the cell, as described above, the first therapeutic protein or first therapeutic nucleic acid is different from said second therapeutic protein or second therapeutic nucleic, respectively.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the second endogenous promoter is induced by activation of the T cell.

In certain embodiments of a T cell wherein a first transgene is integrated at a first site within the genome and a second transgene is integrated at a second site within the genome of the cell, and wherein the first endogenous promoter is constitutive, and the second endogenous promoter is inducible, the first transgene encodes a CAR. In a particular embodiment where the first transgene encodes a CAR, the first endogenous promoter is a T cell receptor promoter. In certain embodiments, the T cell receptor promoter is selected from the group consisting of T cell receptor alpha chain promoter, T cell receptor beta chain promoter, CD3 gamma chain promoter, CD3 delta chain promoter, CD3 epsilon chain promoter, and CD3 zeta chain promoter. In a particular embodiment, the promoter is T cell receptor alpha chain promoter.

In certain embodiments of a T cell described above, except insofar as the foregoing embodiments relate to a transgene encoding a cytokine that is immunoinhibitory, for example, TGFbeta or IL10, the T cell is an immunostimulatory T cell. In certain embodiments where the T cell is an immunoinhibitory T cell, the T cell is selected from the group consisting of cytotoxic T lymphocyte (CTL), CD4+ subtype, CD8+ subtype, central memory T cell (TCM), stem memory T cell (TSCM), effector memory T cell, effector T cell, Th1 cell, Th2 cell, Th9 cell, Th17 cell, Th22 cell, and Tfh (follicular helper) cell. In a specific embodiment, the T cell is CD4+. In a specific embodiment, the T cell is CD8+.

In certain embodiments of a T cell described above, except insofar as the foregoing embodiments relate to a transgene encoding a cytokine that is immunostimulatory, for example, the cytokine is selected from the group consisting of IL2, IL12, IL15, and IL18, the T cell is an immunoinhibitory T cell. In a specific embodiment, the T cell is a regulatory T cell.

In another aspect, provided herein is an isolated population of T cells, which comprises a plurality of the T cell of the embodiments described above. In certain embodiments, the isolated population of T cells comprises the immunostimulatory T cells described above. In certain embodiments, the isolated population of T cells comprises the immunoinhibitory T cells described above.

In another aspect, provided herein is a pharmaceutical composition comprising a therapeutically effective amount of the T cell of the embodiments described above; and a pharmaceutically acceptable carrier. In another aspect, provided herein is a pharmaceutical composition comprising a therapeutically effective amount of a population of T cells, which population comprises a plurality of the T cell of the embodiments described above; and a pharmaceutically acceptable carrier.

In another aspect, provided herein is a pharmaceutical composition comprising a therapeutically effective amount of the T cell of the embodiments described above, wherein the T cell is the immunostimulatory T cell described above; and a pharmaceutically acceptable carrier. In another aspect, provided herein is a pharmaceutical composition comprising a therapeutically effective amount of a population of T cells, which population comprises a plurality of the T cell of the embodiments described above, wherein the T cell is the immunostimulatory T cell described above; and a pharmaceutically acceptable carrier.

In another aspect, provided herein is a pharmaceutical composition comprising a therapeutically effective amount of the T cell of the embodiments described above, wherein the T cell is the immunoinhibitory cell described above; and a pharmaceutically acceptable carrier. In another aspect, provided herein is a pharmaceutical composition comprising a therapeutically effective amount of a population of T cells, which population comprises a plurality of the T cell of the embodiments described above, wherein the T cell is the immunoinhibitory T cell described above; and a pharmaceutically acceptable carrier.

In another aspect, provided herein is a method of treating a subject with T cell therapy in need thereof, comprising administering to the subject a therapeutically effective amount of the T cell of the embodiments described above. In another aspect, also provided herein is a method of treating a subject with T cell therapy in need thereof, comprising administering to the subject a therapeutically effective amount of the T cell population of the embodiments described above. In yet another aspect, provided herein is a method of treating a subject with T cell therapy in need thereof, comprising administering to the subject the pharmaceutical composition of the embodiments described above.

In certain embodiments of methods of the invention described above, the subject is a human, and the T cell is derived from a human. In certain embodiments of the methods of the invention described above, the T cell is autologous to the subject. In certain embodiments of the methods of the invention described above, the T cell is non-autologous to the subject.

In another aspect, provided herein is a method of treating a subject with T cell therapy in need thereof, wherein the subject is in need of a stimulated immune response, comprising administering to the subject a therapeutically effective amount of a cell or population of cells, wherein the cell is a T cell, wherein a transgene is integrated at a first site within the genome of the T cell such that expression of the transgene is under control of an endogenous promoter of the T cell, wherein the transgene encodes a therapeutic protein or therapeutic nucleic acid. In certain embodiments, the cell or cell population is administered to the subject as a pharmaceutical composition. In certain embodiments, the transgene encodes a therapeutic protein. In certain embodiments, the transgene encodes a therapeutic nucleic acid.

In certain embodiments of the methods of treating a subject with T cell therapy in need thereof, wherein the subject is in need of a stimulated immune response as described above, the transgene is integrated at a single site within the genome. In certain embodiments, wherein the transgene is integrated at two sites within the genome of the cell. In certain embodiments, wherein the first site is an an exon of the endogenous gene under control of the endogenous promoter. In a specific embodiment, the first site is within the first exon of the endogenous gene.

In certain embodiments of the methods of treating a subject with T cell therapy in need thereof, wherein the subject is in need of a stimulated immune response as described above, the endogenous promoter is constitutive. In certain embodiments, the constitutive promoter is selected from the group consisting of CD4 promoter, CD8a promoter, CD8b promoter, TCRa promoter, TCRb promoter, CD3d promoter, CD3g promoter, CD3e promoter, and CD3z promoter.

In certain embodiments of the methods of treating a subject with T cell therapy in need thereof, wherein the subject is in need of a stimulated immune response as described above, the endogenous promoter is active in a subset of T cells. In certain embodiments where the endogenous promoter is active in a subset of T cells, the endogenous promoter is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

In certain embodiments of the methods of treating a subject with T cell therapy in need thereof, wherein the subject is in need of a stimulated immune response as described above, the endogenous promoter is inducible.

In certain embodiments of the methods of treating a subject with T cell therapy in need thereof, wherein the subject is in need of a stimulated immune response and the endogenous promoter is inducible, as described above, the endogenous promoter is induced by activation of the T cell. In certain embodiments where the endogenous promoter is induced by activation of the T cell, the promoter is induced by binding of a chimeric antigen receptor (CAR), a chimeric co-stimulatory receptor (CCR), T cell receptor (TCR), CD28, CD27, or 4-1BB expressed by the T cell to its respective binding partner. In certain embodiments, the promoter is induced by binding of a CAR, CCR or TCR expressed by the T cell to its respective binding partner. In certain embodiments where the promoter is induced by binding of a CAR, CCR or TCR expressed by the T cell to its respective binding partner, the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

In certain embodiments of the methods of treating a subject with T cell therapy in need thereof, wherein the subject is in need of a stimulated immune response and the endogenous promoter is inducible, as described above, the promoter is induced by binding of a ligand to an inhibitory receptor expressed by the T cell. In certain embodiments, the inhibitory receptor is selected from the group consisting of PD-1, CTLA4, TRAIL, LAG-3, BTLA, TIM-3, Fas, TIGIT, and 2B4. In certain embodiments where the promoter is induced by binding of a ligand to an inhibitory receptor expressed by the T cell, the promoter is selected from the group consisting of CPT1a promoter and ATGL promoter.

In certain embodiments of the methods of treating a subject with T cell therapy in need thereof, wherein the subject is in need of a stimulated immune response and the endogenous promoter is inducible, as described above, the promoter is induced by binding of a cytokine to a cytokine receptor expressed by the T cell. In certain embodiments, the cytokine is selected from the group consisting of interleukin 2 (IL2), interleukin 7 (IL7), interleukin 15 (IL15), and interleukin 21 (IL21). In certain embodiments where the promoter is induced by binding of a cytokine to a cytokine receptor expressed by the T cell, the promoter is selected from the group consisting of T-bet promoter, Eomes promoter, GATA3 promoter, and CD45RA promoter.

In certain embodiments of the methods of treating a subject with T cell therapy in need thereof, wherein the subject is in need of a stimulated immune response and the endogenous promoter is inducible, as described above, the promoter is induced by contact of the cell with a nucleic acid. In certain embodiments, the nucleic acid is selected from the group consisting of viral DNA, viral RNA, and intracellular microRNA. In certain embodiments where the promoter is induced by contact of the cell with a nucleic acid selected from the group consisting of viral DNA, viral, RNA, and intracellular microRNA, the promoter is selected from the group consisting of Type I interferon (IFN) alpha, Type I IFN beta, IRF3, IRF7, NFkB, AP-1, TNF-alpha, ILL and IL6.

In certain embodiments of the methods of treating a subject with T cell therapy in need thereof, wherein the subject is in need of a stimulated immune response and the endogenous promoter is inducible, as described above, the promoter is induced by contact of the cell with a metabolite. In certain embodiments, the metabolite is selected from the group consisting of pyruvate, glutamine, and beta-hydroxybutyrate.

In certain embodiments of the methods of treating a subject with T cell therapy in need thereof, wherein the subject is in need of a stimulated immune response and the endogenous promoter is inducible, as described above, the promoter is induced by a metabolic change in the cell or contact of the cell with a substance that causes a metabolic change in the cell. In a specific embodiment where the promoter is induced by a metabolic change in the cell or contact of the cell with a substance that causes a metabolic change in the cell, the promoter is PKM2 promoter.

In certain embodiments of the methods of treating a subject with T cell therapy in need thereof, wherein the subject is in need of a stimulated immune response and the endogenous promoter is inducible, as described above, the promoter is induced by a particular ion concentration in the cell or contact of the cell with a particular ion concentration. In certain embodiments, the ion is potassium or calcium. In certain embodiments the promoter is induced by a particular ion concentration in the cell or contact of the cell with a particular ion concentration, the promoter is selected from the group consisting of IL2 promoter, TNFalpha promoter, and IFNgamma promoter.

In certain embodiments of the methods of treating a subject with T cell therapy in need thereof, wherein the subject is in need of a stimulated immune response, as described above, the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

In certain embodiments of the methods of treating a subject with T cell therapy in need thereof, wherein the subject is in need of a stimulated immune response, as described above, the transgene encodes a cytokine. In certain embodiments, optionally the cytokine is immunostimulatory. In certain embodiments where the cytokine is immunostimulatory, the cytokine is selected from the group consisting of IL2, IL12, IL15, and IL18.

In certain embodiments of the methods of treating a subject with T cell therapy in need thereof, wherein the subject is in need of a stimulated immune response, as described above, the transgene encodes an antibody. In certain embodiments, optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

In certain embodiments of the methods of treating a subject with T cell therapy in need thereof, wherein the subject is in need of a stimulated immune response, as described above, the transgene encodes a CAR. In a specific embodiment, the CAR binds to a cancer antigen.

In certain embodiments of the methods of treating a subject with T cell therapy in need thereof, wherein the subject is in need of a stimulated immune response, as described above, the T cell is sensitized to a target antigen.

In certain embodiments of the methods of treating a subject with T cell therapy in need thereof, wherein the subject is in need of a stimulated immune response, as described above, a transgene (hereinafter "reporter transgene") encoding a reporter molecule is integrated within the genome of the T cell such that expression of the reporter transgene is under control of a promoter. Preferably, such a promoter is an endogenous promoter of the T cell.

In certain embodiments of the methods of treating a subject with T cell therapy in need thereof, wherein the subject is in need of a stimulated immune response, as described above, the T cell is derived from a human. In certain embodiments, the T cell is a primary human T cell, a T cell derived from a CD34 hematopoietic stem cell, a T cell derived from an embryonic stem cell, or a T cell derived from an induced pluripotent stem cell.

In certain embodiments of the methods of treating a subject with T cell therapy in need thereof, wherein the subject is in need of a stimulated immune response, as described above, the transgene is integrated into the first site by targeted homologous recombination. IN certain embodiments, the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, Aureus, Meganuclease or a Mega-Tal.

In certain embodiments of the methods of treating a subject with T cell therapy in need thereof, wherein the subject is in need of a stimulated immune response, as described above, the transgene is integrated at a plurality of sites within the genome of the T cell, and such that expression of the transgene at the plurality of sites is under the control of different endogenous promoters.

In certain embodiments of the methods of treating a subject with T cell therapy in need thereof, wherein the subject is in need of a stimulated immune response, as described above, the T cell is an immunostimulatory T cell. In certain embodiments, the T cell is selected from the group consisting of cytotoxic T lymphocyte (CTL), CD4+ subtype, CD8+ subtype, central memory T cell (TCM), stem memory T cell (TSCM), effector memory T cell, effector T cell, Th1 cell, Th2 cell, Th9 cell, Th17 cell, Th22 cell, and Tfh (follicular helper) cell. In a specific embodiment, the T cell is CD4+. In another specific embodiment, the T cell is CD8+.

In certain embodiments of the methods of treating a subject with T cell therapy in need thereof, wherein the subject is in need of a stimulated immune response, as described above the subject has cancer. In a specific embodiment, the cancer is leukemia.

In certain embodiments of the methods of treating a subject with T cell therapy in need thereof, wherein the subject is in need of a stimulated immune response, as described above, the subject has a tumor.

In certain embodiments of the methods of treating a subject with T cell therapy in need thereof, wherein the subject is in need of a stimulated immune response, as described above, the subject is a human, and the T cell is derived from a human.

In certain embodiments of the methods of treating a subject with T cell therapy in need thereof, wherein the subject is in need of a stimulated immune response, as described above, the T cell is autologous to the subject. In certain embodiments of the methods of treating a subject with T cell therapy in need thereof, wherein the subject is in need of a stimulated immune response, as described above, the T cell is non-autologous to the subject.

In another aspect, provided herein is a method of treating a subject with T cell therapy in need thereof, wherein the subject is in need of an inhibited immune response, comprising administering to the subject a therapeutically effective amount of a cell or population of cells, wherein the cell is a T cell, wherein a transgene is integrated at a first site within the genome of the T cell such that expression of the transgene is under control of an endogenous promoter of the T cell, wherein the transgene encodes a therapeutic protein or therapeutic nucleic acid. In certain embodiments, the cell or cell population is administered as a pharmaceutical composition. In certain embodiments, the transgene encodes a therapeutic protein. In certain embodiments, the transgene encodes a therapeutic nucleic acid.

In certain embodiments of the methods of treating a subject with T cell therapy in need thereof, wherein the subject is in need of an inhibited immune response, as described above, the transgene is integrated at a single site within the genome. In certain embodiments, the transgene is integrated at two sites within the genome of the cell. In certain embodiments, the first site is an an exon of the endogenous gene under control of the endogenous promoter. In a particular embodiment, the first site is within the first exon of the endogenous gene.

In certain embodiments of the methods of treating a subject with T cell therapy in need thereof, wherein the subject is in need of an inhibited immune response, as described above, the endogenous promoter is constitutive. In certain embodiments, the constitutive promoter is selected from the group consisting of CD4 promoter, CD8a promoter, CD8b promoter, TCRa promoter, TCRb promoter, CD3d promoter, CD3g promoter, CD3e promoter, and CD3z promoter.

In certain embodiments of the methods of treating a subject with T cell therapy in need thereof, wherein the subject is in need of an inhibited immune response, as described above, the endogenous promoter is active in a subset of T cells. In certain embodiments, the endogenous promoter that is active in a subset of T cells is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

In certain embodiments of the methods of treating a subject with T cell therapy in need thereof, wherein the subject is in need of an inhibited immune response, as described above, the endogenous promoter is inducible.

In certain embodiments of the methods of treating a subject with T cell therapy in need thereof, wherein the subject is in need of an inhibited immune response and the endogenous promoter is inducible, as described above, the endogenous promoter is induced by activation of the T cell. In certain embodiments where the endogenous promoter is induced by activation of the T cell, the promoter is induced by binding of a chimeric antigen receptor (CAR), a chimeric co-stimulatory receptor (CCR), T cell receptor (TCR), CD28, CD27, or 4-1BB expressed by the T cell to its respective binding partner. In certain embodiments, the promoter is induced by binding of a CAR, CCR or TCR expressed by the T cell to its respective binding partner. In certain embodiments where the promoter is induced by binding of a CAR, CCR or TCR expressed by the T cell to its respective binding partner, the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

In certain embodiments of the methods of treating a subject with T cell therapy in need thereof, wherein the subject is in need of an inhibited immune response and the endogenous promoter is inducible, as described above, the promoter is induced by binding of a ligand to an inhibitory receptor expressed by the T cell. In certain embodiments, the inhibitory receptor is selected from the group consisting of PD-1, CTLA4, TRAIL, LAG-3, BTLA, TIM-3, Fas, TIGIT, and 2B4. In certain embodiments where the promoter is induced by binding of a ligand to an inhibitory receptor expressed by the T cell, the promoter is selected from the group consisting of CPT1a promoter and ATGL promoter.

In certain embodiments of the methods of treating a subject with T cell therapy in need thereof, wherein the subject is in need of an inhibited immune response and the endogenous promoter is inducible, as described above, the promoter is induced by binding of a cytokine to a cytokine receptor expressed by the T cell. In certain embodiments, the cytokine is selected from the group consisting of interleukin 10 (IL10) and transforming growth factor β (TGFβ). In certain embodiments where the promoter is induced by binding of a cytokine to a cytokine receptor expressed by the T cell, the promoter is selected from the group consisting of T-bet promoter, Eomes promoter, GATA3 promoter, and CD45RA promoter.

In certain embodiments of the methods of treating a subject with T cell therapy in need thereof, wherein the subject is in need of an inhibited immune response and the endogenous promoter is inducible, as described above, the promoter is induced by contact of the cell with a nucleic acid. In certain embodiments, the nucleic acid is selected from the group consisting of viral DNA, viral, RNA, and intracellular microRNA. In certain embodiments where the promoter is induced by contact of the cell with a nucleic acid selected from the group consisting of viral DNA, viral, RNA, and intracellular microRNA, the promoter is selected from the group consisting of Type I interferon (IFN) alpha, Type I IFN beta, IRF3, IRF7, NFkB, AP-1, TNF-alpha, ILL and IL6.

In certain embodiments of the methods of treating a subject with T cell therapy in need thereof, wherein the subject is in need of an inhibited immune response and the endogenous promoter is inducible, as described above, the promoter is induced by contact of the cell with a metabolite. In certain embodiments, the metabolite is selected from the group consisting of pyruvate, glutamine, and beta-hydroxybutyrate.

In certain embodiments of the methods of treating a subject with T cell therapy in need thereof, wherein the subject is in need of an inhibited immune response and the endogenous promoter is inducible, as described above, the promoter is induced by a metabolic change in the cell or contact of the cell with a substance that causes a metabolic change in the cell. In certain embodiments where the promoter is induced by a metabolic change in the cell or contact of the cell with a substance that causes a metabolic change in the cell, the promoter is PKM2 promoter.

In certain embodiments of the methods of treating a subject with T cell therapy in need thereof, wherein the subject is in need of an inhibited immune response and the endogenous promoter is inducible, as described above, the promoter is induced by a particular ion concentration in the cell or contact of the cell with a particular ion concentration. In certain embodiments, the ion is potassium or calcium. In certain embodiments where the promoter is induced by a particular ion concentration in the cell or contact of the cell with a particular ion concentration, the promoter is selected from the group consisting of IL2 promoter, TNFalpha promoter, and IFNgamma promoter.

In certain embodiments of the methods of treating a subject with T cell therapy in need thereof, wherein the subject is in need of an inhibited immune response, as described above, the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

In certain embodiments of the methods of treating a subject with T cell therapy in need thereof, wherein the subject is in need of an inhibited immune response, as described above, the transgene encodes a cytokine. In certain embodiments, optionally the cytokine is immunoinhibitory. In certain embodiments, the cytokine that is immunoinhibitory is selected from the group consisting of TGFBeta and IL10.

In certain embodiments of the methods of treating a subject with T cell therapy in need thereof, wherein the subject is in need of an inhibited immune response, as described above, the transgene encodes an antibody. In certain embodiments, optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

In certain embodiments of the methods of treating a subject with T cell therapy in need thereof, wherein the subject is in need of an inhibited immune response, as described above, the transgene encodes a CAR. In a specific embodiment, the CAR binds to a cancer antigen.

In certain embodiments of the methods of treating a subject with T cell therapy in need thereof, wherein the subject is in need of an inhibited immune response, as described above, the T cell is sensitized to a target antigen.

In certain embodiments of the methods of treating a subject with T cell therapy in need thereof, wherein the subject is in need of an inhibited immune response, as described above, a transgene (hereinafter "reporter transgene") encoding a reporter molecule is integrated within the genome of the T cell such that expression of the reporter transgene is under control of a promoter. Preferably, the reporter is under control of an endogenous promoter of the T cell.

In certain embodiments of the methods of treating a subject with T cell therapy in need thereof, wherein the subject is in need of an inhibited immune response, as described above, the T cell is derived from a human. In certain embodiments, the T cell is a primary human T cell, a T cell derived from a CD34 hematopoietic stem cell, a T cell derived from an embryonic stem cell, or a T cell derived from an induced pluripotent stem cell.

In certain embodiments of the methods of treating a subject with T cell therapy in need thereof, wherein the subject is in need of an inhibited immune response, as described above, the transgene is integrated into the first site by targeted homologous recombination. In certain embodiments, the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, Aureus, Meganuclease or a Mega-Tal.

In certain embodiments of the methods of treating a subject with T cell therapy in need thereof, wherein the subject is in need of an inhibited immune response, as described above, the transgene is integrated at a plurality of sites within the genome of the T cell, and such that expression of the transgene at said plurality of sites is under the control of different endogenous promoters.

In certain embodiments of the methods of treating a subject with T cell therapy in need thereof, wherein the subject is in need of an inhibited immune response, as described above, the T cell is an immunoinhibitory T cell. In a specific embodiment, the immunoinhibitory T cell is a regulatory T cell.

In certain embodiments of the methods of treating a subject with T cell therapy in need thereof, wherein the subject is in need of an inhibited immune response, as described above, the subject is a human, and the T cell is derived from a human.

In certain embodiments of the methods of treating a subject with T cell therapy in need thereof, wherein the subject is in need of an inhibited immune response, as described above, the cell is autologous to the subject. In certain embodiments of the methods of treating a subject with T cell therapy in need thereof, wherein the subject is in need of an inhibited immune response, as described above, the cell is non-autologous to the subject.

In another aspect, provided herein is a method of generating a T cell that expresses a therapeutic transgene, comprising: introducing into a T cell: (i) a transgene, and (ii) a homologous recombination system suitable for targeted integration of the transgene at a site within the genome of the cell, whereby the homologous recombination system integrates the transgene at the site within the genome of the cell, and wherein expression of the transgene is under the control of an endogenous promoter, wherein the transgene encodes a therapeutic protein or a therapeutic nucleic acid. In certain embodiments, the transgene encodes a therapeutic protein. In certain embodiments, the transgene encodes a therapeutic nucleic acid.

In certain embodiments of the methods of generating a T cell that expresses a therapeutic transgene, as described above, the endogenous promoter is constitutive. In certain embodiments, the endogenous constitutive promoter is selected from the group consisting of CD4 promoter, CD8a promoter, CD8b promoter, TCRa promoter, TCRb promoter, CD3d promoter, CD3g promoter, CD3e promoter, and CD3z promoter.

In certain embodiments of the methods of generating a T cell that expresses a therapeutic transgene, as described above, the endogenous promoter is active in a subset of T cells. In certain embodiments where the endogenous promoter is active in a subset of T cells, the endogenous promoter is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

In certain embodiments of the methods of generating a T cell that expresses a therapeutic transgene, as described above, the endogenous promoter is inducible.

In certain embodiments of the methods of generating a T cell that expresses a therapeutic transgene and where the endogenous promoter is inducible, as described above, the endogenous promoter is induced by activation of the T cell.

In certain embodiments of the methods of generating a T cell that expresses a therapeutic transgene and where the endogenous promoter is inducible, as described above, the promoter is induced by binding of a chimeric antigen receptor (CAR), a chimeric co-stimulatory receptor (CCR), T cell receptor (TCR), CD28, CD27, and 4-1BB expressed by the T cell to its respective binding partner. In certain embodiments, the promoter is induced by binding of a CAR, CCR or TCR expressed by the T cell to its respective binding partner. In certain embodiments where the promoter is induced by binding of a CAR, CCR or TCR expressed by the T cell to its respective binding partner, the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

In certain embodiments of the methods of generating a T cell that expresses a therapeutic transgene and where the endogenous promoter is inducible, as described above, the promoter is induced by binding of a ligand to an inhibitory receptor expressed by the T cell. In certain embodiments, the inhibitory receptor is selected from the group consisting of PD-1, CTLA4, TRAIL, LAG-3, BTLA, TIM-3, Fas, TIGIT, and 2B4. In certain embodiments where the promoter is induced by binding of a ligand to an inhibitory receptor expressed by the T cell, the promoter is selected from the group consisting of CPT1a promoter and ATGL promoter.

In certain embodiments of the methods of generating a T cell that expresses a therapeutic transgene and where the endogenous promoter is inducible, as described above, the promoter is induced by binding of a cytokine to a cytokine receptor expressed by the T cell. In certain embodiments where the promoter is induced by binding of a cytokine to a cytokine receptor expressed by the T cell, the cytokine is selected from the group consisting of interleukin 2 (IL2), interleukin 7 (IL7), interleukin 15 (IL15), and interleukin 21 (IL21). In certain embodiments where the promoter is induced by binding of a cytokine to a cytokine receptor expressed by the T cell, the cytokine is selected from the group consisting of interleukin 10 (IL10) and transforming growth factor β (TGFβ). In certain embodiments where the promoter is induced by binding of a cytokine to a cytokine receptor expressed by the T cell, the promoter is selected from the group consisting of T-bet promoter, Eomes promoter, GATA3 promoter, and CD45RA promoter.

In certain embodiments of the methods of generating a T cell that expresses a therapeutic transgene and where the endogenous promoter is inducible, as described above, the promoter is induced by contact of the cell with a nucleic acid. In certain embodiments, the nucleic acid is selected from the group consisting of viral DNA, viral, RNA, and intracellular microRNA. In certain embodiments where the promoter is induced by contact of the cell with a nucleic acid selected from the group consisting of viral DNA, viral, RNA, and intracellular microRNA, the promoter is selected from the group consisting of Type I interferon (IFN) alpha, Type I IFN beta, IRF3, IRF7, NFkB, AP-1, TNF-alpha, ILL and IL6.

In certain embodiments of the methods of generating a T cell that expresses a therapeutic transgene and where the endogenous promoter is inducible, as described above, the promoter is induced by contact of the cell with a metabolite. In certain embodiments, the metabolite is selected from the group consisting of pyruvate, glutamine, and beta-hydroxybutyrate.

In certain embodiments of the methods of generating a T cell that expresses a therapeutic transgene and where the endogenous promoter is inducible, as described above, the promoter is induced by a metabolic change in the cell or contact of the cell with a substance that causes a metabolic change in the cell. In certain embodiments where the promoter is induced by a metabolic change in the cell or contact of the cell with a substance that causes a metabolic change in the cell, the promoter is PKM2 promoter.

In certain embodiments of the methods of generating a T cell that expresses a therapeutic transgene and where the endogenous promoter is inducible, as described above, the promoter is induced by a particular ion concentration in the cell or contact of the cell with a particular ion concentration. In certain embodiments, the ion is potassium or calcium. In certain embodiments where the promoter is induced by a particular ion concentration in the cell or contact of the cell with a particular ion concentration, the promoter is selected from the group consisting of IL2 promoter, TNFalpha promoter, and IFNgamma promoter.

In certain embodiments of the methods of generating a T cell that expresses a therapeutic transgene, as described above, the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

In certain embodiments of the methods of generating a T cell that expresses a therapeutic transgene, as described above, the transgene encodes a cytokine. In certain embodiments, optionally the cytokine is immunostimulatory. In certain embodiments, the immunostimulatory cytokine is selected from the group consisting of IL2, IL12, IL15, and IL18. In certain embodiments, optionally the cytokine is immunoinhibitory. In certain embodiments, the immunoinhibitory cytokine is selected from the group consisting of TGFBeta and IL10.

In certain embodiments of the methods of generating a T cell that expresses a therapeutic transgene, as described above, the transgene encodes an antibody. In certain embodiments, optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

In certain embodiments of the methods of generating a T cell that expresses a therapeutic transgene, as described above, the transgene encodes a CAR. In a specific embodiment, the CAR binds to a cancer antigen.

In certain embodiments of the methods of generating a T cell that expresses a therapeutic transgene, as described above, the T cell is sensitized to a target antigen.

In certain embodiments of the methods of generating a T cell that expresses a therapeutic transgene, as described above, a transgene (hereinafter "reporter transgene") encoding a reporter molecule is integrated within the genome of the T cell such that expression of the reporter transgene is under control of a promoter, preferably an endogenous promoter of the T cell.

In certain embodiments of the methods of generating a T cell that expresses a therapeutic transgene, as described above, the T cell is derived from a human. In certain embodiments, the T cell is a primary human T cell, a T cell derived from a CD34 hematopoietic stem cell, a T cell derived from an embryonic stem cell, or a T cell derived from an induced pluripotent stem cell.

In certain embodiments of the methods of generating a T cell that expresses a therapeutic transgene, as described above, the transgene is integrated into the first site by targeted homologous recombination. In certain embodiments, the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, Aureus, Meganuclease or a Mega-Tal.

In certain embodiments of the methods of generating a T cell that expresses a therapeutic transgene, as described above, the transgene is integrated at a plurality of sites within the genome of the T cell, and such that expression of the transgene at said plurality of sites is under the control of different endogenous promoters.

In certain embodiments of the methods of generating a T cell that expresses a therapeutic transgene, as described above, the transgene that is introduced into the cell is contained in a targeting construct. In certain embodiments, the targeting construct comprises viral nucleic acid sequences. In certain embodiments, the targeting construct is packaged into a natural or recombinant adeno-associated virus (AVV) viral particle. In a specific embodiment, the AAV particle comprises AAV6 sequences. In certain embodiments, the targeting construct is packaged into a non-integrating gamma-retrovirus.

In certain embodiments of the methods of generating a T cell that expresses a therapeutic transgene, as described above, the transgene in the targeting construct is not operably linked to a promoter.

In certain embodiments of the methods of generating a T cell that expresses a therapeutic transgene, as described above, the method further comprising introducing a second transgene into the T cell. In certain embodiments, the first transgene is under control of an endogenous constitutive promoter and the second transgene is under control of an endogenous inducible promoter. In certain embodiments, the first transgene is a CAR. In certain embodiments where the transgene is a CAR, the endogenous constitutive promoter is a T cell receptor promoter. In certain embodiments where the promoter is a T cell receptor promoter, the promoter is selected from the group consisting of T cell receptor alpha chain promoter, T cell receptor beta chain promoter, CD3 gamma chain promoter, CD3 delta chain promoter, CD3 epsilon chain promoter, and CD3 zeta chain promoter. In a specific embodiment, the promoter is T cell receptor alpha chain promoter.

In another aspect, provided herein is a vector comprising a non-integrating gamma-retrovirus. In certain embodiments, the non-integrating gamma-retrovirus comprises a mutated integrase. In certain embodiments, the mutated integrase is mutated at a DDE motif. In certain embodiments, the mutated integrase has a mutation selected from the group consisting of D124A, D124E, D124N, D124V, D183A, D183N, D124A and D183A, D124A and D183N, D124E and D183A, D124E and D183N, D124N and D183A, D124N and D183N, D124V and D183A, and D124V and D183N.

In another aspect, provided herein is a T cell wherein a recombinant nucleic acid sequence encoding a chimeric antigen receptor (CAR) is integrated at a first site within the genome of the cell such that the CAR is expressed by the cell at the surface of the cell, and wherein integration of the nucleic acid encoding the CAR at the first site reduces or prevents expression of a functional T cell receptor (TCR) complex at the surface of the cell. In certain embodiments, the nucleic acid sequence encoding the CAR is integrated at a single site within the genome. In certain embodiments, the nucleic acid sequence encoding the CAR is integrated at two sites within the genome of the cell. In certain embodiments, the first site is an an exon of the gene encoding a protein of the TCR complex.

In certain embodiments of a T cell wherein a recombinant nucleic acid sequence encoding a CAR is integrated at a first site within the genome of the cell, as described above, integration of the nucleic acid sequence encoding the CAR at the first site reduces or prevents expression of a protein selected from the group consisting of T cell receptor alpha chain, T cell receptor beta chain, CD3 gamma chain, CD3 delta chain, CD3 epsilon chain, and CD3 zeta chain.

In certain embodiments of a T cell wherein a recombinant nucleic acid sequence encoding a CAR is integrated at a first site within the genome of the cell, as described above, expression of the integrated nucleic acid sequence in the T cell is under the control of an endogenous promoter. In certain embodiments, the endogenous promoter is a T cell receptor complex promoter. In certain embodiments, the endogenous promoter is a promoter of a gene encoding a T cell receptor alpha chain, T cell receptor beta chain, CD3 gamma chain, CD3 delta chain, CD3 epsilon chain, or CD3 zeta chain.

In certain embodiments of a T cell wherein a recombinant nucleic acid sequence encoding a CAR is integrated at a first site within the genome of the cell, as described above, the CAR binds to a cancer antigen.

In certain embodiments of a T cell wherein a recombinant nucleic acid sequence encoding a CAR is integrated at a first site within the genome of the cell, as described above, the T cell is selected from the group consisting of cytotoxic T lymphocyte (CTL), CD4+ subtype, CD8+ subtype, central memory T cell (TCM), stem memory T cell (TSCM), effector memory T cell, effector T cell, Th1 cell, Th2 cell, Th9 cell, Th17 cell, Th22 cell, Tfh (follicular helper) cell, and T regulatory cell.

In certain embodiments of a T cell wherein a recombinant nucleic acid sequence encoding a CAR is integrated at a first site within the genome of the cell, as described above, the T cell is derived from a human. In certain embodiments, the T cell is a primary human T cell, a T cell derived from a CD34 hematopoietic stem cell, a T cell derived from an embryonic stem cell, or a T cell derived from an induced pluripotent stem cell.

In certain embodiments of a T cell wherein a recombinant nucleic acid sequence encoding a CAR is integrated at a first site within the genome of the cell, as described above, the nucleic acid sequence encoding the CAR is integrated into the first site by targeted homologous recombination. In certain embodiments, the targeted homologous recombination is carried out using a zinc-finger nuclease (ZFN), a transcription activator-like effector nuclease (TALEN), a clustered regularly-interspersed short palindromic repeats (CRISPR) associated protein 9 (Cas9), Cpf1, Meganuclease or a Mega-Tal.

In certain embodiments of a T cell wherein a recombinant nucleic acid sequence encoding a CAR is integrated at a first site within the genome of the cell, as described above, the nucleic acid sequence encoding the CAR is integrated at a plurality of sites within the genome of the cell, and such that expression of the nucleic acid sequence encoding the CAR at said plurality of sites is under the control of a different endogenous promoter.

In certain embodiments of a T cell wherein a recombinant nucleic acid sequence encoding a CAR is integrated at a first site within the genome of the cell, as described above, the nucleic acid sequence encoding a CAR is also integrated at a second site within the genome of the cell such that the CAR is expressed by the cell at the surface of the cell. In certain embodiments, integration of the nucleic acid encoding the CAR at the second site also reduces or prevents expression of a functional TCR complex at the surface of the cell, wherein the first site and the second site are in different genes.

In certain embodiments of a T cell wherein a recombinant nucleic acid sequence encoding a CAR is integrated at a first site within the genome of the cell, as described above, a second nucleic acid sequence encoding a second CAR is integrated at a second site within the genome of the cell such that the second CAR is expressed by the cell at the surface of the cell, and such that expression of the second nucleic acid sequence is under the control of an endogenous promoter at the second site, wherein the first site and the second site are in different genes.

In another aspect, provided herein is a human T cell wherein a promoter-less recombinant nucleic acid sequence encoding a CAR is integrated at a site in the genome of the cell, the site being the first exon of the TCR alpha chain, such that the CAR is expressed under control of the endogenous TCR alpha chain promoter, to produce the CAR at the surface of the cell, and wherein integration of the CAR at the site reduces or prevents expression of a functional TCR alpha chain. In certain embodiments, the CAR binds to CD19.

In another aspect, provided herein is an isolated population of T cells, which comprises a plurality of the cell described above wherein a recombinant nucleic acid sequence encoding a CAR is integrated at a first site within the genome of the cell, or a plurality of the cell described above that is a human T cell wherein a promoter-less recombinant nucleic acid sequence encoding a CAR is integrated at a site in the genome of the cell.

In another aspect, provided herein is a pharmaceutical composition comprising a therapeutically effective amount of the cell described above wherein a recombinant nucleic acid sequence encoding a CAR is integrated at a first site within the genome of the cell, or the cell described above that is a human T cell wherein a promoter-less recombinant nucleic acid sequence encoding a CAR is integrated at a site in the genome of the cell; and a pharmaceutically acceptable carrier.

In another aspect, provided herein is a pharmaceutical composition comprising a therapeutically effective amount of a population of T cells, which population comprises a plurality of the cell described above wherein a recombinant nucleic acid sequence encoding a CAR is integrated at a first site within the genome of the cell, or the cell described above that is a human T cell wherein a promoter-less recombinant nucleic acid sequence encoding a CAR is integrated at a site in the genome of the cell; and a pharmaceutically acceptable carrier.

In another aspect, provided herein is a method of treating a subject with CAR therapy in need thereof, comprising administering to the subject a therapeutically effective amount of the cell described above wherein a recombinant nucleic acid sequence encoding a CAR is integrated at a first site within the genome of the cell, or the cell described above that is a human T cell wherein a promoter-less recombinant nucleic acid sequence encoding a CAR is integrated at a site in the genome of the cell.

In another aspect, provided herein is a method of treating a subject with CAR therapy in need thereof, comprising administering to the subject a pharmaceutical composition described above comprising c a therapeutically effective amount of the cell described above wherein a recombinant nucleic acid sequence encoding a CAR is integrated at a first site within the genome of the cell, or the cell described above that is a human T cell wherein a promoter-less recombinant nucleic acid sequence encoding a CAR is integrated at a site in the genome of the cell.

In another aspect, provided herein is a method of treating a subject with CAR therapy in need thereof, comprising administering to the subject a therapeutically effective amount of the cell population described above comprising a plurality of the cell described above wherein a recombinant nucleic acid sequence encoding a CAR is integrated at a first site within the genome of the cell, or a plurality of the cell described above that is a human T cell wherein a promoter-less recombinant nucleic acid sequence encoding a CAR is integrated at a site in the genome of the cell.

In another aspect, provided herein is a method of treating a subject with CAR therapy in need thereof, comprising administering to the subject a pharmaceutical composition described above comprising a therapeutically effective amount of a population of T cells, which population comprises a plurality of the cell described above wherein a recombinant nucleic acid sequence encoding a CAR is integrated at a first site within the genome of the cell, or the cell described above that is a human T cell wherein a promoter-less recombinant nucleic acid sequence encoding a CAR is integrated at a site in the genome of the cell.

In certain embodiments of the methods described above for treating a subject with CAR therapy in need thereof, the subject has cancer, and the CAR binds to a cancer antigen of the cancer. In a specific embodiment, the cancer is leukemia.

In certain embodiments of the methods described above for treating a subject with CAR therapy in need thereof, the subject has a tumor.

In certain embodiments of the methods described above for treating a subject with CAR therapy in need thereof, the subject is a human, and the cell is derived from a human.

In certain embodiments of the methods described above for treating a subject with CAR therapy in need thereof, the cell is autologous to the subject. In certain embodiments of the methods described above for treating a subject with CAR therapy in need thereof, the cell is non-autologous to the subject.

In another aspect, provided herein is a method of generating a T cell that expresses a chimeric antigen receptor (CAR) and lacks a functional T cell receptor (TCR) complex, comprising: introducing into a T cell: (i) a nucleic acid sequence encoding a CAR, and (ii) a homologous recombination system suitable for targeted integration of the nucleic acid sequence at a site within the genome of the cell, whereby the homologous recombination system integrates the nucleic acid sequence encoding the CAR at the site within the genome of the cell such that integration of the CAR at the site reduces or prevents expression of a functional T cell receptor complex at the surface of the cell, thereby generating a T cell that expresses the CAR and lacks a functional TCR complex.

In certain embodiments of a method of generating a T cell that expresses a CAR and lacks a functional TCR complex, as described above, expression of the CAR is under the control of an endogenous promoter. In certain embodiments, the endogenous promoter is a promoter of a gene encoding a T cell receptor alpha chain, T cell receptor beta chain, CD3 gamma chain, CD3 delta chain, CD3 epsilon chain, or CD3 zeta chain.

In certain embodiments of a method of generating a T cell that expresses a CAR and lacks a functional TCR complex, as described above, the homologous recombination system comprises a zinc-finger nuclease (ZFN), a transcription activator-like effector nuclease (TALEN), or clustered regularly-interspersed short palindromic repeats (CRISPR) associated protein 9 (Cas9), Cpf1, Meganuclease or a Mega-Tal.

In certain embodiments of a method of generating a T cell that expresses a CAR and lacks a functional TCR complex, as described above, the nucleic acid sequence encoding the CAR that is introduced into the cell is contained in a targeting construct. In certain embodiments, the targeting construct comprises adeno-associated virus 2 (AAV2) sequences. In certain embodiments, the targeting construct is packaged into a natural or recombinant adeno-associated virus (AVV) viral particle. In certain embodiments, the AAV particle comprises AAV6 sequences.

In certain embodiments of a method of generating a T cell that expresses a CAR and lacks a functional TCR complex, as described above, the nucleic acid sequences encoding the CAR in the targeting construct are not operably linked to a promoter.

In certain embodiments of a method of generating a T cell that expresses a CAR and lacks a functional TCR complex, as described above, the targeting construct comprises in 5' to 3' order: a first viral sequence, a left homology arm, a nucleic acid sequence encoding a self-cleaving porcine teschovirus 2A, the nucleic acid sequence encoding the CAR, a polyadenylation sequence, a right homology arm, and a second viral sequence. In certain embodiments, the first or the second viral sequence is from an adeno-associated virus (AAV). In certain embodiments, the AAV is AAV2, AAV5 or AAV6.

In another aspect, provided herein is an induced pluripotent stem cell, wherein a recombinant nucleic acid sequence encoding a chimeric antigen receptor (CAR) is integrated at a first site within the genome of the cell such that the CAR is expressed by the cell at the surface of the cell, and wherein integration of the nucleic acid encoding the CAR at the first site reduces or prevents expression of a functional T cell receptor (TCR) complex at the surface of the cell.

6. DESCRIPTION OF THE DRAWINGS

Figure 1B:
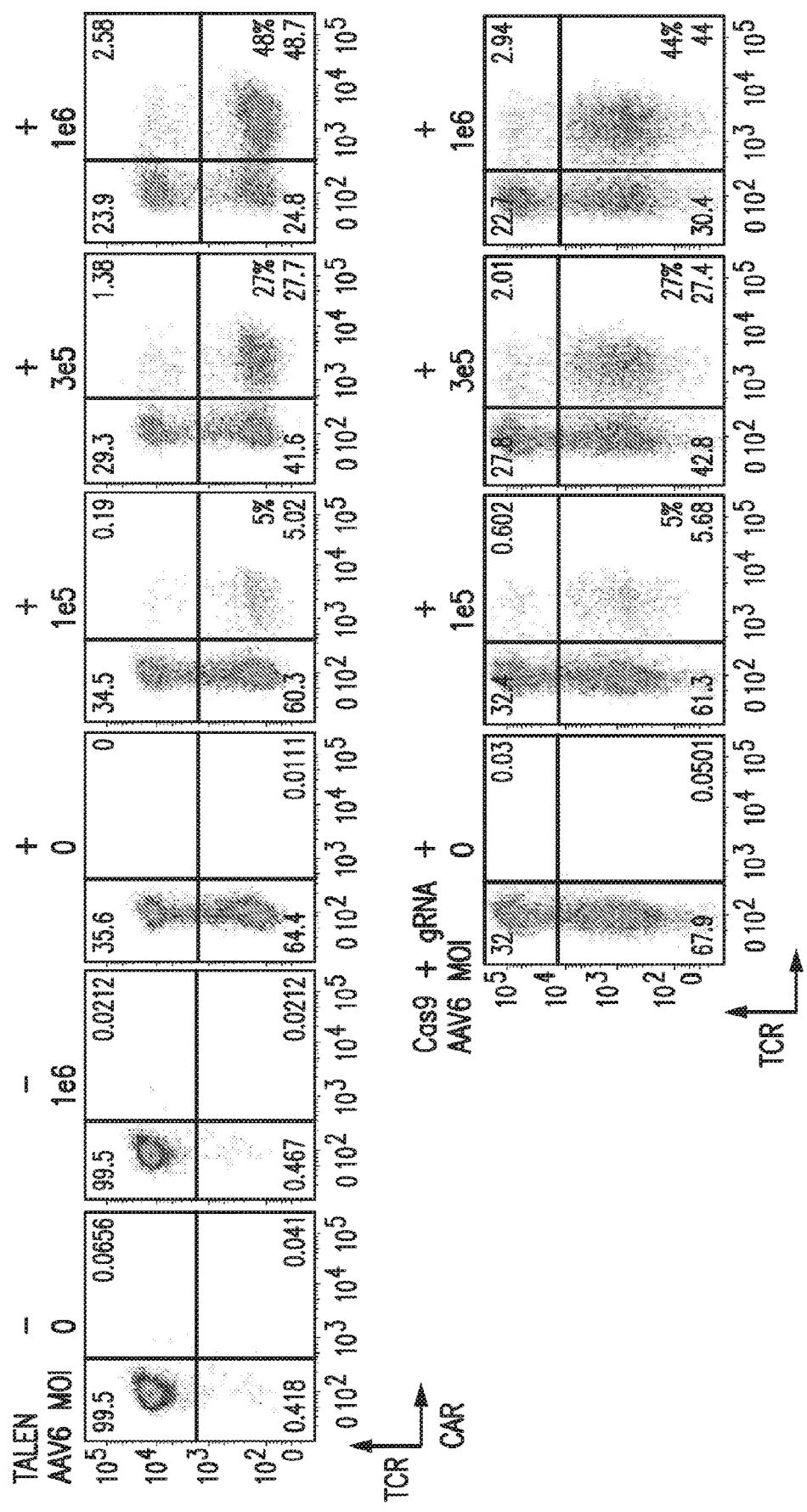

FIGS. 1A-1E show analysis of targeted integration of a CAR into the TCR alpha constant (TRAC) locus. FIG. 1A shows a schematic of tailored nuclease (TALEN or CRISPR/Cas9)-induced targeted integration into TCR alpha constant (TRAC) locus. The targeting construct (AAV6) contains the CAR gene flanked by homology sequences (LHA and RHA). Once integrated CAR expression is driven by the endogenous TCRa promoter while the TRAC locus is disrupted. TRAV: TCR alpha variable region. TRAJ: TCR alpha joining region. 2A: the self cleaving Porcine teschovirus 2A sequence. pA: bovine growth hormone PolyA sequence. FIG. 1B shows representative TCR/CAR flow plot 5 days after transfection of T cells with TRAC TALEN mRNA and addition of AAV6 at the noted MOI (multiplicity of infection). FIG. 1C shows a bar-graph of the percentage of TCR disruption (KO: knockout) and targeted integration (KI: knockin) depending on the AAV6 MOI. Percentages were assessed by FACS analysis. FIG. 1D shows average CAR expression mean fluorescence intensity (MFI) 5 days after CAR vectorization (choosing an adapted vector for expressing the CAR, integration of the CAR coding into the cell) into T cells (n=6 to 8 independent experiments). FIG. 1E shows coefficient of variation of the CAR+ T cells measuring the dispersion in the CAR expression (ratio of the standard deviation to the mean). TRAC-P2A-1928z: Targeted integration into TRAC. SFG-1928z: semi-random integration using the SFG retrovirus. ****P<0.0001 (unpaired T-test).

Figure 2A:
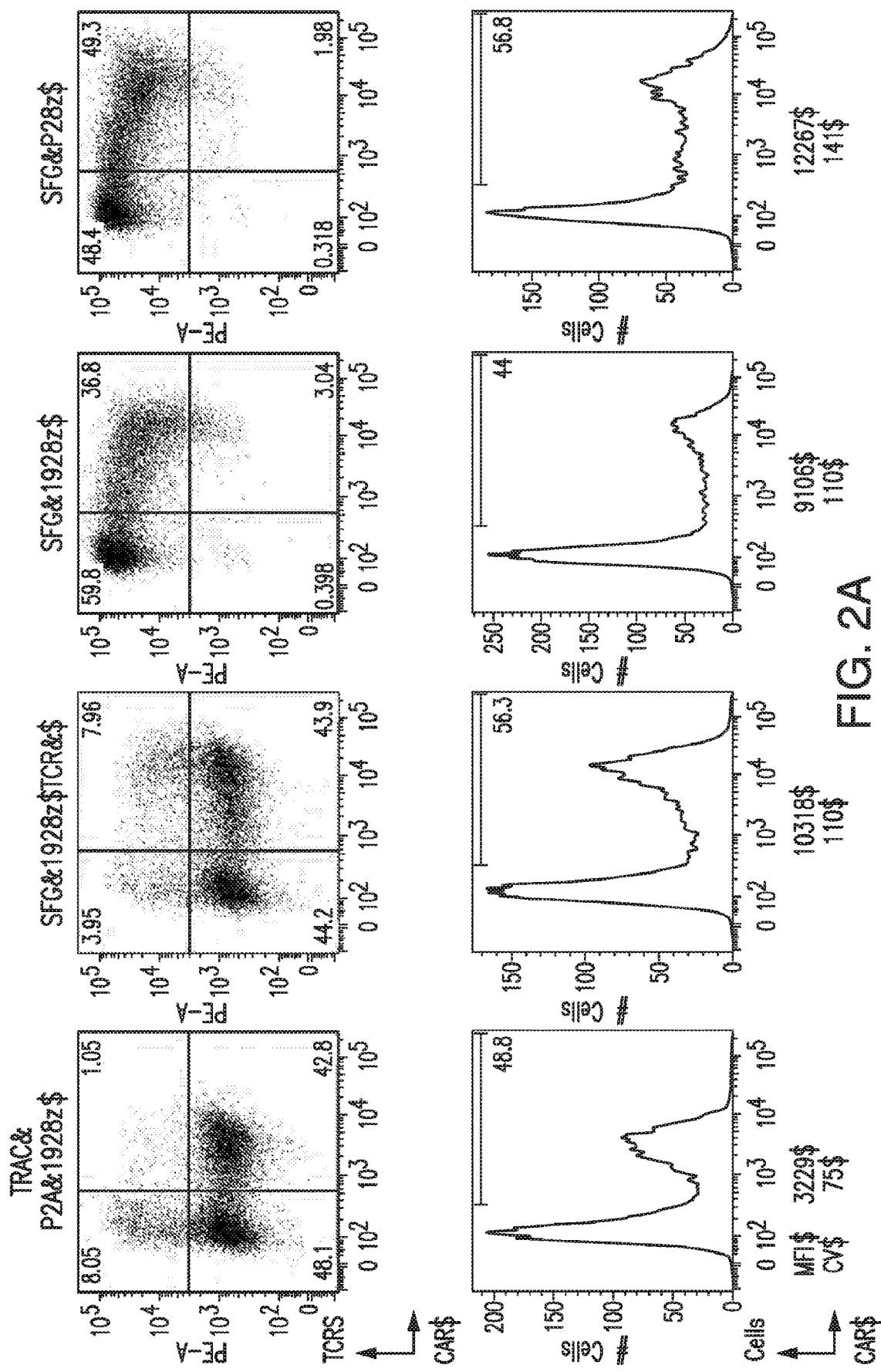
Figure 2B:
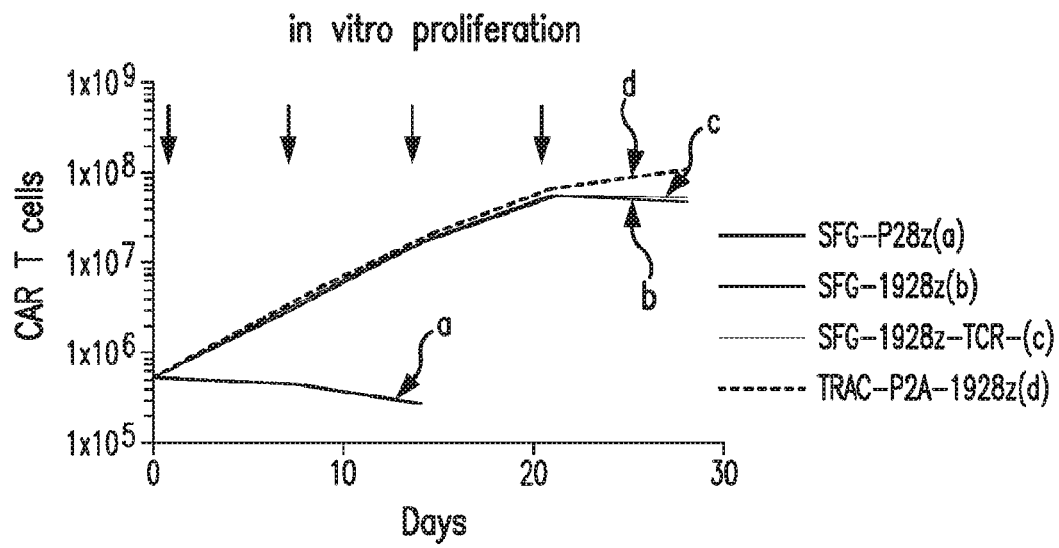
Figure 2C:
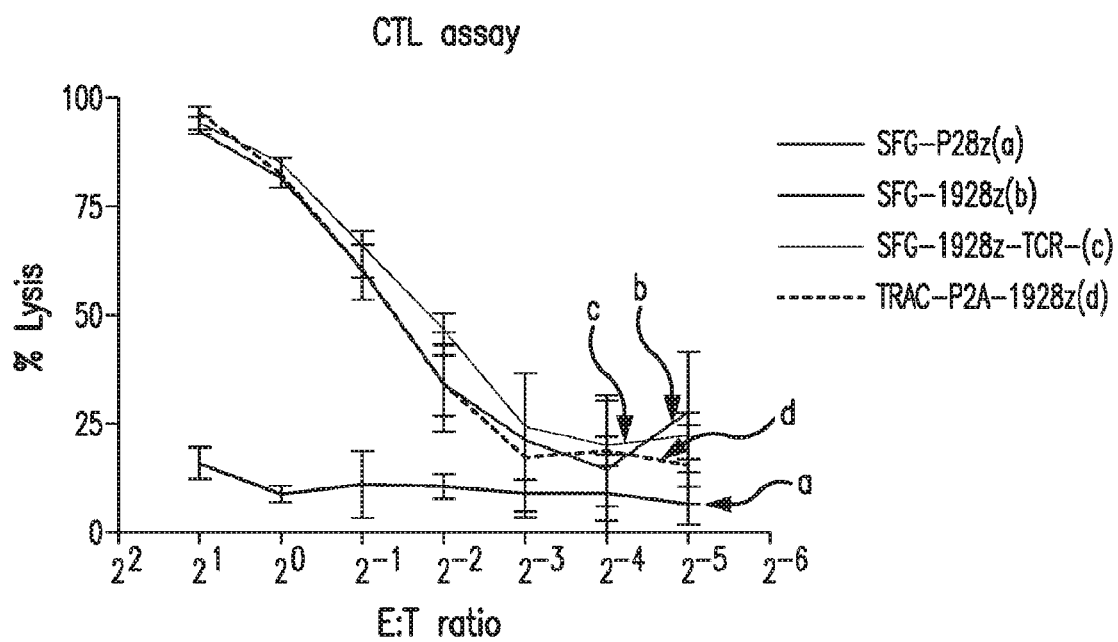
Figure 2D:
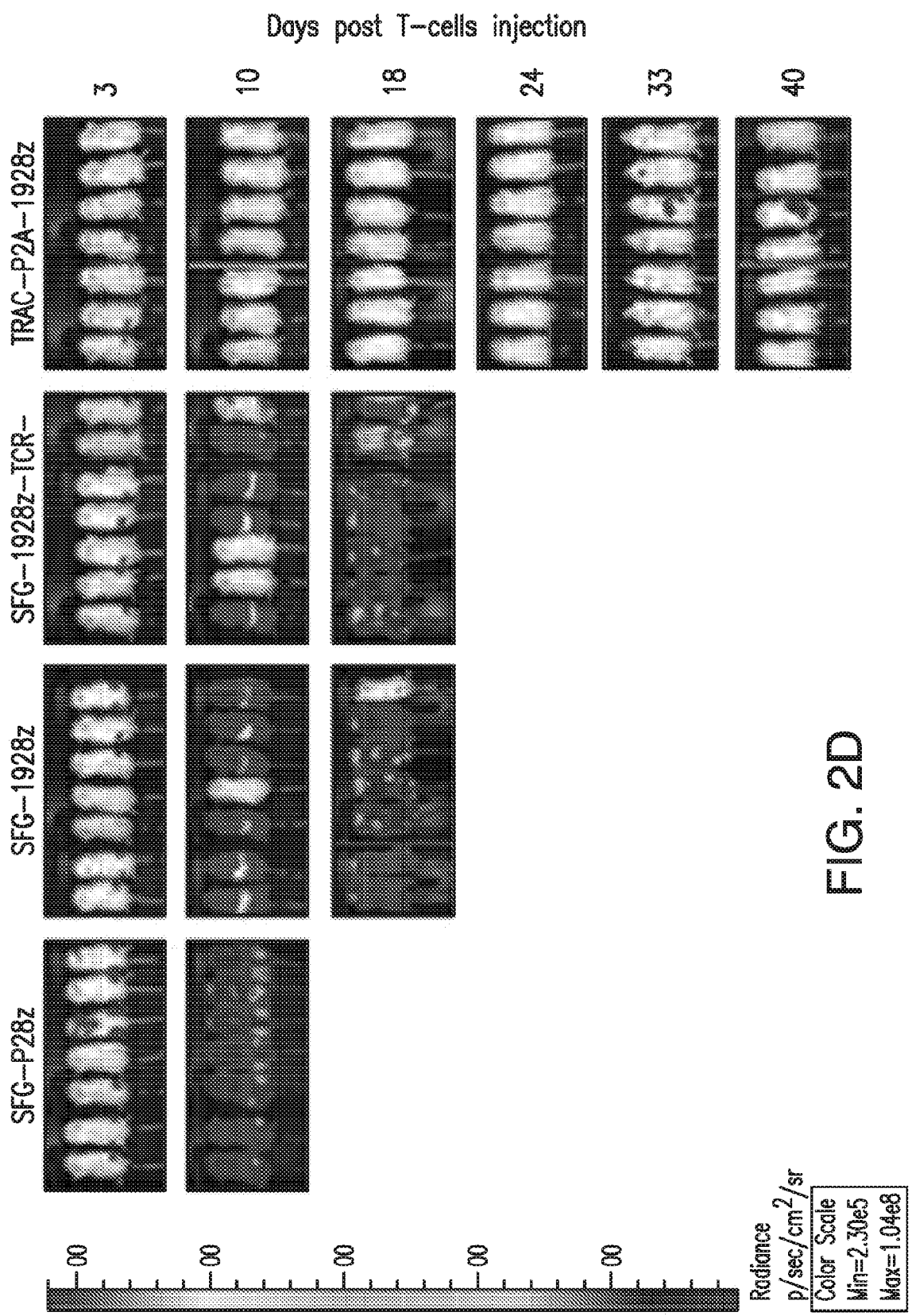
Figure 2E:
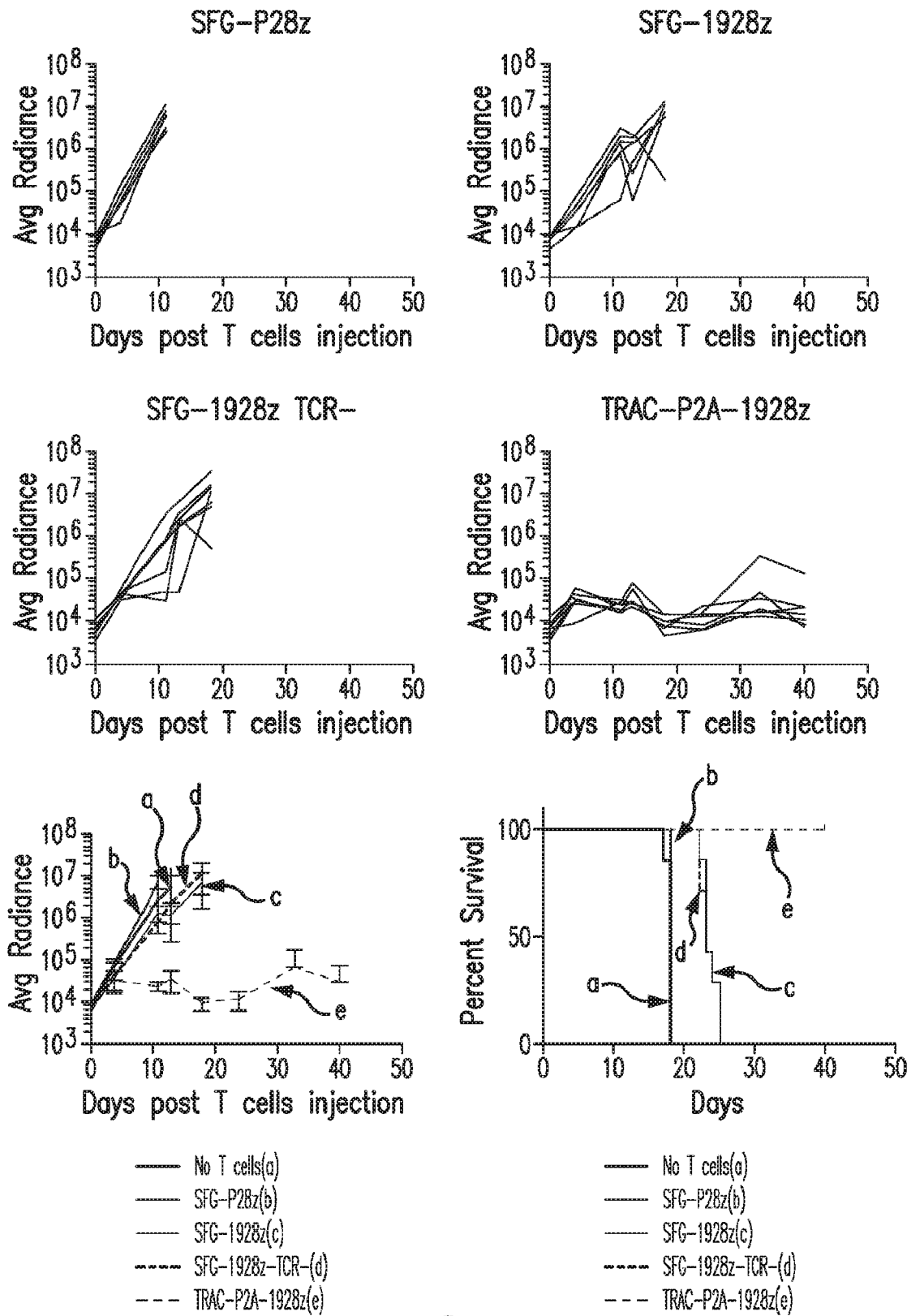

FIGS. 2A-2E show analysis of targeted integration of a CAR into the TCR alpha constant (TRAC) locus. FIG. 2A shows flow cytometry analysis showing CAR and TCR expression. TRAC-P2A-1928z were generated as in FIG. 1; TALEN-generated TCR-cells were transduced with SFG-1928z retrovirus; and TCR+ cells were transduced with either SFG-1928z or SGF-P28z retrovirus. FIG. 2B shows cumulative cell counts of indicated CAR T cells upon weekly stimulation with CD19+ target cells. Arrows indicate stimulation time points. FIG. 2C shows cytotoxic activity using an 18 hr bioluminescence assay, using firefly luciferase (FFL)-expressing NALM6 as targets cells. Data are means±SD. FIGS. 2D and 2E show FFL-NALM6 bearing mice, which were treated with 2×10$^5$ CAR T cells. Tumor burden shown as bioluminescent signal quantified per animal every week over a 40-day period. Quantification is the average photon count of ventral and dorsal acquisitions per animal at all given time points, and it is expressed as radiance. Each line represents one mouse. n=7 mice per group. The lower right figure is Kaplan-Meier analysis of survival of mice in FIGS. 2D and 2E.

Figure 3A:
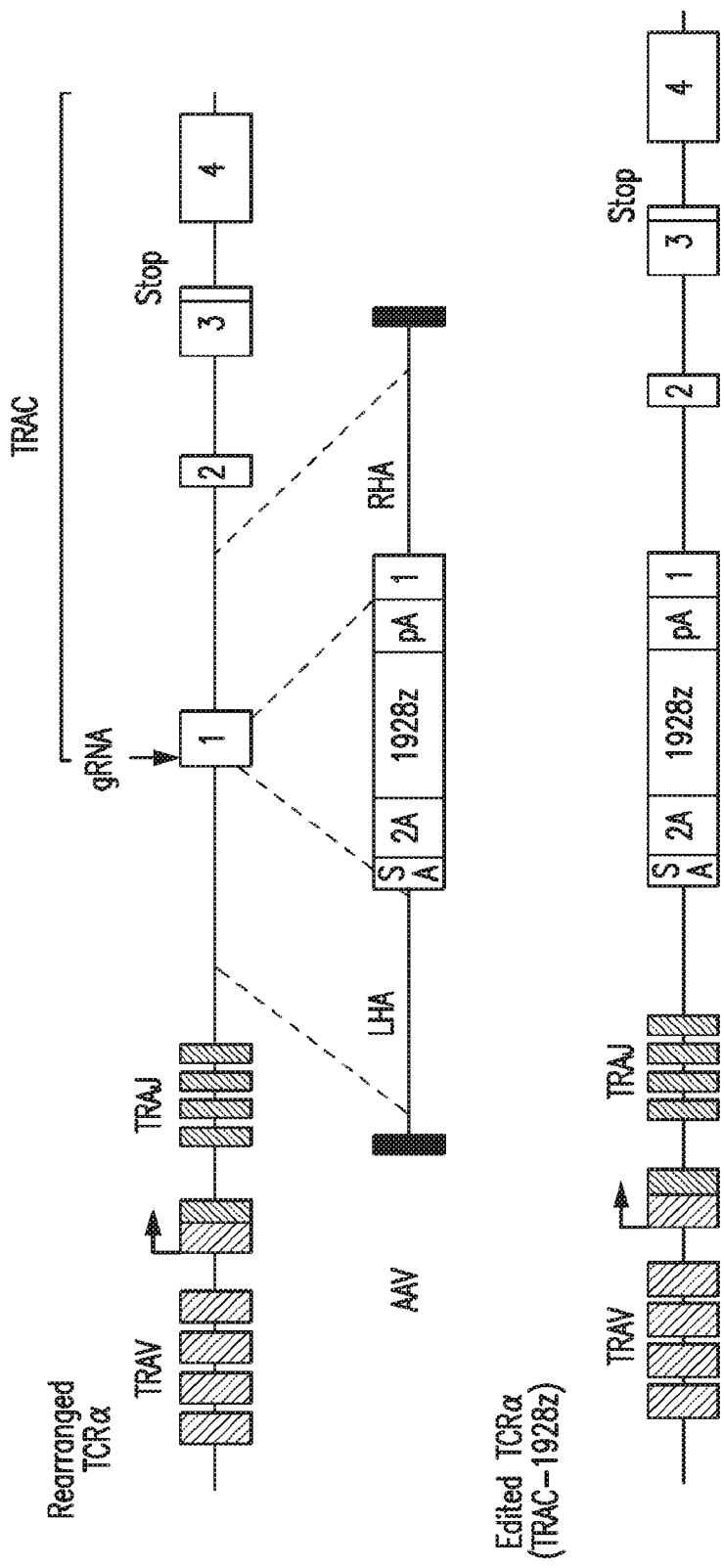
Figure 3B:
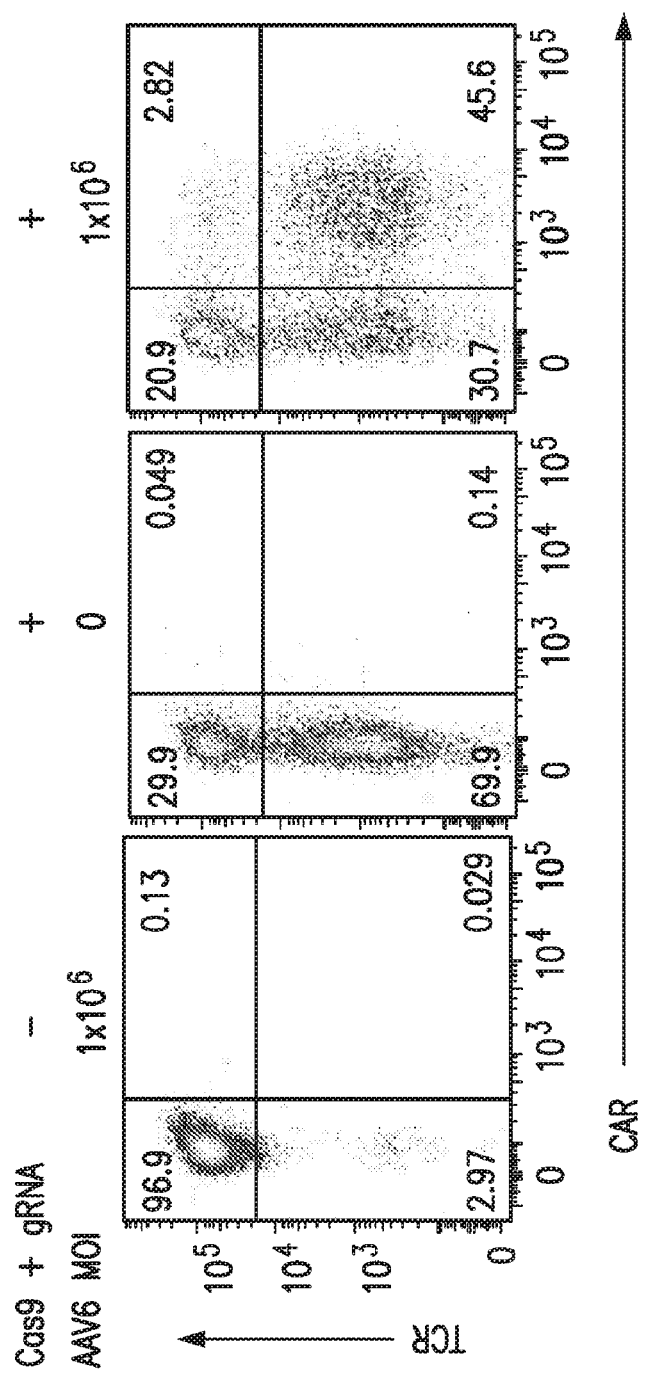
Figure 3C:
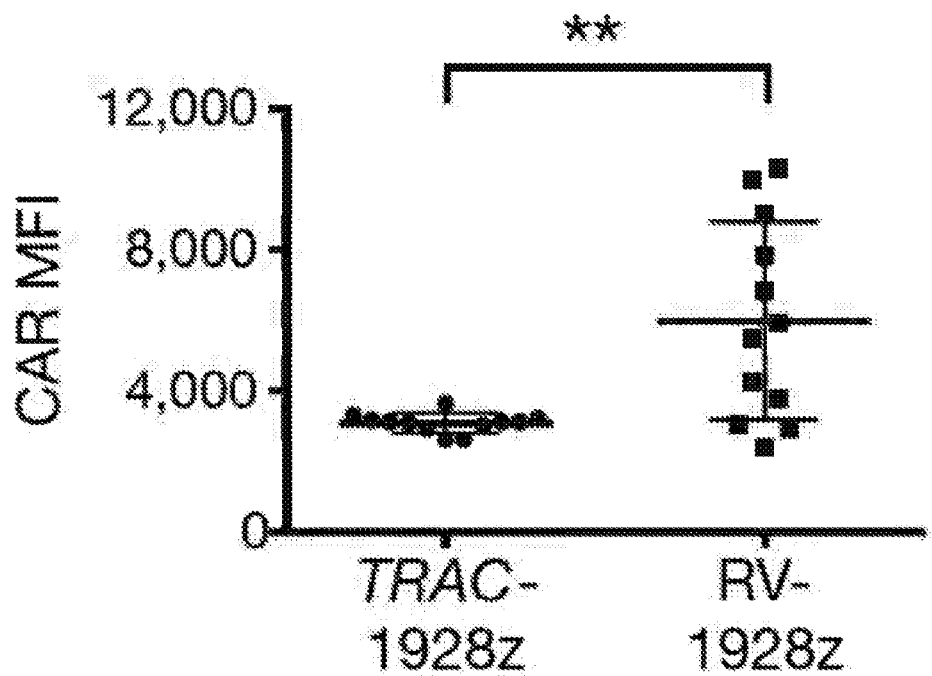
Figure 3D:
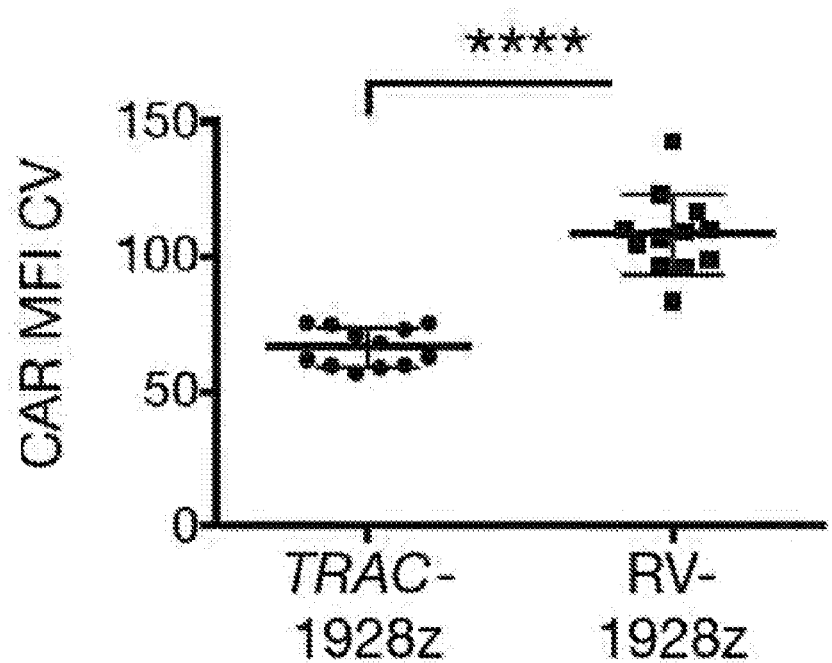
Figure 3E:
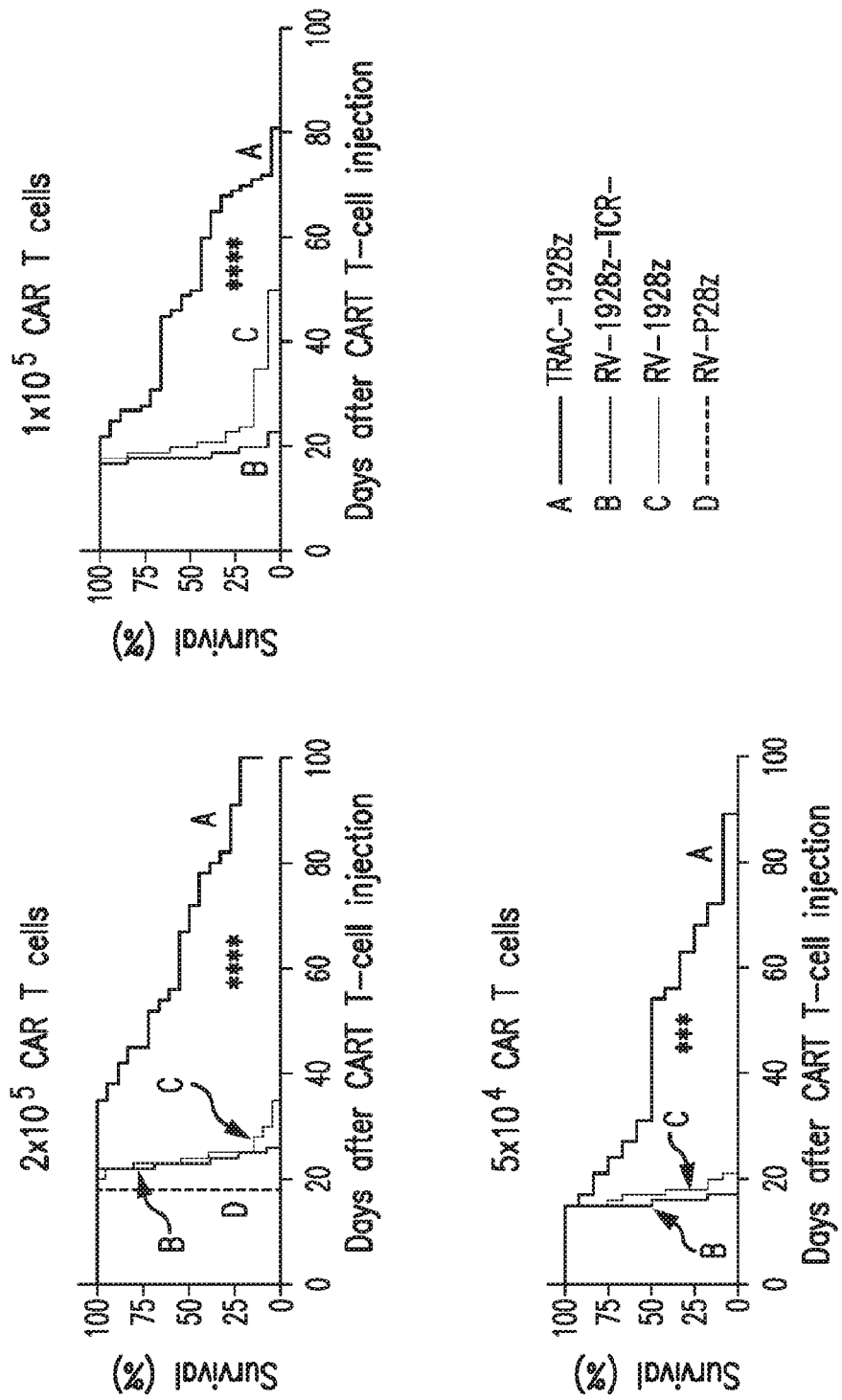
Figure 3F:
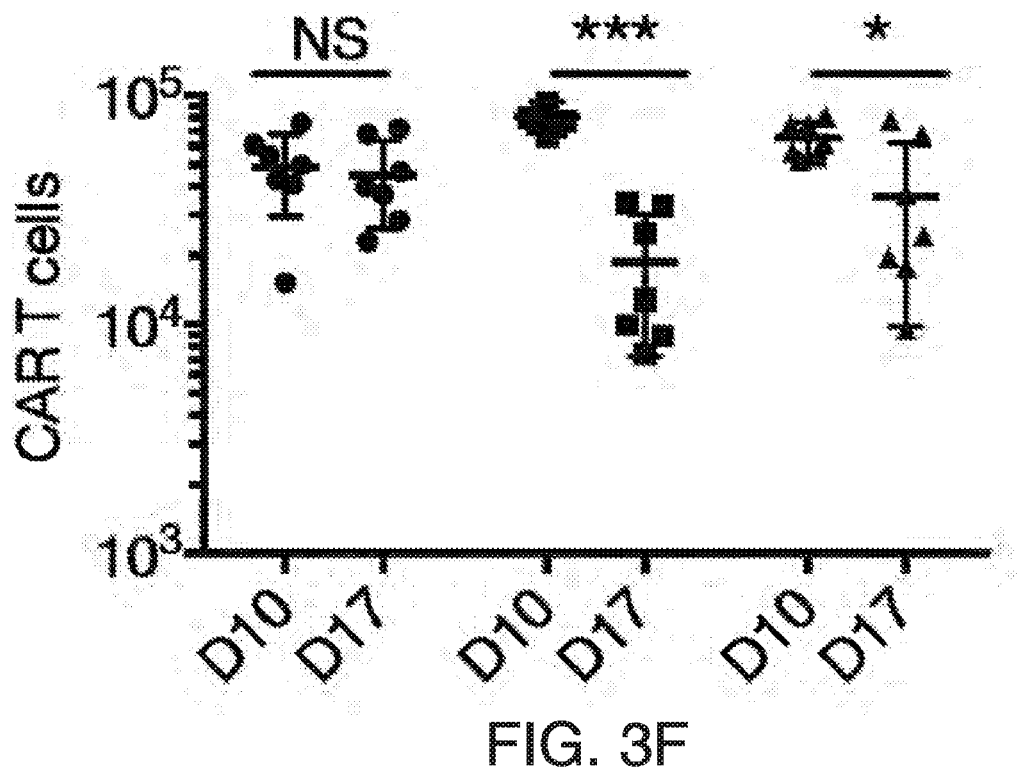
Figure 3G:
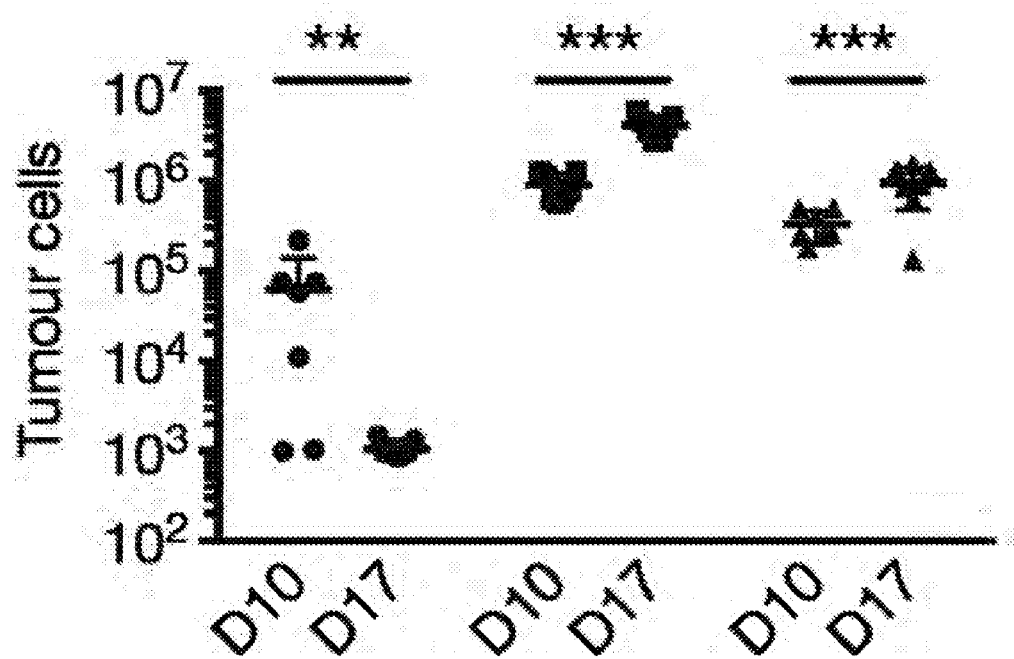
Figure 3H:
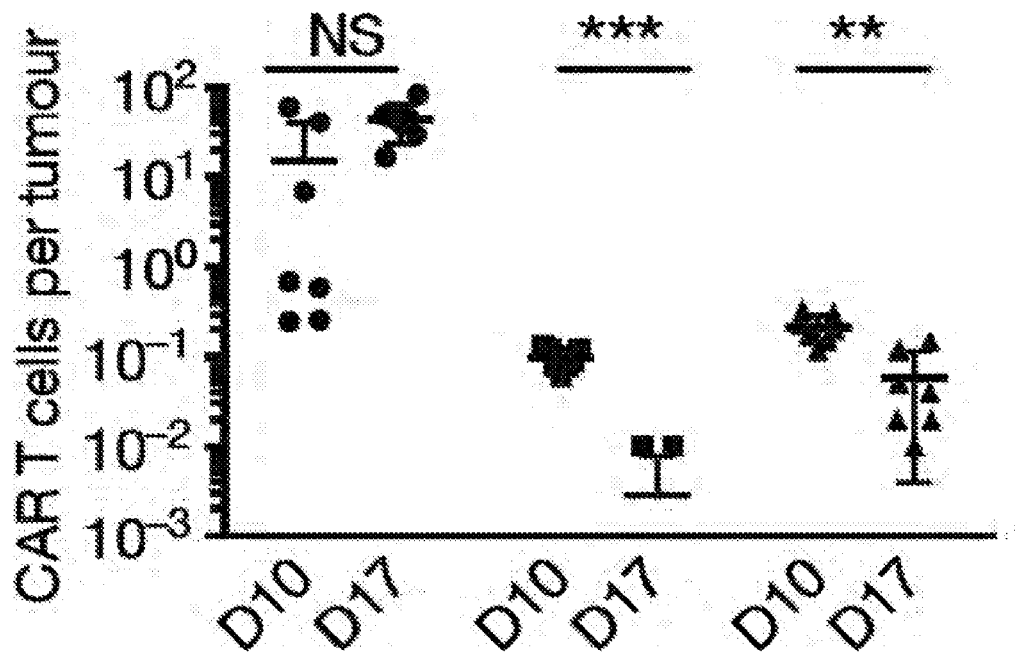
Figure 3I:
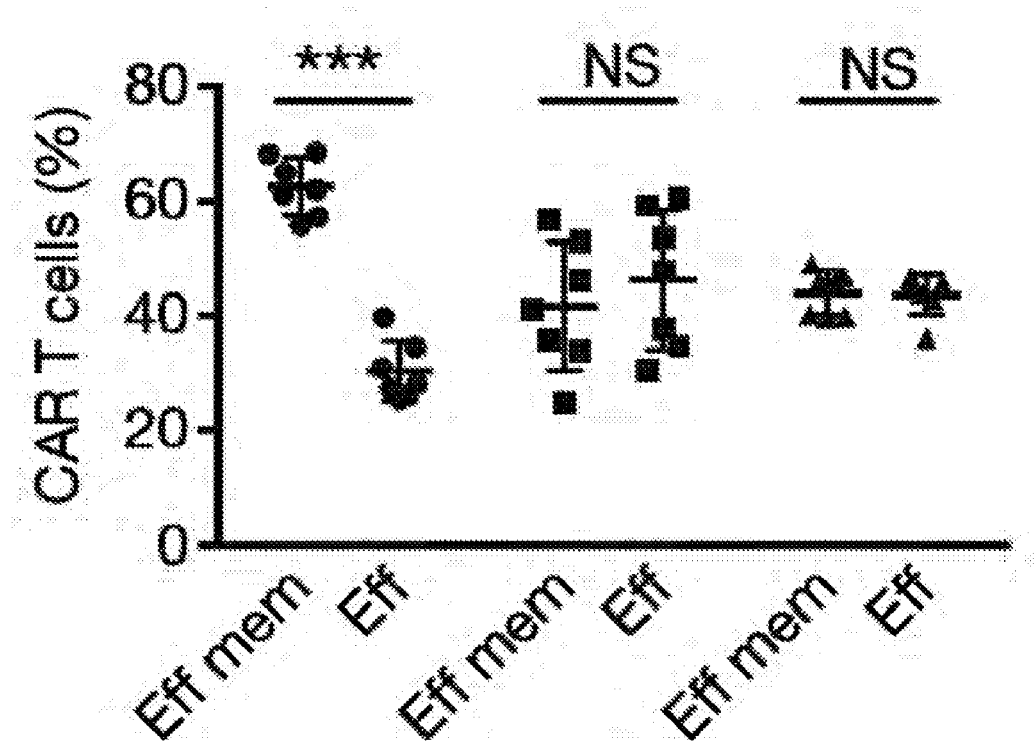
Figure 3J:
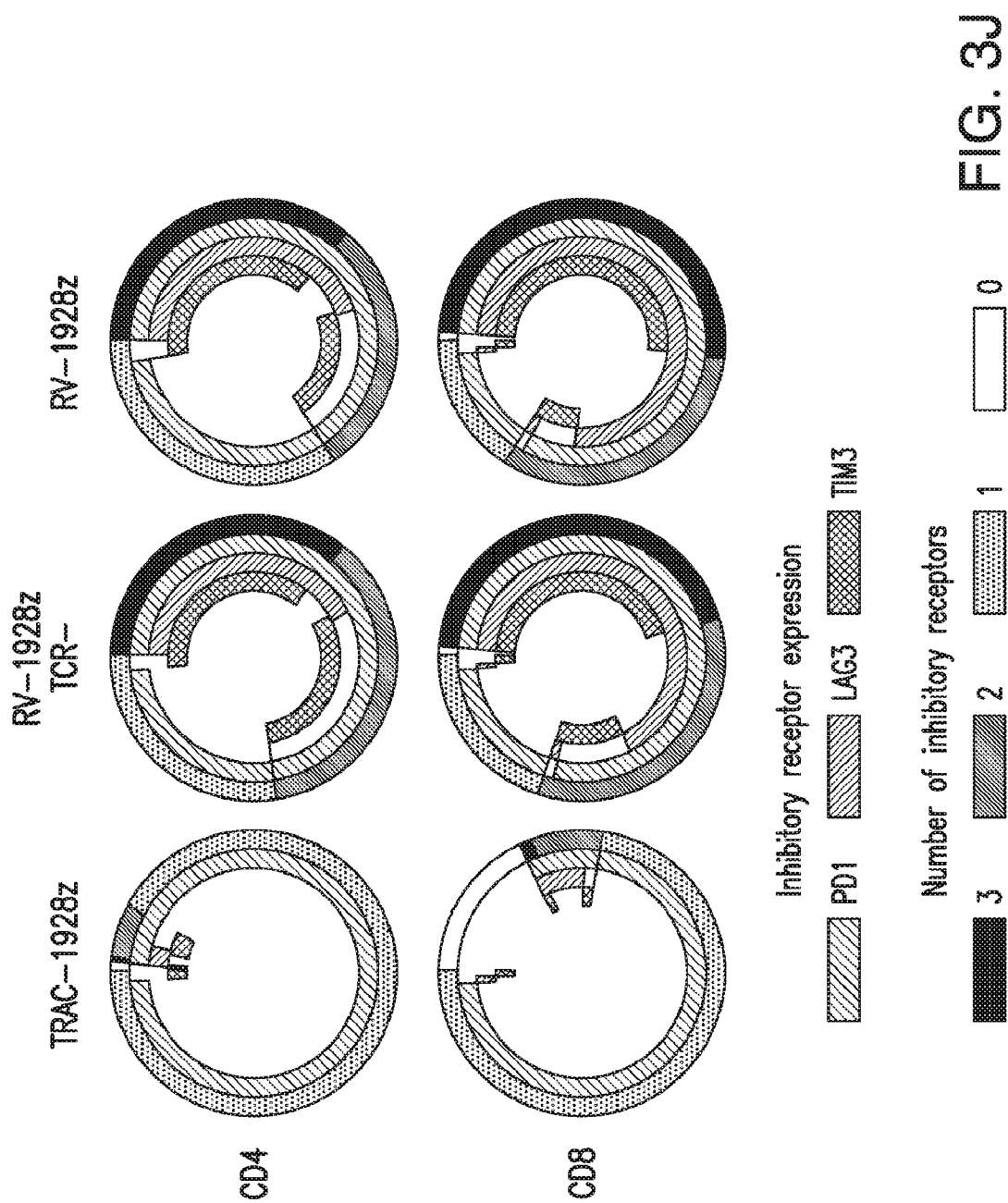

FIGS. 3A-3J show that TRAC-CAR T cells outperform conventional CAR T cells by preventing exhaustion in vivo. FIG. 3A shows CRISPR/Cas9-targeted CAR gene integration into the TRAC locus. Top, TRAC locus; middle, rAAV6 containing the CAR cassette flanked by homology arms; bottom, edited TRAC locus. FIG. 3B shows representative TCR/CAR flow plots 4 days after TRAC targeting. FIGS. 3C and 3D show CAR mean fluorescence intensity (MFI) (FIG. 3C) and CAR MFI coefficient of variance (FIG. 3D) of CAR+ T cells (n=12 independent experiments, 6 donors). FIG. 3E shows Kaplan-Meier analysis of survival of mice. FIGS. 3F-3J show NALM-6-bearing mice were treated with 1×10$^5$ CAR T cells (n=7 per group; dot=one mouse), and euthanized at days 10 and 17 after infusion; bone marrow CAR T cells and NALM-6 cells were analysed and counted by FACS (TRAC-1928z, circles; RV-1928z-TCR-, squares; RV-1928z, triangles). FIG. 3F shows CAR T cells. FIG. 3G shows tumour (GFP+CD19+) cells. FIG. 3H shows CAR T cells to tumour ratio. FIG. 3I shows percentage of effector memory (CD62L−CD45RA−) and effector (CD62L−CD45RA+) in CAR T cells at day 17. FIG. 3J shows percentage of CAR T cells expressing exhaustion markers; quantified by FACS at day 17 (inhibitory receptor expression shown from inner to outer rings TIM3, LAG3 and PD1, respectively). *P<0.05, P<0.01, *P<0.001, ****P<0.0001 (Welch's two samples t-test (FIGS. 3C and 3D); log-rank Mantel-Cox test (FIG. 3E); Mann-Whitney (FIGS. 3F-3I)). All data are means±s.d. See also FIGS. 7-10.

Figure 4A:
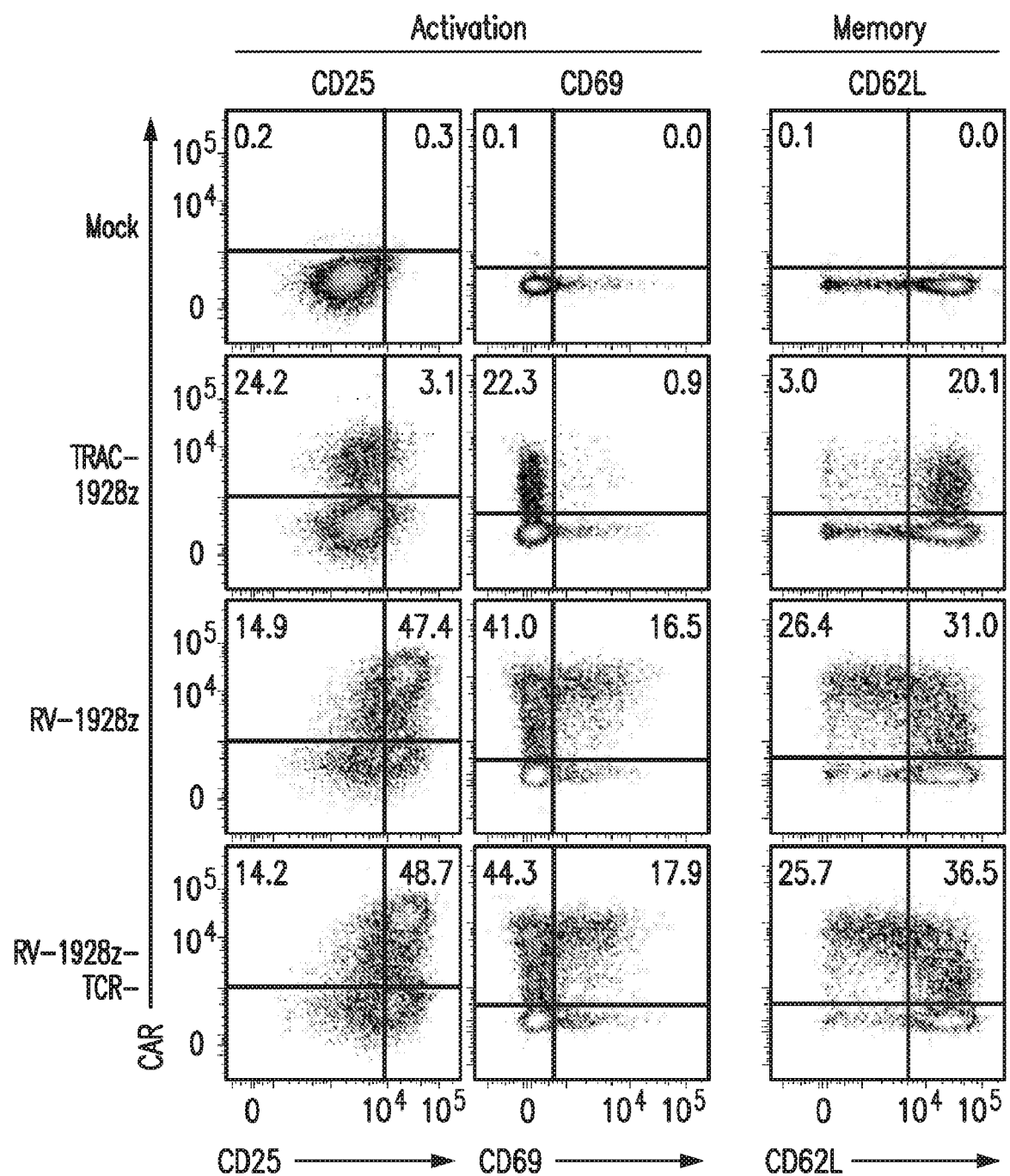
Figure 4A:
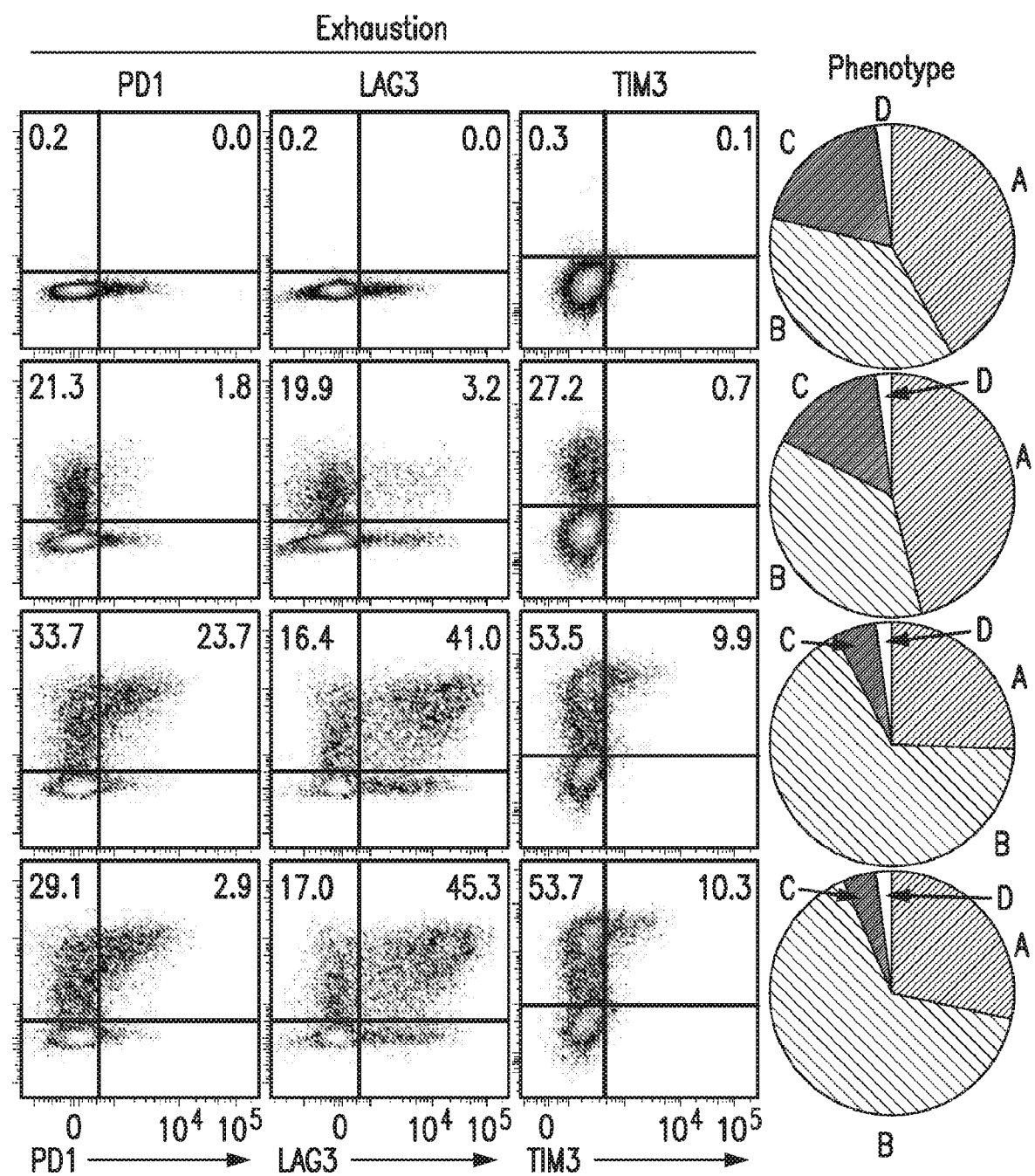
Figure 4B:
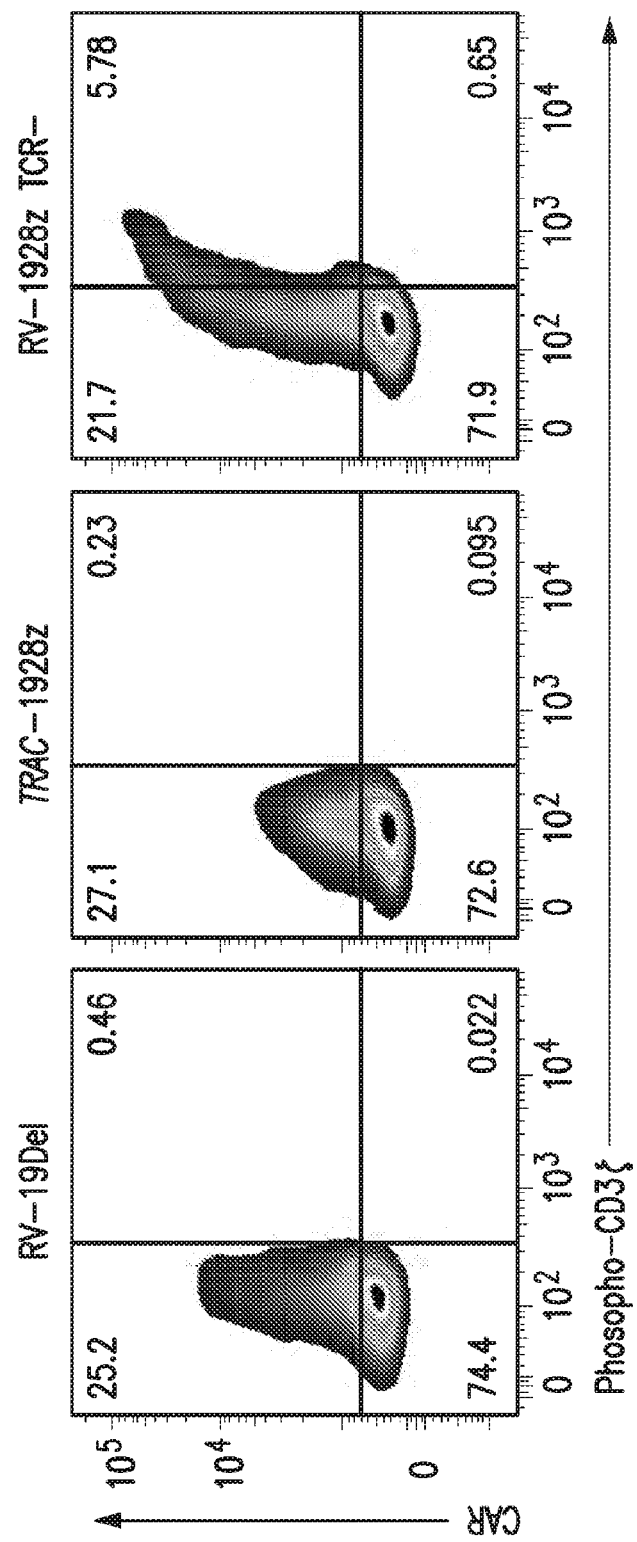
Figure 4C:
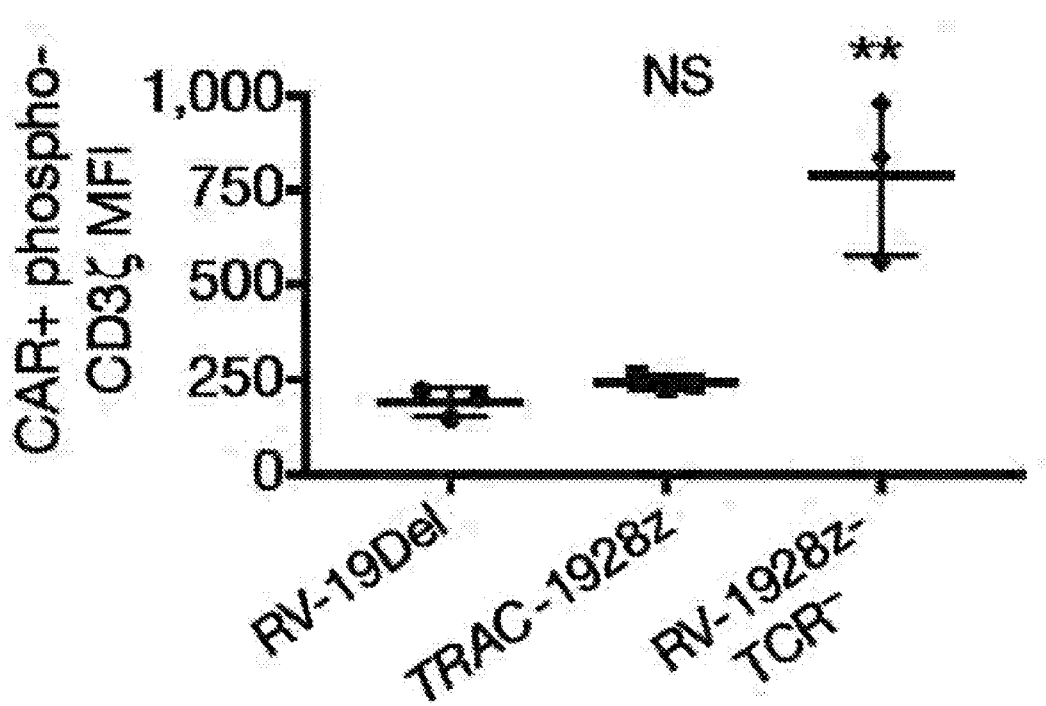
Figure 4E:
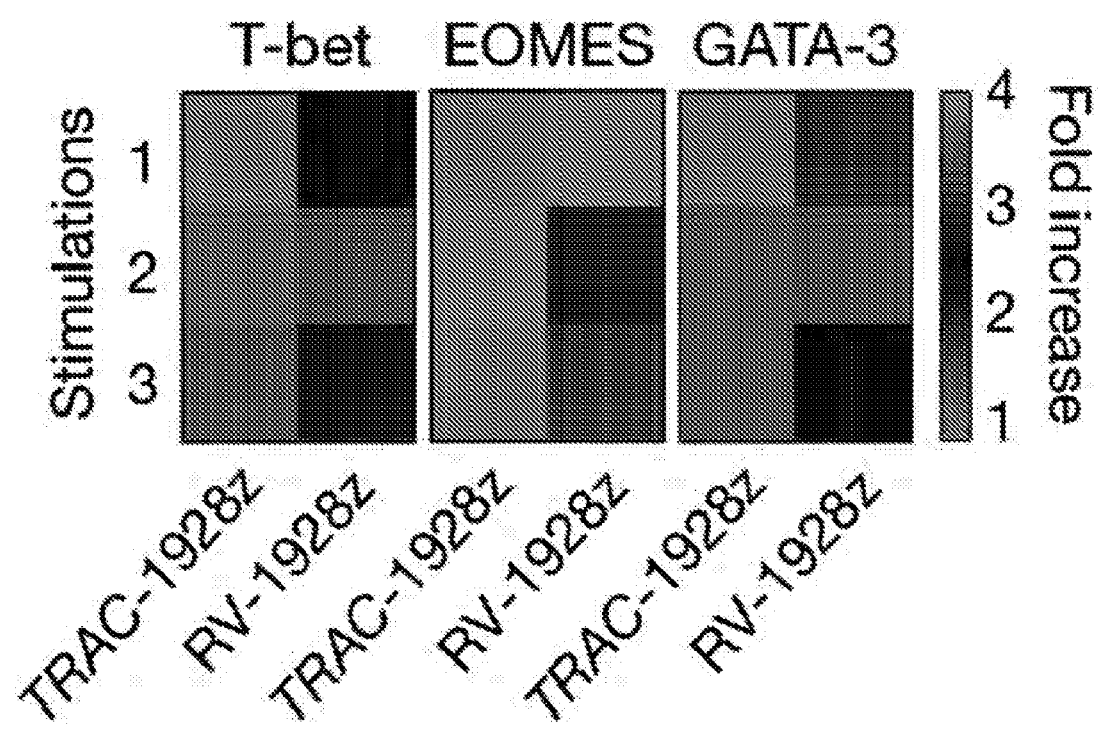

FIGS. 4A-4E show that TRAC-CAR T cells display reduced constitutive signalling and antigen-induced differentiation. FIG. 4A shows FACS analysis of activation, memory and exhaustion markers in T cells (day 5 after infusion; representative of 3 donors; pie chart for CD62L/D45RA expression (n=3, 3 donors). FIG. 4B shows CAR expression and CD3ζ ITAM phosphorylation (representative of 3 donors). RV-19Del, retrovirally expressed CD19-specific CAR lacking signalling domains. FIG. 4C shows phospho-CD3ζ MFI in the CAR+ population (n=3, 3 donors; **P<0.05 Mann-Whitney test). FIG. 4D shows CD62L/CD45RA expression in CAR T cells stimulated 1, 2 or 4 times. Pie charts show the phenotypes of the CAR+ T cells (n=3-5 on different donors) (A, CD45RA+CD62L+; B, CD45RA− CD62L+; C, CD45RA− CD62L−; D, CD45RA+ CD62L−). FIG. 4E shows heat map of T-bet, EOMES and GATA3 expression in CAR T cells collected as in FIG. 4D; fold-increase value of 1 represents to TRAC-1928z, 1 stimulation (n=2, 2 donors). All data are means±s.d. See also FIG. 12.

Figure 5A:
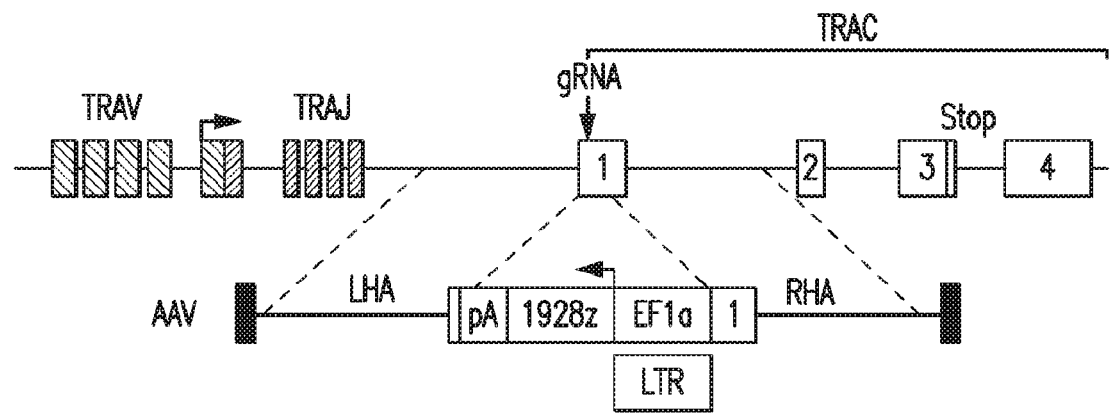
Figure 5B:
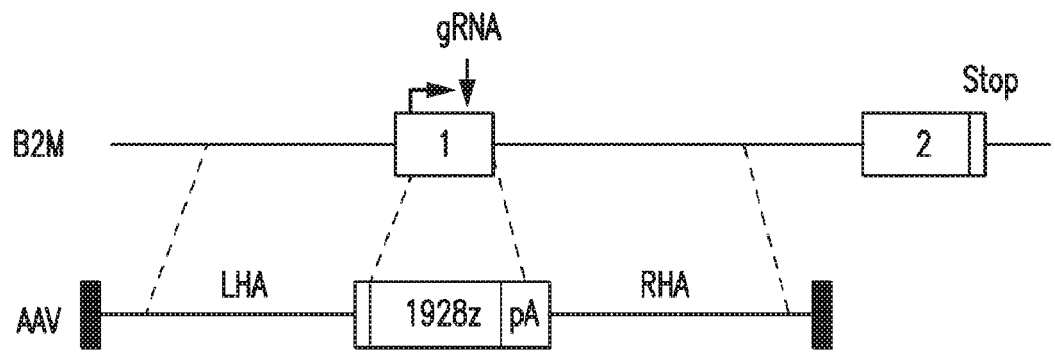
Figure 5C:
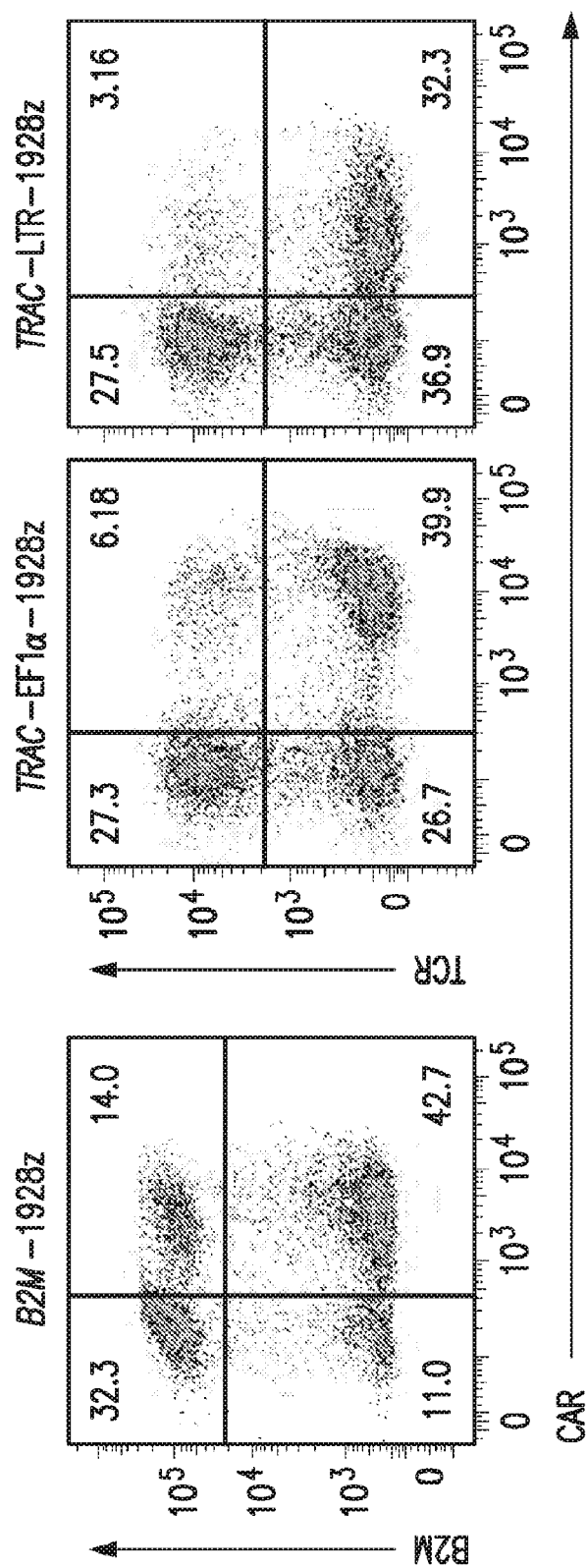
Figure 5D:
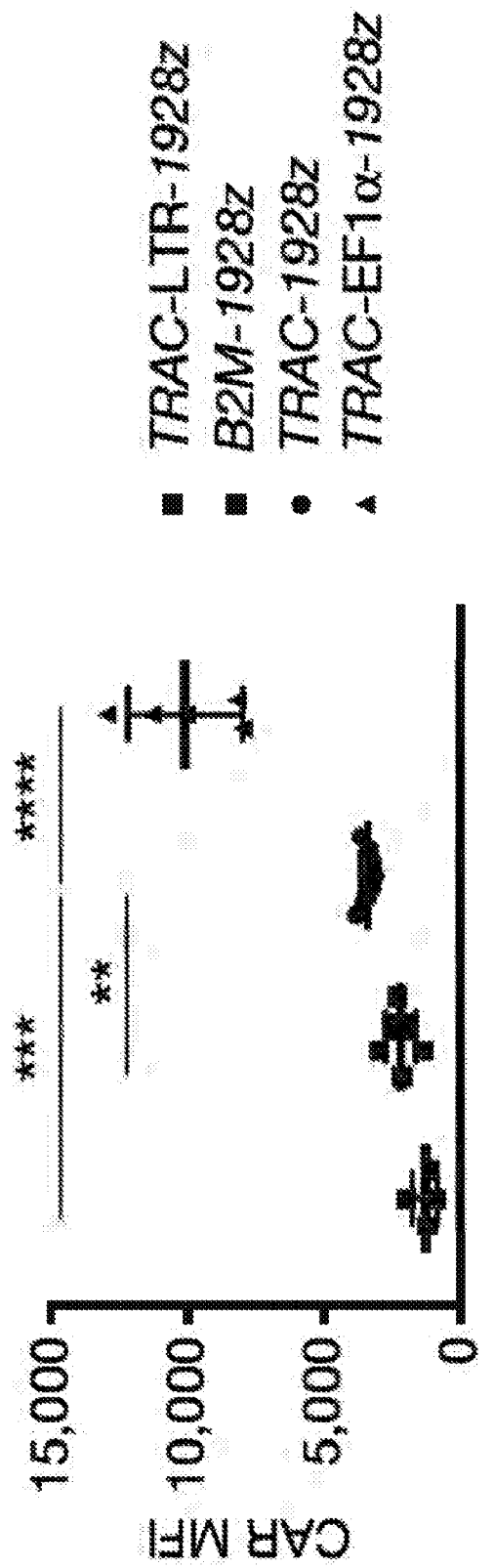
Figure 5E:
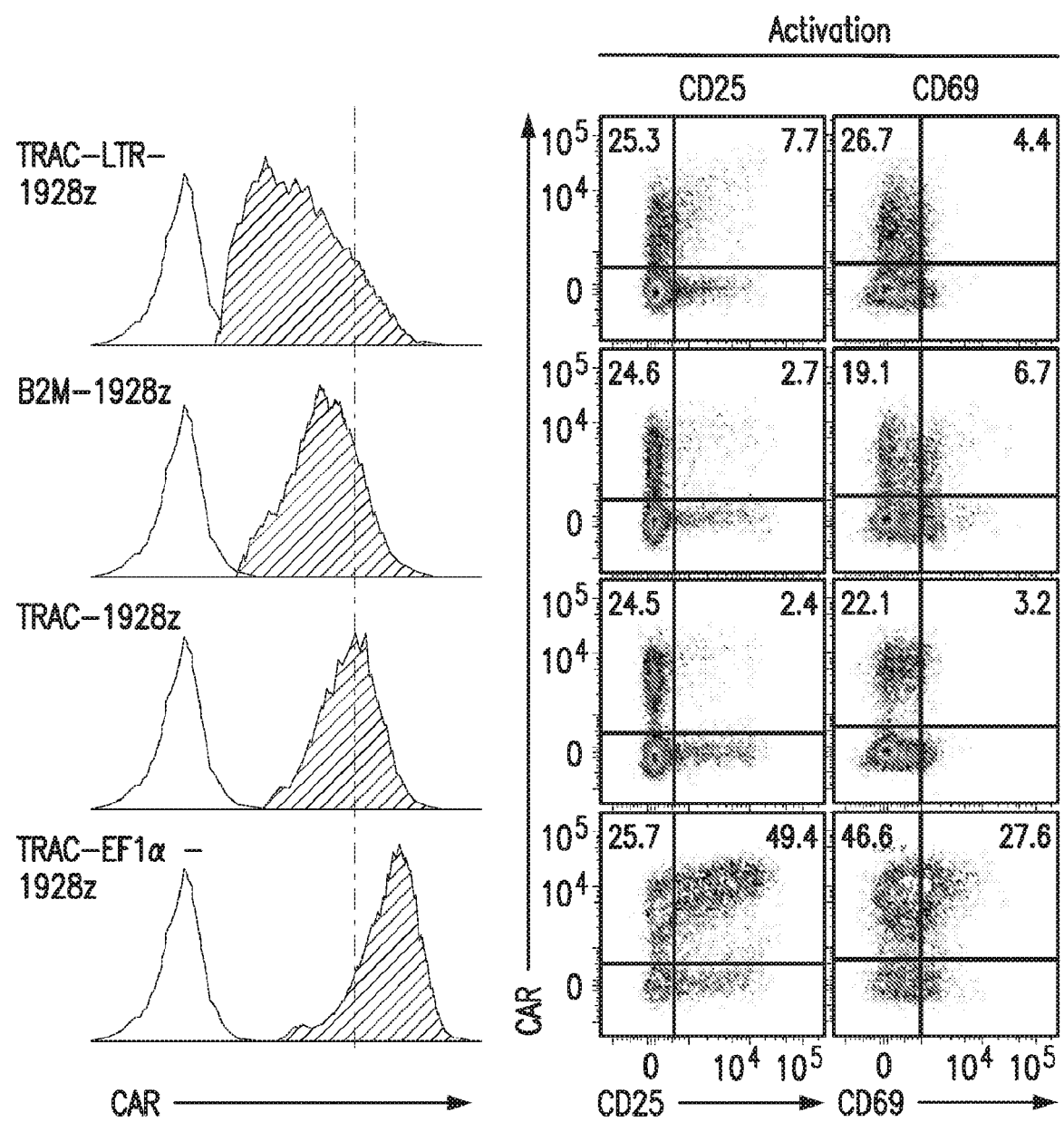
Figure 5E:
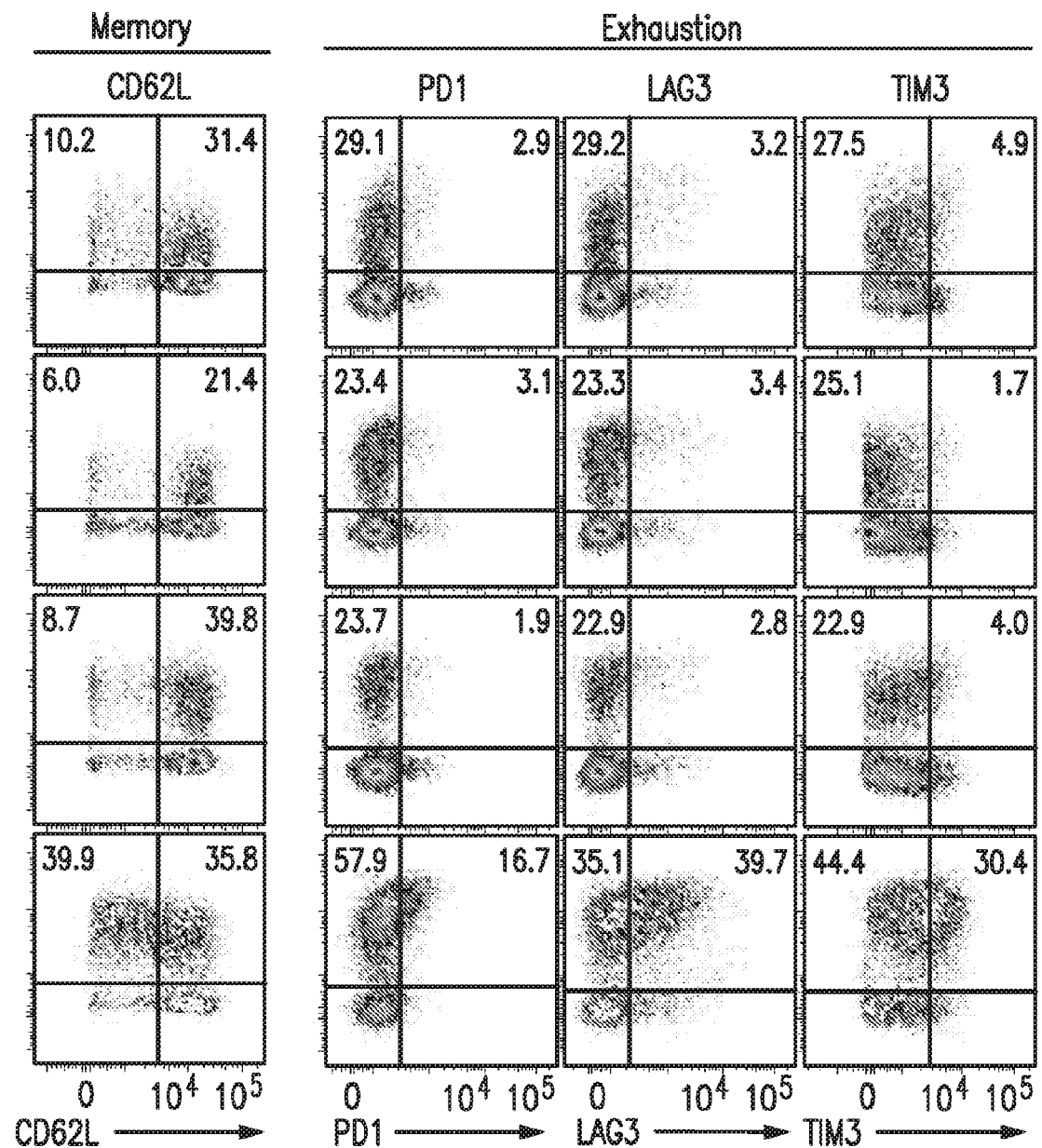
Figure 5F:
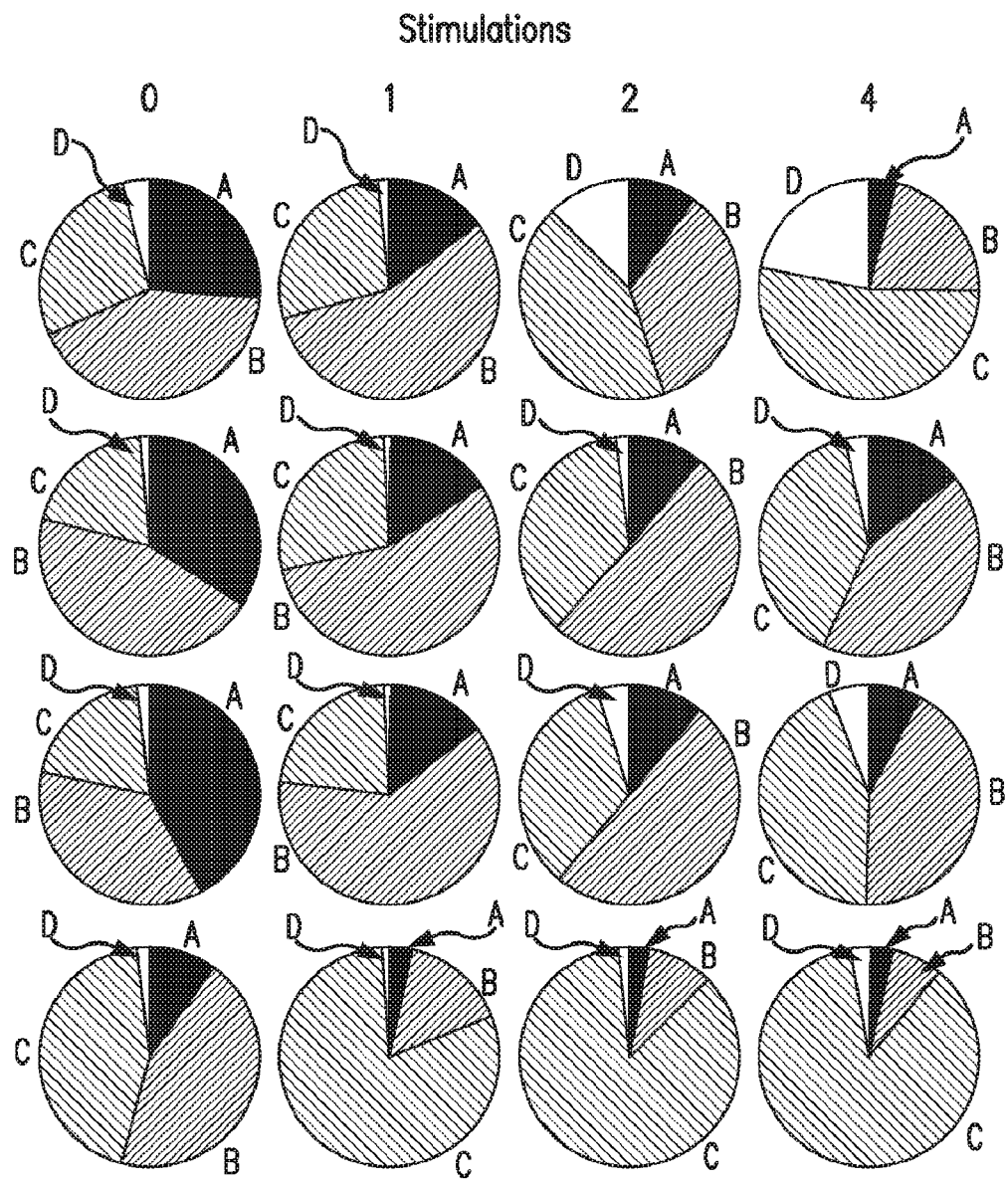
Figure 5G:
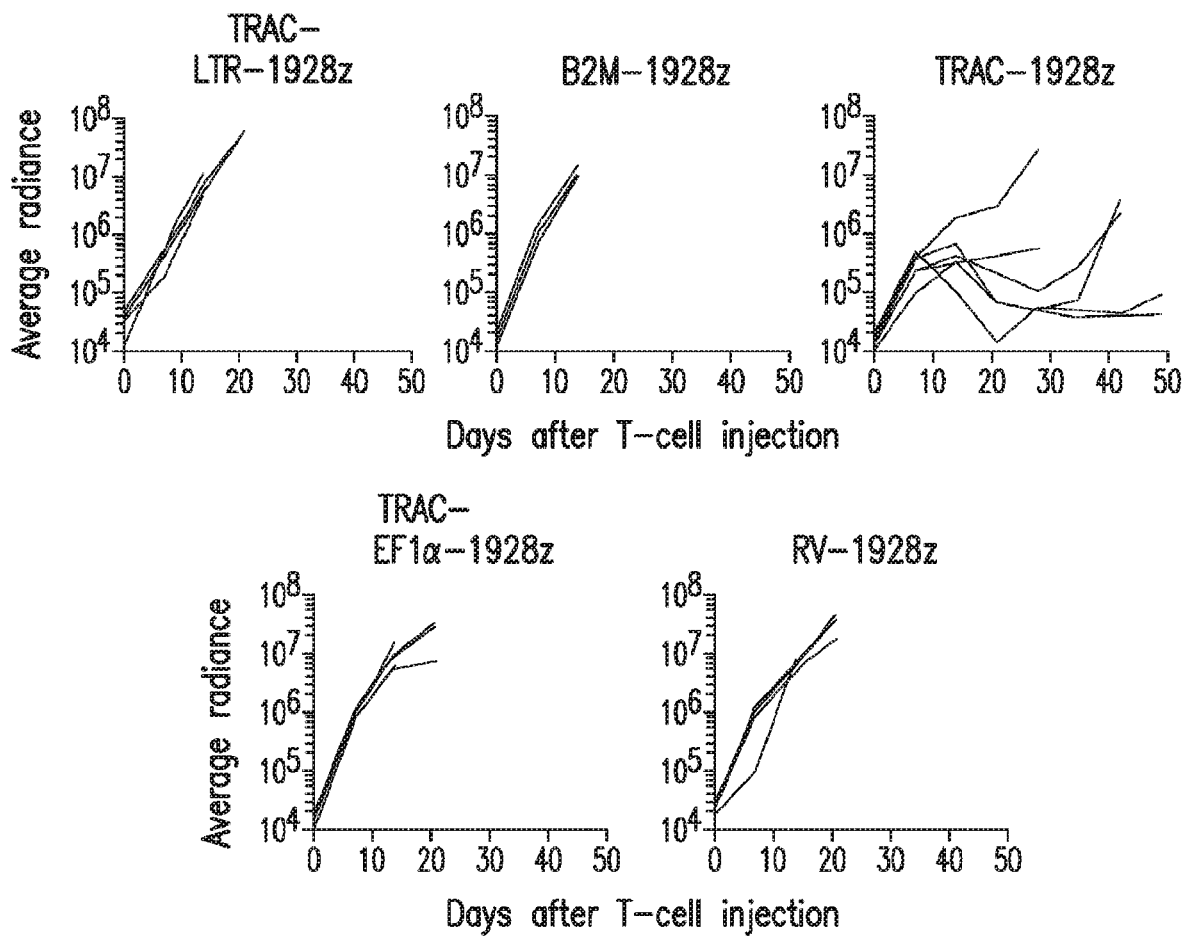
Figure 5H:
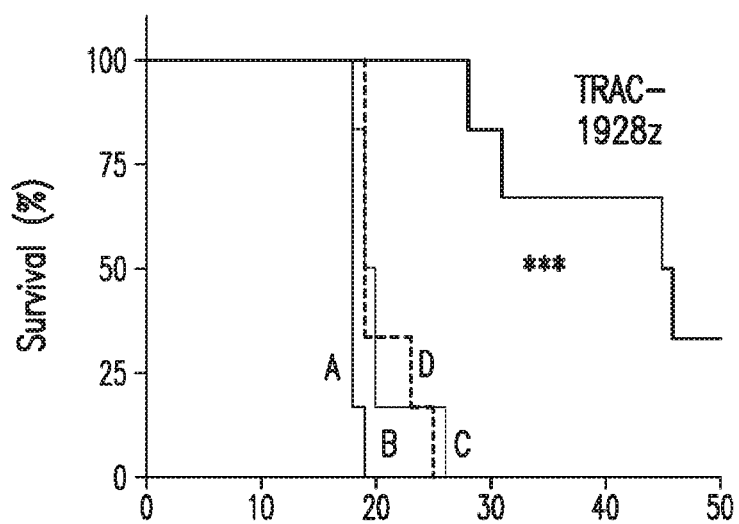

FIGS. 5A-5G show that the endogenous TRAC promoter surpasses other locus/promoter combinations in vivo. FIG. 5A shows a schematic of CRISPR/Cas9-targeted promoter-CAR integration into the TRAC locus. Top: TRAC locus; bottom: rAAV6 containing the promoter-CAR-polyA cassette flanked by homology arms. FIG. 5B shows a schematic of CRISPR/Cas9-targeted promoter-less CAR integration into the B2M locus. Top: B2M locus; bottom: rAAV6 containing a promoter-less CAR cassette flanked by homology arms. FIG. 5C shows representative B2M/CAR or TCR/CAR flow plots 4 days after vectorization of T cells. FIG. 5D shows CAR mean fluorescence intensity (MFI) at day 4 (n=4-7 independent experiments; 4 donors) (TRAC-LTR-1928z, B2M-1928z, TRAC-1928z and TRAC-EF1α-1928z, left to right, respectively). FIG. 5E shows CAR expression. Left panel: CAR expression (representative histogram) at day 4. Right: FACS analysis of activation, memory, and exhaustion markers of CAR T cells at day 5 (representative of 3 donors). FIG. 5F shows CAR T cells stimulated on CD19+ target cells 0, 1, 2 or 4 times. Pie charts show the CD62L/CD45RA phenotypes of CAR+ T cells (n=3-5 independent experiments on different donors) (A, CD45RA+CD62L+; B, CD45RA− CD62L+; C, CD45RA− CD62L−; D, CD45RA+CD62L−). FIG. 5G shows tumour burden (average radiance) of NALM-6-bearing mice treated with $1 \times 10^5$ CAR T cells (n=6; line=one mouse). Tumour burden was quantified weekly over a 50-day period using bioluminescence imaging (BLI). Quantification is the average photon count of ventral and dorsal acquisitions per animal at all given time points. Each line represents one mouse. FIG. 5H shows Kaplan-Meier analysis of the mice survival. (A): TRAC-EF1a-1928z CAR T cells, (B): B2M-1928z CAR T cells, (C): TRAC-LTR-1928z CAR T cells, (D): TRAC-1928z CART cells, TRAC-1928z labeled as indicated. P<0.01, *P<0.001, ****P<0.0001 (Welch's two samples t-test for FIG. 5D); Log-rank Mantel-Cox test for FIG. 5G; Mann-Whitney test for FIG. 5H). All data are means±SD. See also FIGS. 14 and 15.

Figure 6A:
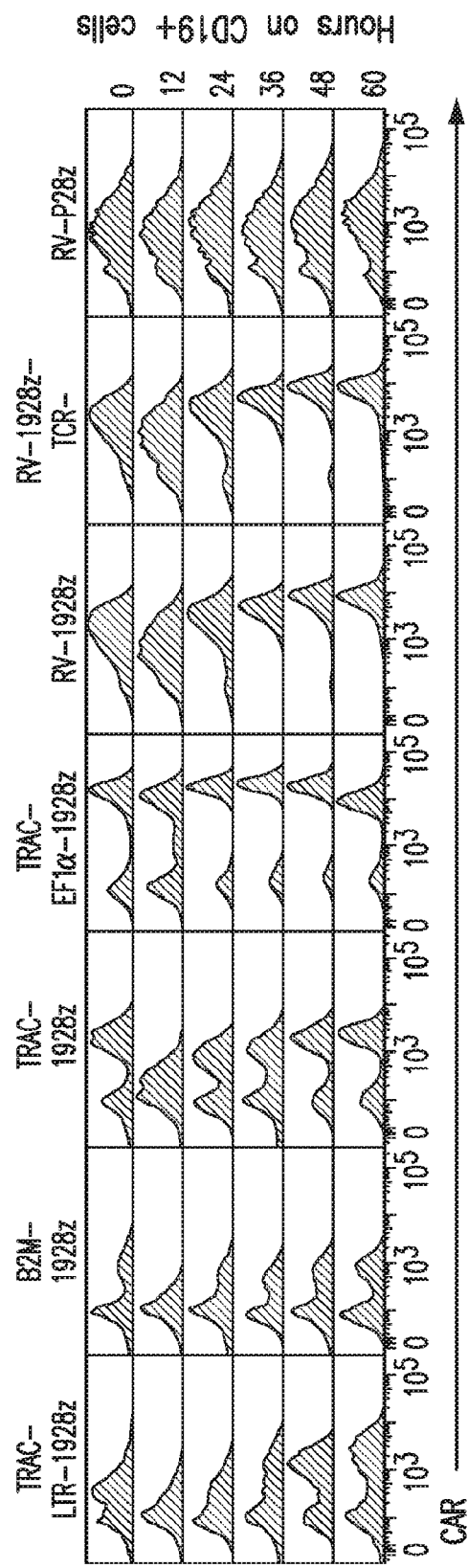
Figure 6B:
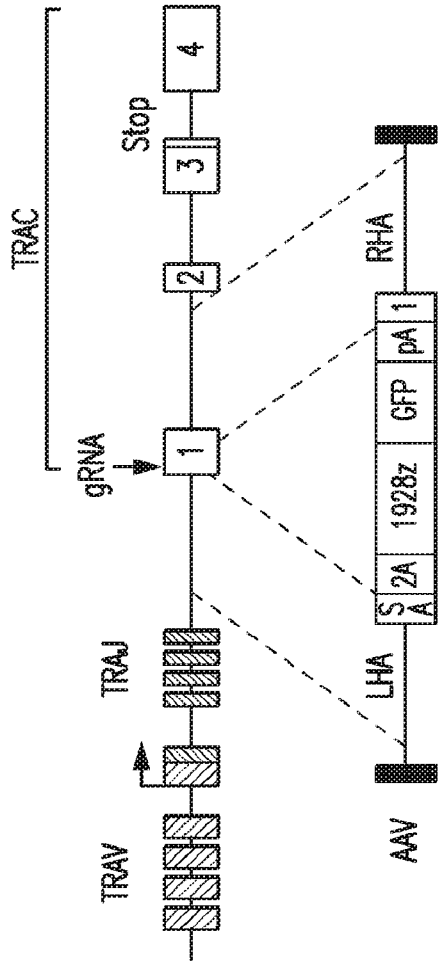
Figure 6C:
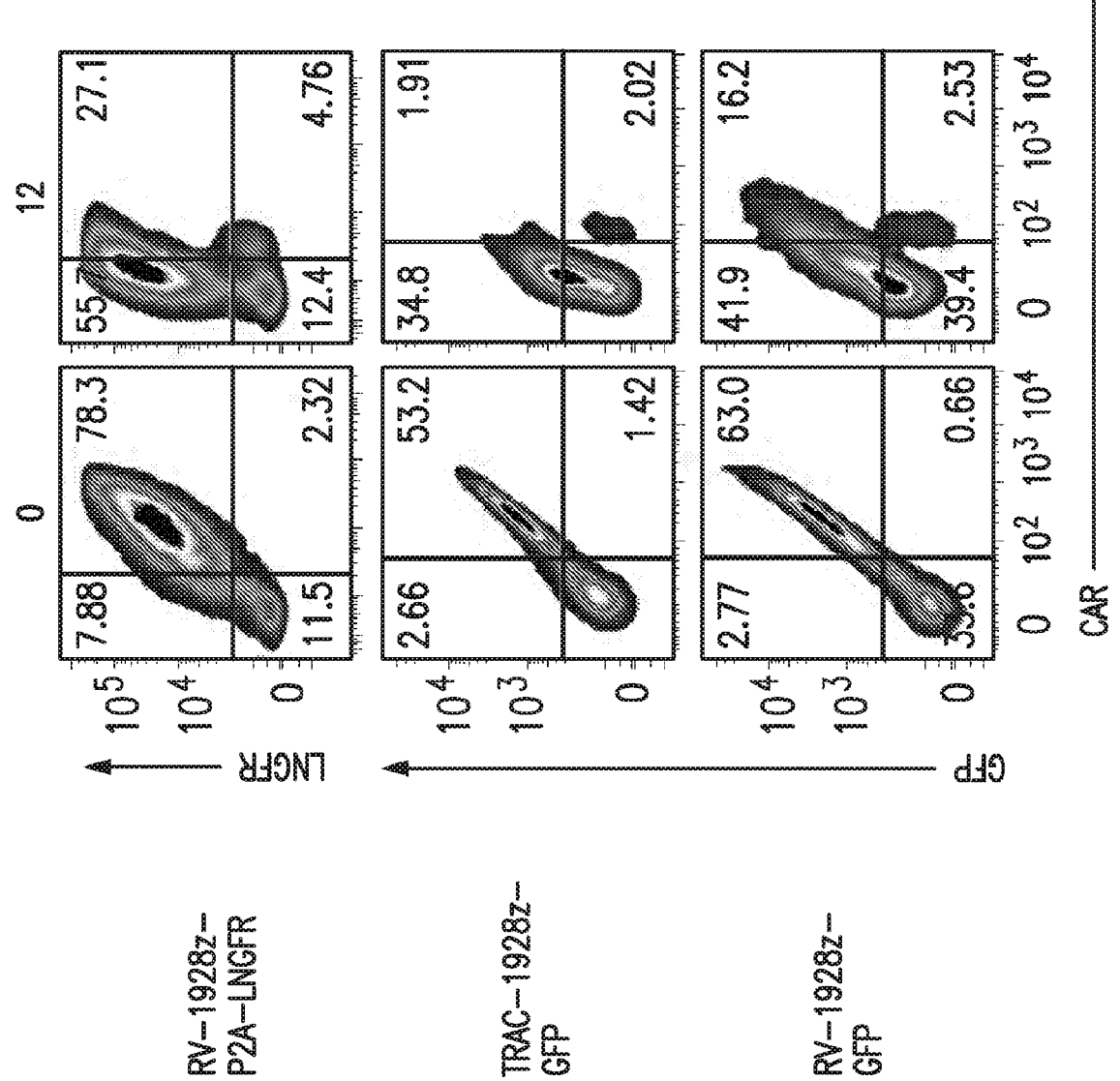
Figure 6D:
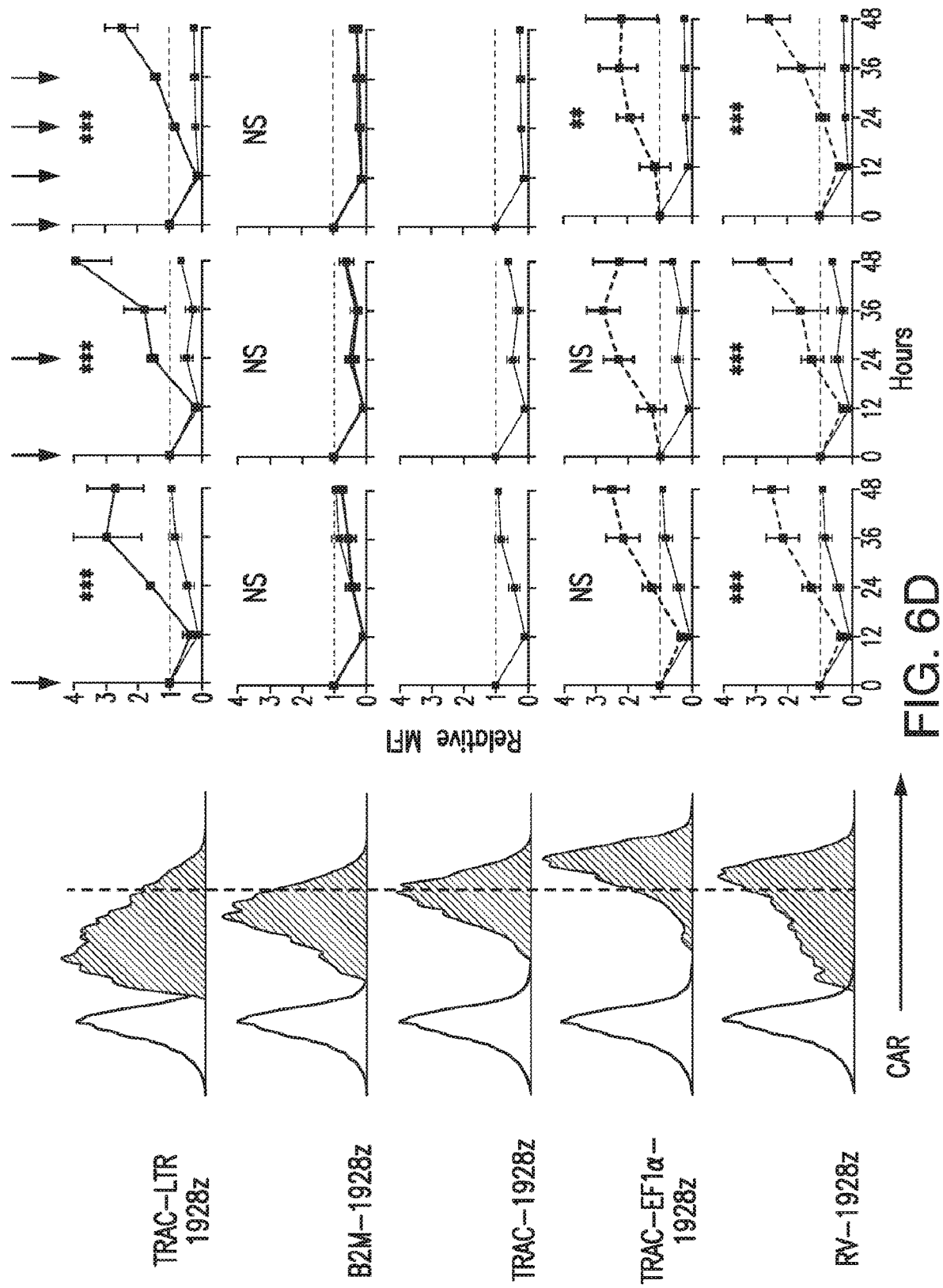
Figure 6E:
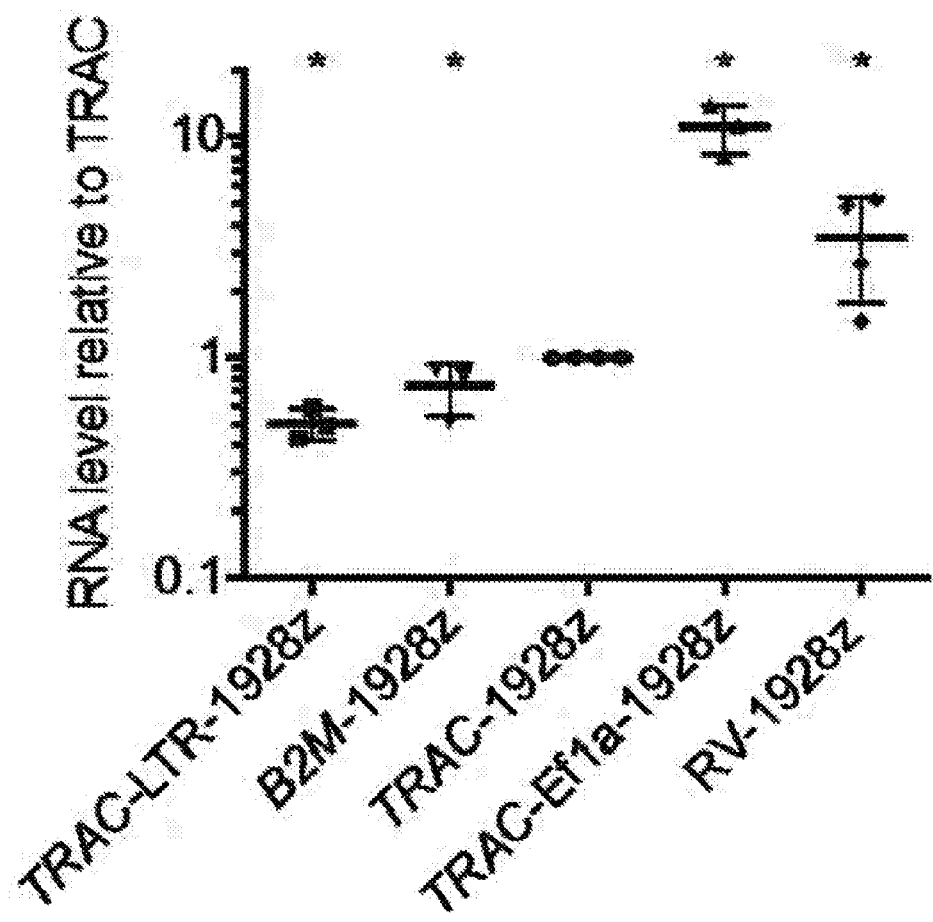
Figure 6F:
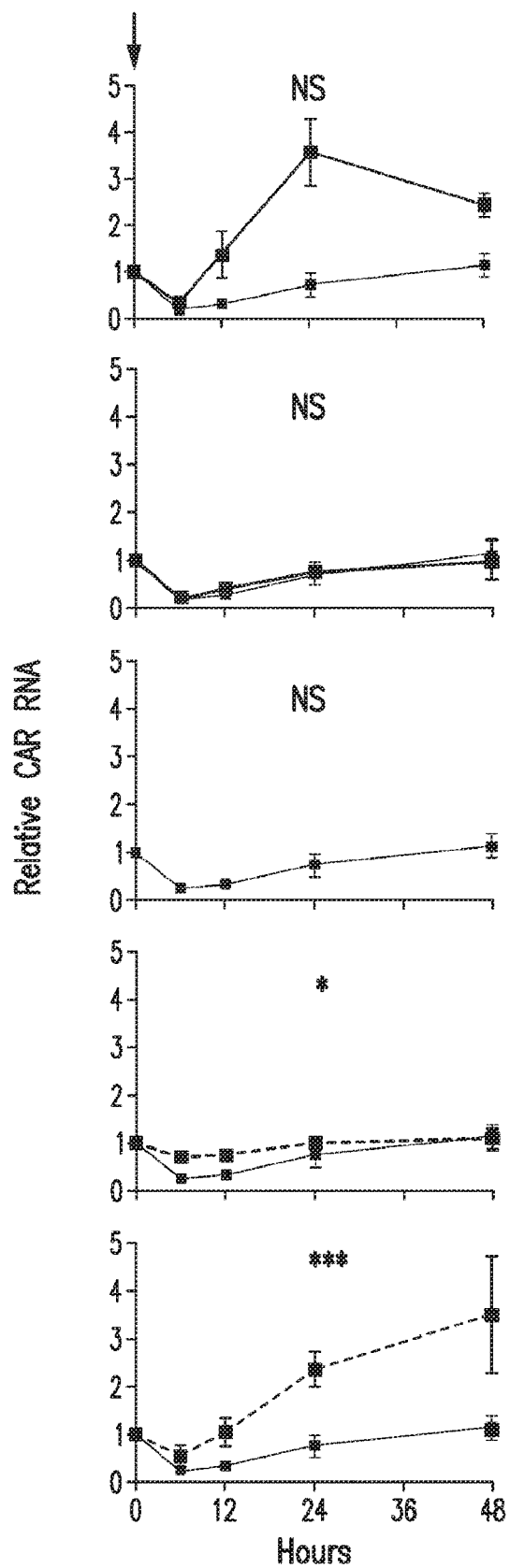

FIGS. 6A-6F show that the TRAC locus affords optimal regulation of cell-surface CAR expression. FIG. 6A shows a representative histogram of CAR expression before and after co-culture with CD19+ target cells. FIG. 6B shows CRISPR/Cas9-targeted integration of a CAR-GFP fusion gene into TRAC locus. FIG. 6C: Upper, LNGFR/CAR expression of the bicistronic CAR-P2A-LNGFR CAR T cells before and after co-culture with CD19+ target cells. Lower, GFP/CAR expression of CAR-GFP fusion targeted into the TRAC locus or randomly integrated with the RV vector (representative of 3 independent experiments on 3 donors). FIG. 6D shows CAR expression. Left panel: representative histogram of the CAR expression 5 days post-vectorization. Right panel: relative CAR MFI (1=MFI at 0 h) of CART cells after 1, 2 or 4 stimulations (indicated by arrows; n=3-7 independent experiments on different donors). FIG. 6E shows relative CAR RNA levels (1=TRAC RNA level) 5 days post-vectorization. FIG. 6F shows a time course analysis of CAR RNA levels (1=RNA level at 0 h) in CAR T cells stimulated once on CD19+ target cells (n=3 independent experiments on 3 donors; CART cells as in FIG. 6D, top to bottom). All data are means±SD. *P<0.05, P<0.01, *P<0.001 (ANOVA F-test with Bonferroni correction (FIG. 6D), and Mann-Whitney test (FIG. 6E)). See also FIG. 16. The lower line represents the CAR surface levels (FIG. 6D) or CAR RNA levels (FIG. 6F) in TRAC-1928z CAR T cells.

Figure 7A:
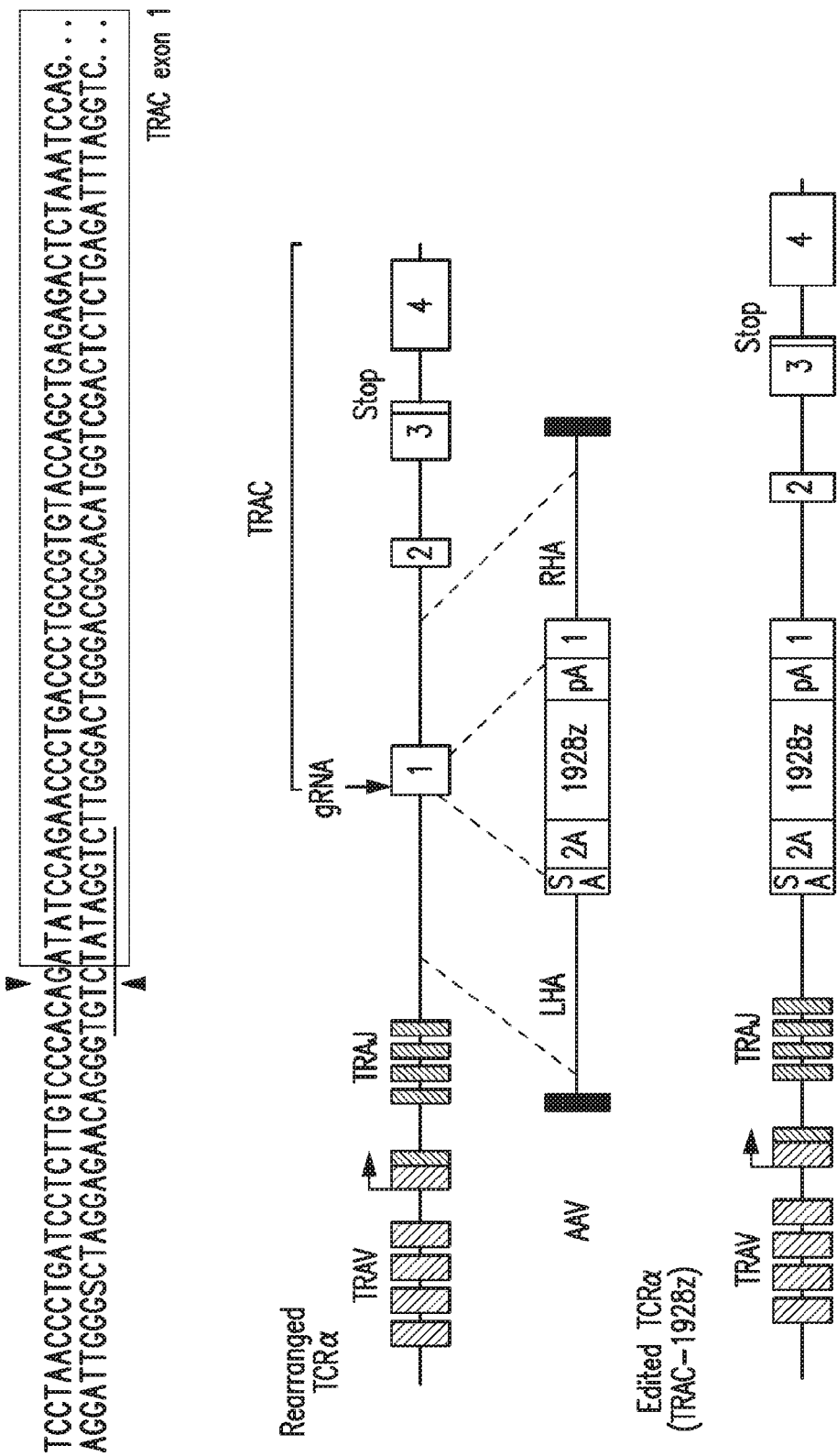
Figure 7B:
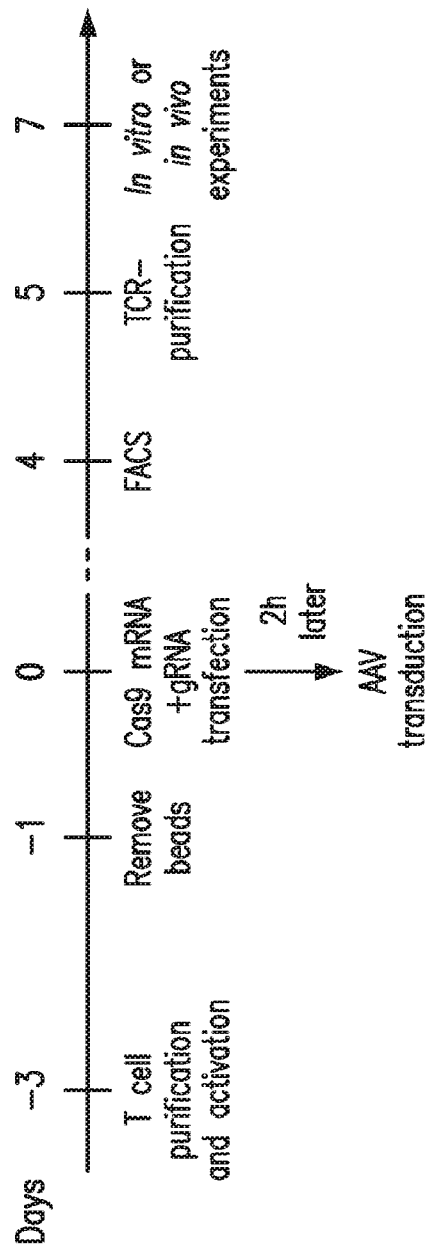
Figure 7C:
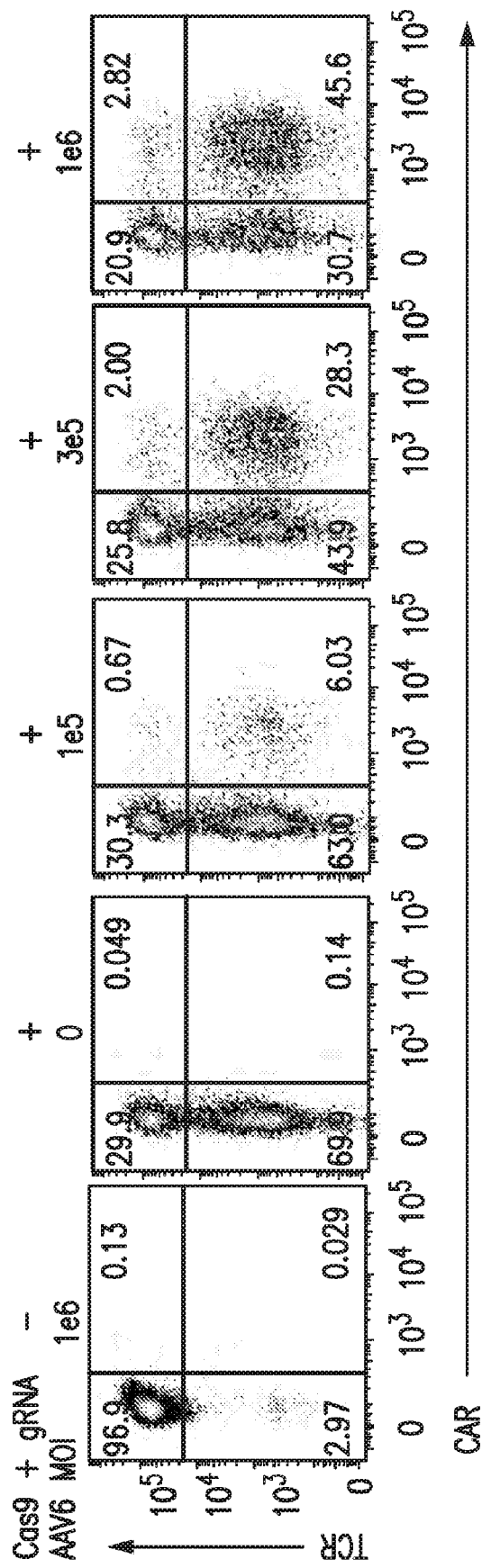

FIGS. 7A-7G show CRISPR/Cas9-mediated CAR gene targeting into the TRAC locus. FIG. 7A, Top, TRAC locus (SEQ ID NO:41) with the 5' end (grey) of the TRAC first exon, the TRAC gRNA (TGT . . . GAC, lower strand) and the corresponding PAM sequence (GGG, immediately left of TGT . . . GAC). The two arrows indicate the predicted Cas9 double strand break. Bottom, CRISPR/Cas9-targeted integration into the TRAC locus. The targeting construct (AAV) contains a splice acceptor (SA), followed by a P2A coding sequence, the 1928z CAR gene and a polyA sequence, flanked by sequences homologous to the TRAC locus (LHA and RHA, left and right homology arm). Once integrated, the endogenous TCRa promoter drives CAR expression, while the TRAC locus is disrupted. TRAV, TCRa variable region; TRAJ, TCRa joining region; 2A, the self-cleaving Porcine teschovirus 2A sequence. pA: bovine growth hormone polyA sequence. FIG. 7B shows a timeline of the CAR targeting into primary T cells. FIG. 7C shows representative TCR/CAR flow plots 4 days after transfection of T cells with Cas9 mRNA and TRAC gRNA and addition of AAV6 at the indicated multiplicity of infection. FIG. 7D shows percentage of TCR disruption 4 days post transfection of the Cas9 mRNA and the TRAC gRNA measured by FACS analysis of the TCR expression (n=5). FIG. 7E shows shows percentage of knock-in depending on the AAV6 multiplicity of infection measured by FACS analysis of the CAR expression (n=4). FIG. 7F shows percentage of CAR+ cells in the TCR-negative population (n=4). FIG. 7G shows percentage of TCR-positive (lower bar) and TCR-negative (upper bar) in the CAR+ population analysed by FACS (n=4).

Figure 8A:
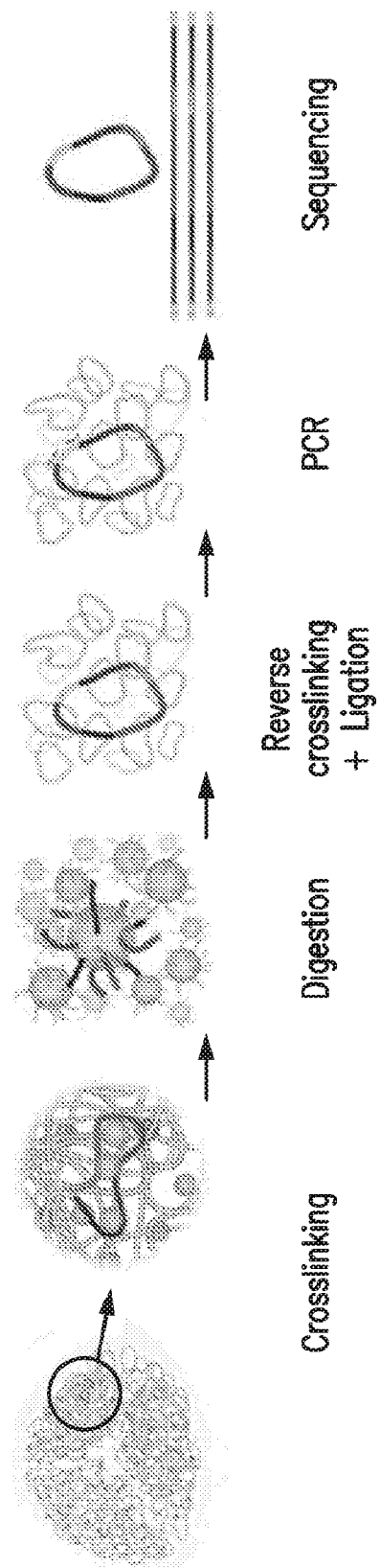
Figure 8B:
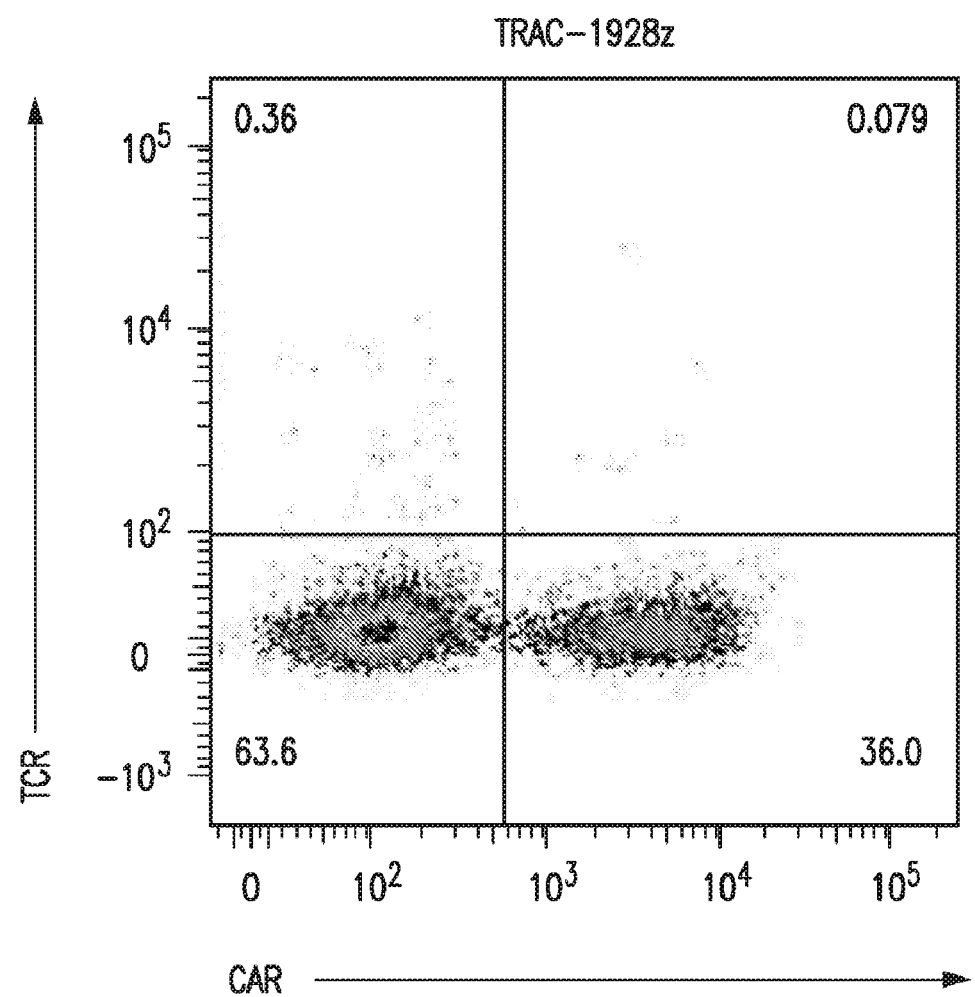
Figure 8C:
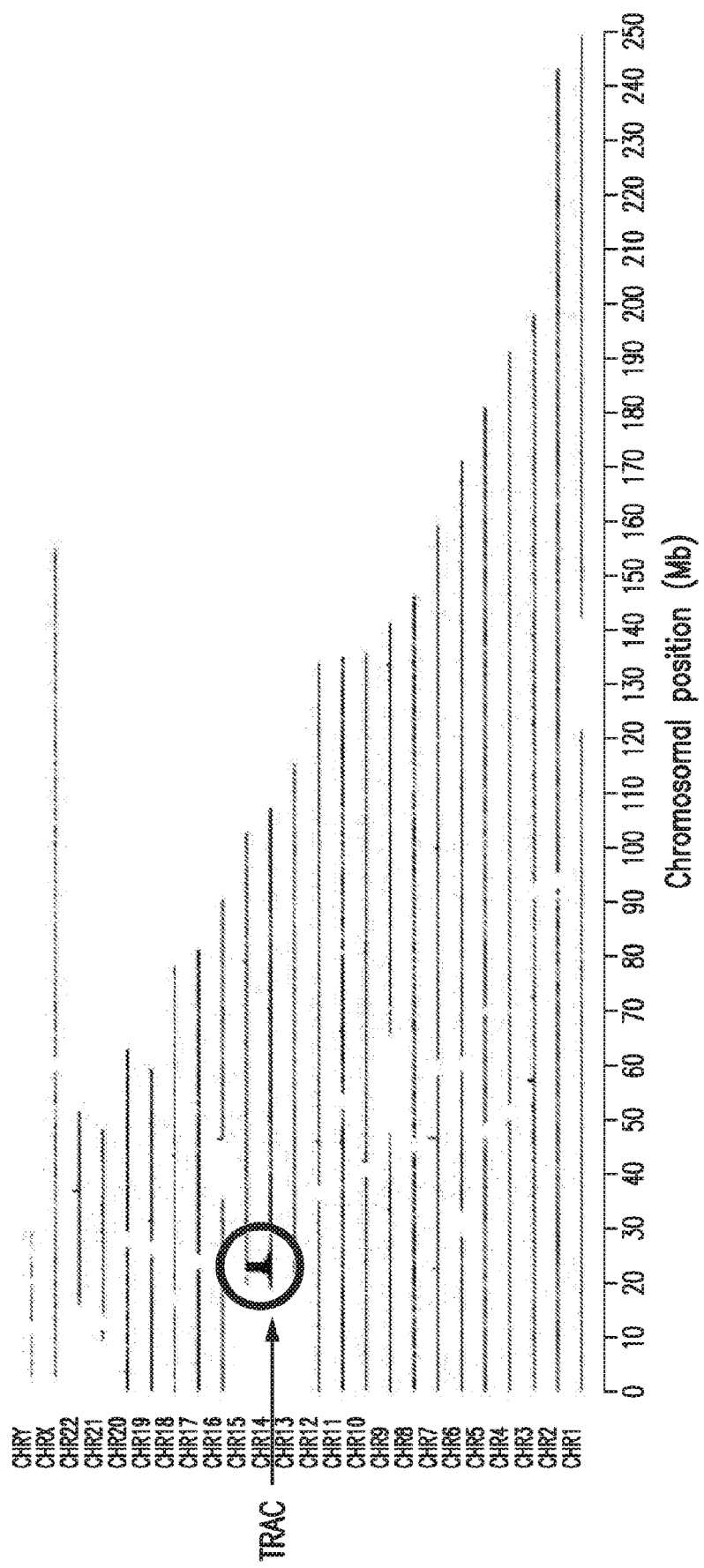
Figures 8D, 8E:
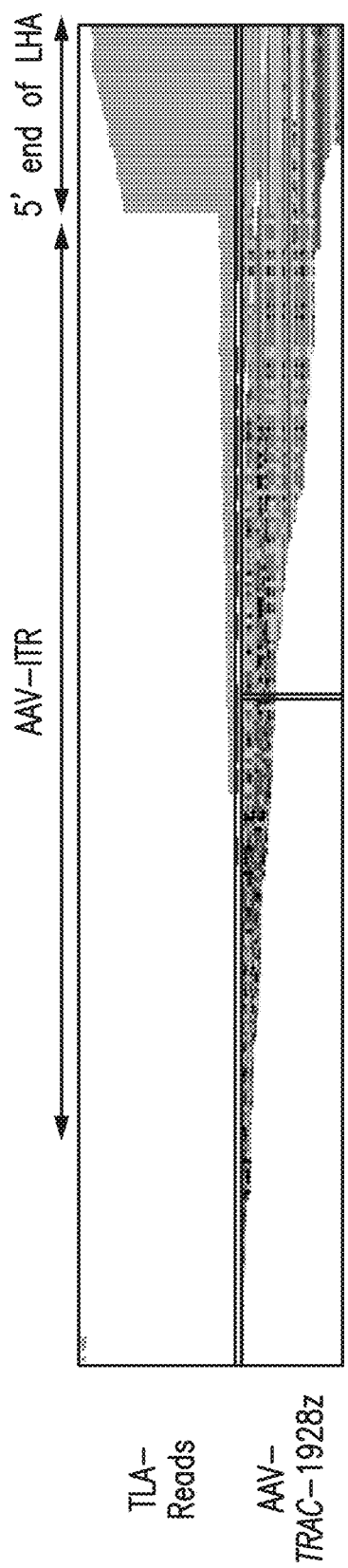

FIGS. 8A-8E show whole-genome mapping of the AAV6 TRAC-1928z integration using the TLA technology. FIG. 8A shows a schematic representation of the TLA technology (de Vree et al., Nat. Biotechnol. 32:1019-1025 (2014)). For this study, two sets of primers targeting the CAR and the left homology arm have been used. FIG. 8B shows TCR/CAR FACS plot of the TRAC-1928z CAR T cells used for the TLA analysis. CAR T cells have been processed as in FIG. 7B and expanded for 2 weeks. FIG. 8C shows TLA sequence coverage across the human genome using 1928z CAR specific primers (CD28-specific forward: 5'-ACAAT-GAGAAGAGCAATGGA-3' (SEQ ID NO:39) and scFV-specific reverse: 5'-GAGATTGTCCTGGTTTCTGT-3' (SEQ ID NO:40)). The chromosomes are indicated on the y axis, the chromosomal position on the x axis. TRAC-encoded CAR T cells were produced as in FIG. 3 and expanded for 10 days before processed for analysis. The primer set was used in an individual TLA amplification. PCR products were purified and library prepped using the Illumina NexteraXT™ protocol and sequenced on an Illumina Miseq™ sequencer. Reads were mapped using BWA-SW, which is a Smith-Waterman alignment tool. This allows partial mapping, which is optimally suited for identifying break-spanning reads. The human genome version hg19 was used for mapping. FIG. 8D shows TLA sequence coverage aligned on the AAV-TRAC-1928z sequence (Targeting sequence flanked by ITRs). The grey vertical bars on top represent the coverage at the shown positions. The coverage showed integration of the AAV ITRs in fraction of reads. The coverage comparison between ITR and CAR integration at the 5' and 3' ends of the TRAC homology arms locus allow the measurement of faithful and unfaithful homologous recombination shown in FIG. 8E. FIG. 8E shows final results from the TLA analysis.

Figure 9A:
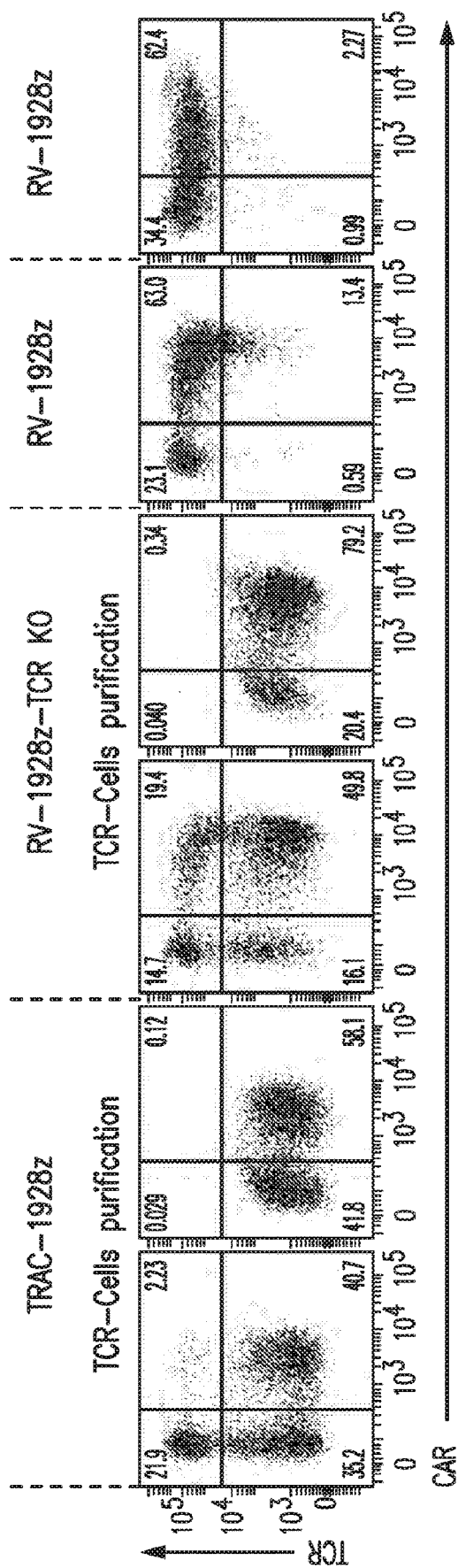
Figure 9B:
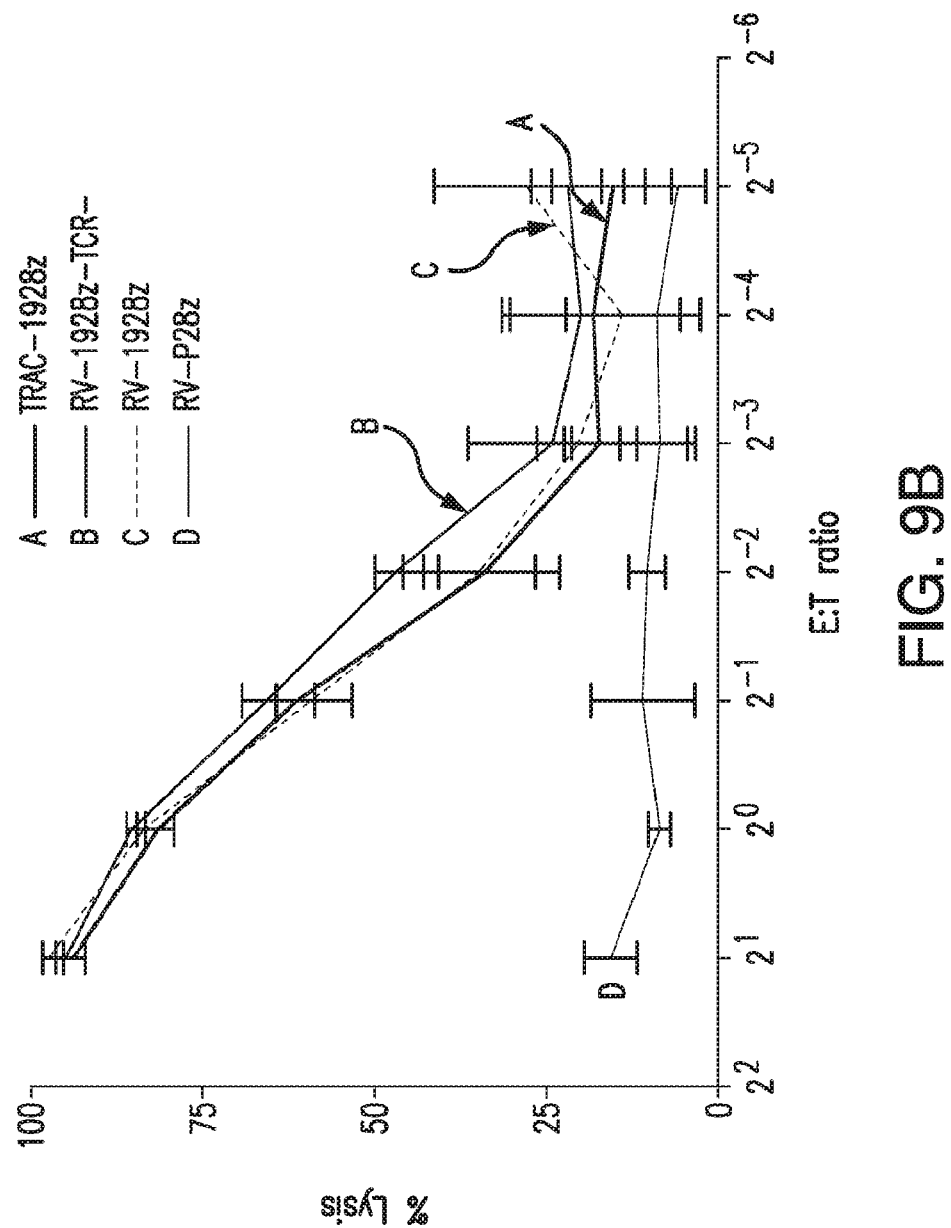
Figure 9C:
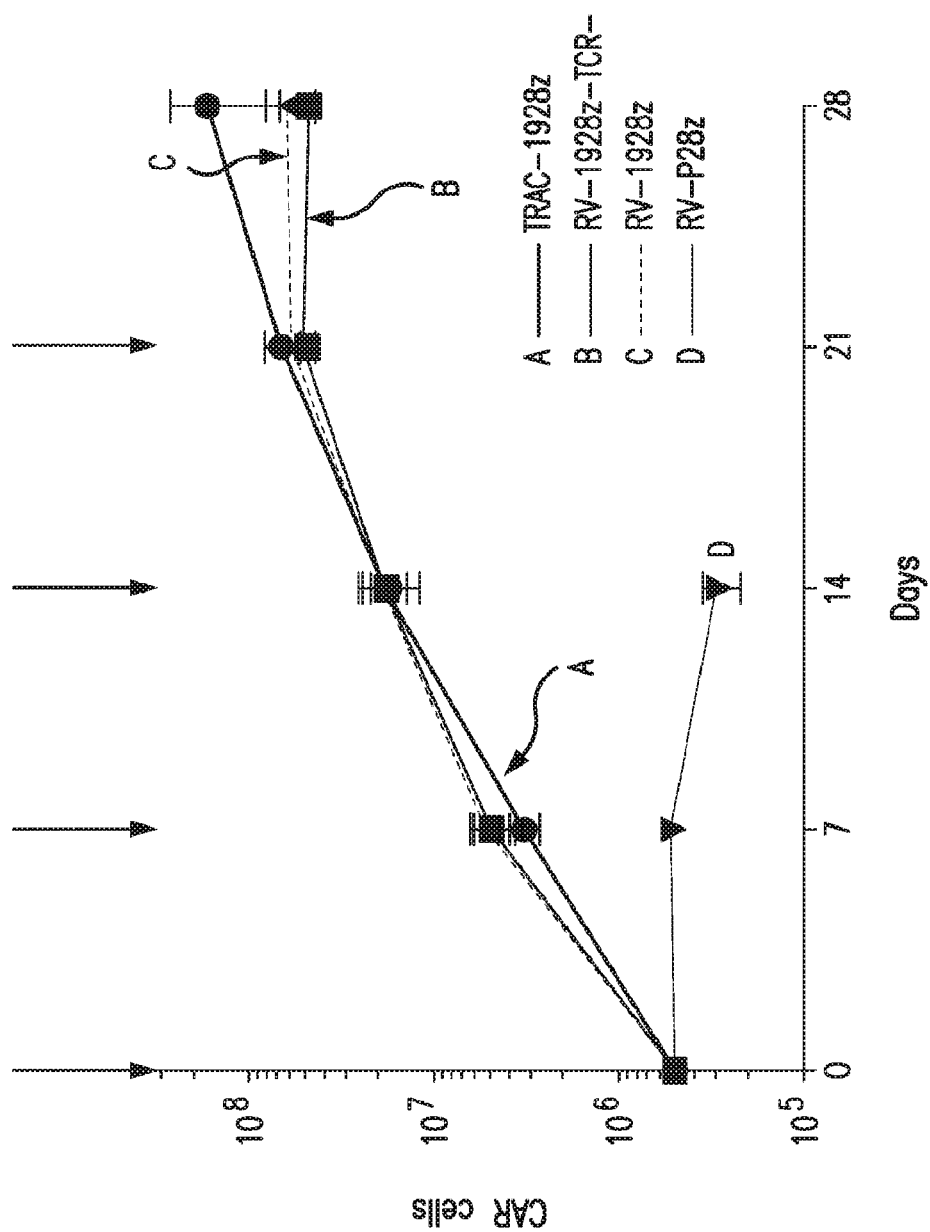

FIGS. 9A-9C show in vitro cytotoxicity activity and proliferation response of TRAC-CAR T cells. FIG. 9A shows representative flow cytometry analysis showing CAR and TCR expression. TRAC-1928z CAR T cells were generated as in FIG. 3B; CRISPR/Cas9-generated TCR− T cells were transduced with RV-1928z retroviral vector; TCR+ cells were transduced with either RV-1928z or RV-P28z (PSMA-specific CAR). TCR-negative T-cell purification was performed using magnetic beads on column. FIG. 9B shows cytotoxic activity using an 18 h bioluminescence assay, using firefly luciferase (FFL)-expressing NALM-6 as targets cells (n=3 independent experiments on 3 healthy donors). FIG. 9C shows representative cumulative cell counts of CAR T cells upon weekly stimulation with CD19+ target cells. Arrows indicate stimulation time points (n=3 independent experiments on 3 healthy donors).

Figure 10A:
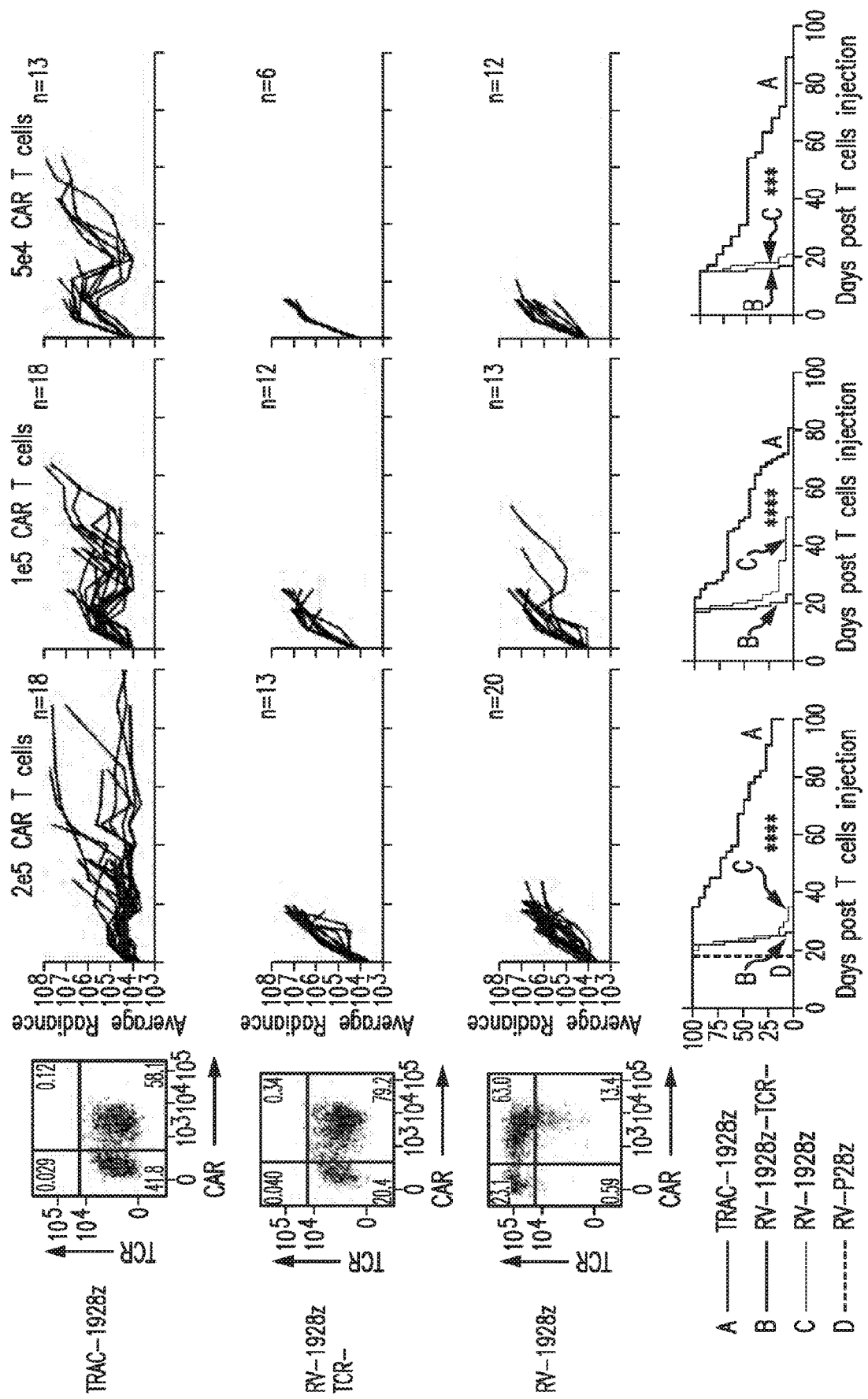
Figure 10B:
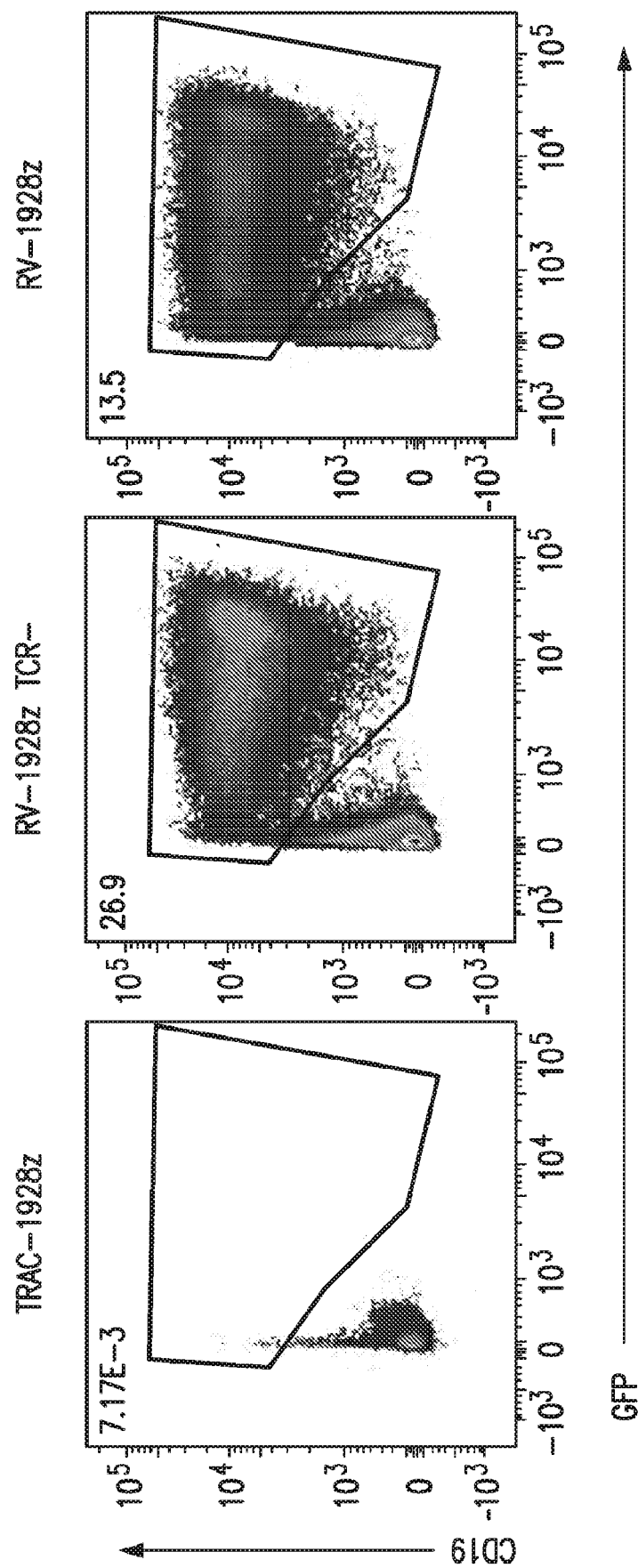
Figure 10C:
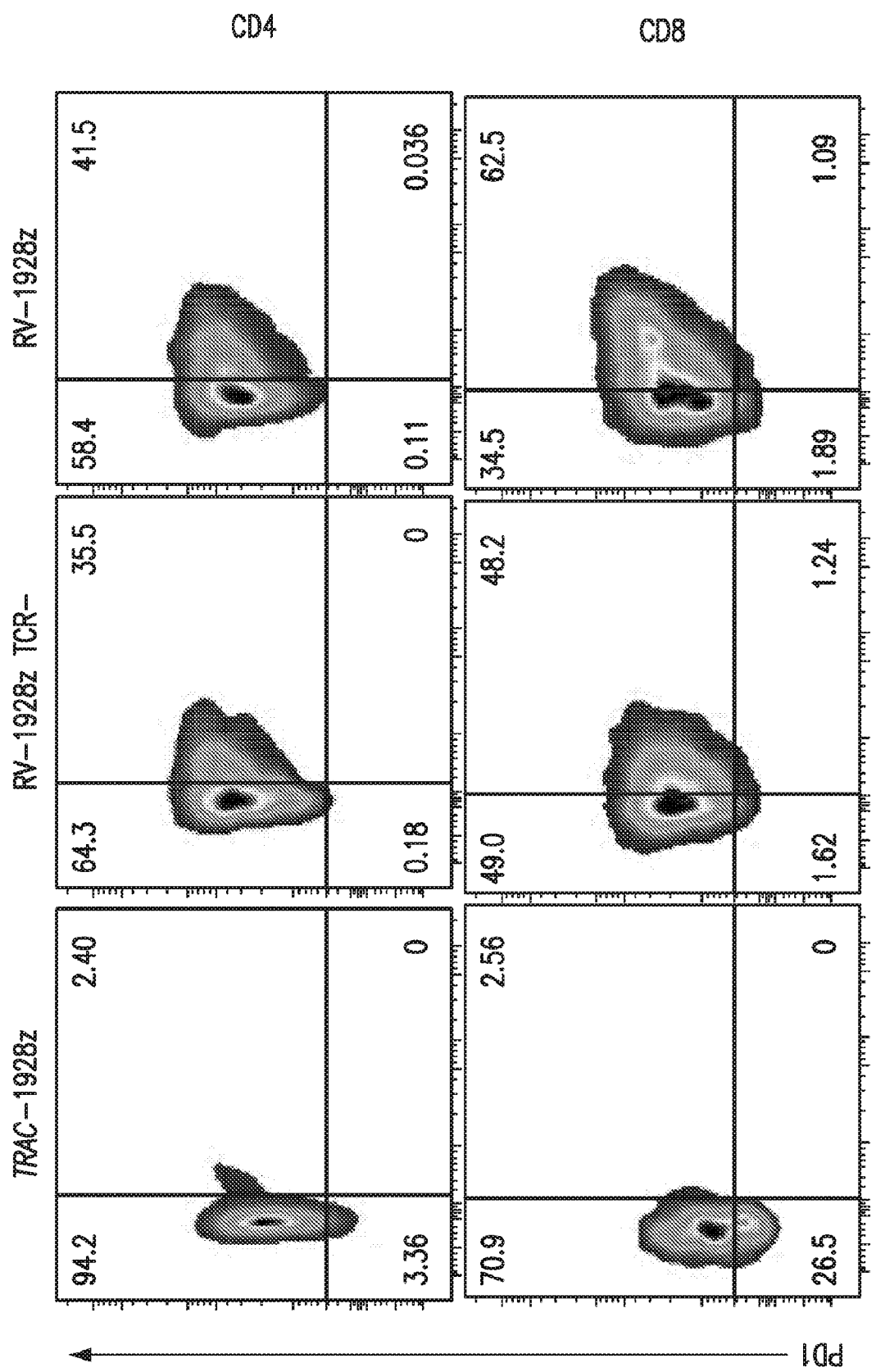
Figure 10D:
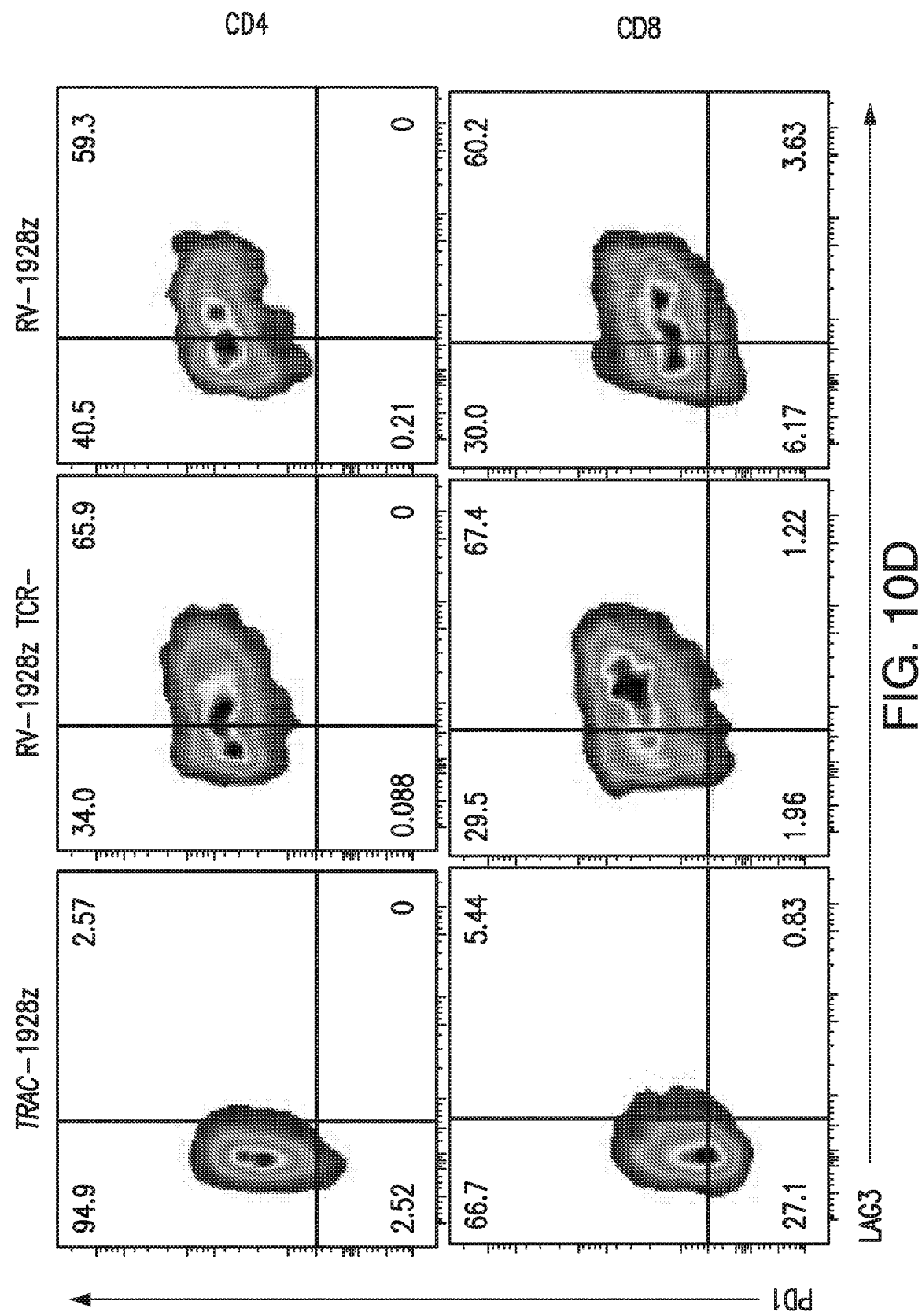
Figure 10E:
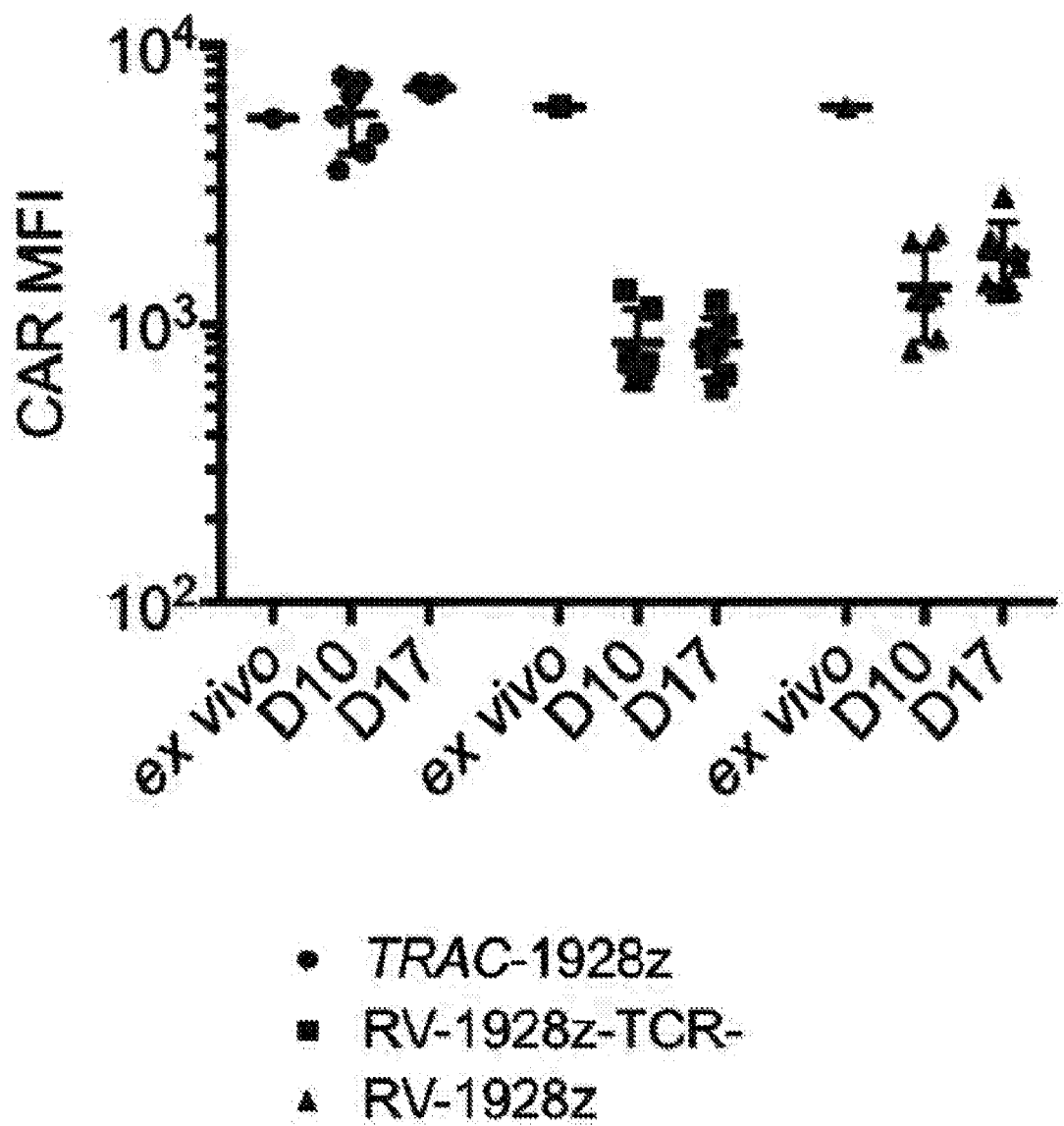
Figure 10F:
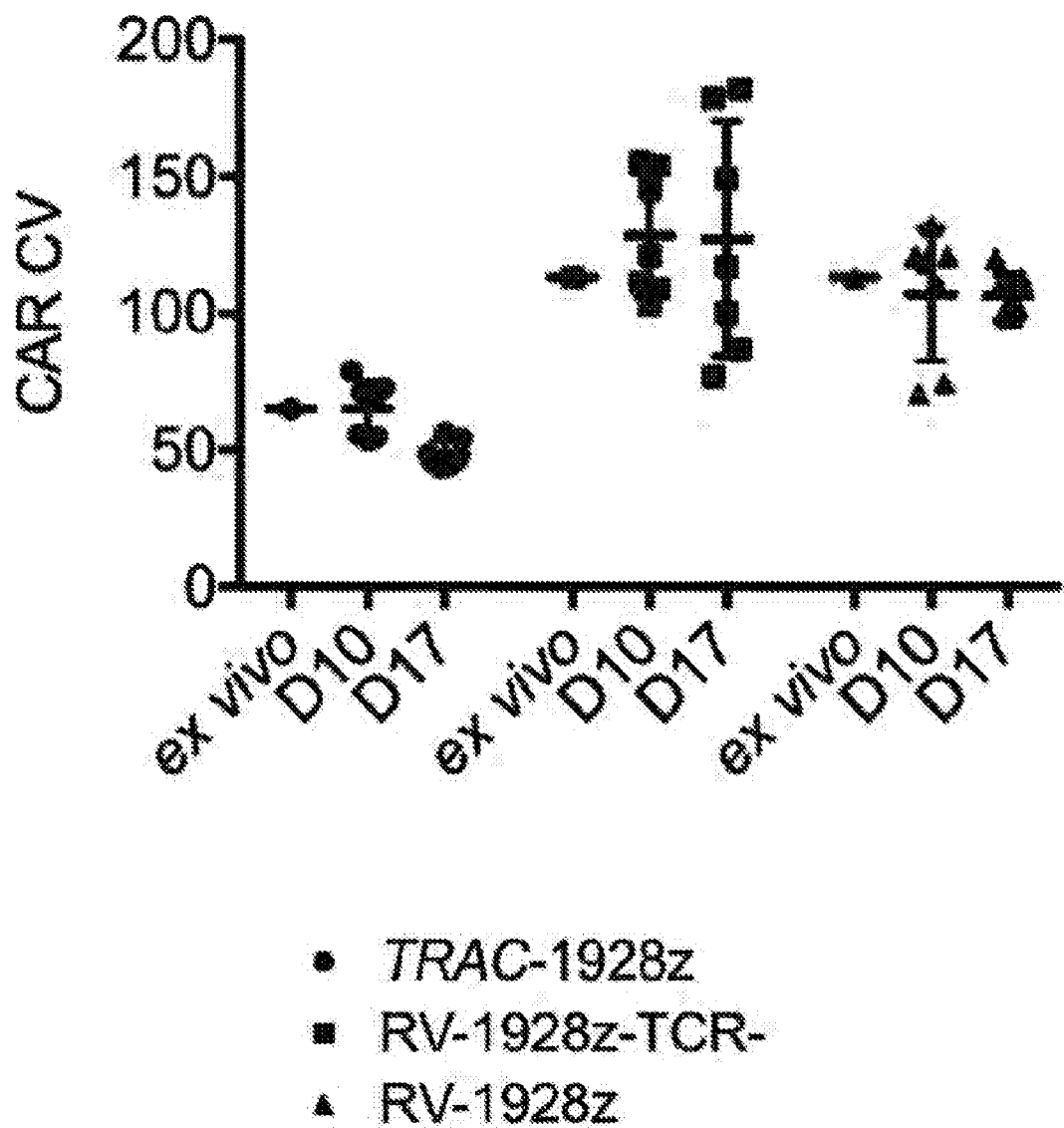
Figure 10G:
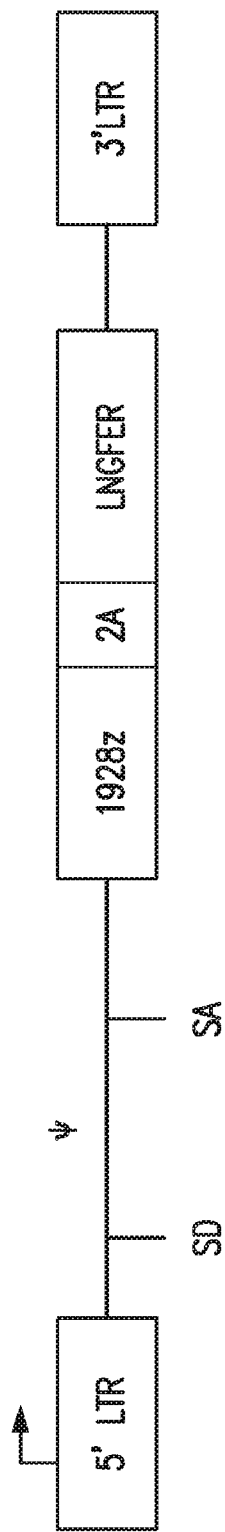
Figure 10H:
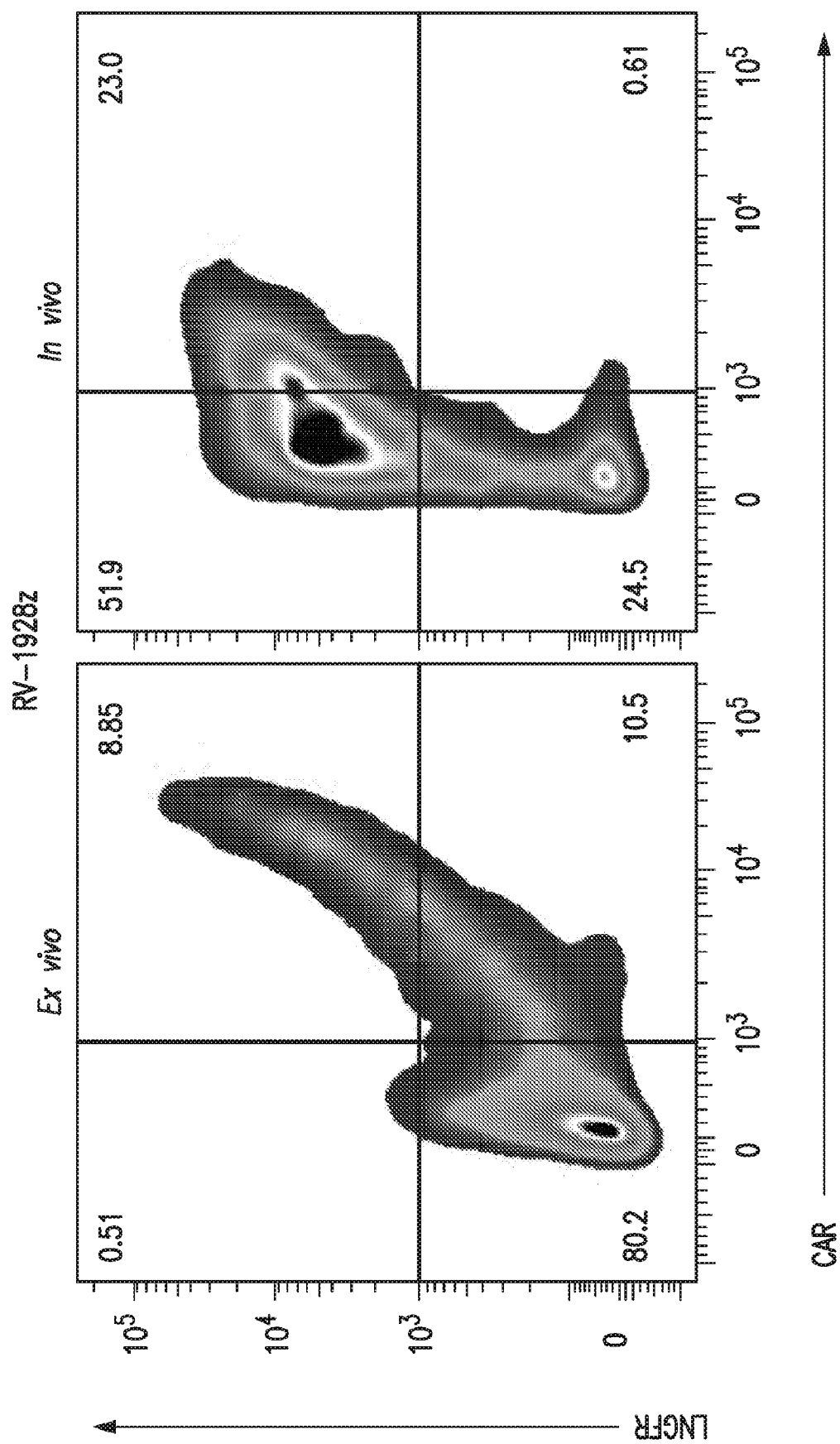
Figure 10I:
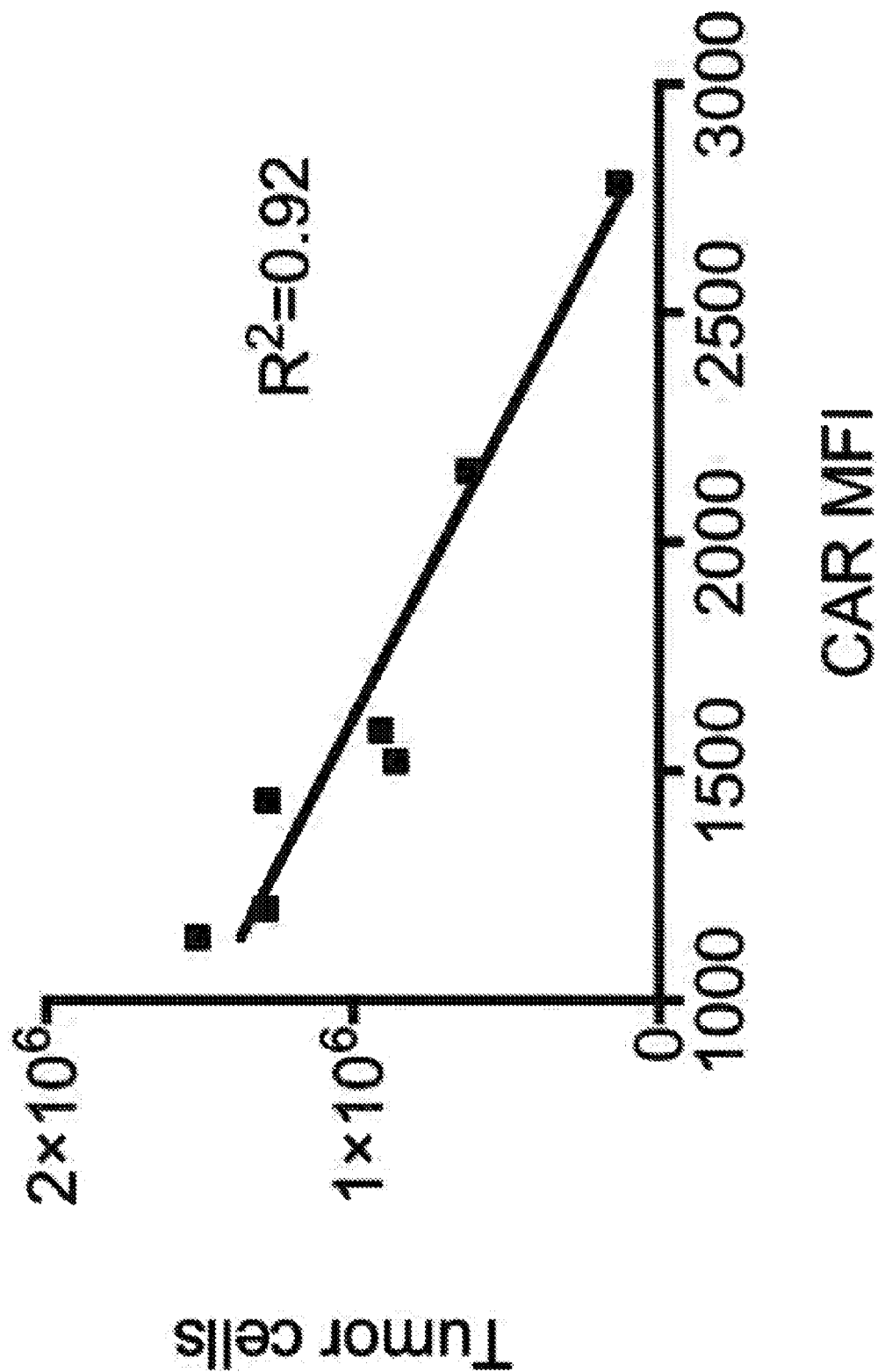

FIGS. 10A-10I show that TRAC-CAR T cells outperform conventional CAR T cells in vivo. FIG. 10A shows NALM- 6-bearing mice were treated with $2 \times 10^5$ (left), $1 \times 10^5$ (middle) or $5 \times 10^4$ (right) CAR T cells. Tumour burden was quantified weekly over a 100-day period using BLI. Quantification is the average photon count of ventral and dorsal acquisitions per animal at all given time points. Each line represents one mouse. Some groups are pooled from two to three independent experiments from different healthy donors, representing n=6-20 mice per group. Lower, Kaplan-Meier analysis of survival of mice. FIGS. 10B-10F show NALM-6-bearing mice were treated with $1 \times 10^5$ indicated CAR T cells. At 10 and 17 days after CAR T-cell infusion, 7 mice per group were euthanized and bone marrow cells were collected. CAR T cells and NALM-6 cells were analysed and counted with flow cytometry. FIG. 10B shows representative FACS analysis of tumour cells (CD19+GFP+) in the bone marrow at day 17. FIG. 10C shows representative FACS analysis of exhaustion markers PD1 and TIM3 in bone marrow CAR T cells at day 17. FIG. 10D show representative FACS analysis of exhaustion markers PD1 and LAG3 in bone marrow CAR T cells at day 17. FIG. 10E shows CAR MFI of the CAR+ cells in the bone marrow (each dot represents one mouse). FIG. 10F shows coefficient of variation measuring the dispersion in the CAR expression of the CAR+ population (ratio of the standard deviation to the mean; each dot represents one mouse). FIG. 10G shows that RV-1928z CAR design allows the co-expression of the CAR and LNGFR from the same LTR promoter by using a self-cleaving P2A sequence. LTR, long terminal repeat, SD, splice donor site; SA, splice acceptor site; 2A, Porcine teschovirus self-cleaving 2A sequence. FIG. 10H shows representative flow cytometry plots of RV-1928z transduced T cells cultured in vitro or in vivo (extracted from bone marrow) and labelled to detect CAR and LNGFR expression. FIG. 10I shows a comparison between CAR MFI in the RV-1928z T cells and the tumour burden (NALM-6 count) in the bone marrow.

Figure 11A:
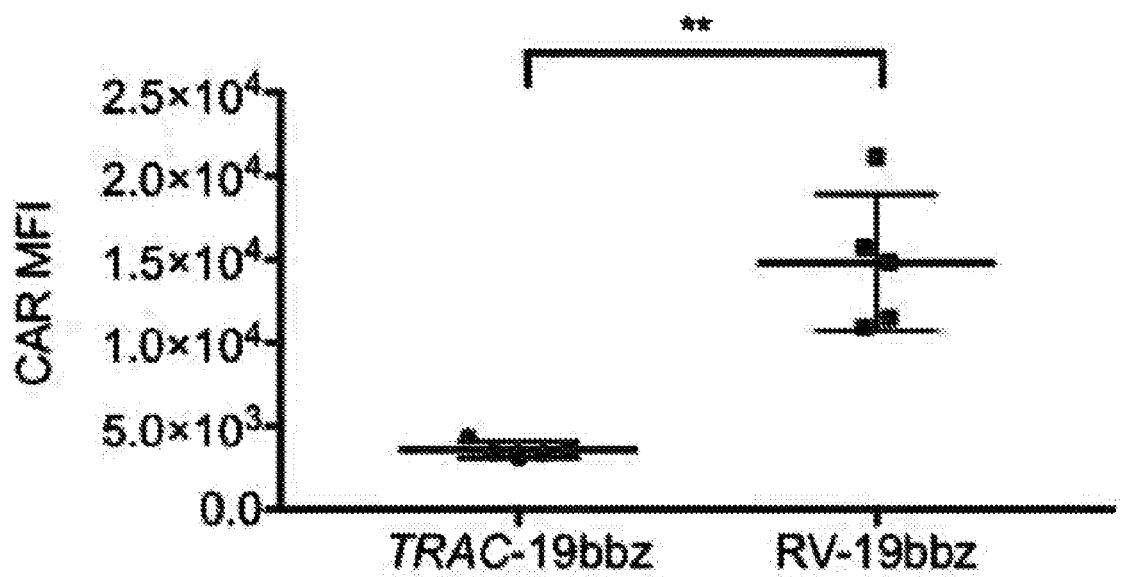
Figure 11B:
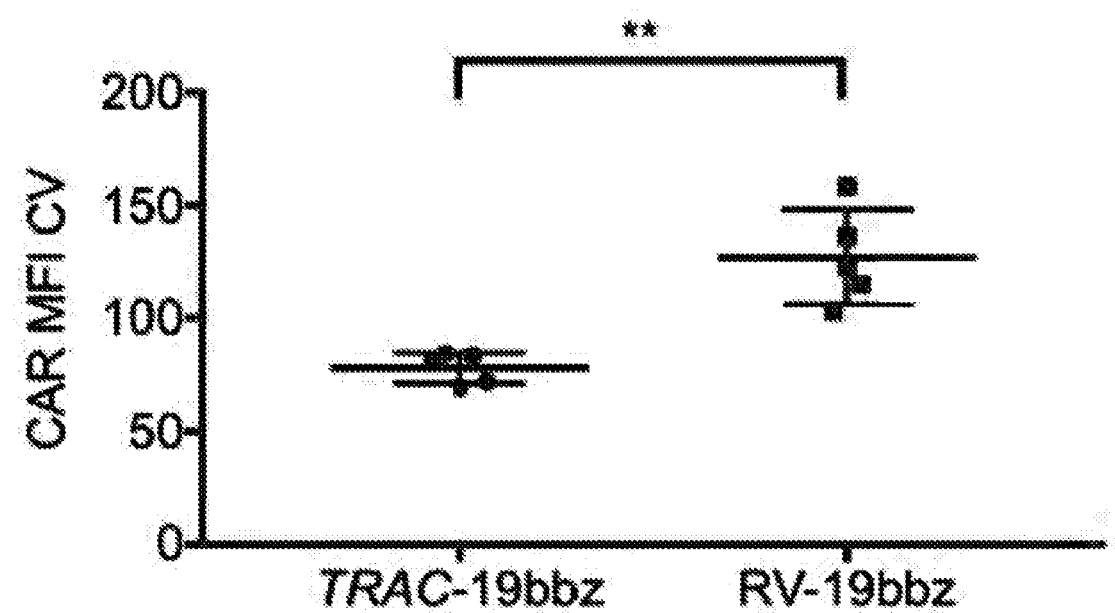
Figure 11C:
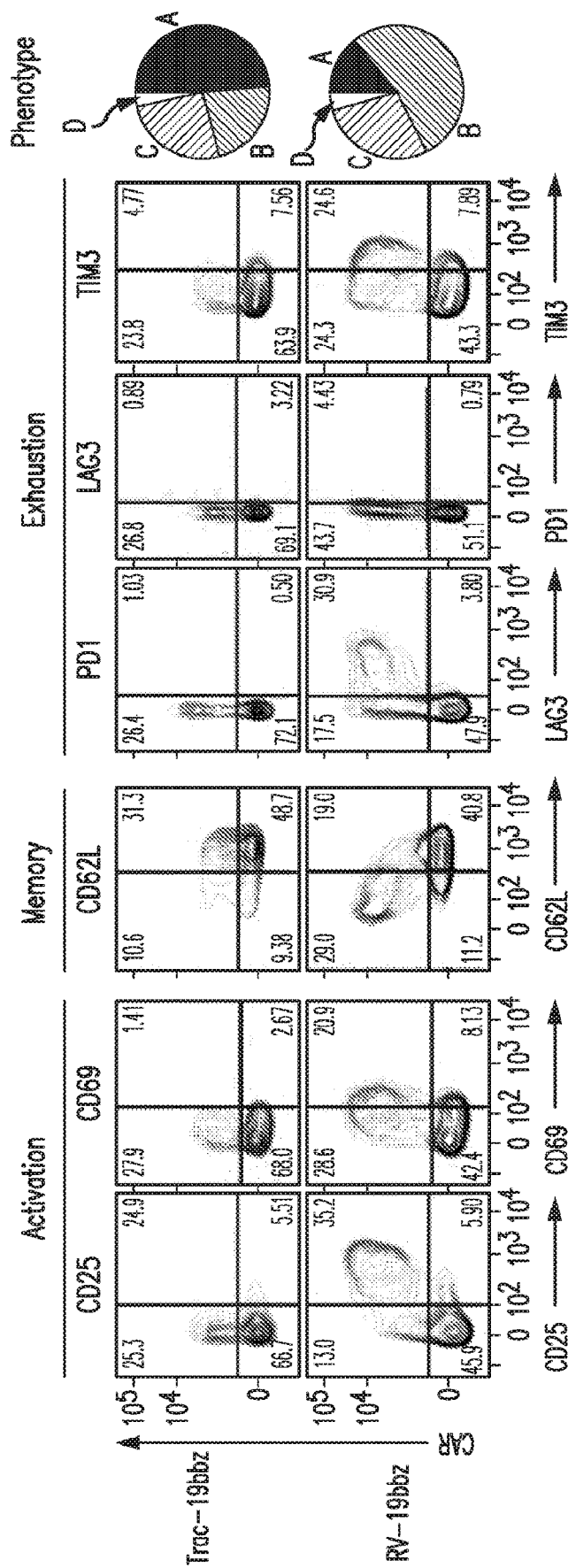
Figure 11D:
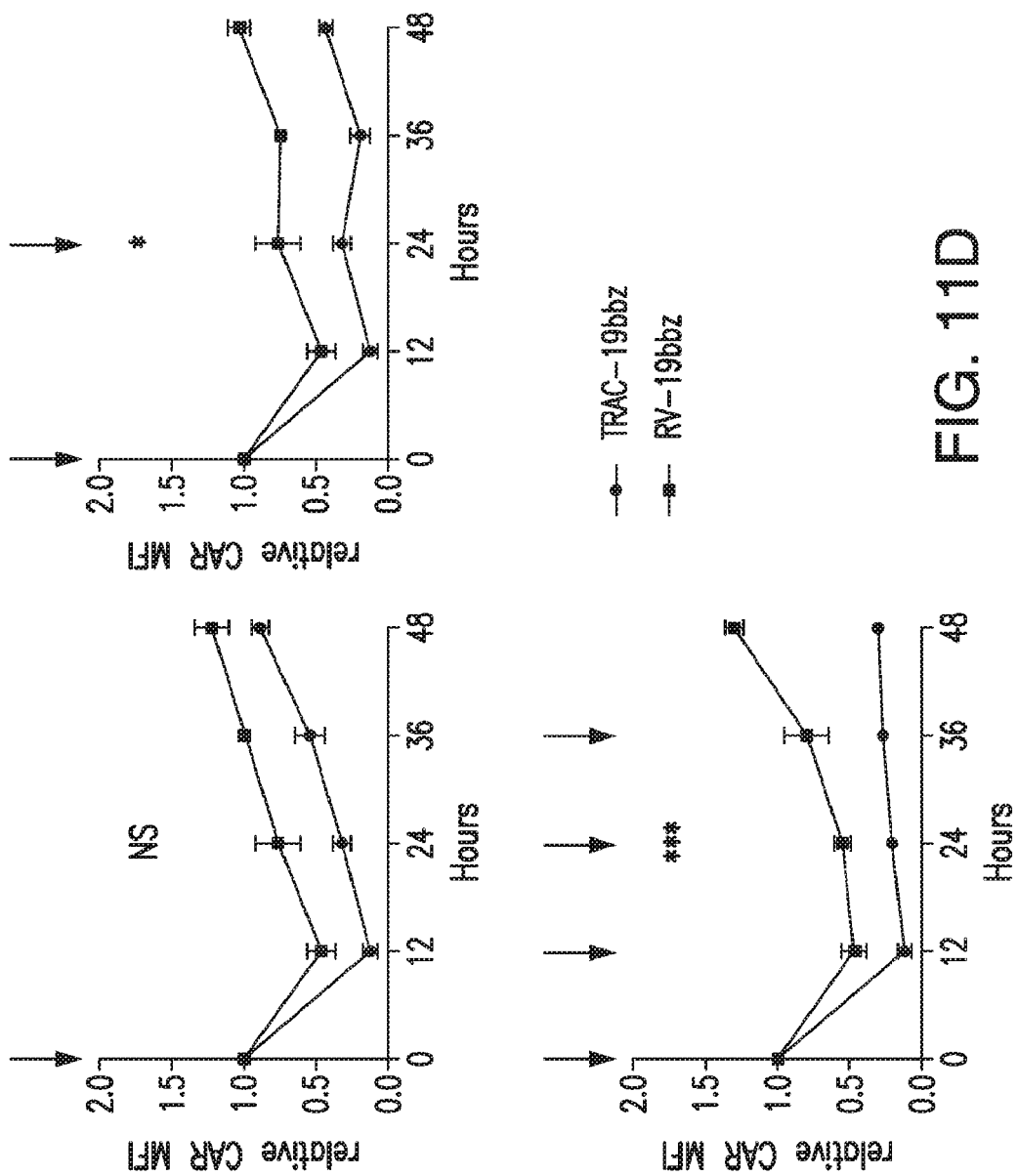
Figure 11E:
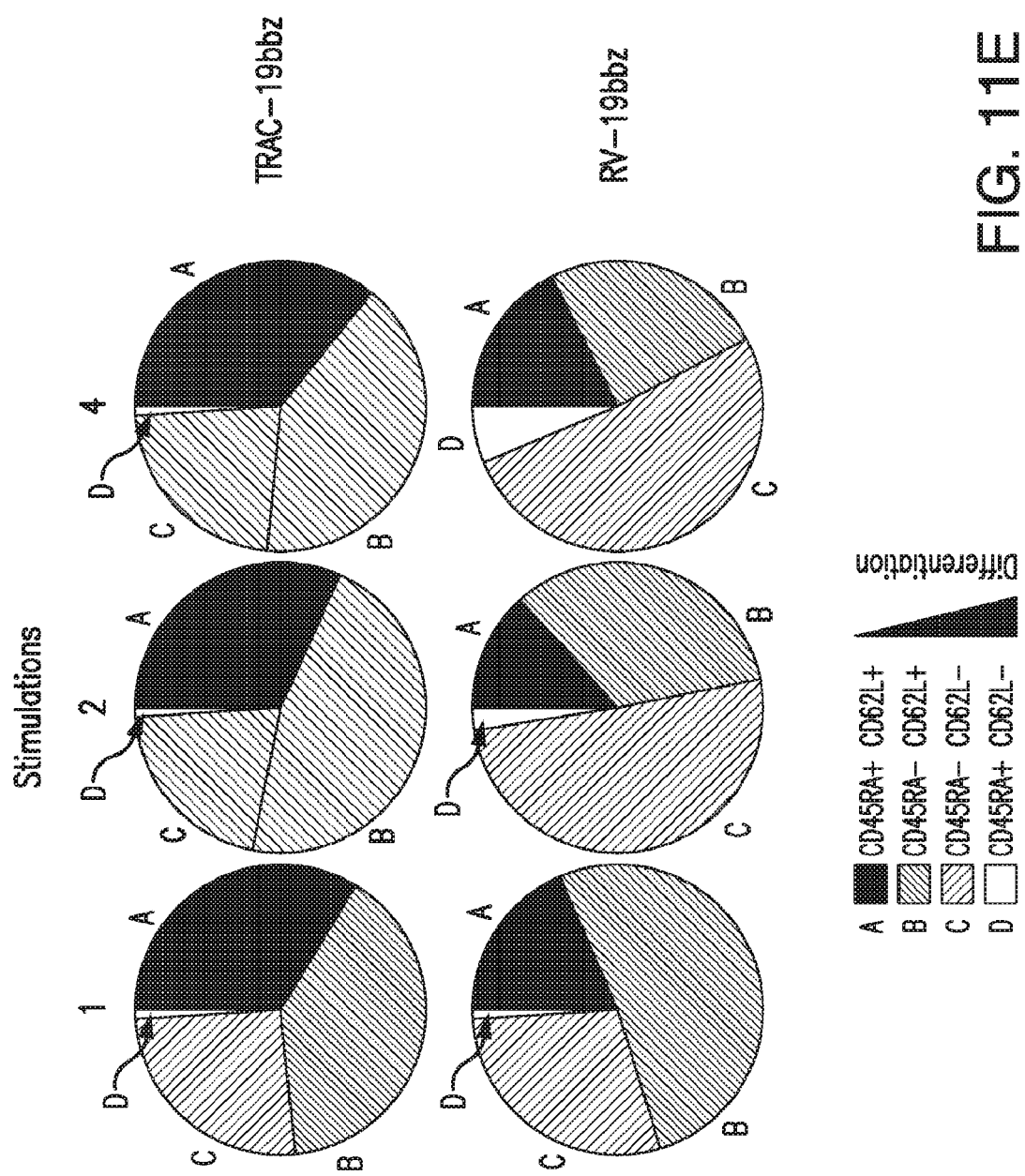
Figure 11F:
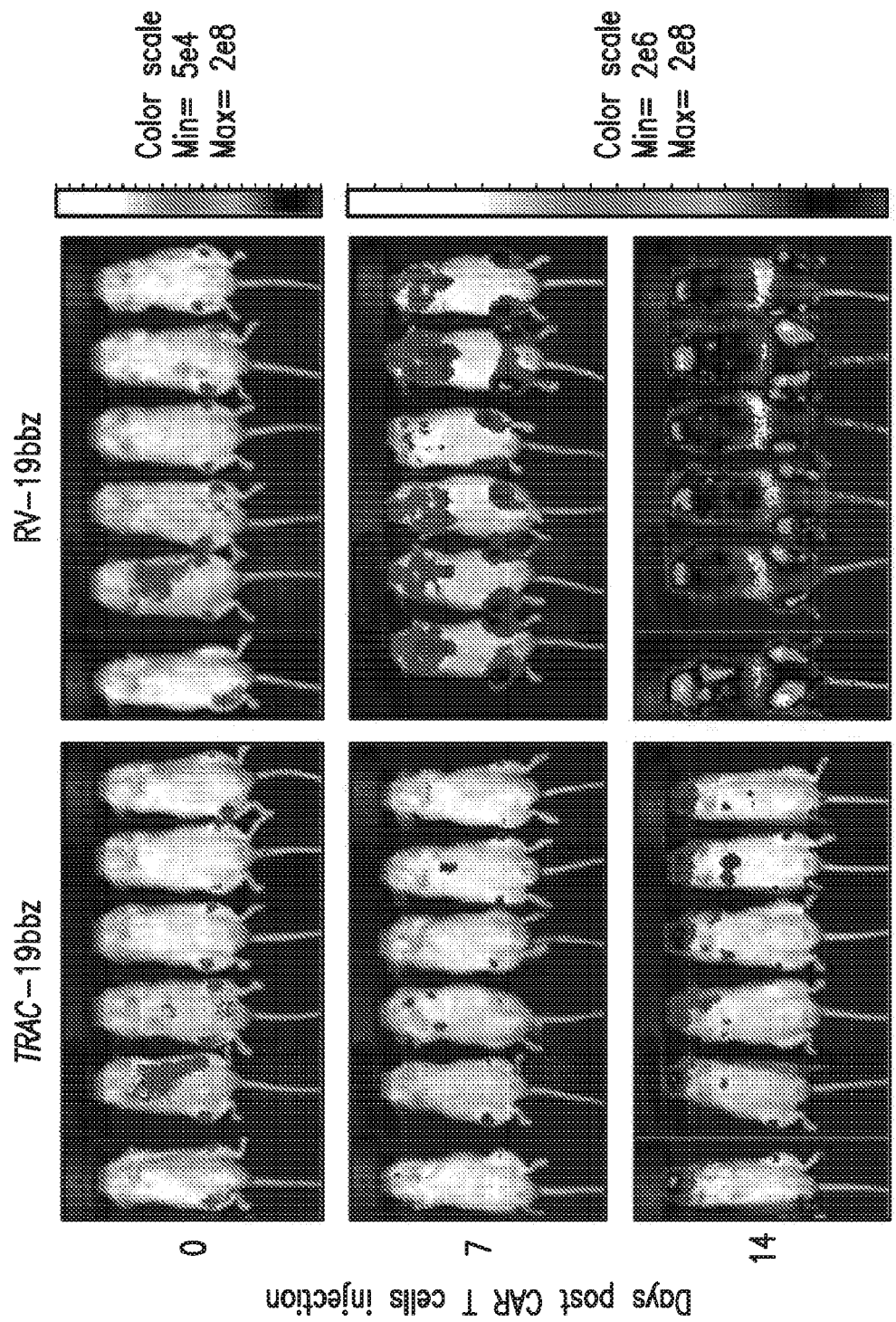
Figure 11G:
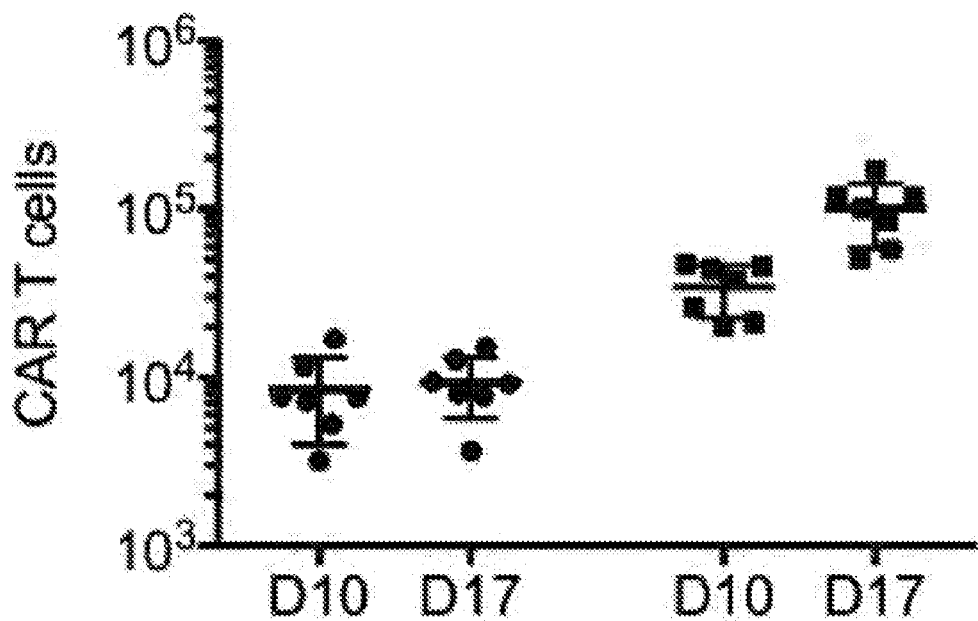
Figure 11H:
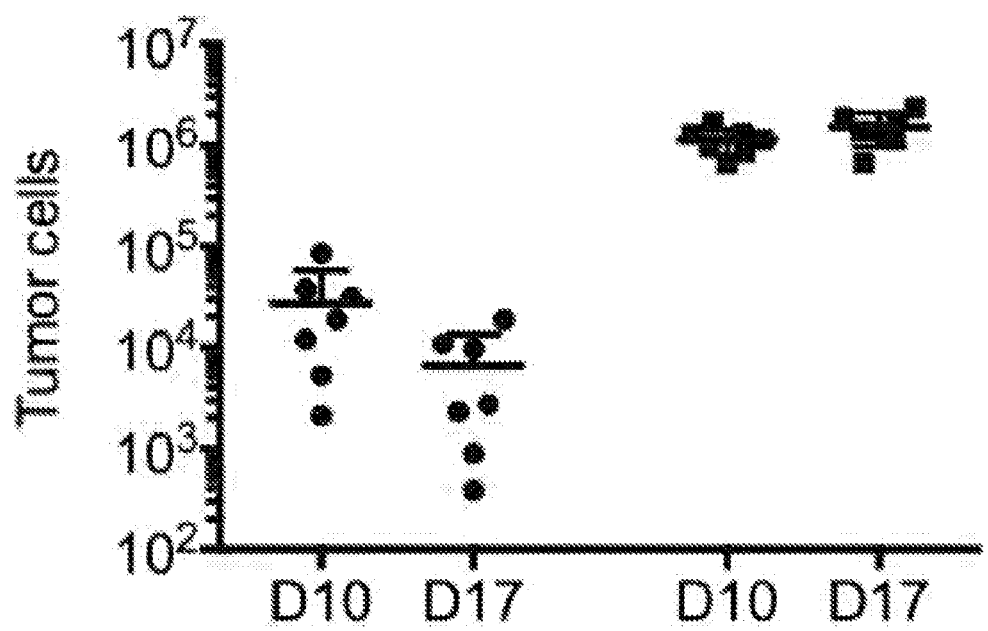
Figure 11I:
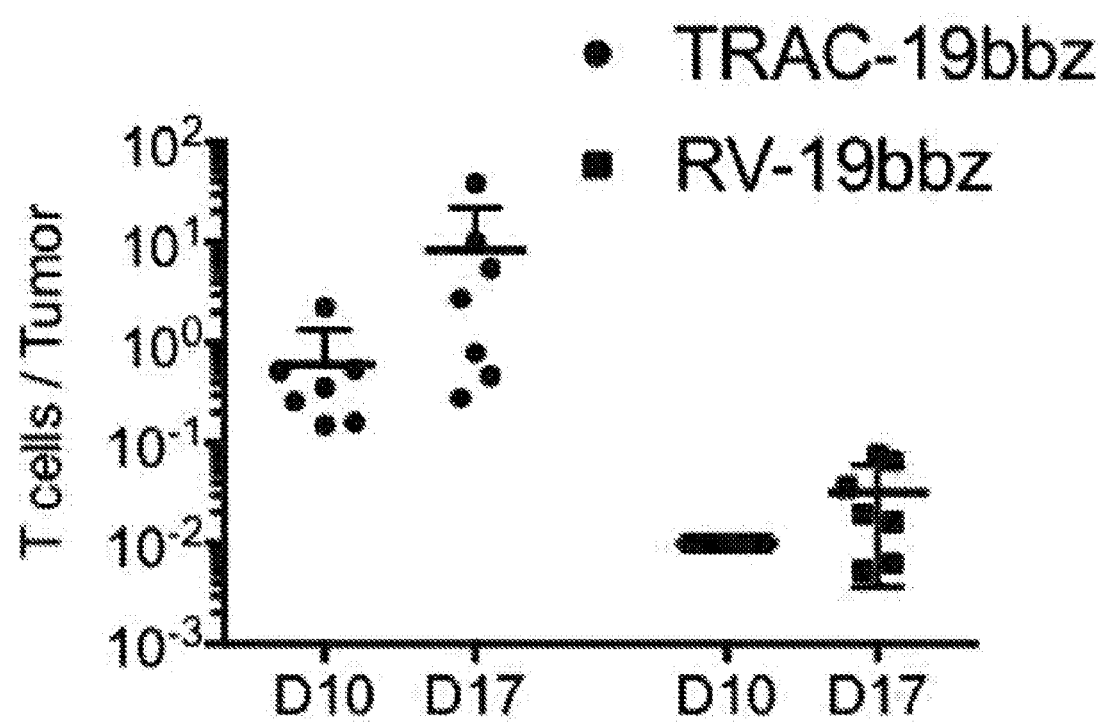
Figure 11J:
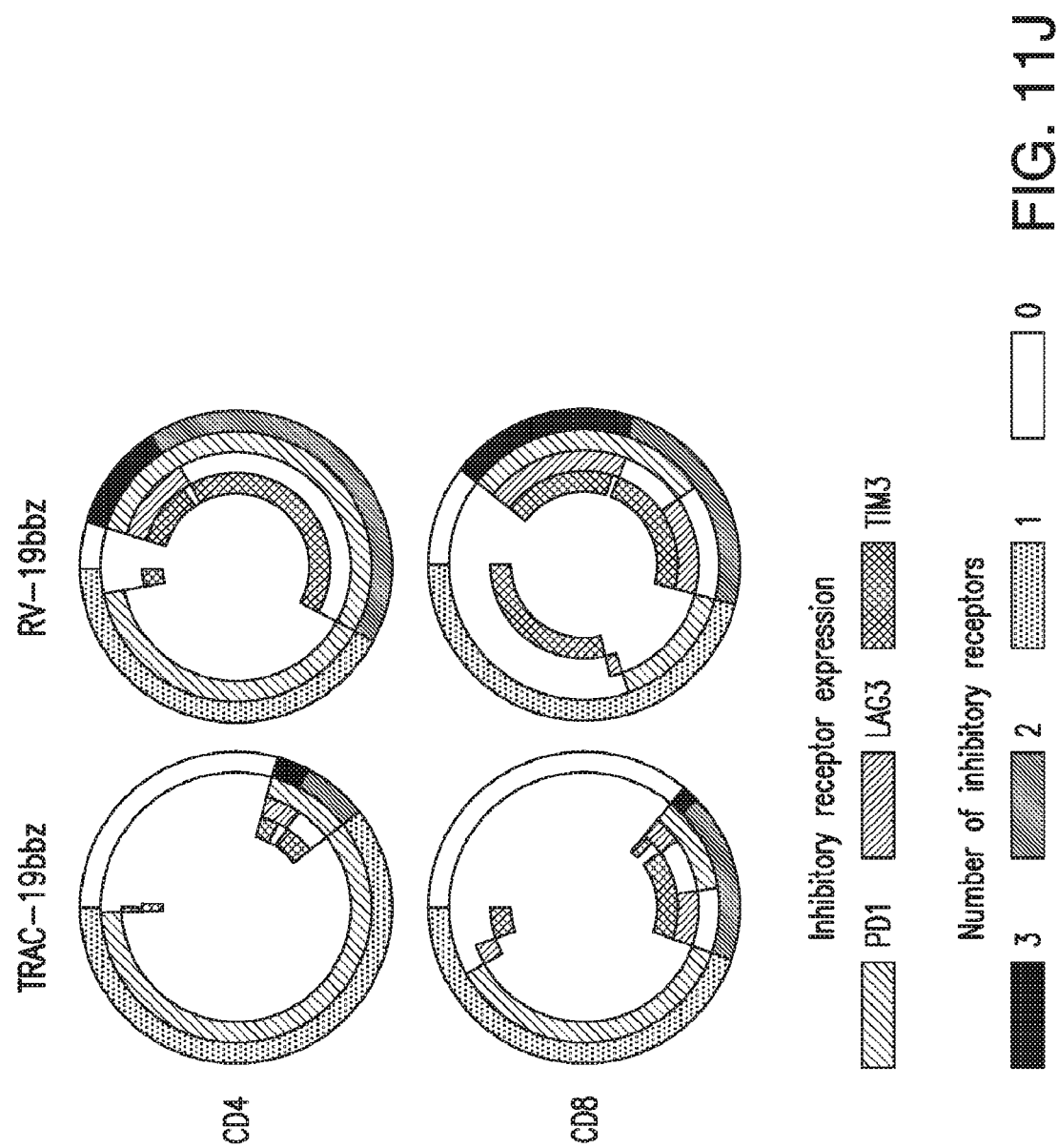

FIGS. 11A-11J show that TRAC-19BBz CAR T cells outperform conventional 19BBz CAR T cells by preventing exhaustion in vivo. FIGS. 11A and 11B show results compiled from the average CAR MFI (FIG. 11A) and coefficient of variation (FIG. 11B) of CAR+ T cells obtained from three independent transfections or transductions. The T cells used for these three experiments have been isolated from blood of three different healthy donors. FIG. 11C: Left, activation, memory, and exhaustion markers of CAR T cells analysed by flow cytometry 5 days after gene transfer. Right, plots indicate the phenotypes of the CAR+ T cells measured by flow cytometry analysis of CD62L and CD45RA expression 5 days after CAR vectorization; A: CD45RA+CD62L+; B: CD45RA− CD62L+; C: CD45RA− CD62L−; D: CD45RA+ CD62L−. FIG. 11D shows relative CAR MFI (1=MFI at 0 h) after CAR T cells being activated 1, 2 or 4 times on CD19+ target cells over a 48 h periods (n=3 independent experiments, arrows indicate stimulation time points) (TRAC-19bbz lower line, RV-19bbz upper line). FIG. 11E shows CAR T cells stimulated on CD19+ target cells either 1, 2 or 4 times in 48 h period were analysed by flow cytometry. Plots indicate the phenotypes of the CAR+ T cells measured by flow cytometry analysis of CD62L and CD45RA expression (average proportion from 3 independent experiments). FIG. 11F shows FFL-NALM-6-bearing mice were treated with $1 \times 10^5$ CAR T cells. Tumour burden shown as bioluminescent signal quantified per animal every week over a 21-day period. n=6 mice per group. FIGS. 11G-11J show NALM-6-bearing mice were treated with $1 \times 10^5$ CAR T cells. At 10 and 17 days after CAR T-cell infusion, 7 mice per group were euthanized and bone marrow cells were collected. CAR T cells and NALM-6 cells were analysed and counted with flow cytometry. Each dot represents one mouse. FIG. 11G shows CAR T cells count in marrow (n=7). FIG. 11H shows tumour (CD19+ GFP+ NALM-6) cells count in bone marrow (n=7). FIG. 11I shows effector/tumour ratio in the bone marrow (n=7). FIG. 11J shows exhaustion marker analysis from bone marrow T cells collected at day 17 and analysed by flow cytometry (inhibitory receptor expression shown from inner to outer rings TIM3, LAG3 and PD1, respectively). Represented as the average percentage of cells expressing the indicated markers (n=7). *P<0.05, P<0.01, *P<0.001 (Mann-Whitney test (FIGS. 11A and 11B) ANOVA F-test (FIG. 11D).

Figure 12A:
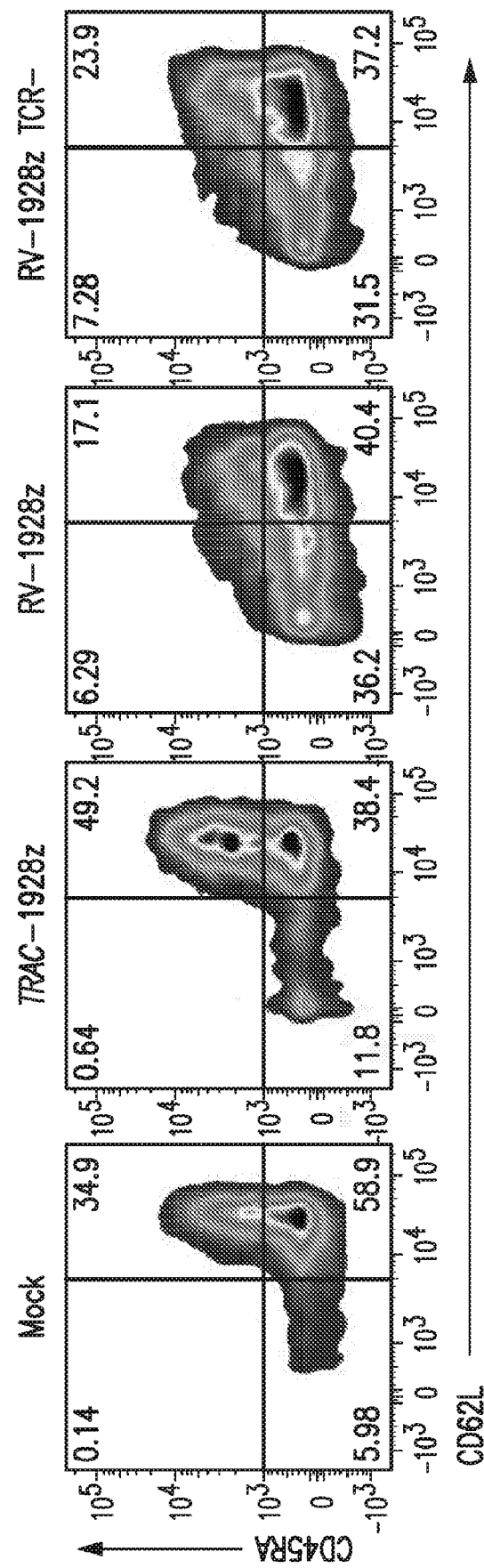
Figure 12B:
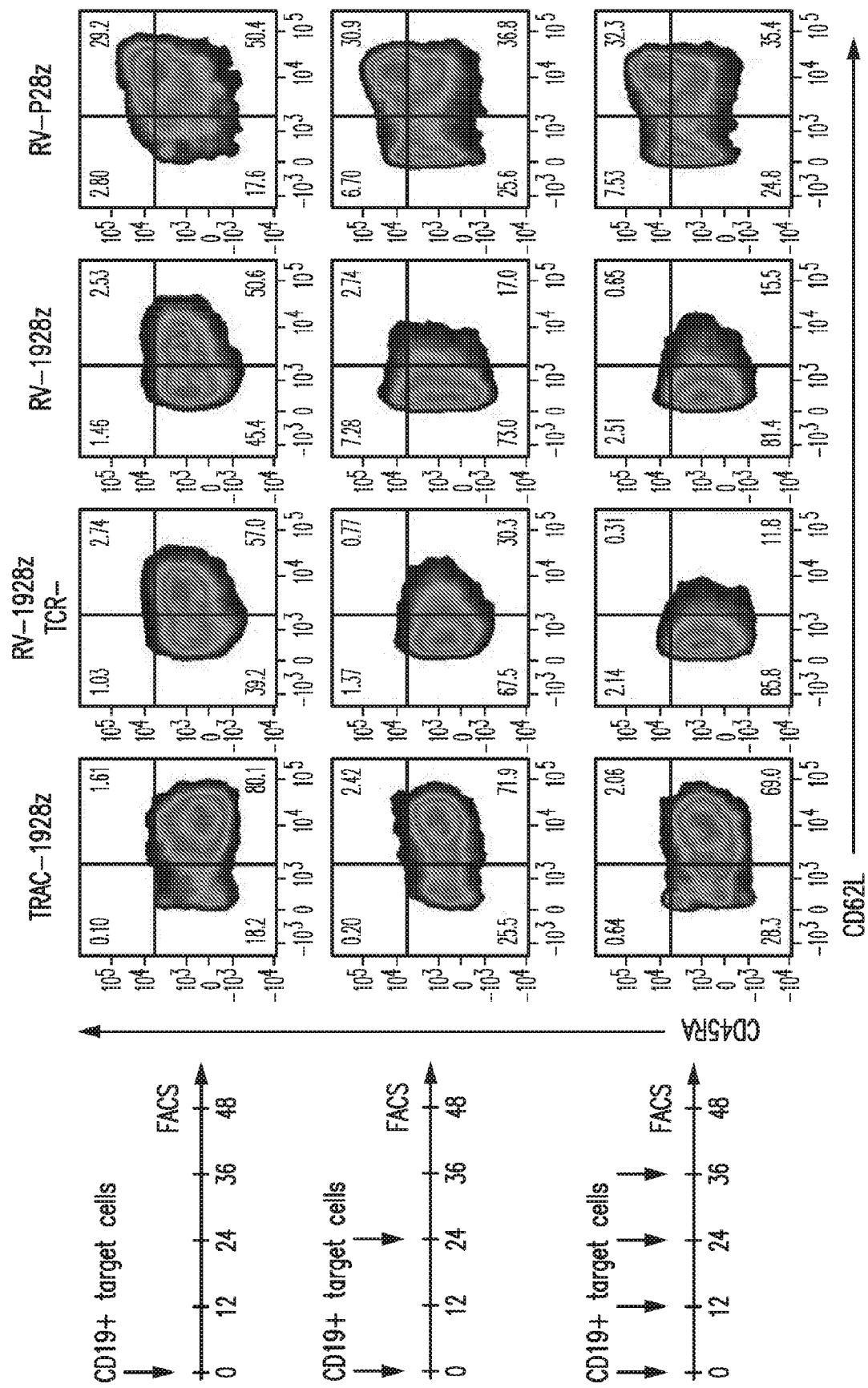
Figure 12C:
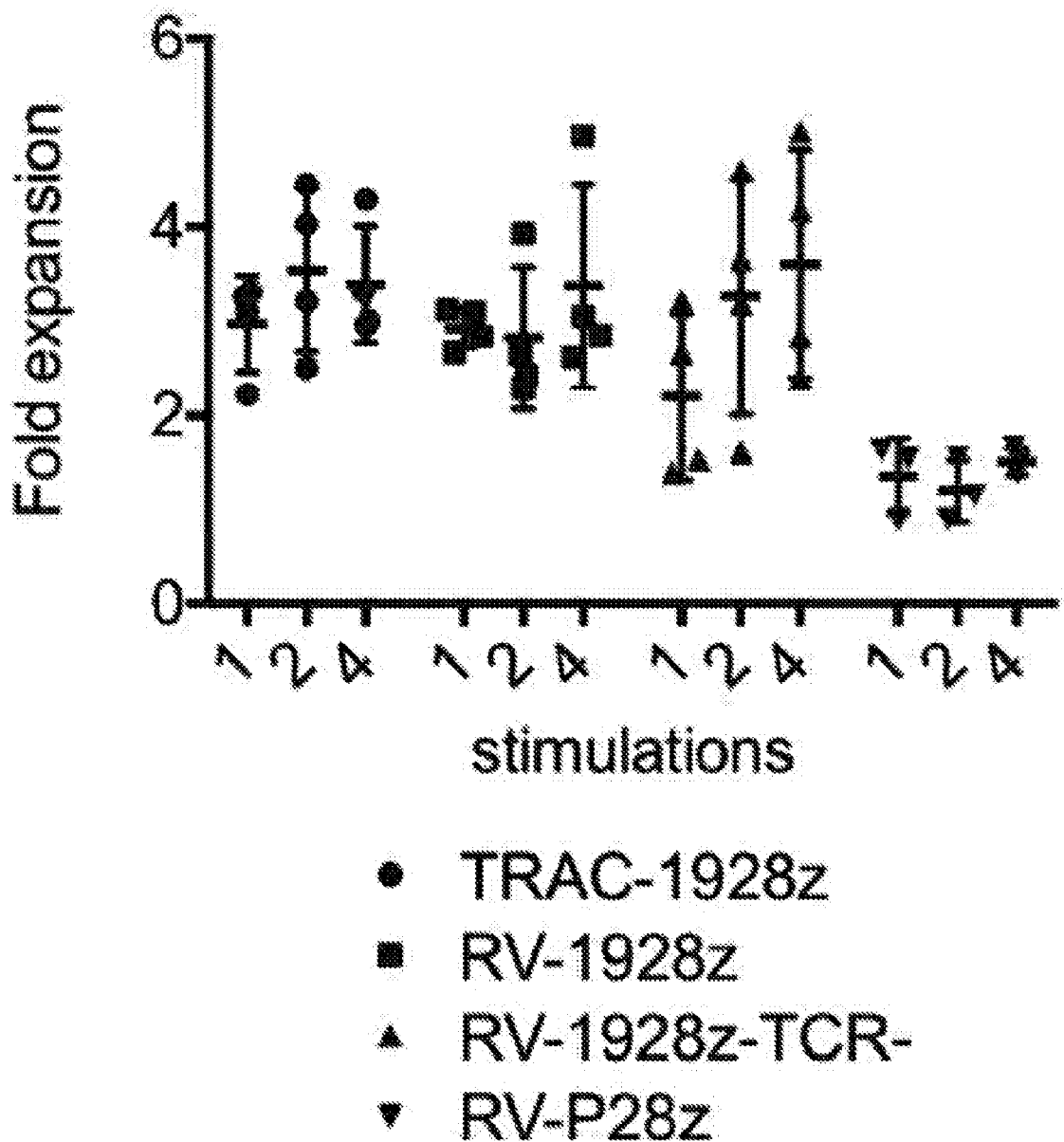
Figure 12D:
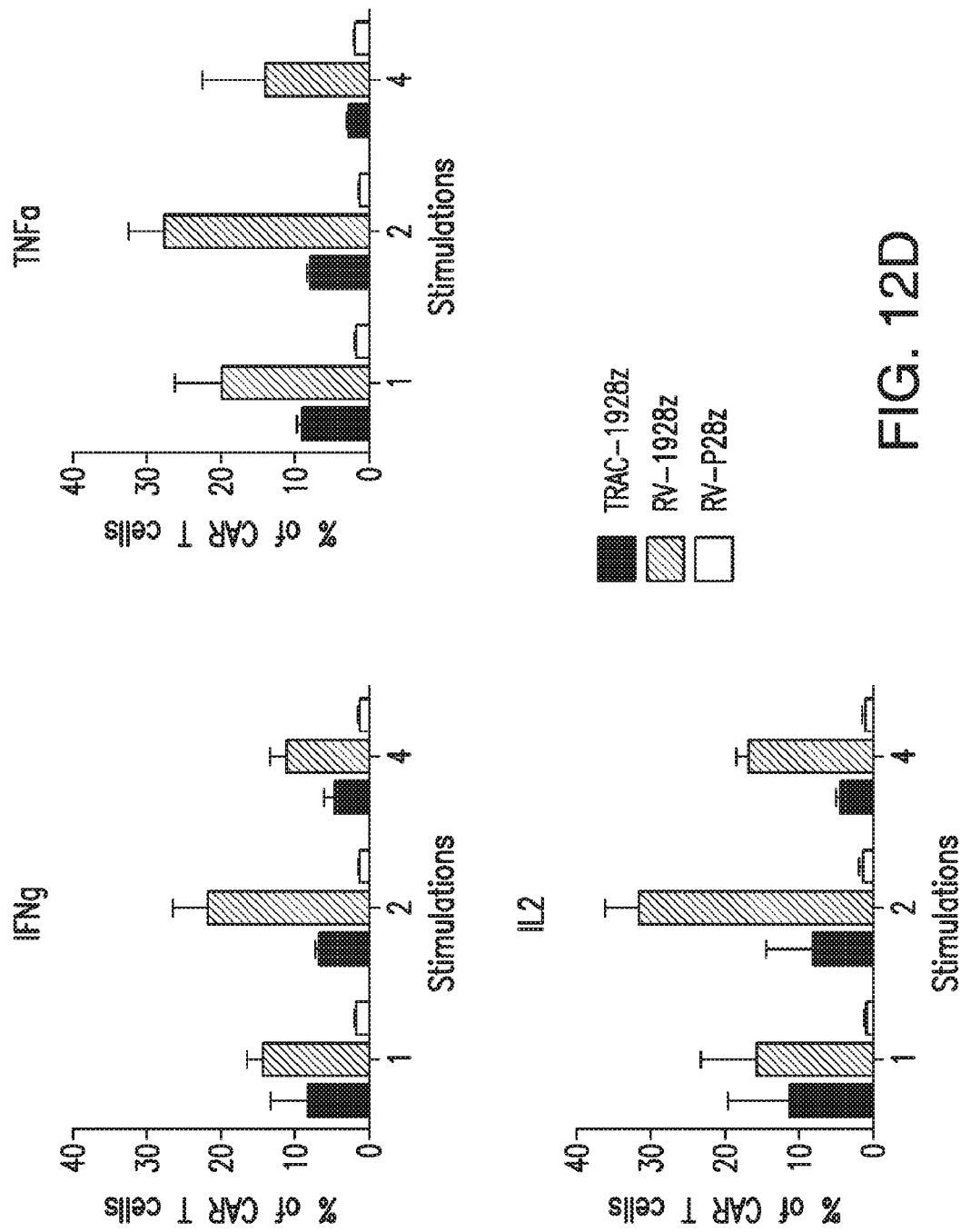

FIGS. 12A-12D show that TRAC-CAR T cells show reduced tonic signalling and antigen-induced differentiation in vitro. FIG. 12A shows representative FACS analysis of T cells differentiation markers 5 days after the CAR gene transfer. FIG. 12B shows representative FACS analysis of the CAR T cell differentiation markers after 1, 2 or 4 stimulations on CD19+ target cells. FIG. 12C shows CAR T cells expansion when stimulated 1, 2 or 4 times on CD19+ target cells over a 48 h period. No noticeable difference in the proliferation was found between the three 1928z CAR T cells conditions. FIG. 12D shows percentage of CAR T cells with positive expression of IFNγ, TNFα or IL-2 after intracellular staining at the end of the protocol in FIG. 4D (n=2 independent experiments on 2 donors) (groups of bars left to right TRAC-1928z, RV1928z and RV-P28z, respectively).

Figure 13A:
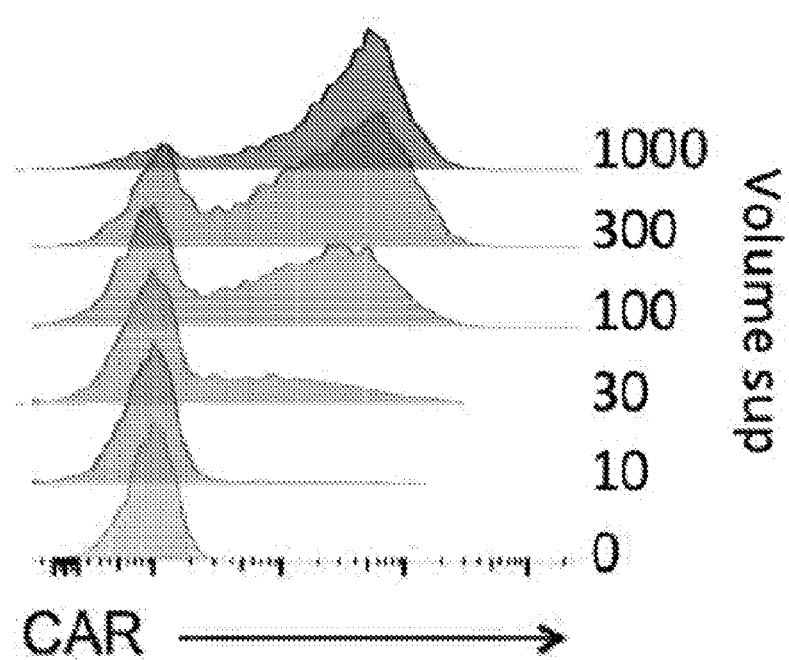
Figure 13B:
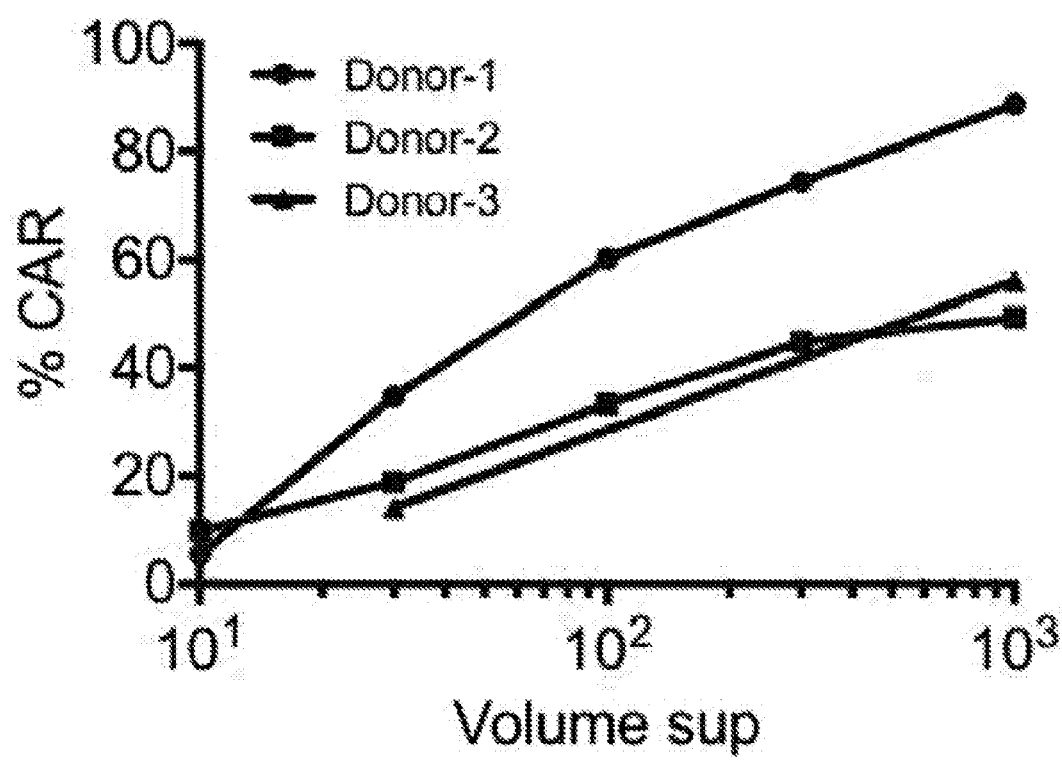
Figure 13C:
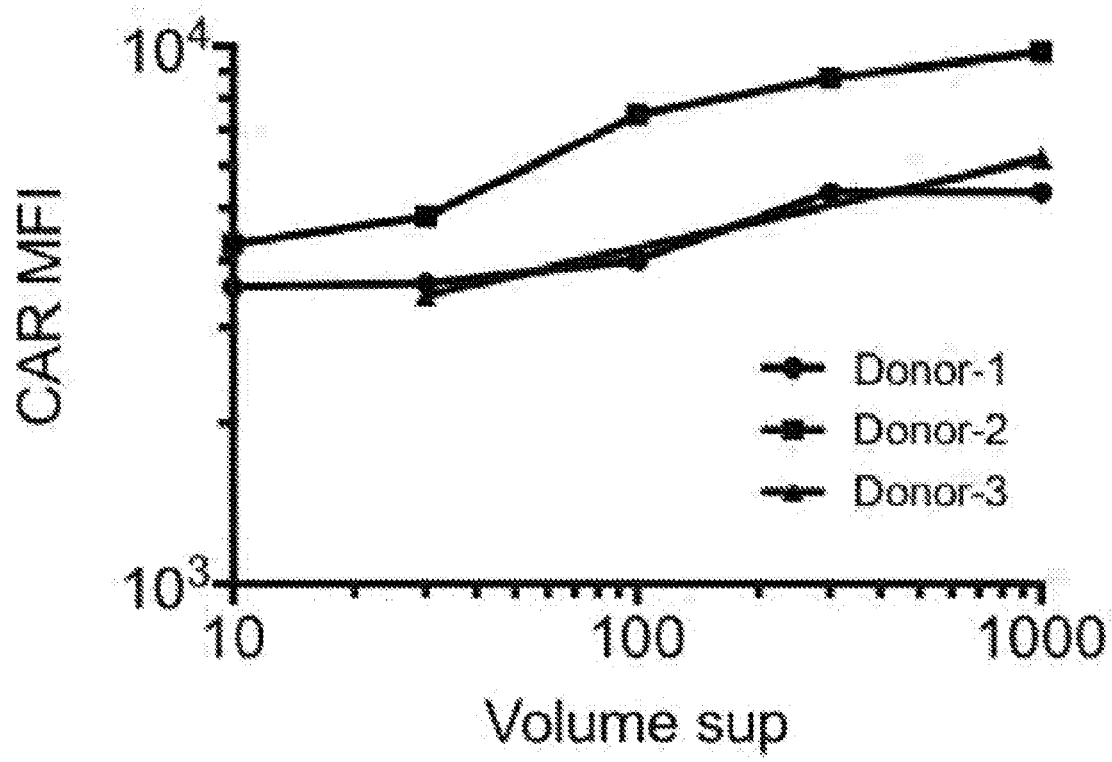
Figure 13D:
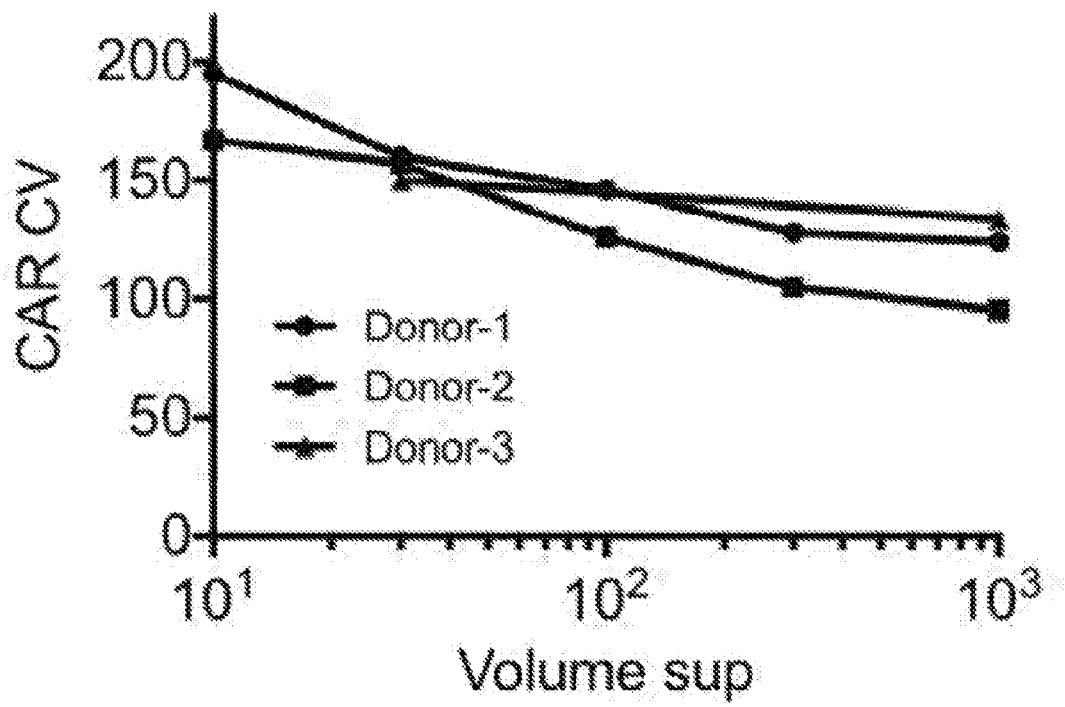
Figure 13E:
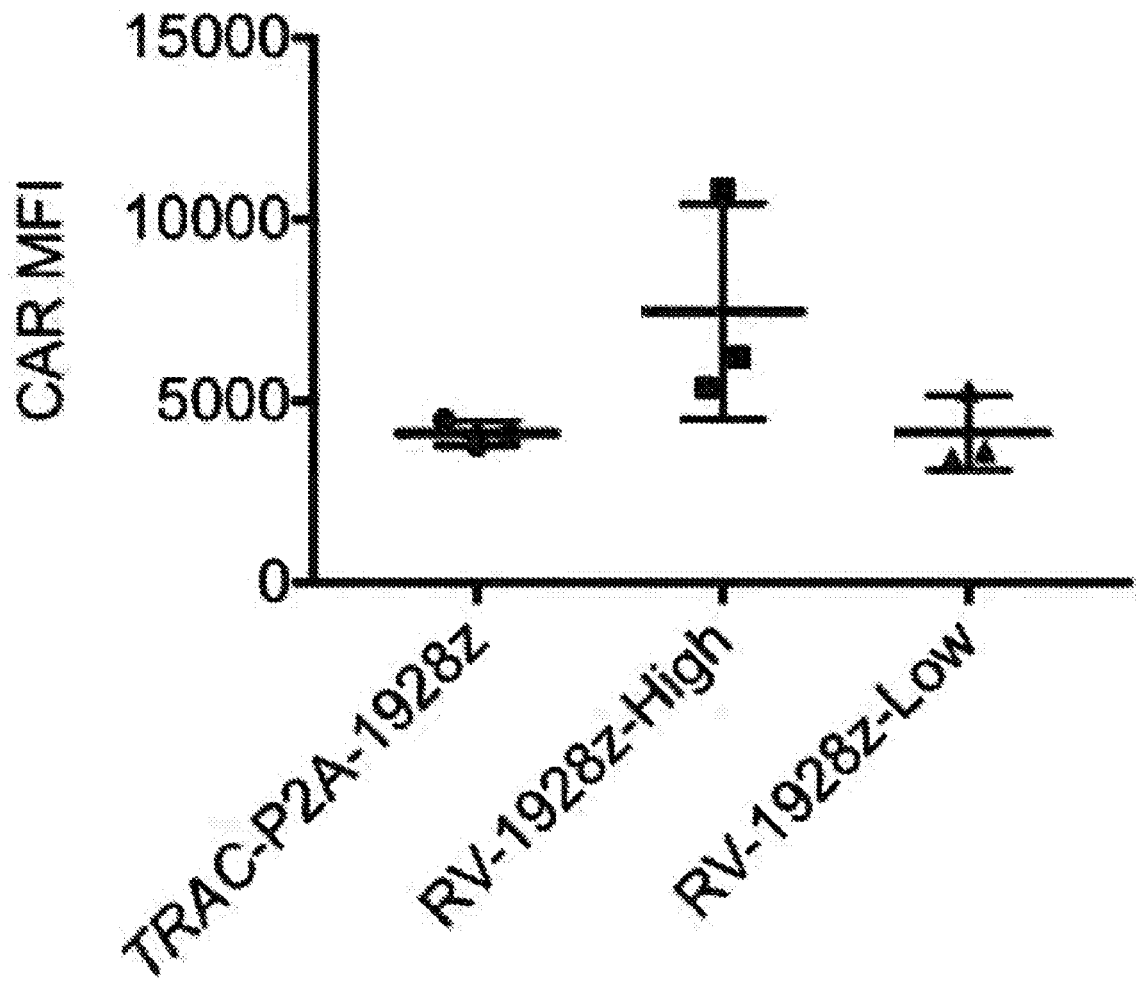
Figure 13F:
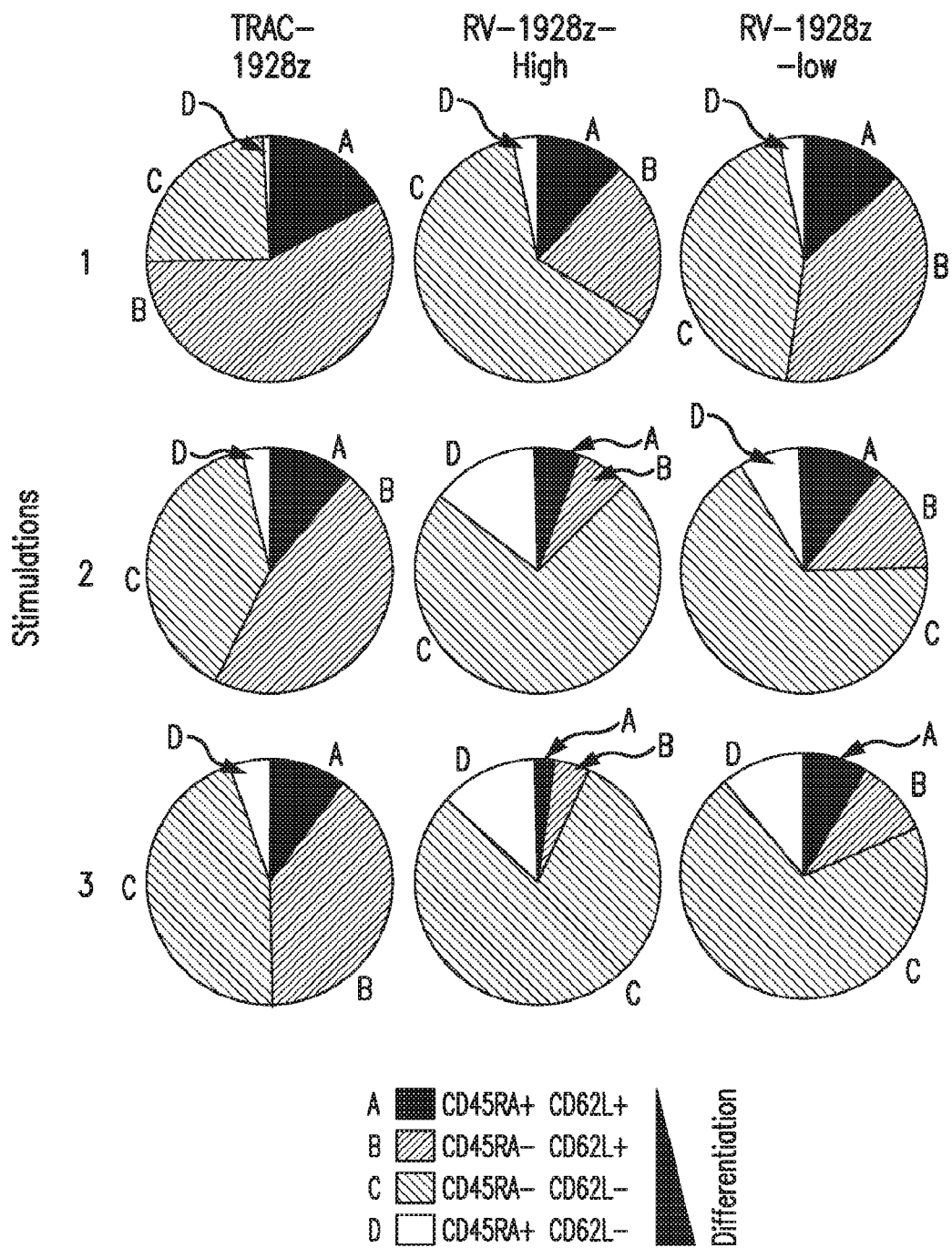

FIGS. 13A-13F show that TRAC-CAR T cells show delayed in vitro antigen-induced differentiation compared to lowly or highly transduced RV-CAR T cells. FIG. 13A shows a representative histogram of the CAR expression 5 days after transduction of different volumes of retroviral supernatant in µl (representative of 3 independent experiments; total transduction volume 2 ml). FIG. 13B shows percentage of CAR+ T cells as a function of the volume of retroviral supernatant analysed by FACS 5 days after transduction (n=3 donors). FIG. 13C shows CAR mean fluorescence intensity (MFI) of T cells as a function of the volume of retroviral supernatant analysed by FACS 5 days after transduction (n=3 donors). FIG. 13D shows CAR coefficient of variation as a function of the volume of retroviral supernatant analysed by FACS 5 days after transduction (n=3 donors). FIG. 13E shows average CAR MFI of CAR T cells 5 days after transduction (n=3 donors). High=1,000 µl, and low=30 µl. FIG. 13F shows CAR T cells stimulated on CD19+ target cells either 1, 2 or 4 times in 48 h period were analysed by flow cytometry. Plots indicate the phenotypes of the CAR-positive T cells measured by flow cytometry analysis of CD62L and CD45RA expression (average proportion from of 3 independent experiments) (A, CD45RA+ CD62L+; B, CD45RA−CD62L+; C, CD45RA−CD62L−; D, CD45RA+CD62L−).

Figure 14C:
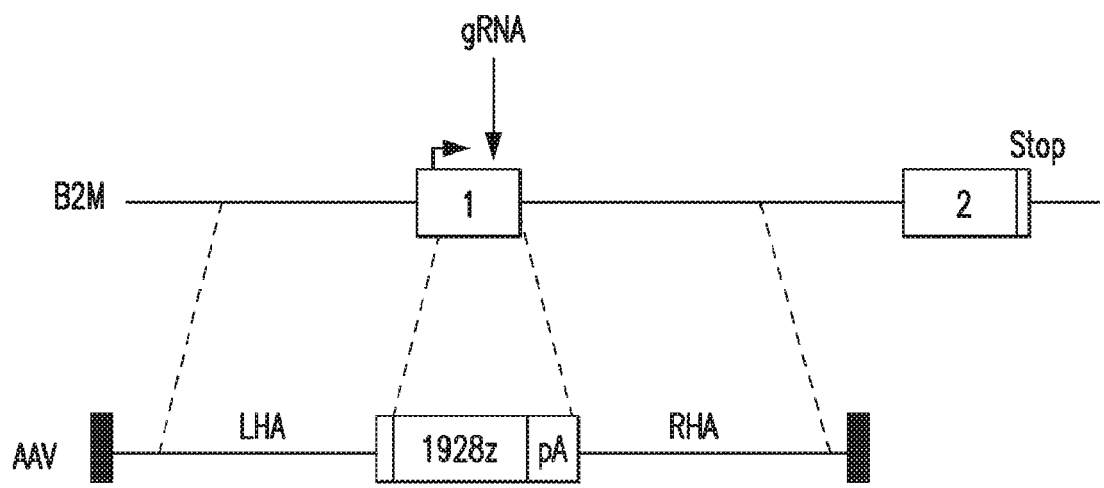
Figure 14D:
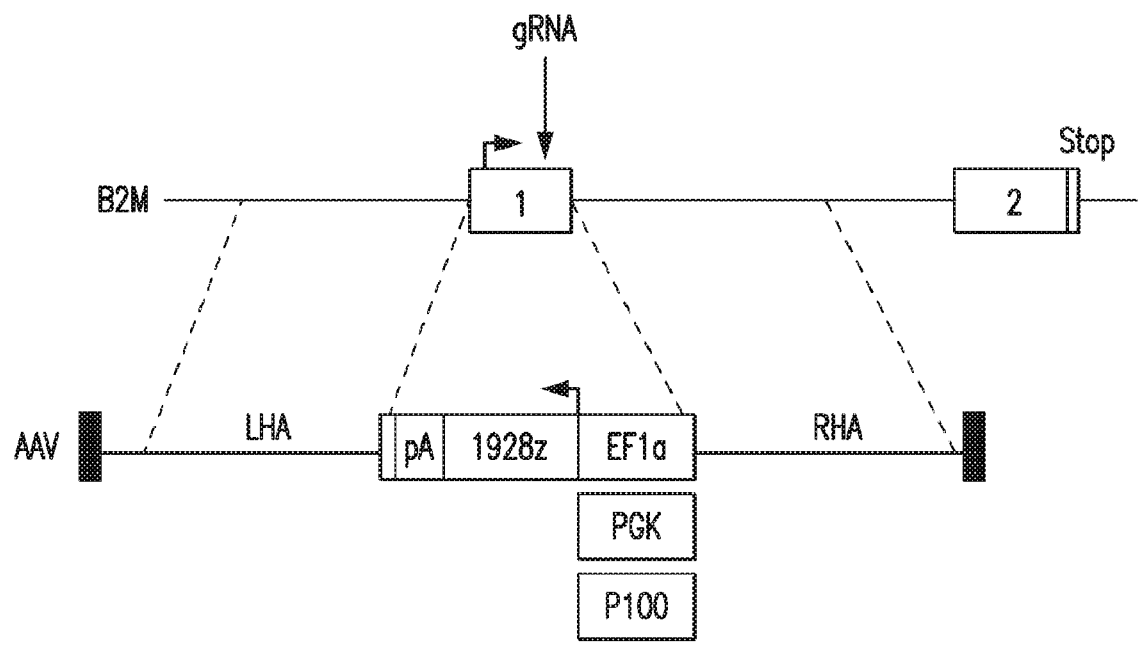
Figure 14E:
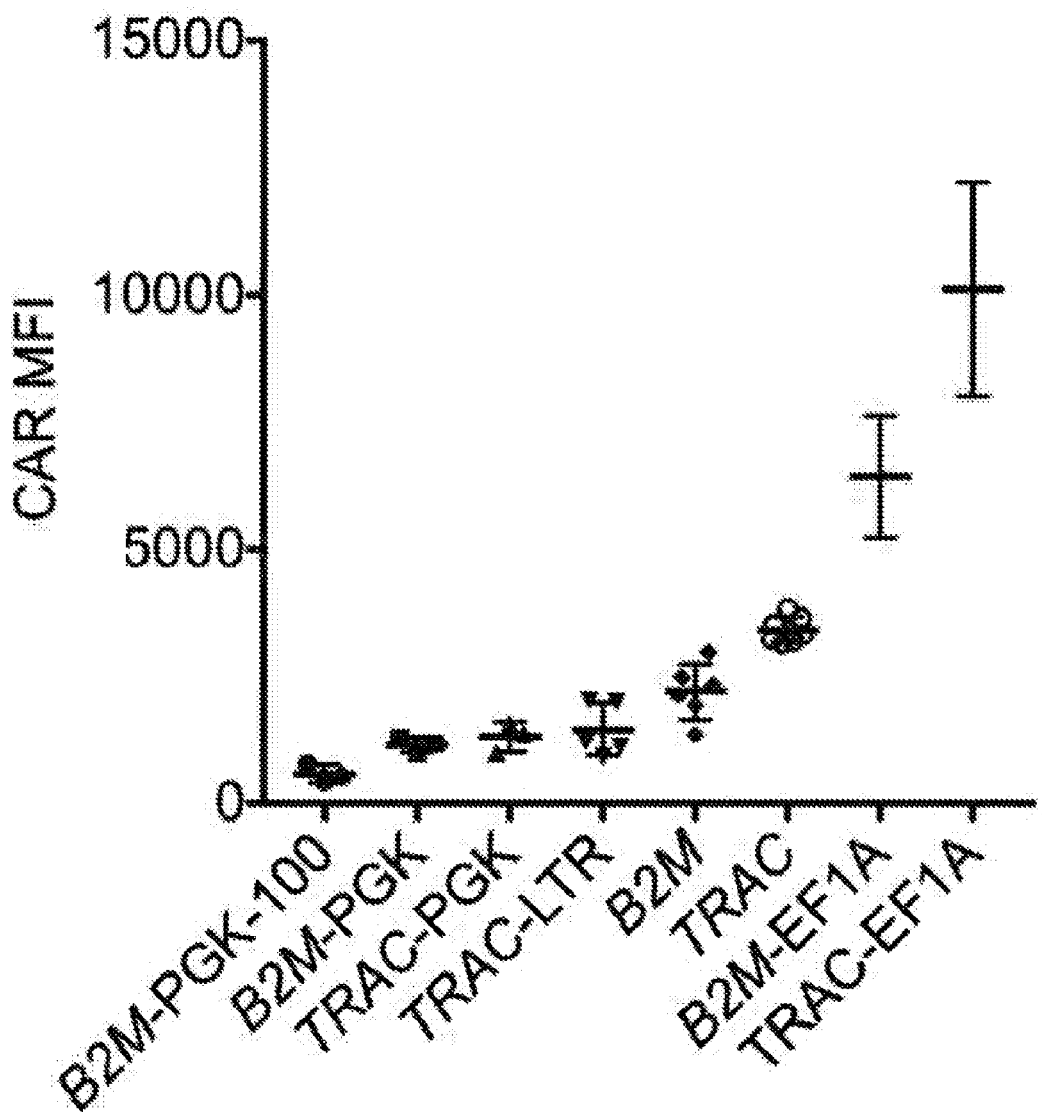
Figure 14F:
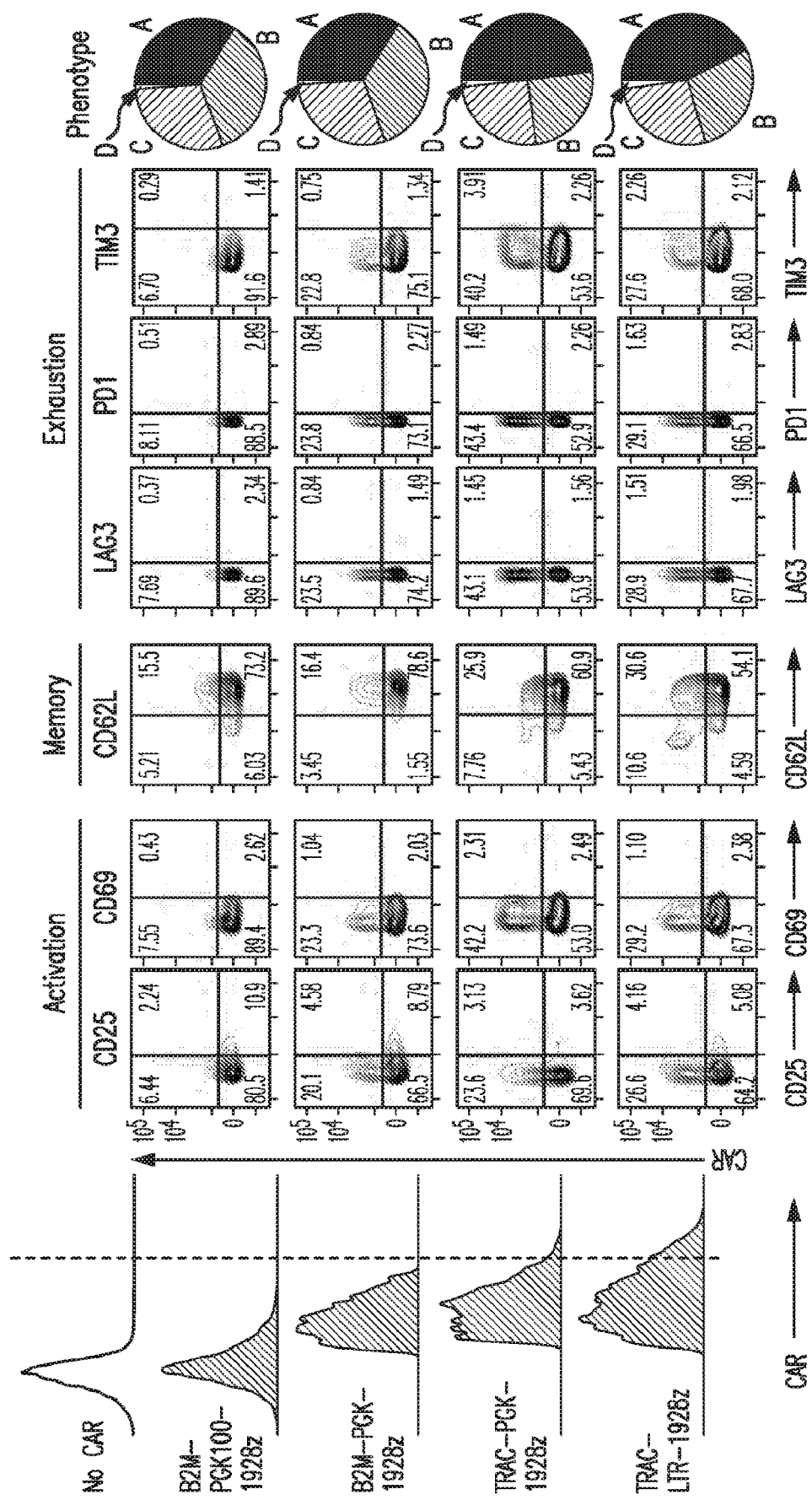
Figure 14F:
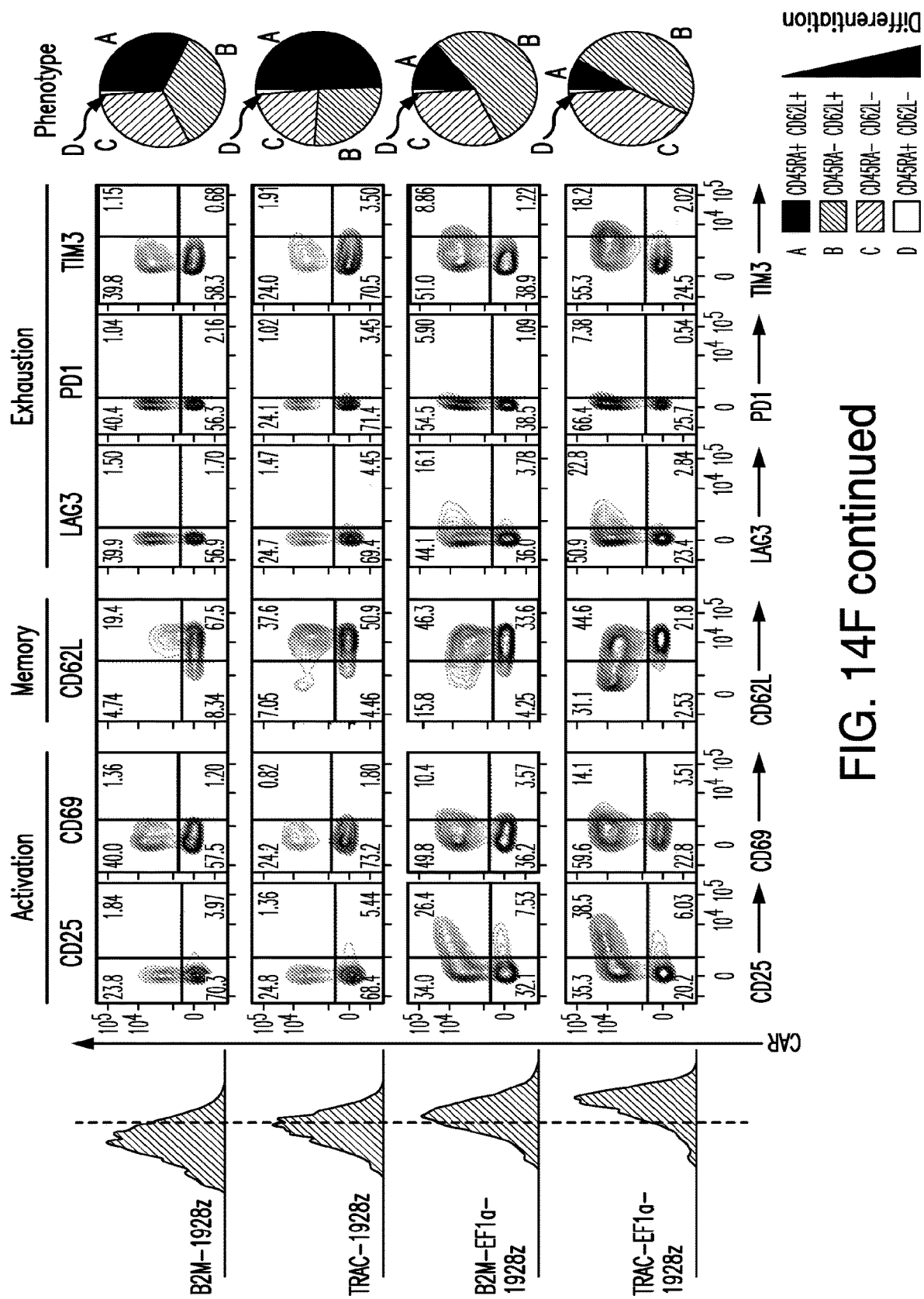

FIGS. 14A-14F CAR gene expression using different promoters at distinct loci influences tonic signalling levels in vitro. FIG. 14A shows a diagram of CRISPR/Cas9-targeted integration into the TRAC locus. The targeting construct (AAV) contains a splice acceptor (SA), followed by a P2A coding sequence, the 1928z CAR gene and a polyA sequence, flanked by sequences homologous to the TRAC locus (LHA and RHA: left and right homology arm). Once integrated, the endogenous TCRa promoter drives CAR expression, while TRAC locus is disrupted. TRAV: TCR alpha variable region. TRAJ: TCR alpha joining region 2A: the self-cleaving Porcine teschovirus 2A sequence. FIG. 14B shows a diagram of CRISPR/Cas9-targeted promoter integration into the TRAC locus. The targeting construct (AAV) contains the 1928z CAR coding sequence in the reverse orientation, under the control of an exogenous promoter, the long version of the human elongation factor 1 alpha promoter (EF1α), the enhancer sequence from the gamma retrovirus used in FIGS. 3 and 4 (Mo-MLV LTR here called LTR) or the phosphoglycerate kinase (PGK) promoter and a polyA sequence, flanked by sequences homologous to the TRAC locus (LHA and RHA: left and right homology arm). TRAV: TCR alpha variable region. TRAJ: TCR alpha joining region. FIG. 14C shows a schematic of tailored CRISPR/Cas9-induced targeted integration into the B2A1 locus. The targeting construct (AAV) contains the CAR gene flanked by homology sequences (LHA and RHA). Once integrated, the endogenous B2A1 promoter drives CAR expression. FIG. 14D shows a schematic of CRISPR/Cas9-targeted promoter integration into the B2A1 locus. The targeting construct (AAV) contains the 1928z CAR gene in the reverse orientation, under the control of an exogenous promoter, the human elongation factor 1 alpha promoter (EF1α), the phosphoglycerate kinase (PGK) promoter or a truncated version of the PGK (PGK100) and a polyA sequence, flanked by sequences homologous to the B2A1 locus (LHA and RHA: left and right homology arm). FIG. 14E shows average CAR mean fluorescence intensity (MFI) analysed by FACS 4 days after transduction (n=3 to 7 independent experiments and 4 different donors). pA: bovine growth hormone polyA sequence for all targeting constructs. FIG. 14F shows analysis of CAR T cells 5 days after vectorization. Left panel: representative histogram of the CAR expression 5 days after its vectorization into T cells. Middle panel: Activation, memory, and exhaustion markers of CAR T cells analysed by flow cytometry 5 days after the vectorization of the CAR. Right panel: Plots indicate the phenotypes of the CAR positive T cells measured by flow cytometry analysis of CD62L and CD45RA expression 5 days after vectorization of the CAR (A, CD45RA+CD62L+; B, CD45RA−CD62L+; C, CD45RA−CD62L−; D, CD45RA+CD62L−).

Figure 15A:
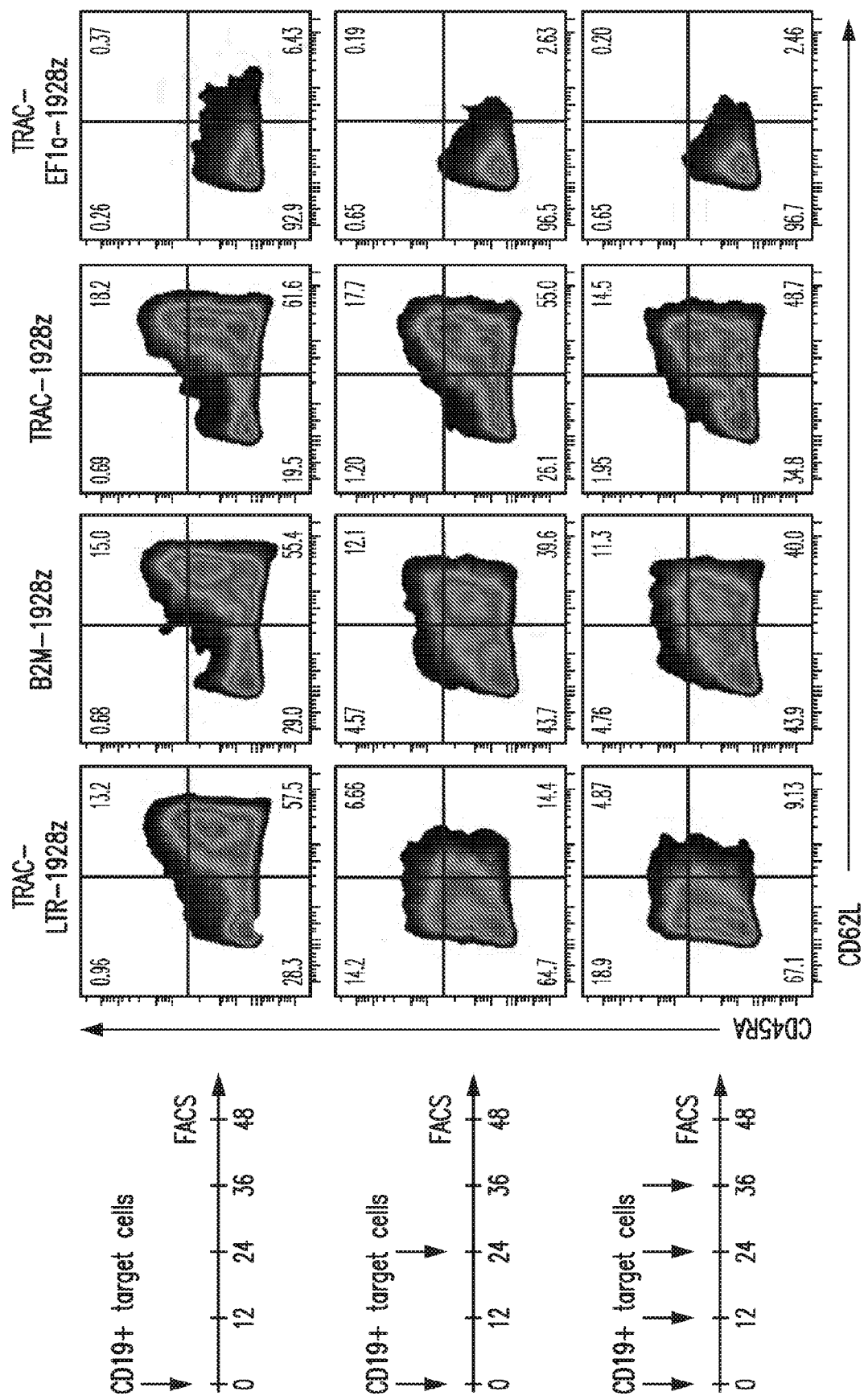
Figure 15B:
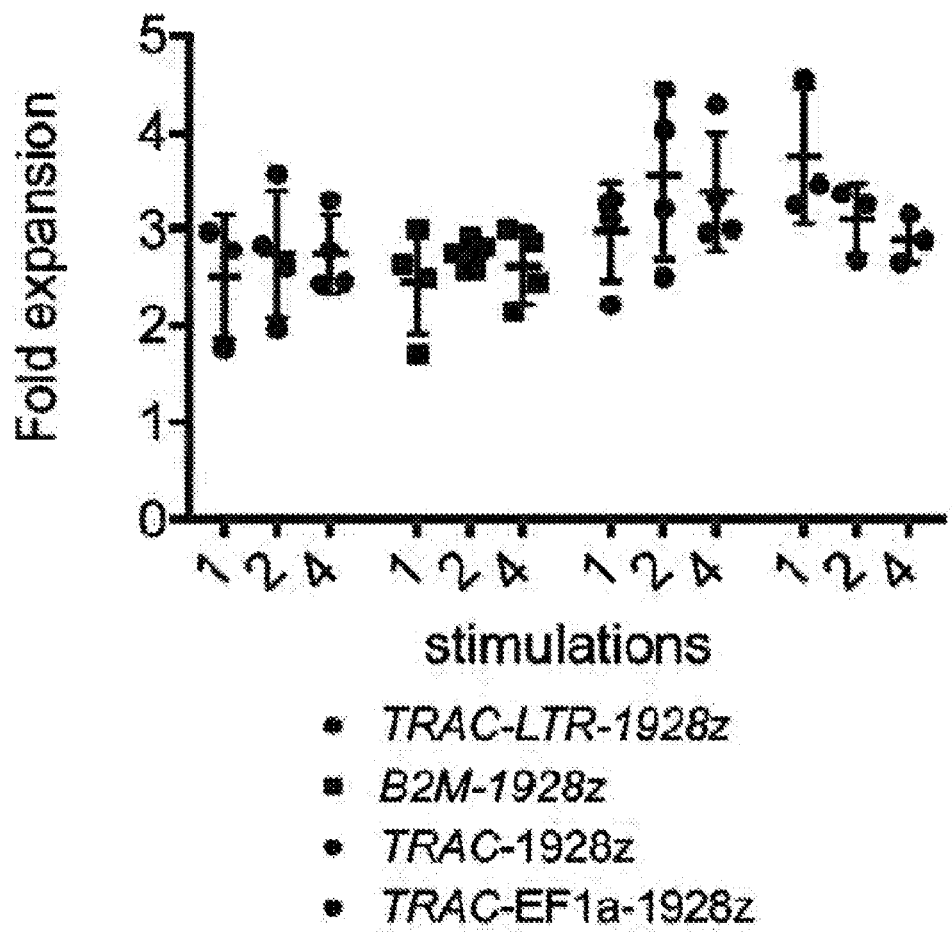
Figure 15C:
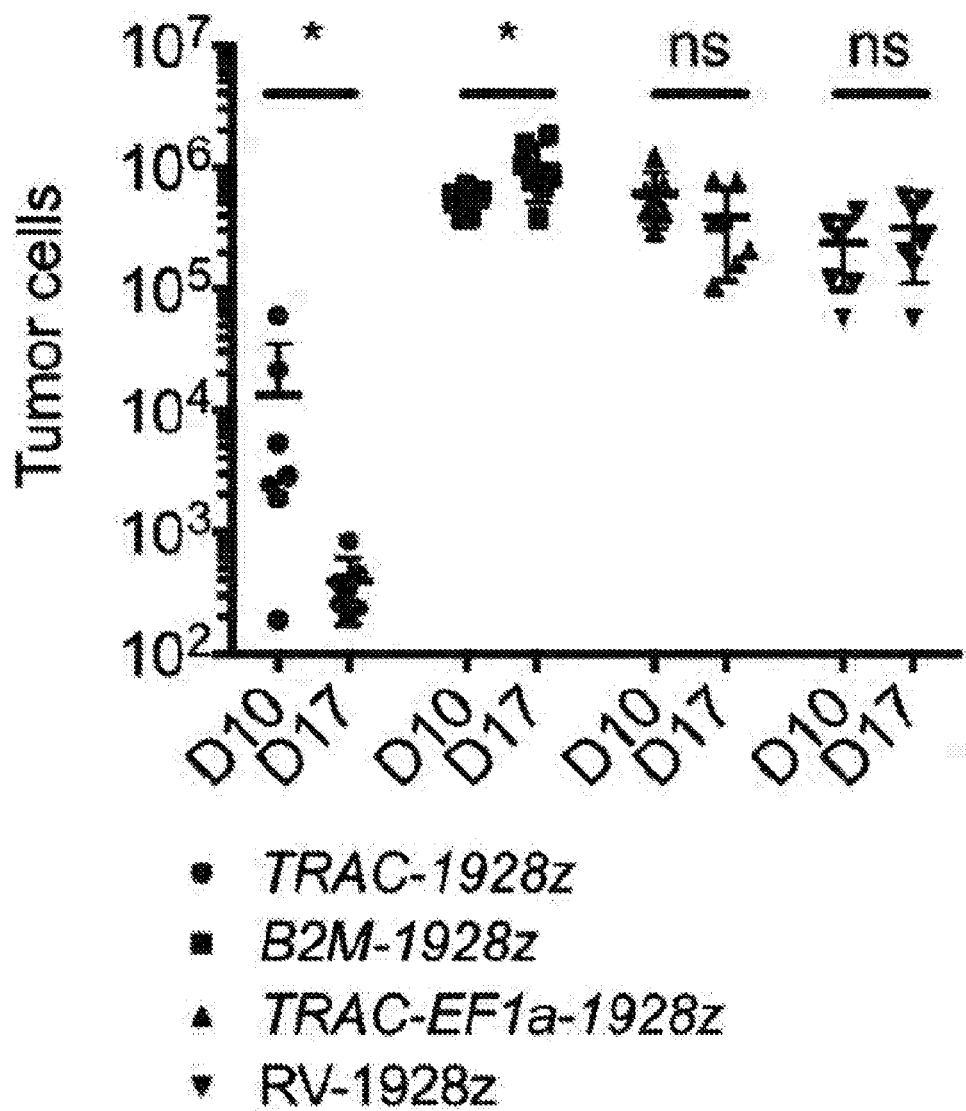
Figure 15D:
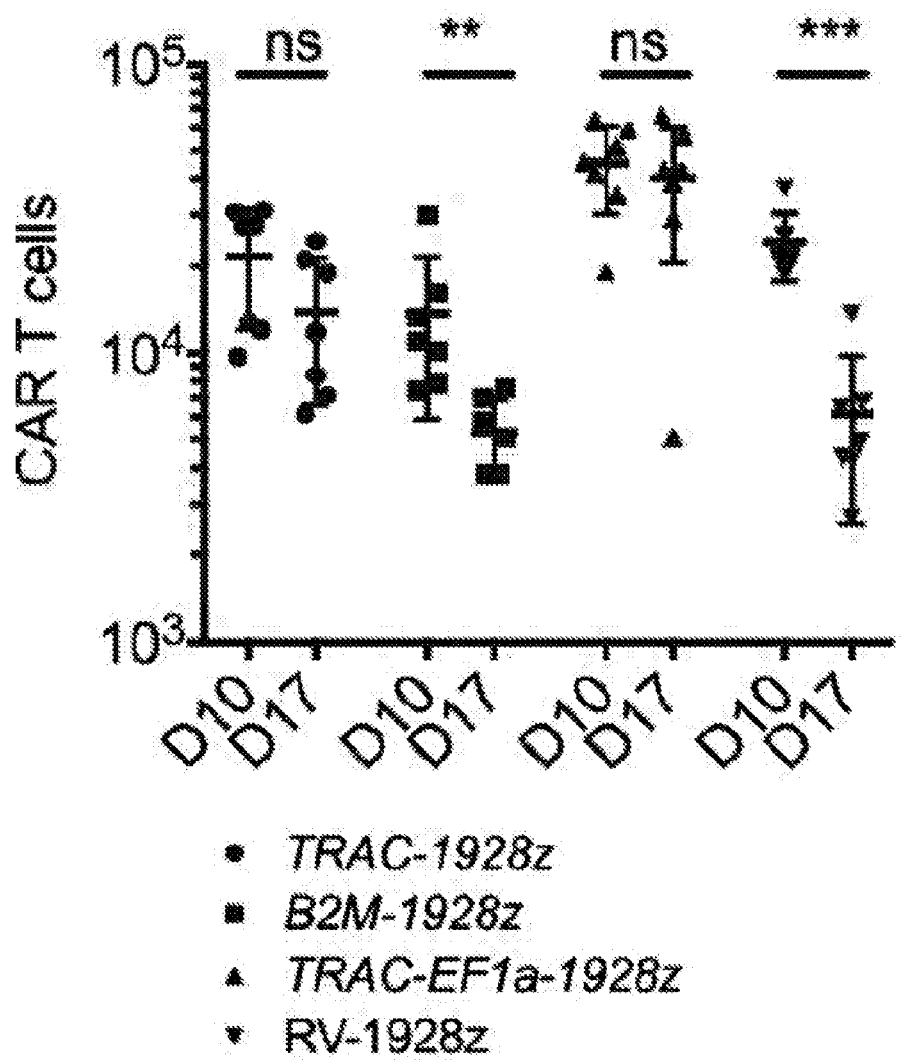
Figure 15E:
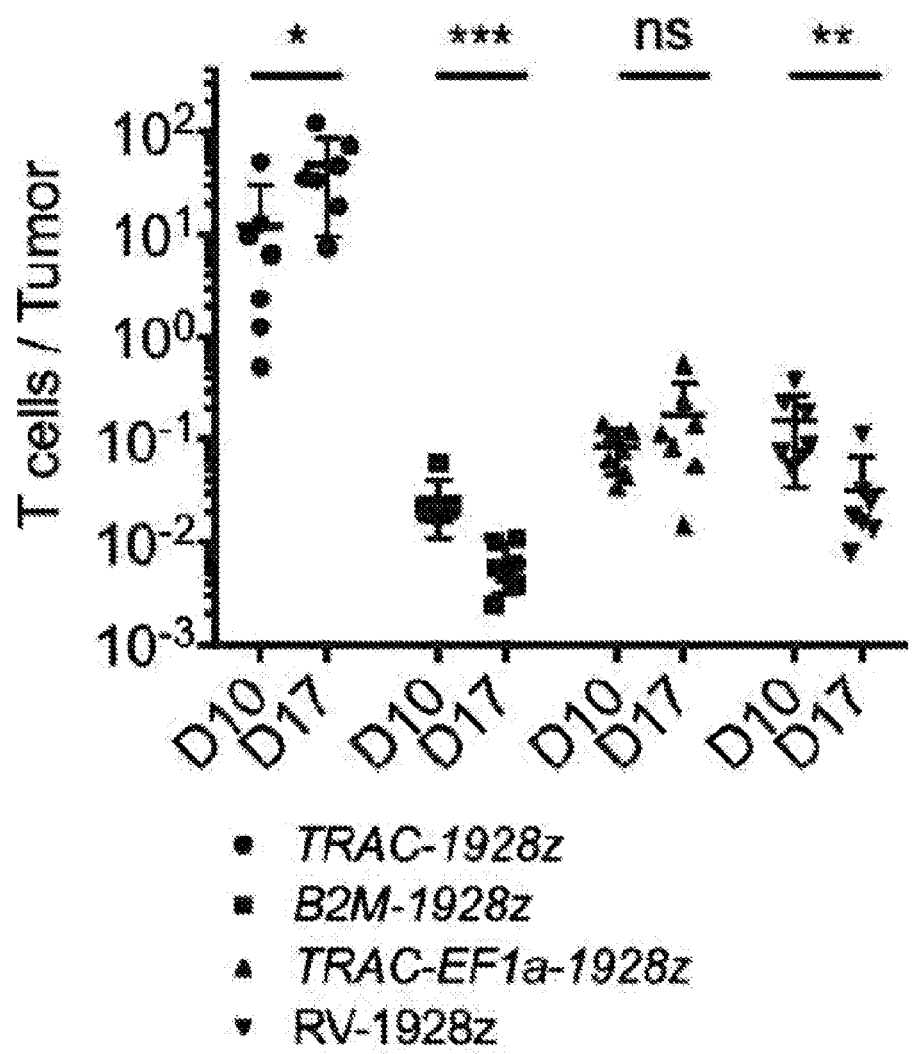
Figure 15F:
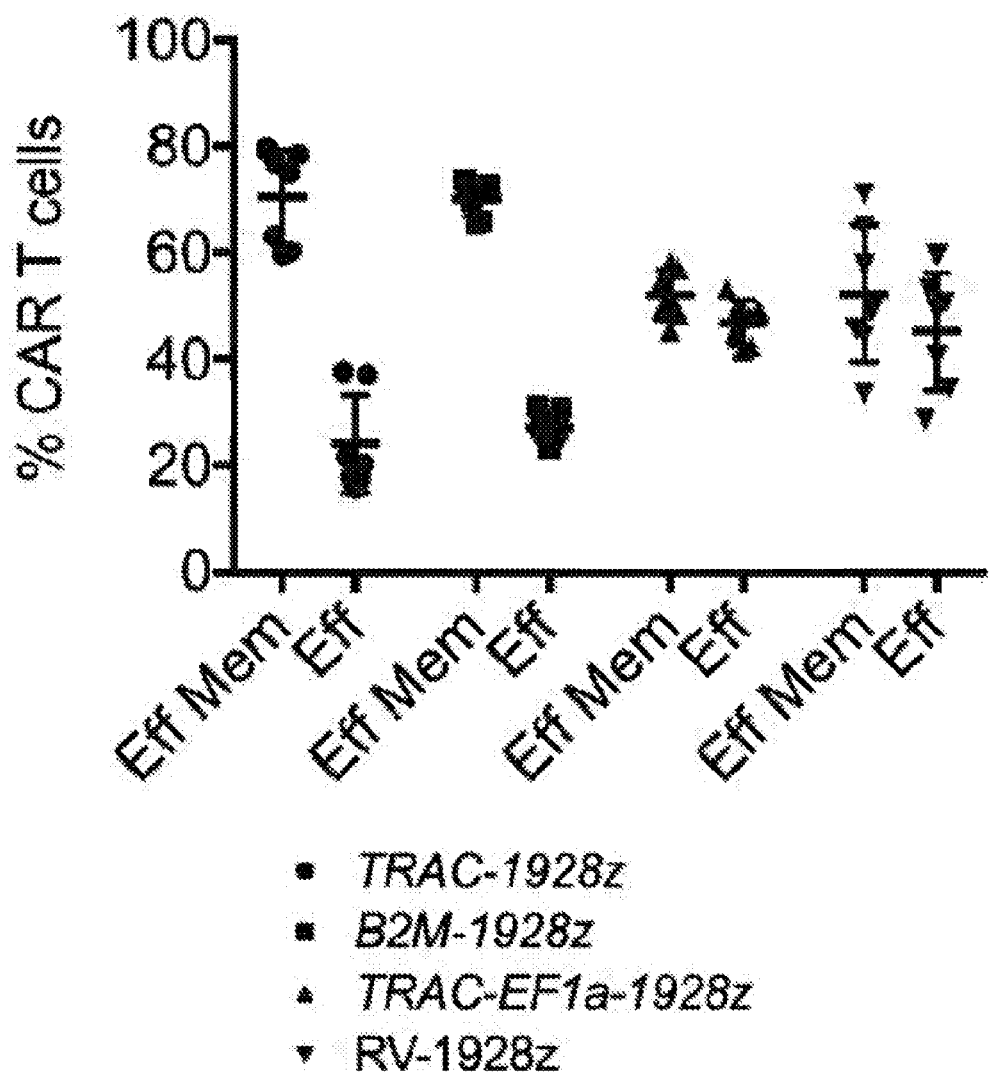
Figure 15G:
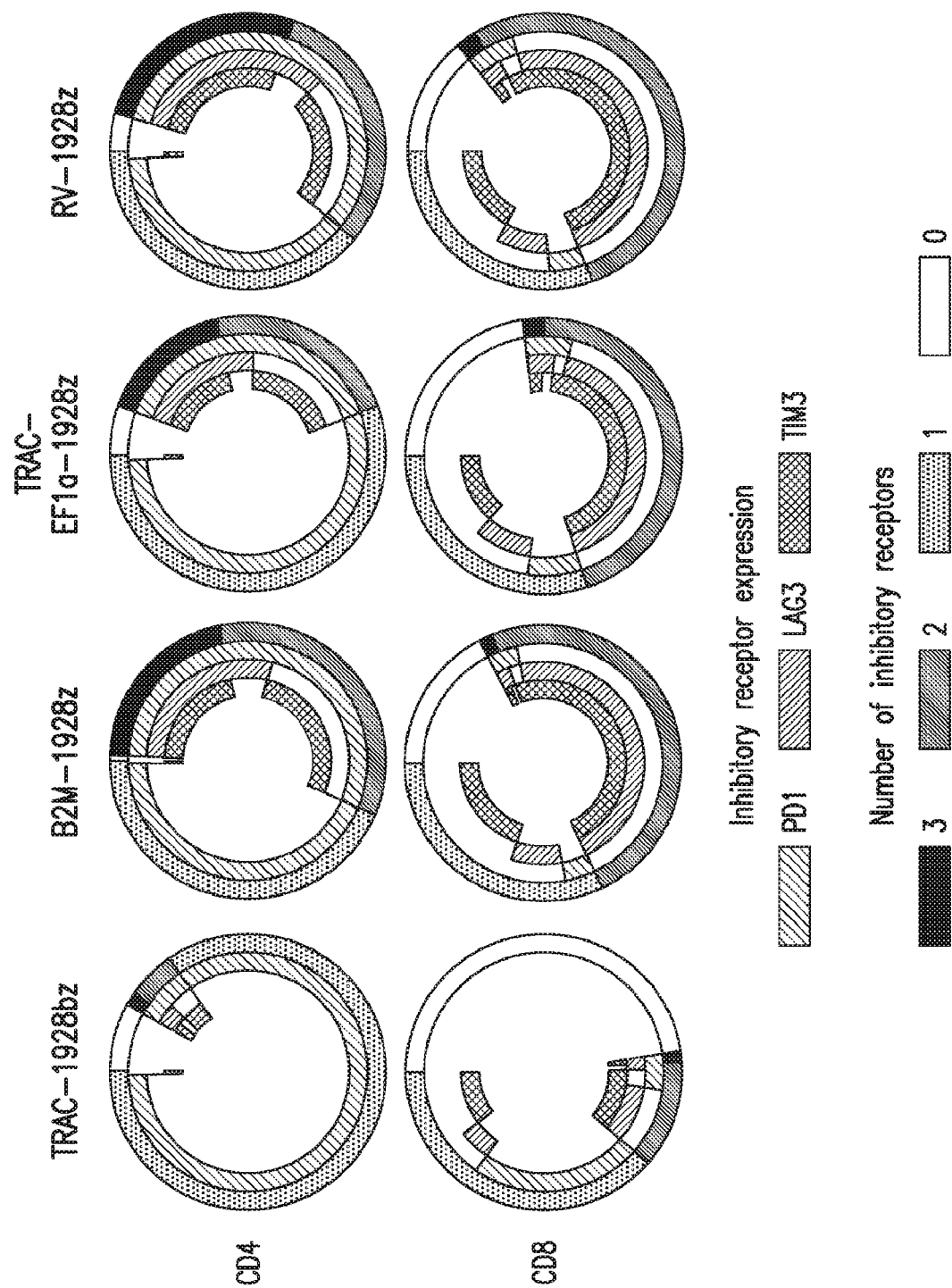

FIGS. 15A-15G show that CAR gene expression using different promoters at distinct loci influences antigen-induced differentiation and exhaustion in vivo. FIG. 15A shows representative FACS analysis of the CAR T-cell differentiation markers after 1, 2 or 4 stimulations on CD19+ target cells. FIG. 15B shows CAR T-cell expansion when stimulated 1, 2 or 4 times on CD19+ target cells over a 48 h period (groups of dots left to right TRAC-LTR-1928z, B2M-1928z, TRAC-1928z and TRAC-EF1a-1928z, respectively). No apparent difference in the proliferation was found between the four 1928z CAR T cells conditions. FIGS. 15C-15E show NALM-6− bearing mice were treated with $1 \times 10^5$ CART cells. At 10 and 17 days after CAR T cell infusion, 7 mice per group were euthanized and bone marrow cells were collected. CAR T cells and NALM-6 cells were analysed and counted with flow cytometry. Each dot represents one mouse. FIG. 15F shows percentage of effector memory ('Eff mem', CD62L−CD45RA−) and effector ('Eff', CD62L−CD45RA+) in the bone marrow CAR T cells at day 17 (n=7 mice). FIG. 15G shows exhaustion marker analysis from bone marrow T cells collected at day 17 and analysed by flow cytometry. Represented as the average percentage of cells expressing the indicated markers (n=7 mice) (inhibitory receptor expression shown from inner to outer rings TIM3, LAG3 and PD1, respectively).

Figure 16A:
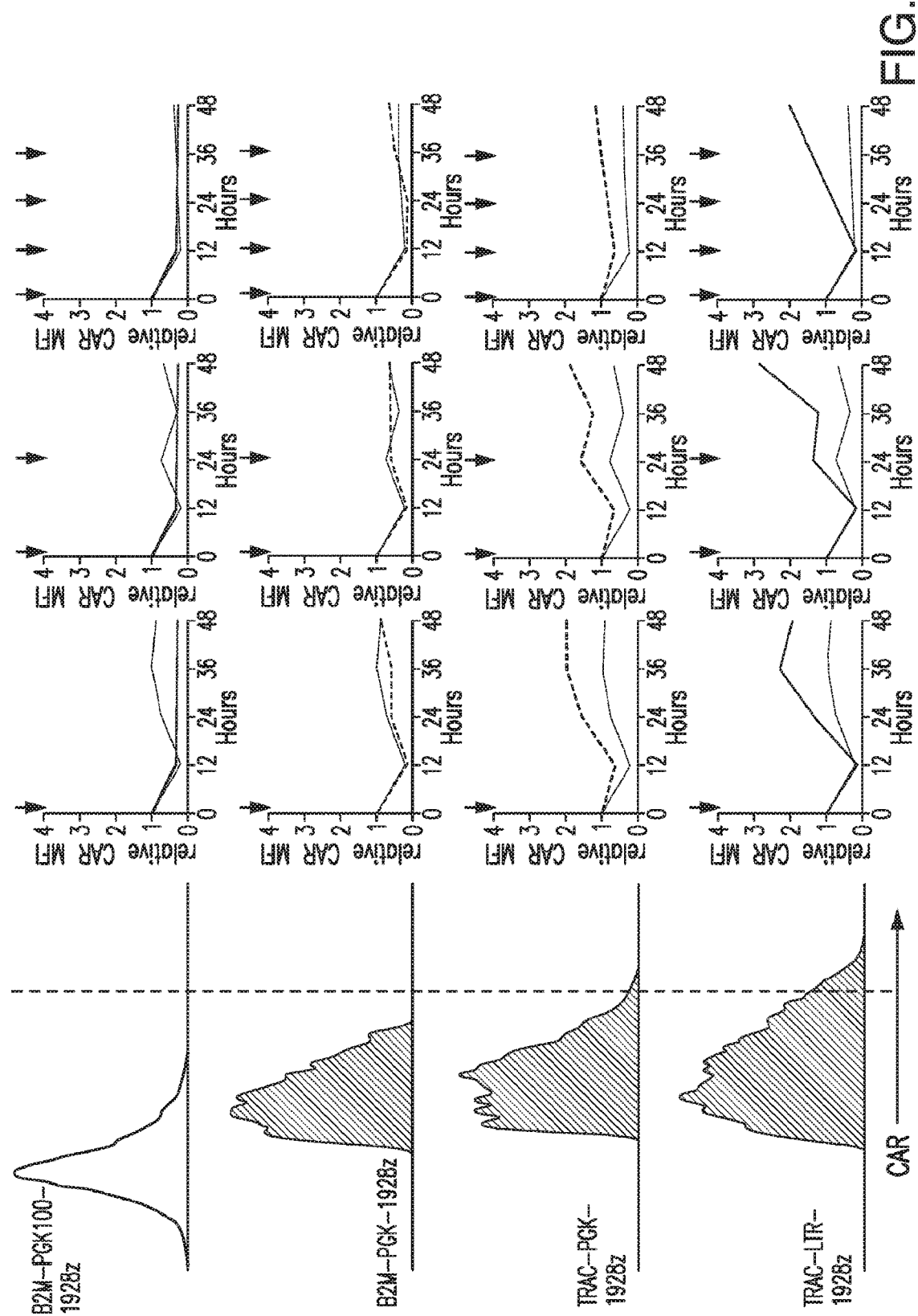
Figure 16A:
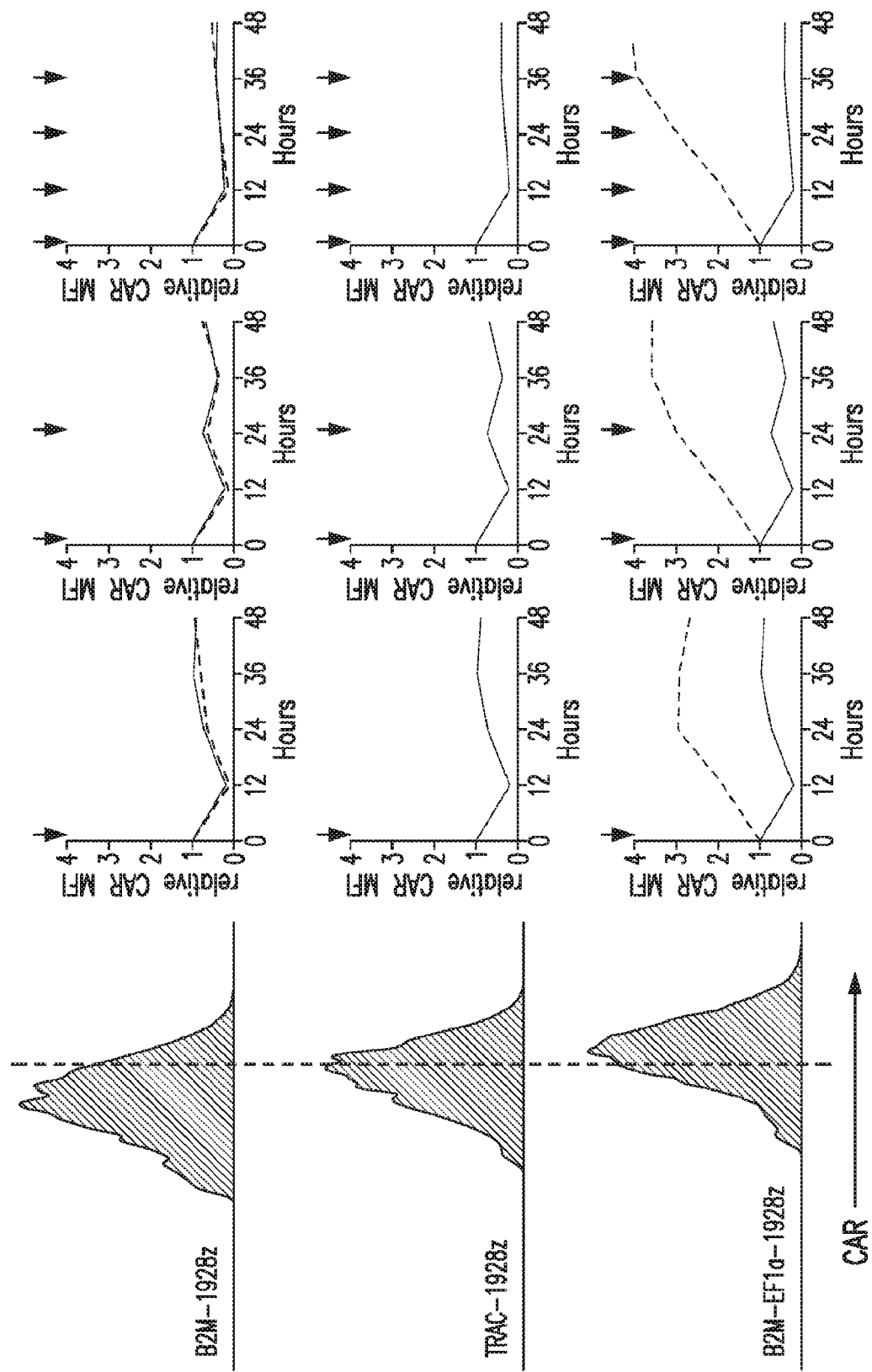
Figure 16A:
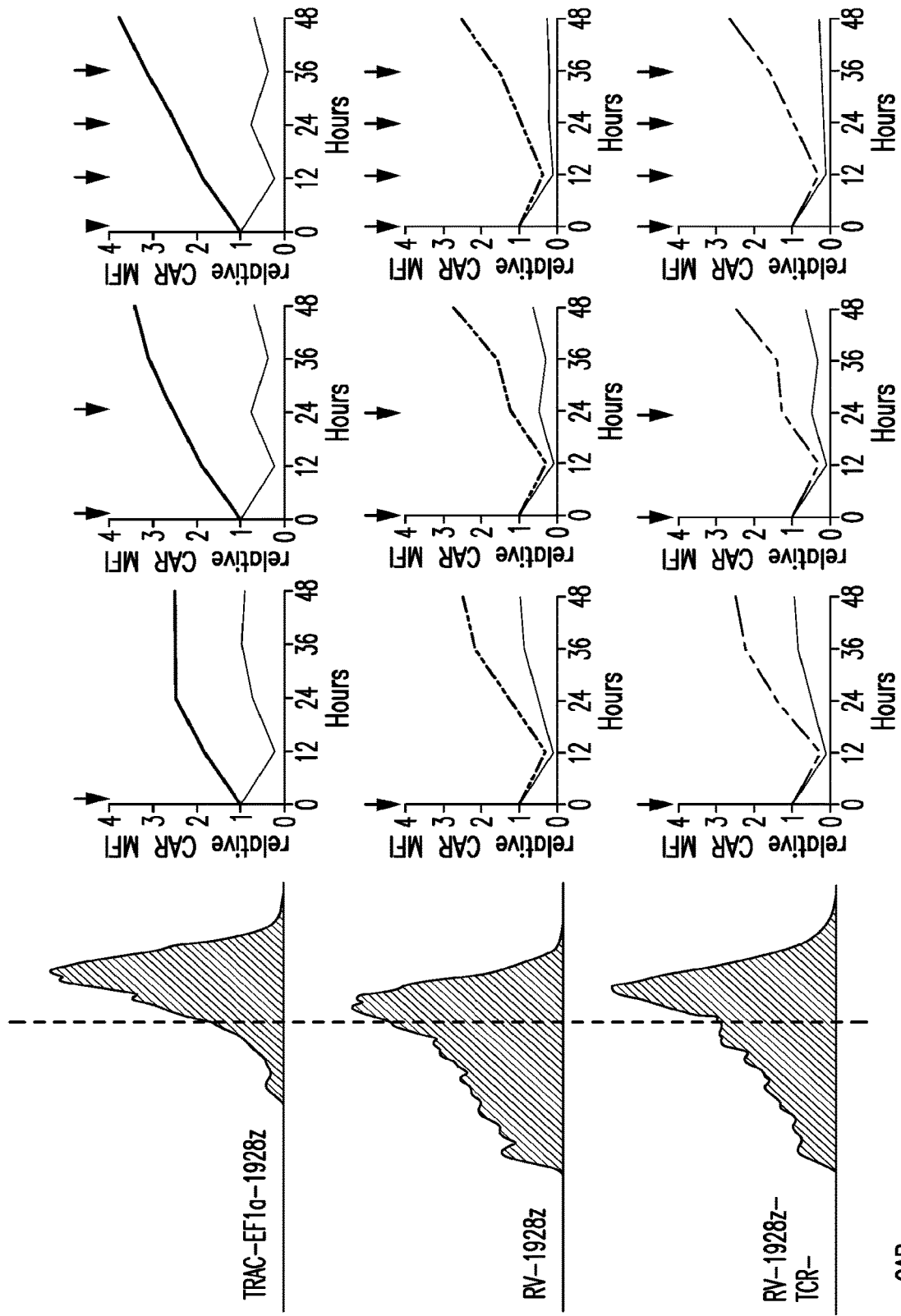
Figure 16B:
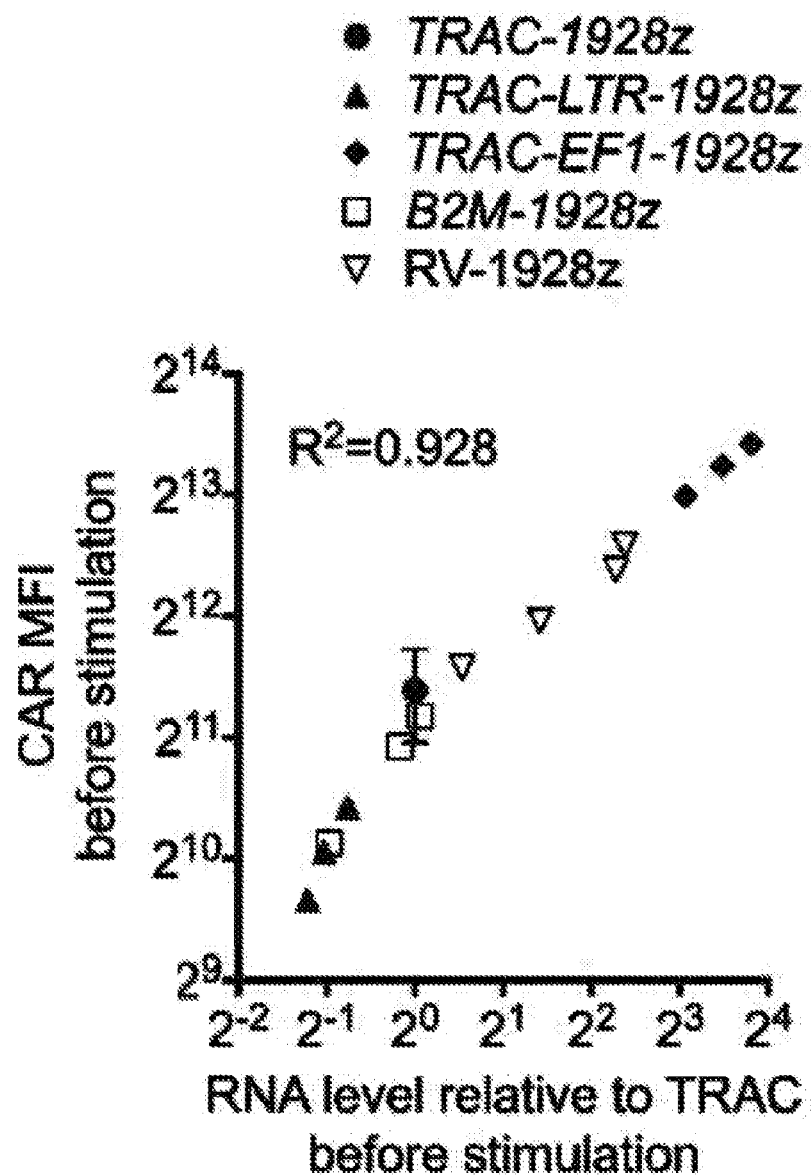

FIGS. 16A-16B show that locus-promoter configuration controls CAR protein expression and transcriptional response upon CAR T cell activation. FIG. 16A: Left panel: representative histogram of the CAR expression 5 days after its vectorization into T cells. Right panel: relative CAR MFI (1=MFI at 0 h) after CAR T cells being activated 1, 2 or 4 times on CD19+ target cells over a 48 h period. FIG. 16B shows a comparison between CAR MFI and CAR RNA relative level before stimulation (n=3 independent experiments on 3 donors). The lower line represents the CAR surface levels in TRAC-1928z CAR T cells.

Figure 17:
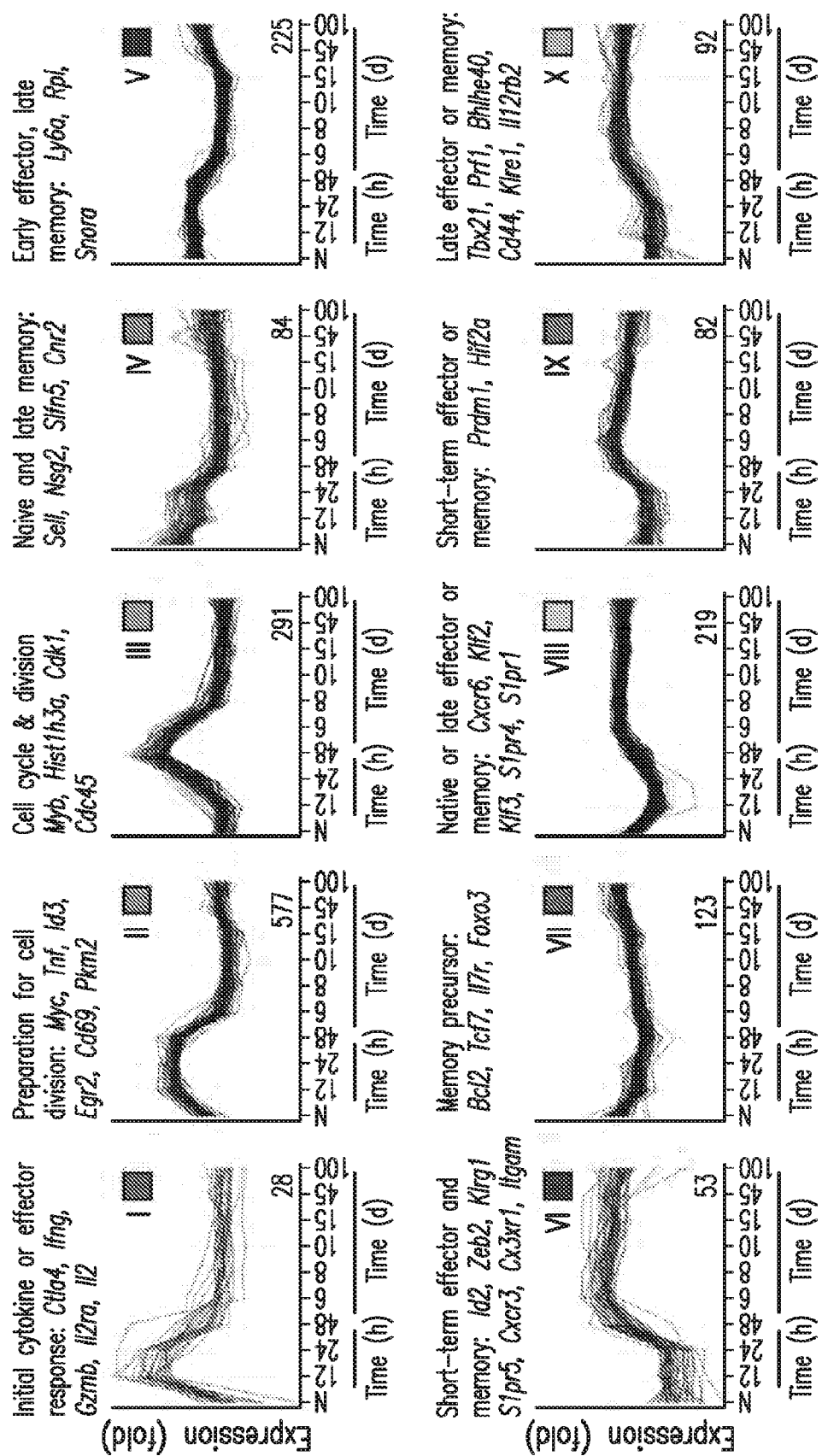

FIG. 17 shows gene-expression profiles associated with the activation and memory formation of CD8+ T cells. Genes upregulated (Up) or downregulated (Down) in infection-exposed OT-I cells relative to their expression in naive OT-I cells was quantified at various time points during infection. Ten clusters with the most dynamic expression by K-means clustering analysis are shown, with a change in expression of over 1.4-fold. Each line represents a single probe; numbers in bottom right corners indicate number of probes; above plots, genes of interest in each cluster (taken from Best et al., Nature Immunol. 14:404-413 (2013)).

FIG. 18 shows Moloney murine leukemia virus (MLV) amino acid sequence of integrase wild type (SEQ ID NO:1) and mutants D124A (SEQ ID NO:2), D124E (SEQ ID NO:3), D124N (SEQ ID NO:4), D124V (SEQ ID NO:5), D183A (SEQ ID NO:6), D183N (SEQ ID NO:7), D124A and D183A (SEQ ID NO:8), D124A and D183N (SEQ ID NO:9), D124E and D183A (SEQ ID NO:10), D124E and D183N (SEQ ID NO:11), D124N and D183A (SEQ ID NO:12), D124N and D183N (SEQ ID NO:13), D124V and D183A (SEQ ID NO:14), and D124V and D183N (SEQ ID NO:15).

Where reference is made in the description of the drawings to color, the drawings have been converted to grayscale.

7. DETAILED DESCRIPTION OF THE INVENTION

The present invention relates to immunotherapy and specifically to targeted cell therapies based on genetically engineering T cells to express a therapeutic transgene under desired conditions. Described herein is a method for generating T cells for immunotherapy by targeting the integration of a therapeutic transgene into the genome of a T cell such that the transgene is placed under control of an endogenous promoter. It will be understood that reference to a transgene (in the singular) as described herein applies also to one or more transgenes (in the plural) unless context indicates otherwise. The invention provides a strategy for T cell therapy that utilizes genome editing to place one or several therapeutic transgenes under the control of one or more endogenous promoters to provide controlled spatio-temporal expression in therapeutic T cells. The invention provides for a T cell to be engineered to express a therapeutic transgene, or a variety of therapeutic transgenes, where expression of the transgene can be made dependent on the location of the T cell (e.g., expression of a transgene only in proximity to a tumor), or at defined time points (e.g., before or after engaging a tumor cell) by use of endogenous promoters that provide for expression accordingly. The cells and methods of the invention can thus be used to increase the efficacy and safety of therapeutic T cells.

The invention relates to placing a therapeutic transgene under control of an endogenous promoter to achieve a desired transgene expression profile in the T cell. An endogenous promoter is selected so as to regulate the expression characteristics of the transgene, for example, the timing of transgene expression and/or the level of transgene expression. Regulating expression of the transgene by placing it under control of an endogenous promoter eliminates the need for administering small molecule drugs to induce expression of a transgene, immunogenic components, and viral vectors encoding internal promoters and transgenes. By utilizing endogenous promoters, the T cells are engineered to autonomously regulate expression of transgenes such that transgene expression, for example, where and when transgene expression is activated, preferably occurs in a defined program that relies on the coordinated endogenous response of the T cell to environmental cues (e.g., proximity to a target antigen, cytokine, and/or costimulatory ligand). Thus, in a specific embodiment, the T cell is engineered such that an endogenous promoter is used that responds to microenvironmental cues, resulting in spatially and temporally predictable transgene expression governed by the endogenous promoter.

In a specific embodiment, the therapeutic transgene encodes a therapeutic protein. In another specific embodiment, the therapeutic transgene encodes a therapeutic RNA.

In a preferred embodiment, the present invention relates to immunotherapy and specifically to targeted cell therapies based on the genetic replacement of a component of the T cell receptor (TCR) complex with sequences encoding a CAR that reprograms T cell specificity and function. As disclosed by way of example herein, gene editing was utilized to generate histocompatible T cell products with stable and homogeneous CAR expression. In addition, the gene editing approach results in the disruption of the targeted gene encoding a component of the TCR complex, which enhances the function of the CAR-T cells by reducing graft versus host reactivity that would have been mediated by the TCR complex. It also can be used for patient auto-immune diseases, usually not included in the clinical Trial. Inactivating their TCR can be used to improve safety for these patients.

In a specific embodiment, described herein is a method for a one-step generation of universal CAR T cells by targeting the integration of a CAR gene cassette, preferably promoter-less, into a gene encoding a polypeptide required for functional expression of a T cell receptor (TCR) complex. The term "universal" denotes that the T cells are not limited to autologous use, but can also be used non-autologously. In one embodiment, this approach can take advantage of the regulated expression of a component of the TCR complex to drive the expression of the CAR in the cell. In addition, the integration of the CAR cassette disrupts or reduces the expression of a polypeptide required for a functional TCR complex, for example, by preventing the proper assembly of the TCR complex at the cell surface, leading to TCR negative cells. The method is suitable with the commonly used genome editing platforms, such as zinc-finger nuclease (ZFN), transcription activator-like effector nuclease (TALEN), and clustered regularly-interspersed short palindromic repeats (CRISPR) associated protein 9 (Cas9), Cpf1, Meganuclease or a Mega-Tal, and results in homologous recombination at a target site in the genome of the cell. As disclosed herein, conditions were established yielding up to 50% of universal CAR T cells, combining target gene disruption and CAR targeted insertion in a single step. The results disclosed herein shows that the methods utilizing an endogenous TCR promoter provided the benefits of single integration as well as consistent and predictable expression. In addition, the method provided unexpected benefits of improved T cell function and persistence. Most importantly, T cells expressing the CAR from the TCR locus exhibited higher in vitro and in vivo tumor lysis activity, increased proliferation and persistence than retrovirally-transduced CAR T cells, while removing their Graft versus host disease potential. Moreover, this new methodology opens the possibility of generating autologous CAR T cells for patients suffering from autoimmune disorders. The methods described herein, which combine the scalability of universal T cell manufacturing with the uniformity and safety of targeted CAR gene integration, are useful for CAR therapy and for the development of off-the-shelf CAR therapy.

7.1 T Cells

In one embodiment, the invention provides a T cell, wherein a therapeutic transgene is integrated at a site within the genome of the cell such that expression of the transgene is under control of an endogenous promoter of the T cell. In a preferred embodiment, the invention provides a T cell, wherein a recombinant nucleic acid sequence encoding a chimeric antigen receptor (CAR) is integrated at a site within the genome of the cell such that the CAR is expressed by the cell at the surface of the cell, and wherein integration of the nucleic acid encoding the CAR at the site reduces or prevents expression of a functional T cell receptor (TCR) complex at the surface of the cell. In a preferred embodiment, the recombinant cells can be used to enhance or provide an immune response against a desired target. In another embodiment, the recombinant cells can be used to inhibit an undesirable immune response. Preferably, the cells are derived from a human (are of human origin prior to being made recombinant) (and human-derived cells are particularly preferred for administration to a human in the methods of treatment of the invention).

In a specific embodiment, the present invention relates to the targeted integration of a promoter-less expression cassette into a chromosomal transcription unit in T cells, preferably human T cells, to take advantage of an endogenous promoter to optimize transgene expression and enhance the function of the engineered T cells, wherein the transgene is a CAR or other therapeutic transgene. In a preferred embodiment, by engineering T cells this way, stable and homogenous CAR expression was obtained, and T cell function and persistence was enhanced relative to previous methods for CAR therapy. Depending on the cassette design, the method can be used to disrupt, or not, the expression of the endogenous gene. In the case where endogenous gene expression is disrupted, the endogenous gene is a non-essential gene, i.e., a gene that is not necessary for cell viability or proliferation of the cell. In a particular embodiment, the therapeutic transgene is a CAR. In a preferred embodiment, the integration of the CAR-encoding nucleic acid sequences disrupts the expression of an endogenous gene encoding a protein required for a functional T cell receptor complex. This approach can be applied to any gene, having either stable, spatially, and/or temporally regulated expression. In a specific embodiment, the targeting of a gene that is expressed from only one allele, for example, TCR alpha, TCR beta, Y or X chromosome-specific genes, can be utilized to ensure that only one transgene copy per cell is expressed. Each T cells expresses a unique T cell receptor resulting from association of one recombined TCR alpha and one recombined TCR beta chains. The process of generating the TCR diversity happens during lymphopoiesis in the thymus, where both TCR alpha and beta genes recombine (VJ and VDJ recombination respectively), and only one allele of each gene is expressed through a process called allele exclusion (Honey, *Nat. Rev. Immunol.* 5, 95 doi:10.1038/nri1560 (2005)). In the case of targeting a recombined TCR alpha or beta chain, this process provides that only one copy of the integrated CAR will be expressed. The other allele can be targeted but would not result in CAR expression.

The T cells of the invention are immune cells of the lymphoid lineage. T cells express the T cell receptor (TCR), with most cells expressing α and β chains and a smaller population expressing γ and δ chains. T cells useful as immune cells of the invention can be CD4+ or CD8+ and can include, but are not limited to, T helper cells (CD4+), cytotoxic T cells (also referred to as cytotoxic T lymphocytes, CTL; CD8+ T cells), and memory T cells, including central memory T cells (TCM), stem memory T cells (TSCM), stem-cell-like memory T cells (or stem-like memory T cells), and effector memory T cells, for example, $T_{EM}$ cells and $T_{EMRA}$ (CD45RA+) cells, effector T cells, Th1 cells, Th2 cells, Th9 cells, Th17 cells, Th22 cells, Tfh (follicular helper) cells, T regulatory cells, natural killer T cells, mucosal associated invariant T cells (MAIT), and γδ T cells. Major T cell subtypes include $T_N$ (naive), $T_{SCM}$ (stem cell memory), $T_{CM}$ (central memory), $T_{TM}$ (Transitional Memory), $T_{EM}$ (Effector memory), and $T_{TE}$ (Terminal Effector). In one embodiment, the T cells of the invention are immunostimulatory cells, i.e., cells that mediate an immune response. Exemplary T cells that are immunostimulatory include, but are not limited to, T helper cells (CD4+), cytotoxic T cells (also referred to as cytotoxic T lymphocytes, CTL; CD8+ T cells), and memory T cells, including central memory T cells (TCM), stem memory T cells (TSCM), stem-cell-like memory T cells (or stem-like memory T cells), and effector memory T cells, for example, $T_{EM}$ cells and $T_{EMRA}$ (CD45RA+) cells, effector T cells, Th1 cells, Th2 cells, Th9 cells, Th17 cells, Th22 cells, Tfh (follicular helper) cells, natural killer T cells, mucosal associated invariant T cells (MAIT), and γδ T cells. In another embodiment, the T cells of the invention are immunoinhibitory cells, i.e., cells that inhibit an immune response. Exemplary T cells that are immunoinhibitory include regulatory T cells (T regulatory cells, Treg) and follicular regulatory T cells (Tfh) cells. T cells can optionally be generated from embryonic stem cells or induced pluripotent stem cells (iPSCs)(see, for example, Themeli et al., *Nat. Biotechnol.* 31(10):928-933 (2013)). Optionally, precursor cells of T cells that can be used, which recombinantly express a transgene, preferably a CAR, are, by way of example, hematopoietic stem and/or progenitor cells. Hematopoietic stem and/or progenitor cells can be derived from bone marrow, umbilical cord blood, adult peripheral blood after cytokine mobilization, and the like, by methods known in the art, and then are genetically engineered to recombinantly express a transgene, preferably a CAR. Particularly useful precursor cells are those that can differentiate into the lymphoid lineage, for example, hematopoietic stem cells or progenitor cells of the lymphoid lineage that can differentiate into T cells. In another embodiment, an iPSC can be utilized as a cell for expression of a transgene. In a preferred embodiment, an iPSC can be utilized as a cell for expression of a CAR, wherein a recombinant nucleic acid encoding a CAR is integrated into a site in the genome of the cell such that the CAR is expressed by the cell at the surface of the cell, and wherein integration of the nucleic acid encoding the CAR at the site reduces or prevents expression of a functional T cell receptor complex at the surface of the cell. In another embodiment, a T cell, preferably a CAR T cell, as disclosed herein can be used to produce an iPSC. It is understood that embodiments disclosed herein relating to a T cell shall be deemed as applicable to an iPSC or stem cell, as context permits. An iPSC can be used to produce a T cell of the invention, and an iPSC can also be derived therefrom.

The type of T cell selected for expressing a transgene will take into consideration whether it is desired to stimulate an immune response or inhibit an immune response. For example, a regulatory T cell (CD4+CD25high FoxpP3+) would be used for treating a subject in need of an inhibited immune response such as someone having an autoimmune disease and, by way of example, the T cell would express a transgene encoding an immuno-inhibitory cytokine, while CD4+(except Treg)/CD8+ T cells are used to treat a subject in need of a stimulated immune response, for example, a subject having cancer, and, by way of example, the T cell would express an immunostimulatory cytokine.

T cells can be isolated by methods well known in the art, including commercially available isolation methods (see, for example, Rowland-Jones et al., *Lymphocytes: A Practical Approach*, Oxford University Press, New York (1999)). Sources for the T cells include, but are not limited to, peripheral blood, umbilical cord blood, bone marrow, or other sources of hematopoietic cells. Various techniques can be employed to separate the cells to isolate or enrich for desired immune cells such as T cells. For instance, negative selection methods can be used to remove cells that are not the desired immune cells. Additionally, positive selection methods can be used to isolate or enrich for desired T cells, or a combination of positive and negative selection methods can be employed. Monoclonal antibodies (MAbs) are particularly useful for identifying markers associated with particular cell lineages and/or stages of differentiation for both positive and negative selections. If a particular type of T cell is to be isolated, various cell surface markers or combinations of markers, including but not limited to, CD3, CD4, CD8, CD34 (for hematopoietic stem and progenitor cells) and the like, can be used to separate the cells, as is well known in the art (see Kearse, *T Cell Protocols: Development and Activation*, Humana Press, Totowa NJ (2000); De Libero, *T Cell Protocols*, Vol. 514 of *Methods in Molecular Biology*, Humana Press, Totowa NJ (2009)).

Methods for isolating and expanding regulatory T cells are well known in the art (see, for example, Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. Tranplant.* 13:3010-3020 (2013); Lee et al., *Cancer Res.* 71:2871-2881 (2011); MacDonald et al., *J Clin. Invest.* 126:1413-1424 (2016)). In vitro generation of regulatory T cells (iTregs) has also been described (see, for example, Lan et al., *J. Mol. Cell. Biol.* 4:22-28 (2012); Yamagiwa et al., *J. Immunol.* 166:7282-7289 (2001); Zheng et al., *J. Immunol.* 169:4183-4189 (2002)). Generally, regulatory T cells of the invention are CD4+, for example, CD4+CD25+, and in particular CD4+CD127$^{lo/-}$CD25+. Such regulatory T cells express Foxp3 (forkhead box P3), which is in the forkhead/winged-helix family of transcription factors (Bluestone et al., *J. Clin. Invest.* 125:2250-2260 (2015); Riley et al., *Immunity* 30:656-665 (2009)). A regulatory T cell that is an immunoinhibitory cell of the invention can also be a CD8+ regulatory T cell (Guillonneau et al., *Curr. Opin. Organ Transplant.* 15:751-756 (2010)). Methods for isolating and expanding regulatory T cells are also commercially available (see, for example, BD Biosciences, San Jose, CA;

STEMCELL Technologies Inc., Vancouver, Canada; eBioscience, San Diego, CA; Invitrogen, Carlsbad, CA). An immunoinhibitory T cell of the invention can also be a follicular regulatory T cell (T(FR)) (Sage et al., *Nat. Immunol.* 14:152-161 (2013)). In a particular embodiment, the follicular regulatory T cells of the invention are CD4$^+$ CXCR5$^+$ and express Foxp3 (Sage et al., supra, 2013).

Procedures for separation of cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique (see, for example, Recktenwald et al., *Cell Separation Methods and Applications*, Marcel Dekker, Inc., New York (1998)).

The T cells can be autologous or non-autologous to the subject to which they are administered in the methods of treatment of the invention. Autologous cells are isolated from the subject to which the engineered T cells are to be administered. In a preferred embodiment, autologous cells are isolated from the subject to which the engineered cells recombinantly expressing a CAR are to be administered. Optionally, the cells can be obtained by leukapheresis, where leukocytes are selectively removed from withdrawn blood, made recombinant, and then retransfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. For both autologous and and non-autologous cells, the cells can optionally be cryopreserved until ready to be used for genetic manipulation and/or administration to a subject using methods well known in the art.

Various methods for isolating T cells that can be used for recombinant expression of a CAR have been described previously, and can be used, including but not limited to, using peripheral donor lymphocytes (Sadelain et al., *Nat. Rev. Cancer* 3:35-45 (2003); Morgan et al., Science 314: 126-129 (2006), using lymphocyte cultures derived from tumor infiltrating lymphocytes (TILs) in tumor biopsies (Panelli et al., *J. Immunol.* 164:495-504 (2000); Panelli et al., *J. Immunol.* 164:4382-4392 (2000)), and using selectively in vitro-expanded antigen-specific peripheral blood leukocytes employing artificial antigen-presenting cells (AAPCs) or dendritic cells (Dupont et al., *Cancer Res.* 65:5417-5427 (2005); Papanicolaou et al., *Blood* 102:2498-2505 (2003)). In the case of using stem cells, the cells can be isolated by methods well known in the art (see, for example, Klug et al., *Hematopoietic Stem Cell Protocols*, Humana Press, New Jersey (2002); Freshney et al., *Culture of Human Stem Cells*, John Wiley & Sons (2007)).

In a specific embodiment, isolated T cells are genetically engineered ex vivo for recombinant expression of a transgene. In a preferred embodiment, isolated T cells are genetically engineered ex vivo for recombinant expression of a CAR. The cells can be genetically engineered for recombinant expression by methods well known in the art.

In another embodiment, the invention provides T cells that recognize and are sensitized to a target antigen that are then genetically engineered for recombinant expression of a transgene. Such T cells can but need not express a CAR that binds to a target antigen, since the cells already are target antigen-specific so that their immune response (for example, cytotoxicity) is stimulated specifically by such target antigen. Such T cells that recognize and are sensitized to a target antigen can be obtained by known methods, by way of example, in vitro sensitization methods using naive T cells (see, for example, Wolfl et al., *Nat. Protocols* 9:950-966 (2014)) or hematopoietic progenitor cells (see van Lent et al., *J. Immunol.* 179:4959-4968 (2007)); or obtained from a subject that has been exposed to and is mounting an immune response against the target antigen (i.e., in vivo sensitized T cells). Methods for isolating an antigen-specific T cell from a subject are well known in the art. Such methods include, but are not limited to, a cytokine capture system or cytokine secretion assay, which is based on the secretion of cytokines from antigen stimulated T cells that can be used to identify and isolate antigen-specific cells, and expansion of cells in vitro (see Assenmacher et al., *Cytometric Cytokine Secretion Assay*, in *Analyzing T Cell Responses: How to Analyze Cellular Immune Responses Against Tumor Associated Antigens*, Nagorsen et al., eds., Chapter 10, pp. 183-195, Springer, The Netherlands (2005); Haney et al., *J. Immunol. Methods* 369:33-41 (2011); Bunos et al., *Vox Sanguinis* DOI: 10.1111/vox.12291 (2015); Montes et al., *Clin. Exp. Immunol.* 142:292-302 (2005); Adusumilli et al., *Sci Transl Med.* 6:261ra151 (2014)). Such cytokines include, but are not limited to interferon-γ and tumor necrosis factor-α. Methods for isolating an antigen-specific regulatory T cell from a subject are well known in the art (see, for example, Noyan et al., *Eur. J. Immunol.* 44:2592-2602 (2014); Brusko et al., *PLoS One* 5(7) e11726 (doi: 10.1371) (2010); Bacher et al., *Mucosal Immunol.* 7:916-928 (2014); Koenen et al., *J. Immunol.* 174:7573-7583 (2005)). The antigen-specific T cells can be isolated using well known techniques as described above for isolating T cells, which include, but are not limited to, flow cytometry, magnetic beads, panning on a solid phase, and so forth. Antigen-specific T cell isolation techniques are also commercially available, which can be used or adapted for clinical applications (see, for example, Miltenyi Biotec, Cambridge, MA; Proimmune, Oxford, UK; and the like).

The T cells can be subjected to conditions that favor maintenance or expansion of the cells (see Kearse, *T Cell Protocols: Development and Activation*, Humana Press, Totowa NJ (2000); De Libero, *T Cell Protocols*, Vol. 514 of *Methods in Molecular Biology*, Humana Press, Totowa NJ (2009); Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1999); Quinn et al., *Hum. Gene Ther.* 9:1457-1467 (1998); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011); MacDonald et al., *J. Clin. Invest.* 126:1413-1424 (2016); see also commercially available methods such as Dynabeads™ human T cell activator products, Thermo Fisher Scientific, Waltham, MA)). The cells can optionally be expanded prior to or after ex vivo genetic engineering. Expansion of the cells is particularly useful to increase the number of cells for administration to a subject. Such methods for expansion of immune cells such as T cells are well known in the art (see Kaiser et al., *Cancer Gene Therapy* 22:72-78 (2015); Wolfl et al., *Nat. Protocols* 9:950-966 (2014)). Furthermore, the cells can optionally be cryopreserved after isolation and/or genetic engineering, and/or expansion of genetically engineered cells (see Kaiser et al., supra, 2015)). Methods for cyropreserving cells are well known in the art (see, for example, Freshney, *Culture of Animal Cells: A Manual of Basic Techniques*, 4th ed., Wiley-Liss, New York (2000); Harrison and Rae, *General Techniques of Cell Culture*, Cambridge University Press (1997)).

7.2 Targeted Integration Methods

With respect to generating cells recombinantly expressing a transgene under control of an endogenous T cell promoter, the transgene is introduced into the genome of the T cell. In a preferred embodiment, with respect to generating cells recombinantly expressing a CAR, a nucleic acid encoding the CAR is introduced into the T cell. Traditionally, such methods have utilized a suitable expression vector, in which case the T cells are transduced with a transgene, for example, a nucleic acid encoding a CAR. In the present invention, a transgene is cloned into a targeting construct, which provides for targeted integration of the transgene at a site within the genome. In a preferred embodiment, a nucleic acid encoding a CAR is cloned into a targeting construct, which provides for targeted integration of the nucleic acid sequence encoding the CAR at a site within the genome, in a particular embodiment, a site that disrupts expression of a gene encoding a protein required for expression of a functional TCR complex in the cell. For example, a transgene, for example, a polynucleotide encoding a CAR, of the invention can be cloned into a suitable targeting construct, or a suitable vector such as a retroviral vector, and introduced into the T cell using well known molecular biology techniques (see Ausubel et al., Current Protocols in Molecular Biology, John Wiley and Sons, Baltimore, MD (1999)).

Any suitable targeting construct suitable for expression in a cell of the invention, particularly a human T cell, can be employed. In a particular embodiment, the targeting construct is compatible for use with a homologous recombination system suitable for targeted integration of the nucleic acid sequence (transgene) at a site within the genome of the cell. Exemplary homologous recombination systems are well known in the art and include, but are not limited to, technologies utilizing a nuclease, for example, transcription activator-like effector nucleases (TALENs), Zinc-finger nucleases (ZFNs), clustered regularly interspaced short palindromic repeats (CRISPRs) systems such as and CRISPR associated protein 9 (Cas9) and Cpf1, and/or Meganuclease or a Mega-Tal (fusion of a Tal domain and a Meganuclease) and the like, which provide for homologous recombination, for example, a desired target site within the genome of the cell (see Examples; see also U.S. Pat. No. 8,697,359; US publication 20140068797; Gaj et al., *Trends Biotechnol.* 31:397-405 (2013); Gersbach et al., *Nucl. Acids Res.* 39:7868-7878 (2011); Vasileva, et al. *Cell Death Dis.* 6:e1831. (Jul. 23, 2015); Sontheimer, *Hum. Gene Ther.* 26(7):413-424 (2015); Osborn et al., *Mol. Ther.* 24(3):570-581 (2016))). Such methods are well known in the art and commercially available (ThermoFisher, Carlsbad, CA; GenScript, Piscataway, NJ; Clontech, Mountain View, CA). Other CRISPR based systems include pyrogen and *Aureus*. Such methods can be used to carry out or promote homologous recombination.

7.3 Vectors and Targeting Constructs

A suitable targeting construct can comprise any nucleic acid sequence that is compatible with a homologous recombination system employed in the invention. In one embodiment, the targeting construct comprises adeno-associated virus (AAV) sequences. The targeting construct can have nucleic acid sequences from one or more AAV serotypes. For example, the targeting construct can comprise AAV2 sequences or other serotype sequences such as AAV5. The AAV nucleic acid sequences that function as part of a targeting construct can be packaged in several natural or recombinant AAV capsids or particles. In a particular embodiment, the AAV particle is AAV6. In a particular embodiment, an AAV2-based targeting construct is delivered to the target cell using AAV6 viral particles. In a particular embodiment, the AAV sequences are AAV2, AAV5 or AAV6 sequences. In a particular embodiment, the AAV sequences are from AAV2. In another particular embodiment, the AAV sequences are from AAV6. In another particular embodiment, the targeting construct comprises in 5' to 3' order: a first viral sequence, a left homology arm, a nucleic acid sequence encoding a self-cleaving porcine teschovirus 2A, a transgene, a polyadenylation sequence, a right homology arm and a second viral sequence. In a preferred embodiment, the targeting construct comprises in 5' to 3' order: a first viral sequence, a left homology arm, a nucleic acid sequence encoding a self-cleaving porcine teschovirus 2A, a nucleic acid sequence encoding a CAR, a polyadenylation sequence, a right homology arm and a second viral sequence. Another suitable targeting construct can comprise sequences from an integrative-deficient Lentivirus (see, for example, Wanisch et al., *Mol. Ther.* 17(8): 1316-1332 (2009)). In a particular embodiment, the viral nucleic acid sequence comprises sequences of an integrative-deficient Lentivirus. It is understood that any suitable targeting construction compatible with a homologous recombination system employed can be utilized.

Viral vector sequences that can be included in a target construct include but are not limited to retroviral, adenoviral, lentiviral, and adeno-associated viral vectors, vaccinia virus, bovine papilloma virus derived vectors, and herpes virus vectors, such as Epstein-Barr Virus (see, for example, Miller, *Hum. Gene Ther.* 1(1):5-14 (1990); Friedman, *Science* 244:1275-1281 (1989); Eglitis et al., *BioTechniques* 6:608-614 (1988); Tolstoshev et al., *Current Opin. Biotechnol.* 1:55-61 (1990); Sharp, *Lancet* 337:1277-1278 (1991); Cornetta et al., *Prog. Nucleic Acid Res. Mol. Biol.* 36:311-322 (1989); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995); Rosenberg et al., *N. Engl. J. Med.* 323:370 (1990); Anderson et al., U.S. Pat. No. 5,399,346; Scholler et al., *Sci. Transl. Med.* 4:132-153 (2012; Parente-Pereira et al., *J. Biol. Methods* 1(2):e7 (1-9)(2014); Lamers et al., *Blood* 117(1):72-82 (2011); Reviere et al., *Proc. Natl. Acad. Sci. USA* 92:6733-6737 (1995); Wang et al., *Gene Therapy* 15:1454-1459 (2008)).

Particularly useful vectors for generating a target construct that provides transgene vectorization for homologous recombination-mediated targeting include, but are not limited to, recombinant Adeno-Associated Virus (rAAV), recombinant non-integrating lentivirus (rNILV), recombinant non-integrating gamma-retrovirus (rNIgRV), single-stranded DNA (linear or circular), and the like. Such vectors can be used to introduce a transgene into a T cell of the invention by making a target construct, as described above.

In one embodiment, the vector is a recombinant non-integrating gamma-retrovirus (rNIgRV). In one embodiment, the rNIgRVs is obtained by using a gamma-retrovirus integrase that is mutated at the DDE motif, which abolishes integrase activity. Thus, a gamma-retrovirus is converted to a non-integrating gamma-retrovirus by inactivation of its integrase (see Example 4 and FIG. 18). In a particular embodiment, the integrase comprises a DDE mutation selected from the group consisting of D164A, D164E, D164N, D164V, D183A, D183N, D164A and D168A, D164A and D183N, D164N and D183A, D164N and D183N, D164V and D168A, D164V and D183N, D164V and D183A, and D164V and D183N. Such a rNIgRV vector is advantageous since it is easier and cheaper to produce than traditionally used vectors.

It will be readily understood that a rNIgRV vector can be utilized to introduce any desired DNA into any cell. Thus, a rNIgRV can be used to introduce any type of desired DNA into a cell of any type in which the vector functions.

In methods of the present invention that employ an endogenous promoter for controlling the expression of a transgene that is integrated within a site in the genome of a cell, the targeting construct preferably is promoter-less. In a preferred embodiment of methods of the present invention that employ an endogenous promoter for controlling the expression of a nucleic acid sequence encoding a CAR that is integrated within a site in the genome of a cell, the targeting construct preferably is promoter-less. Such a construct allows the integration of the transgene, such as the nucleic acid sequence encoding a CAR, into a site within the genome such that the integrated nucleic acid sequence (transgene) is under the control of an endogenous promoter. In one embodiment, the endogenous promoter is a TCR promoter. In a particular embodiment, the endogenous promoter is a promoter of a gene encoding a T cell receptor alpha chain, T cell receptor beta chain, CD3 gamma chain, CD3 delta chain, CD3 epsilon chain, or CD3 zeta chain. In a specific embodiment, the nucleic acid sequences encoding a CAR are integrated.

Although the methods of the invention preferably utilize an endogenous promoter to control expression of the recombinant transgene, such as the nucleic acid sequence encoding a CAR, it is understood that a vector that employs a suitable promoter for expression in a particular host cell can be utilized, for example, a vector that incorporates an endogenous promoter such as a TCR promoter. Such a vector could provide for expression in a manner similar to that provided by an endogenous promoter, such as a TCR promoter. Such a vector can be useful, for example, if the site of integration does not provide for efficient expression of a transgene, or if disruption of the endogenous gene controlled by the endogenous promoter would be detrimental to the T cell or would result in a decrease in its effectiveness in T cell therapy. In a preferred embodiment, such a vector can be useful, for example, if the site of integration does not provide for efficient expression of nucleic acid sequence encoding a CAR. The promoter can be an inducible promoter or a constitutive promoter. Expression of a nucleic acid sequence under the control of an endogenous or vector-associated promoter occurs under suitable conditions for the cell to express the nucleic acid, for example, growth conditions, or in the presence of an inducer with an inducible promoter, and the like. Such conditions are well understood by those skilled in the art.

The targeting construct can optionally be designed to include a P2A sequence directly upstream of the nucleic acid sequences encoding the transgene. In a preferred embodiment, the targeting construct can optionally be designed to include a P2A sequence directly upstream of the nucleic acid sequences encoding a CAR. P2A is a self-cleaving peptide sequence, which can be used for bicistronic or multicistronic expression of protein sequences (see Szymczak et al., *Expert Opin. Biol. Therapy* 5(5):627-638 (2005)). If desired, the targeting construct can optionally be designed to include a reporter, for example, a reporter protein that provides for identification of transduced cells. Exemplary reporter proteins include, but are not limited to, fluorescent proteins, such as mCherry, green fluorescent protein (GFP), blue fluorescent protein, for example, EBFP, EBFP2, Azurite, and mKalama1, cyan fluorescent protein, for example, ECFP, Cerulean, and CyPet, and yellow fluorescent protein, for example, YFP, Citrine, Venus, and YPet.

Preferably, the targeting construct comprises a polyadenylation (poly A) sequence 3' of the transgene. In a preferred embodiment, the targeting construct comprises a polyadenylation (poly A) sequence 3' of the nucleic acid sequences encoding a CAR.

As disclosed herein, in a specific embodiment, a nucleic acid encoding a CAR is integrated at a site within the genome of the cell such that the CAR can be expressed in the cell and produced at the cell surface. The site of integration reduces or prevents expression of a functional T cell receptor (TCR) complex at the surface of the cell. The cell thereby can become a TCR negative cell. Such a TCR negative cell can be useful, for example, in the case of utilizing non-autologous T cells, for reducing graft versus host disease (GVHD) in the recipient. Generating a TCR negative cell also can be used to treat a subject having an autoimmune disease with autologous cells, since the autoimmune reaction provided by the subject's own T cells can be reduced by reducing or preventing expression of a functional TCR complex that targets an autoantigen.

The T cell receptor (TCR) is a heterodimer of TCR-α and TCR-β chains. The TCR complex is formed by TCR and CD3 gamma (γ), CD3 delta (δ), CD3 epsilon (ε), and CD3 zeta (ζ) (see, for example, Call et al., *Cell* 111:967-979 (2002)). Disruption or reduced expression of one or more of a T cell receptor alpha chain, T cell receptor beta chain, CD3 gamma chain, CD3 delta chain, CD3 epsilon chain, or CD3 zeta chain can be used to reduce or prevent formation of a functional T cell receptor (TCR) complex. By reducing or preventing the formation of a functional TCR complex, the T cell no longer mediates an immune response through its TCR complex. In one embodiment, a nucleic acid encoding a CAR is integrated at a site within the genome that disrupts or reduces the expression of a T cell receptor alpha chain, T cell receptor beta chain, CD3 gamma chain, CD3 delta chain, CD3 epsilon chain, or CD3 zeta chain. While the reduction of one of the TCR complex proteins can be sufficient, it is understood that more than one component of the TCR complex can be reduced, if desired.

It is understood that the site of integration in the genome of the cell is targeted to place the transgene under control of an endogenous promoter. The integration can be, by way of example but not limitation, integration into an exon, integration into an intron, or integration at the 5' end of the gene. In one embodiment, integration of the transgene results in disruption of the endogenous gene at the site of integration.

In a preferred embodiment, it is understood that the site of integration in the genome of the cell is targeted to reduce or disrupt expression of a component of the TCR complex, for example, T cell receptor alpha chain, T cell receptor beta chain, CD3 gamma chain, CD3 delta chain, CD3 epsilon chain, or CD3 zeta chain. One skilled in the art can readily determine a suitable position within a gene encoding a T cell receptor alpha chain, T cell receptor beta chain, CD3 gamma chain, CD3 delta chain, CD3 epsilon chain, or CD3 zeta chain to integrate a CAR encoding nucleic acid to reduce or disrupt expression of T cell receptor alpha chain, T cell receptor beta chain, CD3 gamma chain, CD3 delta chain, CD3 epsilon chain, or CD3 zeta chain. Such methods are well known in the art and can include, but are not limited to, integration into an exon, integration into an intron, integration at the 5' end of the gene, and the like. It is understood that any intron or exon of the gene can support the targeting construct. One skilled in the art can readily determine a suitable site for targeted integration of a transgene that, if desired, will reduce or disrupt expression of an endogenous gene under control of the endogenous promoter at the site of integration. In a particular embodiment, the site of integration is within the first exon. It is understood that, when selecting a site for integration of a transgene, the integration site occurs in a non-essential gene, i.e., a gene that is not necessary for cell viability or proliferation of the cell, particularly in the case where expression of the endogenous gene will be disrupted. In a preferred embodiment, one skilled in the art can readily determine a suitable site for targeted integration of a nucleic acid sequence encoding a CAR that will reduce or disrupt expression of TCR complex protein such as T cell receptor alpha chain, T cell receptor beta chain, CD3 gamma chain, CD3 delta chain, CD3 epsilon chain, or CD3 zeta chain, and/or place the CAR encoding nucleic acid sequence under the control of the endogenous promoter of the respective gene encoding the TCR complex component. In one embodiment, the site of integration is within the first exon (see Example). In a particular embodiment, the site of integration is within the first exon of the TCR alpha constant chain (TRAC). In a preferred embodiment, a transgene, such as a nucleic acid encoding a CAR, is placed under control of an endogenous TCR promoter. Details thereof are described in provisional application Nos. 62/323,623, filed Apr. 15, 2016, and 62/323,675, filed Apr. 16, 2106, which are incorporated herein by reference in their entireties.

If desired, the integration site and targeting construct can be designed to provide integration of a transgene in frame with the endogenous gene, resulting in expression of a fusion protein of the transgene and the endogenous gene (see also US20130280222). In a preferred embodiment, the integration site and targeting construct can be designed to provide integration in frame with the endogenous gene, resulting in expression of a fusion protein of a CAR and the TCR complex protein. Optionally, such a construct can contain a P2A directly 5' of the transgene, allowing the expression of the transgene at a desired location in the cell without being fused to the gene product of the endogenous gene. Such a construct provides for expression of both the transgene and the endogenous gene at the site of integration, and such a construct can be utilized if disruption of the endogenous gene is detrimental to the T cell or would result in a decrease in its effectiveness in T cell therapy. In a preferred embodiment, such a construct can contain a P2A directly 5' of the nucleic acid sequence encoding the CAR, allowing the expression of the CAR at the surface of the cell without being fused to TCR complex protein. It is further understood that another gene also can be integrated into the genome such as a gene encoding a second CAR, or a safety switch (e.g., inducible caspase 9 (iCasp9) or herpes simplex virus thymidine kinase (HSVtk), see Tey, *Clin. Transl. Immunology* 3(6):e17), or an immunomodulatory molecule, and the like. In one embodiment, integration of the same or different genes (transgenes) occurs in different target genes, respectively. In a specific aspect, different genes (transgenes) are integrated at the different integration sites, respectively.

The homologous recombination system is designed using methods well known in the art to target a desired site within the genome, for example, a site within the gene encoding T cell receptor alpha chain (Chromosome 14, NC_000014.9 (22547506..22552132)), T cell receptor beta chain (Chromosome 7, NC_000007.14 (142299011..142813287)), CD3 gamma chain (Chromosome 11, NC_000011.10 (118344316..118353782)), CD3 delta chain (Chromosome 11, NC_000011.10 (118339074..118342744)), CD3 epsilon chain (Chromosome 11, NC_000011.10 (118304580..118316175)), or CD3 zeta chain (Chromosome 1, NC_000001.11 (167430640..167518616)), as is known in the art (Chromosome location numbers correspond to the current assembly: GRCh38. p2).

As described herein, in one embodiment, the integration site can target a gene that is expressed from only one allele, for example, TCR alpha, TCR beta, Y or X chromosome-specific genes. In such a case, it can be sufficient to integrate a transgene at a single site within the genome. In a preferred embodiment wherein the transgene encodes a CAR, in such a case, it can be sufficient to integrate a nucleic acid encoding a CAR at a single site within the genome. This strategy can be utilized to ensure that only one transgene copy per cell is expressed. Optionally, in the case where a gene to be targeted for integration is present on two alleles, targeted homologous recombination can occur at both alleles. In such a case, the targeted integration can occur at one locus or two loci.

Assays can be used to determine the transduction efficiency of a transgene, preferably encoding a CAR, using routine molecular biology techniques. Gene transfer efficiency can be monitored by fluorescence activated cell sorting (FACS) analysis to quantify the fraction of transduced T cells, and/or by quantitative PCR. Using a well-established cocultivation system (Gade et al., *Cancer Res.* 65:9080-9088 (2005); Gong et al., *Neoplasia* 1:123-127 (1999); Latouche et al., *Nat. Biotechnol.* 18:405-409 (2000)) it can be determined whether fibroblast AAPCs expressing cancer antigen (vs. controls) direct cytokine release from transduced T cells expressing a CAR (cell supernatant LUMINEX (Austin TX) assay for IL-2, IL-4, IL-10, IFN-γ, TNF-α, and GM-CSF), T cell proliferation (by carboxyfluorescein succinimidyl ester (CFSE) labeling), and T cell survival (by Annexin V staining). T cells expressing a CAR can be exposed to repeated stimulation by target antigen positive cells, and it can be determined whether T cell proliferation and cytokine response remain similar or diminished with repeated stimulation. In a preferred embodiment, T cells expressing a CAR can be exposed to repeated stimulation by cancer antigen positive target cells, and it can be determined whether T cell proliferation and cytokine response remain similar or diminished with repeated stimulation. Cytotoxicity assays with multiple E:T ratios can be conducted using chromium-release assays.

7.4 Endogenous T Cell Promoters

The invention relates to expressing a therapeutic transgene in a T cell by integrating the transgene at a site within the genome of the T cell such that the transgene is placed under the control of an endogenous promoter of the T cell. By utilizing an endogenous promoter, T cells are engineered to express a therapeutic transgene, or a variety of therapeutic transgenes under the control of different endogenous promoters. In a specific embodiment, expression of the transgene is dependent on the microenvironment of the T cell. For example, expression of a therapeutic transgene can be made dependent on the location of the T cell (e.g., expression of a transgene only in proximity to a tumor) by using an endogenous promoter that is induced when the T cell is at a particular location (e.g., when the T cell is at the location of a tumor and is activated by binding to tumor antigen, thereby inducing the endogenous promoter), or can be at defined time points (e.g., by using an endogenous promoter that is induced at a defined time point, e.g. by activation of the T cell upon encountering a tumor cell). The promoter is selected based on, for example, how soon it is activated or inhibited after encounter of the T cell with an antigen, how strongly it is expressed, and for how long. The promoter is selected to accommodate the pharmacology for the transgene whose expression it regulates (e.g., some transgenes are more effective at low levels, other transgenes are more effective at high levels of expression, and the like). It will be understood that the description in this disclosure with respect to use of an endogenous promoter (singular) controlling the expression of a transgene in a T cell will apply equally to the use of more than one endogenous promoter, each controlling the expression of a transgene (that can be the same or different from the other transgenes), in the T cell, unless context indicates otherwise. One skilled in the art can readily select appropriate endogenous promoters to provide desired expression and/or regulation of one or more transgenes to enhance the effectiveness of a T cell for use in T cell therapy.

The endogenous T cell promoters can be constitutive or inducible. In a specific embodiment, the endogenous promoter is specific for a subset of T cells. In the case where more than one transgene is expressed in a T cell, the transgenes (which may be different from each other) can be placed under control of a combination of constitutive and inducible promoters, respectively, of which one or more can be, for example, specific for a subset of T cells.

In one aspect of the embodiments described herein, the endogenous promoter is not an interleukin 4 (IL4) promoter.

In one embodiment, the endogenous T cell promoter is constitutive. In another embodiment, the endogenous T cell promoter is inducible. In a specific embodiment, the endogenous T cell promoter is active in a subset of T cells. In one embodiment, two or more transgenes are integrated into the genome of the T cell, such that expression of each transgene is under the control of a different endogenous promoter of the T cell. In a specific embodiment, two transgenes are thus integrated. In a particular embodiment, the expression of each of two transgenes is under the control of different endogenous promoters that are constitutive. In another particular embodiment, the expression of each of two transgenes is under the control of different endogenous promoters that are inducible. In another particular embodiment, the expression of a first transgene is under control of a constitutive endogenous promoter and expression of a second transgene is under control of an inducible endogenous promoter. In another particular embodiment, three transgenes are integrated into the genome of the T cell, such that expression of each transgene is under the control of a different endogenous promoter of the T cell, where expression of a first transgene is under control of a constitutive endogenous promoter and expression of second and third transgenes is under control of two different inducible, endogenous promoters, respectively. It is understood that, depending on the transgene to be expressed in the T cell, a promoter can be selected to provide an appropriate expression level, time of expression, expression when the T cell is in a particular microenvironment, and so forth. For example, expression of transgene 1 can be under control of a constitutive promoter, expression of transgene 2 can be under control of an inducible promoter that is activated shortly after contact with an antigen recognized by the T cell, and expression of transgene 3 can be under control of a different inducible promoter that is activated at a later time or at a different level than for transgene 2. In this particular example, transgene 1 is expressed constitutively, and transgenes 2 and 3 are under control of inducible promoters with distinct characteristics.

Engineering of T cells of the invention to express a transgene from an endogenous T cell promoter provides for autonomous regulation of transgene expression by the T cell. Thus, the microenvironment of the T cell can be used to coordinate the expression of multiple transgenes to provide optimized activity of the transgenic T cell, particularly when at least one gene is under control of an inducible promoter. For example, T cell therapy can be accompanied by administration of a T cell stimulatory cytokine (see Sadelain et al., *Cancer Disc.* 3:388-398 (2013)). In one embodiment, the T cells of the invention can be engineered to co-express a CAR and a second transgene, such as a T cell activating cytokine. For example, a CAR can be placed under control of a constitutive promoter, and a second transgene such as a T cell activating cytokine (e.g., interleukin 12 (IL12)) can be placed under control of an inducible promoter such that activation of the inducible promoter controlling the second transgene occurs when the T cell is in proximity to an antigen recognized by the CAR such as on a tumor, for example, when the T cell engages a target tumor antigen by binding to the CAR. In this example, such a construct obviates the need for systemic or localized administration of a T cell activating cytokine, which can result in toxicity. In addition, in the case where the T cell is engineered to express a T cell activation cytokine under control of an inducible promoter that can be regulated by administration of a drug, such a construct obviates the need to administer the drug. In such a case, instead of needing to administer a drug to induce expression of a transgene, regulation of transgene expression is under control of an endogenous promoter, which provides for expression of the transgene. Instead, the T cell itself, upon engagement with a target antigen, activates expression of a T cell activating cytokine, providing localized expression of the cytokine, and therefore spatio-temporal regulation of expression of transgenes to optimize the effectiveness of the T cells to be used for immunotherapy.

In another example, a T cell expressing a CAR can sometimes exhibit toxicities. To reduce such toxicity, in a specific embodiment, a transgene encoding a CAR can therefore be placed under control of an inducible promoter such that the promoter is not induced, and expression of the CAR does not occur, until the T cell is engaged with a target recognized by the CAR, such as a target tumor. In yet another embodiment, a T cell can be engineered to have higher selectivity for a particular target. For example, in some cases a target antigen on a tumor may not be expressed on the tumor only. Therefore, targeting of a T cell to the target antigen could result in an immune response against non-target cells or tissues that express the same antigen. Accordingly, in one embodiment, a T cell of the invention is engineered to recognize two antigens on a target tumor, which provides higher selectivity for the target tumor. For example, the T cell can be engineered to express two CARs specific for two different tumor antigens. In this case, selective binding of the T cell to a target bearing two target antigens can be coupled with a third transgene under control of an inducible endogenous promoter, such as a T cell activating cytokine as described above, thereby stimulating activation of the T cell with the cytokine only upon selective engagement with the target. A person skilled in the art will readily understand that selection of suitable therapeutic transgenes to be expressed under the control of suitable endogenous T cell promoters, either constitutive, specific for a subtype of T cells, inducible, or a combination thereof, can be used to generate autonomously regulated expression of transgenes to provide more effective T cell therapy. In one embodiment, instead of using a fully competent CAR targeting one antigen, two sub-optimal CAR targeting two different antigens need to be engaged for a full antitumor response. If healthy tissues express one or the other antigen, they healthy tissue will not fully engage a CAR T cell response. If the tumor expresses the two antigen, it will then trigger a complete CAR T cell activity.

The invention relates to optionally using both constitutive and inducible promoters, since a T cell can be engineered to specifically respond to a particular molecular cue to produce new therapeutic molecules at a chosen location and time. For example, a transgene encoding an antigen-specific cell-surface receptor can be expressed from a constitutive promoter and will only signal upon interaction with that particular antigen. Then, this interaction induces the activation of a specific promoter that controls the expression of a therapeutic molecule. The therapeutic benefit of this particular engineered T cell depends on the function of both constitutive and inducible promoters. In a particular embodiment, a CAR can be under the under the control of a constitutive promoter (e.g., TRAC, CD3s, B2M . . . ). In a particular embodiment, another therapeutic transgene (monoclonal antibody (checkpoint inhibitor, and the like) or cytokines (e.g., IL12, IL18 and the like) are under the control of promoter activated by CAR engagement (e.g., IL2, IFNg, CD69 . . . ). In such a case, the transgene would be expressed upon CAR activation and specifically be expressed in the tumor.

In one embodiment, the invention relates to expressing 3 transgenes, or more. For example, transgene 1 can be constitutive, transgene 2 can come in shortly after contact with antigen, and transgene 3 can come on later or at a different level than transgene 2. In this example, expression of transgene 1 is under the control of an endogenous constitutive promoter, expression of transgene 2 begins shortly after contact with antigen by virtue of being controlled by an endogenous promoter induced by antigen engagement, and expression of transgene 3 begins later or at a different level than transgene 2 by virtue of being controlled by an endogenous promoter induced later or providing for a different level of expression than the endogenous promoter regulating transgene 2. In this example, transgene 1 is constitutive and transgenes 2 and 3 are inducible (each with distinct kinetic characteristics). In a particular embodiment, transgene 1 encodes a CAR specific for antigen A, e.g., on tumor cells, where transgene 1 is constitutively expressed. After binding to antigen A, transgene 2 is expressed, which encodes another CAR specific for antigen B (e.g., also expressed on tumor cells or on other cells within the tumor microenvironment). Transgene 3 can be, for example, a third CAR; this third CAR can recognize antigen C, e.g., also on the tumor cells or other cells within the tumor microenvironment. This example is a form of "combinatorial targeting" using temporal/sequential expression of different CARs by the same T cell. In another particular embodiment, transgene 1 encodes a CAR (or TCR) specific for antigen A; transgene B encodes a cytokine, and transgene 3 encodes another cytokine or a costimulatory ligand or an scFv, for example, recognizing an antigen on the same cells (e.g., tumor cells) that express antigen A or cells in the same microenvironment. This is an example of sequential gene activation designed to increase T cell potency and safety by confining gene expression to a microenvironment such as the tumor microenvironment. Thus, a person skilled in the art can select an endogenous T cell promoter for placement of a desired transgene to provide desired expression characteristics of the transgene.

It is further understood that certain transgenes (e.g., immunostimulatory transgenes—those that when expressed provide an immunostimulatory effect) are desirable to express in a T cell that is immunostimulatory, whereas other transgenes (e.g., immunoinhibitory transgenes—those that when expressed provide an immunoinhibitory effect) are desirable to express in a T cell that is immunoinhibitory. It is understood that a person skilled in the can readily determine suitable transgenes to express in a T cell depending on whether it is desired to stimulate or inhibit an immune response. As will be clear, in preferred embodiments, an immunostimulatory transgene is expressed in an immunostimulatory T cell to stimulate an immune response in the subject to which the T cell is administered, and an immunoinhibitory transgene is expressed in an immunoinhibitory T cell to inhibit an immune response in the subject to which the T cell is administered.

Constitutive Promoters. In one embodiment, a therapeutic transgene is integrated at a site within the genome of a T cell such that expression of the transgene is placed under control of an endogenous promoter that is constitutive. The constitutive promoters can be used to express a transgene such as a CAR or CCR to activate the immune response. A constitutive promoter can also be used to inhibit an immune response if controls expression of an inhibitory CAR (iCAR) containing PD1 and or cTLA4 intracellular domain, and the like.

In one embodiment, a constitutive promoter is a TCR promoter, i.e., a promoter of a protein of the T cell receptor complex (TCR) (see Examples). In a particular embodiment, the endogenous promoter is a promoter of a gene encoding a T cell receptor alpha chain, T cell receptor beta chain, CD3 gamma chain, CD3 delta chain, CD3 epsilon chain, or CD3 zeta chain.

In another embodiment, a constitutive promoter can be, but is not limited to, a promoter such as CD4 promoter, CD8a promoter, CD8b promoter, TCRa promoter, TCRb promoter, CD3d promoter, CD3g promoter, CD3e promoter, and CD3z promoter, or the like (see also Table 1, promoters indicated as constitutive).

TABLE 1

Exemplary Constitutive and Inducible Promoters and Corresponding Inducers.

| T cells subset | Promoter | Inducer | Immunue response | Reference |
|---|---|---|---|---|
| CD4 | CD4 | constitutive | Activation/inhibition | |
| CD8 | CD8a | constitutive | Activation/inhibition | |
| | CD8b | constitutive | Activation/inhibition | |
| CD3 | TCRa | constitutive | Activation/inhibition | |
| | TCRb | constitutive | Activation/inhibition | |
| | CD3d | constitutive | Activation/inhibition | |
| | CD3g | constitutive | Activation/inhibition | |
| | CD3e | constitutive | Activation/inhibition | |
| | CD3z | constitutive | | |
| CD3 | Actin | NFAT/AP1/NFkb activated (Ca2+ dependent - CAR/TCR + CD28) | | |
| | CD25 | NFAT/AP1/NFkb activated (Ca2+ dependent - CAR/TCR + CD28) | | |
| | IL2 | NFAT/AP1/NFkb activated (Ca2+ dependent - CAR/TCR + CD28) | | 1 |
| | CD69 | NFAT/AP1/NFkb activated (Ca2+ dependent - CAR/TCR + CD28) | | 2 |
| | GzmB | NFAT/AP1/NFkb activated (Ca2+ dependent - CAR/TCR + CD28) | | |
| Th1 | T-bet | IFNg-IFNg-R - (STAT1) + TCR activation (NFAT, AP-1, NFkb) | | 3 |
| | IFNg | T-bet + IL2 (STAT5) | | |
| | TIM3 | T-bet | | 4 |
| Th2 | IL4 | IL4-IL4R (STAT6) + TCR activation (NFAT, AP-1, NFkb) + Th2 commitment (GATA-3, c-MAF) | | 5 |
| | GATA3 | IL4-IL4R (STAT6) | | |
| | IL5 | Th2 commitment (GATA-3, c-MAF) + NFAT1 | | |
| | IL13 | Th2 commitment (GATA-3, c-MAF) + NFAT1 | | |
| | IL10 | NFAT + IRF4 | | 6 |
| | | IL27 (STAT 1/3) - IL6 (STAT3) | | 7 |
| Th17 | IL17A | IL6-IL6R (STAT3 - ROR) + IL23-IL23R + TGFB-TGFBR | | |
| | IL6 | IL6-IL6R (STAT3 - ROR) - TCR activation (NFAT, AP-1, NFkb) | | 8 |
| | IL21 | IL6-IL6R (STAT3 - ROR) - TCR activation (NFAT, AP-1, NFkb) - IL21-IL21R | | 9 |
| | IL23R | IL21-IL21R - IL23-IL23R - TGFB-TGFBR | | 10 |
| iTregs | FoxP3 | TGFB-TGFBR (SMAD), IL2/15 (STAT5) + low affinity Antigen TCR activation (NFAT but no AP1) | | 11 |
| | CTLA4 | NFAT + FoxP3 | | 12 |
| | CD25 | NFAT + FoxP3 | | |
| | PD1 | NFAT/AP1/NFkb activated (Ca2+ dependent - CAR/TCR + CD28) | | 13 |

1. Jain, J., C. Loh, and A. Rao. 1995. Transcriptional regulation of the IL-2 gene. Curr. Opin. Immunol. 7: 333-342. +Kim H P, Leonard W J. The basis for TCR-mediated regulation of the IL-2 receptor alpha chain gene: role of widely separated regulatory elements. EMBO J 2002; 21: 3051-3059.
2. Ziegler S F, Ramsdell F, Alderson M R (1994) The activation antigen CD69. Stem Cells 12: 456-465.
3. Afkarian M, Sedy J R, Yang J, et al. T-bet is a STAT1-induced regulator of IL-12R expression in naive CD4+ T cells. Nat Immunol 2002; 3: 549-557
4. Anderson A C1, Lord G M, Dardalhon V, Lee D H, Sabatos-Peyton C A, Glimcher L H, Kuchroo V K.. 2010. Th1 transcription factor T-bet regulates the expression of Tim-3. Eur J Immunol. 2010 March; 40(3): 859-66. doi: 10.1002/eji.200939842.
5. Chuvpilo S, Schomberg C, Gerwig R, et al. Multiple closely-linked NFAT/octamer and HMG I(Y) binding sites are part of the interleukin-4 promoter. Nucleic Acids Res 1993; 21: 5694-5704.
6. Lee C G, Kang K H, So J S, et al. A distal cis-regulatory element, CNS-9, controls NFAT1 and IRF4-mediated IL-10 gene activation in T helper cells. Mol Immunol 2009; 46: 613-621
7. Iyer S S, Cheng G. 2012. Role of Interleukin 10 Transcriptional Regulation in Inflammation and Autoimmune Disease - Crit Rev Immunol. 2012; 32(1): 23-63.
8. Macian F. NFAT proteins: key regulators of T-cell development and function. Nat Rev Immunol 2005; 5: 472-484.
9. Mehta D S, Wurster A L, Weinmann A S, Grusby M J. NFATc2 and T-bet contribute to T-helper-cell-subset-specific regulation of IL-21 expression. Proc Natl Acad Sci USA 2005
10. Zhou L, Lopes J E, Chong M M, et al. TGFβ induced Foxp3 inhibits Th17 cell differentiation by antagonizing RORgammat function. Nature 2008; 453: 236-240.
11. Fantini M C, Becker C, Monteleone G, Pallone F, Galle P R, Neurath M F. Cutting edge: TGFbeta induces a regulatory phenotype in CD4+CD25− T cells through Foxp3 induction and down-regulationof Smad7. J Immunol 2004; 172: 5149-5153.
12. Wu Y, Borde M, Heissmeyer V, et al. Foxp3 controls regulatory T cell function through cooperation with NFAT. Cell 2006; 126: 375-387.
13. Oestreich K J, Yoon H, Ahmed R, Boss J M. 2008. NFATc1 Regulates PD-1 Expression upon T Cell Activation1. J Immunol.; 181(7): 4832-9.

T Cell Subset-Specific Promoters. In one embodiment, a therapeutic transgene is integrated at a site within the genome of a T cell such that expression of the transgene is placed under control of an endogenous promoter that is active in a subset of T cells. It is understood that such promoters that are active in a subset of T cells are inactive or have low activity in other T cells. Exemplary promoters that are active in a subset of T cells include, but are not limited to, promoters such as CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFN-gamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter (see Tables 1 and 2).

In Table 2, the expression levels are compared to naive T cells in the different T cells differentiation subsets, as reported by Mahnke et al., *Eur. J. Immunol.* 43(11):2797-809. doi: 10.1002/eji.201343751 (2013). After activation by a TCR or a CAR, T cells are going through differentiation, and specific genes are being activated or repressed. The inducer is the initial activation by a TCR or CAR, but signaling also continues the co-stimulations that will impact on the differentiation of the T cell (see also Mahnke et al., *Eur. J. Immunol.* 43(11):2797-809. doi: 10.1002/eji.201343751 (2013)).

TABLE 2

Exemplary Promoters Specific for T Cell Subsets
(see Mahnke et al., Eur. J.
Immunol. 43(11):2797-809. doi: 10.1002/eji.201343751 (2013)).

|  |  | Naïve | stem cell mem | central mem | transition al mem | effector mem | terminal eff |
|---|---|---|---|---|---|---|---|
| CD45RO |  | − | − | + | + | + | − |
| CCR7 |  | + | + | + | − | − | − |
| CD28 |  | + | + | + | + | − | − |
| CD95 |  | − | + | + | + | + | + |
| CD28 |  | + | ++ | ++ | ++ | − | − |
| CD27 |  | ++ | + | + | + | −/+ | − |
| CD127 |  | ++ | +++ | +++ | ++ | −/+ | − |
| PD-1 |  | − | −/+ | + | ++ | + | + |
| CD122 |  | − | + | ++ | +++ | +++ | +++ |
| CD132 |  | + | + | + | + | + | + |
| KLRG-1 |  | − | ND | −/+ | + | ++ | +++ |
| HLA-DR |  | − | − | −/+ | −/+ | + | − |
| CD38 |  | + | −/+ | − | − | − | − |
| CD69 |  | − | − | − | − | − | − |
| Ki-67 |  | − | − | −/+ | −/+ | −/+ | − |
| CD11a |  | + | ++ | ++ | +++ | +++ | +++ |
| CD58 |  | − | + | ++ | +++ | +++ | +++ |
| CD99 |  | −/+ | + | ++ | ++ | ++ | ++ |
| CD62L |  | + | + | + | − | − | − |
| CD103 |  | − | − | − | − | + | − |
| CCR4 |  | −/+ | + | ++ | +++ | +++ | −/+ |
| CCR5 |  | − | − | + | ++ | +++ | ++ |
| CCR6 |  | − | − | ++ | +++ | +++ | − |
| CCR9 | CD4 | − | ND | + | − | − | − |
|  | CD8 | − | ND | + | ++ | ++ | − |
| CCR10 |  | − | − | + | ND | ++ | − |
| CXCR3 | CD4 | − | −/+ | + | ++ | +++ | +++ |
|  | CD8 | ++ | +++ | +++ | ++ | + | + |

TABLE 2-continued

Exemplary Promoters Specific for T Cell Subsets
(see Mahnke et al., Eur. J.
Immunol. 43(11):2797-809. doi: 10.1002/eji.201343751 (2013)).

|  |  | Naïve | stem cell mem | central mem | transition al mem | effector mem | terminal eff |
|---|---|---|---|---|---|---|---|
| CXCR4 |  | + | ++ | +++ | +++ | ++ | ++ |
| CLA |  | − | ND | + | ND | ++ | ND |
| Granzyme A | CD4 | − | − | − | − | −/+ | + |
|  | CD8 | − | − | −/+ | ++ | +++ | +++ |
| Granzyme B | CD4 | − | − | − | − | −/+ | −/+ |
|  | CD8 | − | − | − | + | ++ | +++ |
| Perforin | CD4 | − | − | − | − | −/+ | −/+ |
|  | CD8 | − | − | −/+ | + | ++ | +++ |
| CD57 |  | − | − | − | −/+ | ++ | +++ |
| CD161 |  | − | − | −/+ | + | +++ | +++ |
| IL-18Ra |  | − | −/+ | + | ++ | +++ | +++ |
| c-Kit |  | − | − | − | ND | +++ | ND |
| CD130 |  | ++ | + | −/+ | − | − | − |

In general, there is usually not a single inducer for a single promoter, but signal pathways engaging and activation/repression loops that lead to promoter activation. These signaling pathways are triggered by multiple inducers and result in the commitment of the T cells to a subset or a phenotype. However, certain genes expression patterns are very specific to subsets and phenotypes; and their promoter can be targeted, e.g., T-bet and INFgamma in Th1; GATA3, IL4 and IL10 in Th2; IL6 in Th17; FoxP3 in Treg. Thus, an endogenous promoter can be selected for integration of a transgene to provide for expression of the transgene in a particular T cell subtype.

Inducible Promoters. In one embodiment, a therapeutic transgene is integrated at a site within the genome of a T cell such that expression of the transgene is placed under control of an endogenous promoter that is inducible. An inducible promoter is one that is responsive to an inducer that propagates a signal to the nucleus, resulting in activation of the inducible promoter (see, for example, Table 1). In general, the inducer is a binding partner of a molecule expressed by the T cell. For example, in the case of a receptor, the binding partner can be its cognate ligand, or in the case of a CAR, CCR or TCR, the binding partner can be a target antigen.

In one embodiment, the endogenous inducible promoter is induced by activation of the T cell. In one embodiment, the endogenous inducible promoter is induced by binding of a chimeric antigen receptor (CAR) or a chimeric co-stimulatory receptor (CCR) expressed by the T cell to its respective binding partner, for example, upon interaction with its corresponding antigen. A more detailed description of CARs and CCRs are provided under the section below describing therapeutic transgenes. Briefly, both CARs and CCRs contain intracellular signaling domains. In the case of a CAR, the intracellular signaling domain activates a T cell, and optionally contains a co-stimulatory domain (in the case of second and third generation CARs) (see Sadelain et al., *Cancer Discov.* 3(4):388-398 (2013)). In the case of a CCR, it contains a co-stimulatory signal but does not have a T cell activation signal (Sadelain et al., supra, 2013). Binding of a corresponding antigen to a CAR or CCR results in activation of the T cell signaling domain and/or the co-stimulatory domain. The activation of these signaling domains results in propagation of a signal to the nucleus and activation of certain endogenous promoters in the T cell. Intracellular signaling domains of a CAR or CCR include, but are not limited to, the intracellular domains of CD28, 4-1BB, CD27, ICOS, CD3z, and the like, as well as other intracellular signaling domains disclosed herein. Signaling can also occur with mutated (e.g., mutated ITAMs), truncated or fused versions of these domains.

In another embodiment, the endogenous inducible promoter is induced by binding of the T cell receptor (TCR), CD28, CD27, 4-1BB, and the like, expressed by the T cell to its respective binding partner. These molecules contain intracellular signaling domains. Upon activation, the signaling domain results in propagation of a signal to the nucleus and activation of certain endogenous promoters in the T cell. In another embodiment, the endogenous inducible promoter is induced by binding of an iCAR (CAR with inhibitory intracellular domain such as PD1, CTLA4) or truncated CAR (no intracellular domain). In one embodiment, the iCAR functions as a 'break' for the T cells activation upon target encounter through the signaling of CTLA4 or PD1 intracellular domains. Thus promoters that are regulated by PD1 or CTLA4 can be used to express a transgene upon iCAR encounter with the antigen. The transgene could for example be an immunosuppressive molecule to further control T cell activation.

We believe that truncated CARs would allow to address the T cell to a specific location where its target is expressed. We also believe that the created contact between CAR T cells and target cells would eventually regulate promoters than thus can be targeted for transgene expression.

In a particular embodiment, the promoter that is induced by a CAR, CCR or TCR is selected from the group consisting of nuclear factor of activated T cells (NFAT) promoter, PD-1 promoter, TIM-3 promoter, CTLA4 promoter, LAG3 promoter, TRAIL promoter, BTLA promoter, CD25 promoter, CD69 promoter, FasL promoter, TIGIT promoter, and 2B4 promoter. In a particular embodiment, CAR and TCR can both regulate promoters that are in the signal pathway of CD3 ITAM phosphorylation and regulated by Ca2+-dependent transcription factors (e.g., NFAT, NFkB, AP1 or CREB regulated genes such as IL2). Such promoters result in increased expression upon signaling from the pathway. For CAR and CCR, genes regulated upon antigen encounter depend on the domains the CAR and CCR, respectively, are composed of, e.g., a CD28 co-stimulatory domain induces promoters activated by the PI3K pathway, while 41BB co-stimulatory domain activation induces promoters activated by the TRAF pathway. Timely regulation of promoters, in response for example to TCR/CD28 (as well as CARs composed of CD28 and CD3zeta) activation, can be used to regulate the timing of expression of a transgene (see FIG. 17; Best et al., Nat. Immunol. 14:404-413 (2013)). For example, upon activation and memory formation of CD8+ T cells, promoters in cluster 1 (12-24 hours) include, for example, CTLA4 promoter, IFNgamma promoter, Gzmb promoter, IL2ra promoter, IL2 promoter, and the like; promoters in cluster 2 (12-48 hours) include, for example, CD69 promoter and Pkm2 promoter, and the like; and promoters in cluster 3 (24 hours to days) include, for example, Id2 promoter, KLRg1 promoter, Cxcr3 promoter, Cxcr3r1 promoter, Itgam promoter, and the like (see also FIG. 17 for additional exemplary promoters and Best et al., supra, 2013). An exemplary inducible promoter is 4-1BB promoter. Another exemplary inducible promoter is H1F1alpha, involved in the metabolic response to hypoxia.

In another embodiment, the endogenous inducible promoter is induced by binding of a ligand to an inhibitory receptor expressed on the T cell. Exemplary inhibitory receptors include, but are not limited to, the receptors programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), tumor necrosis factor (TNF)-related apoptosis-inducing ligand (TRAIL, receptors 1 and 2), Fas, T-cell immunoreceptor with Ig and ITIM domains (TIGIT), and 2B4 (CD244). The corresponding ligands for these inhibitory receptors include, for example, PD-L1 (for PD-1); PD-L2 (for PD-1); CD80, CD86 (for CTLA-4); HVEM (for BTLA); Galectin-9, HMGB1 (for TIM-3); MHC II (for LAG-3); TRAIL (for TRAIL receptor 1 and TRAIL receptor 2); Fas ligand (FasL) (for Fas), and the like (see Chen et al., Nat. Rev. Immunol. 13(4):227-242 (2013); Tollefson et al., J. Virol. 75:8875-8887 (2001); Waring et al., Immunol. Cell Biol. 77:312-317 (1999)).

In a particular embodiment, the promoter that is induced by binding of a ligand to an inhibitory receptor is selected from the group consisting of CPT1a promoter and ATGL promoter.

In another embodiment, the endogenous inducible promoter is induced by binding of a cytokine to a cytokine receptor expressed by the T cell. In one embodiment, the cytokine is an immunostimulatory cytokine selected from the group consisting of interleukin 2 (IL2), interleukin 7 (IL7), interleukin 15 (IL15), and interleukin 21 (IL21). In another embodiment, the cytokine is an immunoinhibitory cytokine, such as interleukin 10 (IL10), transforming growth factor-β (TGFβ); IL4, IL9, or Thymic stromal lymphopoietin (TSLP).

In a particular embodiment, the promoter is induced by a cytokine selected from the group consisting of T-bet promoter, Eomes promoter, GATA3 promoter, and CD45RA promoter.

In another embodiment, the endogenous inducible promoter is induced by contact of a cell with a nucleic acid. In a particular embodiment, the nucleic acid is selected from the group consisting of viral DNA, viral RNA, and intracellular microRNA. Exemplary promoters that are induced by contact of the cell with a nucleic acid include, but are not limited to, promoters of the Type I interferons (IFNs) (alpha and beta), IRF3 and IRF7 transcription factors, NFkB and AP-1 transcription factors, pro-inflammatory cytokines (TNF-alpha, IL1, IL6), and the like.

In another embodiment, the endogenous inducible promoter is induced by a metabolite. In a particular embodiment, the metabolite is selected from the group consisting of pyruvate, glutamine, beta-hydroxybutyrate, lactate, and serine. These metabolites are generated or taken up during T cell activation, which translates into a metabolic change in the T cell. Exemplary promoters that are induced by a metabolite are those of: c-Myc, HIF-1alpha, ERRalpha, CD98, SLC1A5, Psat1, Phgdh, psph, Mthfd2, Mthfd1, Mat2a, Mtrr, Mtr, Shmt1, Shmt2 (see Wang et al., Immunity 35:871-882 (2011); Chang et al., Nat. Immunol. 17: 364-368 (2016); Ma et al., Cell Metab. 25:345-357 (2017)).

In another embodiment, the endogenous inducible promoter is induced by a metabolic change. This refers to the metabolic state of the cells. For example, when naive T cells rely on oxidative phosphorylation to generate energy, and when they became activated and differentiate into effector T cell, they switch to glycolysis to generate energy. Hypoxia and low-pH also induce metabolic changes (Chang et al., Nat. Immunol 17:364-368 (2016); McNamee et al., Immunol. Res. 55: 58-70 (2013)).

In a particular embodiment, the promoter induced by a metabolic change is PKM2 promoter. The PKM2 promoter is the same as for PKM1. PKM2 is generated through alternative splicing when cells switch from oxidative phosphorylation to glycolysis.

In another embodiment, the endogenous inducible promoter is induced by an ion, such as a particular ion concentration. In one embodiment, the ion is potassium or calcium. Exemplary promoters induced by an ion include, but are not limited to the promoters of, IL2, TNFalpha, and IFNgamma, which are activated in a NFAT-dependent manner. NFAT is activated by increased levels of intracellular calcium.

7.5 Therapeutic Transgenes

The invention relates to expressing a therapeutic transgene in a T cell by integrating the transgene at a site within the genome of the T cell such that expression of the transgene is under the control of an endogenous promoter of the T cell. A therapeutic transgene is a nucleotide (e.g., DNA or a modified form thereof) sequence encoding a therapeutic protein or therapeutic nucleic acid. The therapeutic protein or therapeutic nucleic acid when expressed by the T cell has use in treating a human or veterinary disease or disorder. The therapeutic nucleic acid is preferably a therapeutic RNA. The therapeutic protein can be a peptide or polypeptide.

In one aspect of the embodiments described herein, the therapeutic transgene does not encode a membrane-bound form of interleukin 4 (IL4).

Therapeutic transgenes include, but not limited to, those encoding a CAR, chimeric co-stimulatory receptor (CCR), TRC, cytokine, dominant negative, microenvironment modulator, antibody, biosensor, chimeric receptor ligand (CRL), chimeric immune receptor ligands (CIRL), soluble receptor, enzyme, ribozyme, genetic circuit, reporter, epigenetic modifier, transcriptional activator or repressor, noncoding RNA, or the like.

It is understood that a transgene can encode, for example, a cDNA, a gene, miRNA or lncRNA, or the like. Additionally, the transgene can be a polycistronic message, i.e., arrayed cDNAs or arrayed miRNAs. One exemplary polycistronic transgene is the TCR chains. Polycistronic messages can be engineered in the T cells to express multiple transgenes under control of the same endogenous promoter. Thus, by knocking 3 bicistronic transgenes at 3 selected loci, one could express 6 gene products in an engineered T cell. Thus, a number of transgenes can be expressed in a T cell (1, 2, 3, 4, 5, 6 and so forth, as desired), each under control of separate endogenous promoters, or with some transgenes (i.e., polycistronic transgenes) under the control of the same endogenous promoter. The multiple transgenes can be placed independently under the control of a constitutive promoter or inducible. Thus, a combination of constitutive and/or inducible promoters can be used in a T cell to express multiple transgenes in the same cell.

In a specific embodiment, the transgene is polycistronic, e.g., bicistronic. In a specific embodiment, the transgene is polycistronic and encodes more than one therapeutic protein or therapeutic RNA, where expression of both are under the control of the same endogenous promoter of the T cell. In a specific embodiment, the transgene is bicistronic and encodes two therapeutic proteins (for example, scFvs), wherein the expression of the scFvs are both under the control of the same endogenous promoter of the T cell.

In one embodiment, the therapeutic transgene encodes a TCR. In the case of a transgene that is encoded on more than one polypeptide chain, the transgene can be expressed from more than one polynucleotide, i.e., the two encoding nucleic acids (e.g., cDNAs) are coexpressed in a T cell. Accordingly, where a multi-subunit protein is desired to be expressed, the different polypeptide subunits can be expressed from different transgenes, i.e., the two encoding nucleotide sequences (e.g., cDNA sequences) are coexpressed in a T cell from different transgenes regulated by different endogenous T cell promoters. In one embodiment, the a and b chains of a TCR is expressed.

Chimeric Antigen Receptors (CARs). A chimeric antigen receptor (CAR) is an exemplary product encoded by a therapeutic transgene of the invention. The CAR that is recombinantly expressed by a cell of the invention has an antigen binding domain that binds to an antigen. The antigen is associated with a disease or disorder present in the subject or desired to be prevented in the subject to which the T cell is administered.

In specific embodiments, the CAR can be a "first generation," "second generation" or "third generation" CAR (see, for example, Sadelain et al., *Cancer Discov.* 3(4):388-398 (2013); Jensen et al., *Immunol. Rev.* 257:127-133 (2014); Sharpe et al., *Dis. Model Mech.* 8(4):337-350 (2015); Brentjens et al., *Clin. Cancer Res.* 13:5426-5435 (2007); Gade et al., *Cancer Res.* 65:9080-9088 (2005); Maher et al., *Nat. Biotechnol.* 20:70-75 (2002); Kershaw et al., *J. Immunol.* 173:2143-2150 (2004); Sadelain et al., *Curr. Opin. Immunol.* (2009); Hollyman et al., *J. Immunother.* 32:169-180 (2009)).

"First generation" CARs are typically composed of an extracellular antigen binding domain, for example, a single-chain variable fragment (scFv), fused to a transmembrane domain, which is fused to a cytoplasmic/intracellular domain of the T cell receptor chain. "First generation" CARs typically have the intracellular domain from the CD3-chain, which is the primary transmitter of signals from endogenous T cell receptors (TCRs) (see exemplary first generation CAR in FIG. 1A). "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second-generation" CARs for use in the invention comprise an antigen-binding domain fused to an intracellular signaling domain capable of activating T cells and a co-stimulatory domain designed to augment T cell potency and persistence (Sadelain et al., *Cancer Discov.* 3:388-398 (2013)). CAR design can therefore combine antigen recognition with signal transduction, two functions that are physiologically borne by two separate complexes, the TCR heterodimer and the CD3 complex. "Second generation" CARs include an intracellular domain from various co-stimulatory molecules, for example, CD28, 4-1BB, ICOS, OX40, and the like, in the cytoplasmic tail of the CAR to provide additional signals to the cell (see exemplary second generation CAR in FIG. 1A). "Second generation" CARs provide both co-stimulation, for example, by CD28 or 4-1BB domains, and activation, for example, by a CD3t signaling domain. Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL) (Davila et al., *Oncoimmunol.* 1(9): 1577-1583 (2012)). "Third generation" CARs provide multiple co-stimulation, for example, by comprising both CD28 and 4-1BB domains, and activation, for example, by comprising a CD3t activation domain.

In the embodiments disclosed herein, the CARs generally comprise an extracellular antigen binding domain, a transmembrane domain and an intracellular domain, as described above, where the extracellular antigen binding domain binds to an antigen of interest, such as a cancer antigen or an antigen of an infectious pathogen, or of an autoimmune disorder, or of a transplanted tissue. In a particular non-limiting embodiment, the extracellular antigen-binding domain is an scFv.

As disclosed herein, the methods of the invention involve administering cells that have been engineered to express a CAR. The extracellular antigen-binding domain of a CAR is usually derived from a monoclonal antibody (mAb) or from receptors or their ligands.

The design of CARs is well known in the art (see, for example, reviews by Sadelain et al., *Cancer Discov.* 3(4): 388-398 (2013); Jensen et al., *Immunol. Rev.* 257:127-133 (2014); Sharpe et al., *Dis. Model Mech.* 8(4):337-350 (2015), and references cited therein). A CAR directed to a desired antigen can be generated using well known methods for designing a CAR, including those as described herein. A CAR, whether a first, second or third generation CAR, can be readily designed by fusing a target antigen binding activity, for example, a cancer antigen binding activity, such as an scFv antibody directed to the antigen, to an immune cell signaling domain, such as a T cell receptor cytoplasmic/intracellular domain. As described above, the CAR generally has the structure of a cell surface receptor, with the antigen binding activity, such as an scFv, as at least a portion of the extracellular domain, fused to a transmembrane domain, which is fused to an intracellular domain that has cell signaling activity in a T cell. The CAR can include co-stimulatory molecules, as described herein. One skilled in the art can readily select appropriate transmembrane domains, as described herein and known in the art, and intracellular domains to provide the desired signaling capability in the T cell.

A CAR for use in the present invention comprises an extracellular domain that includes an antigen binding domain that binds to an antigen. In a specific embodiment, the antigen binding domain binds to an antigen on the target cancer cell or tissue. Such an antigen binding domain is generally derived from an antibody. In one embodiment, the antigen binding domain can be an scFv or a Fab, or any suitable antigen binding fragment of an antibody (see Sadelain et al., *Cancer Discov.* 3:38-398 (2013)). Many antibodies or antigen binding domains derived from antibodies that bind to an antigen, such as a cancer antigen, are known in the art. Alternatively, such antibodies or antigen binding domains can be produced by routine methods. Methods of generating an antibody are well known in the art, including methods of producing a monoclonal antibody or screening a library to obtain an antigen binding polypeptide, including screening a library of human Fabs (Winter and Harris, *Immunol. Today* 14:243-246 (1993); Ward et al., *Nature* 341:544-546 (1989); Harlow and Lane, Antibodies: A Laboratory Manual, Cold Spring Harbor Laboratory Press (1988); Hilyard et al., *Protein Engineering: A practical approach* (IRL Press 1992); Borrabeck, *Antibody Engineering*, 2nd ed. (Oxford University Press 1995); Huse et al., *Science* 246:1275-1281 (1989)). For the CAR, the antigen binding domain derived from an antibody can be human, humanized, chimeric, CDR-grafted, and the like, as desired. For example, if a mouse monoclonal antibody is a source antibody for generating the antigen binding domain of a CAR, such an antibody can be humanized by grafting CDRs of the mouse antibody onto a human framework (see Borrabeck, supra, 1995), which can be beneficial for administering the CAR to a human subject. In a preferred embodiment, the antigen binding domain is an scFv. The generation of scFvs is well known in the art (see, for example, Huston, et al., *Proc. Nat. Acad. Sci. USA* 85:5879-5883 (1988); Ahmad et al., *Clin. Dev. Immunol.* 2012: ID980250 (2012); U.S. Pat. Nos. 5,091,513, 5,132,405 and 4,956,778; and U.S. Patent Publication Nos. 20050196754 and 20050196754)).

With respect to obtaining an antigen binding activity, one skilled in the art can readily obtain a suitable antigen binding activity, such as an antibody, using any of the well known methods for generating and screening for an antibody that binds to a desired antigen, as disclosed herein, including the generation of an scFv that binds to an antigen, which is particularly useful in a CAR. In addition, a number of antigen antibodies, in particular monoclonal antibodies, such as cancer antigens or other antigens are commercially available and can also be used as a source for an antigen binding activity, such as an scFv, to generate a CAR.

Alternatively to using an antigen binding domain derived from an antibody, a CAR extracellular domain can comprise a ligand or extracellular ligand binding domain of a receptor (see Sadelain et al., *Cancer Discov.* 3:388-398 (2013); Sharpe et al., *Dis. Model Mech.* 8:337-350 (2015)). In this case, the ligand or extracellular ligand binding domain of a receptor provides to the CAR the ability to target the cell expressing the CAR to the corresponding receptor or ligand. In a specific embodiment, the ligand or extracellular ligand binding domain is selected such that the cell expressing the CAR is targeted to a cancer cell or tumor (see Sadelain et al., *Cancer Discov.* 3:388-398 (2013); Sharpe et al., *Dis. Model Mech.* 8:337-350 (2015), and references cited therein). In an embodiment of the invention, the ligand or extracellular ligand binding domain is selected to bind to an antigen that is the corresponding receptor or ligand (see Sadelain et al, *Cancer Discov.* 3:388-398 (2013)).

For a CAR directed to a target antigen, the antigen binding domain of the CAR is selected to bind to the target antigen (an antigen expressed on a target cell). Such a target antigen can be uniquely expressed on a target cell, or the target antigen can be overexpressed in a target cell relative to non-target cells or tissues. The target antigen to be bound by the CAR is chosen to provide targeting of the cell expressing the CAR over non-target cells or tissues. In a preferred embodiment, for a CAR directed to a cancer antigen, the antigen binding domain of the CAR is selected to bind to an antigen expressed on a cancer cell. Such a cancer antigen can be uniquely expressed on a cancer cell, or the cancer antigen can be overexpressed in a cancer cell relative to noncancerous cells or tissues. The cancer antigen to be bound by the CAR is chosen to provide targeting of the cell expressing the CAR over noncancerous cells or tissues. In one embodiment of the methods of the invention for treating a cancer, a T cell is designed to treat a cancer patient by expressing in the cell a CAR that binds to a suitable cancer antigen of the patient's cancer, as described herein. Similarly, where a CAR is used to target an antigen of an infectious disease pathogen, or an autoimmune disorder, or of a transplanted tissue, the antigen can be uniquely expressed on the target or at the target site, or overexpressed relative to non-target tissues or non-target sites.

The cancer antigen can be a tumor antigen. Any suitable cancer antigen can be chosen based on the type of cancer exhibited by a subject (cancer patient) to be treated. It is understood that the selected cancer antigen is expressed in a manner such that the cancer antigen is accessible for binding by the CAR. Generally, the cancer antigen to be targeted by a cell expressing a CAR is expressed on the cell surface of a cancer cell. However, it is understood that any cancer antigen that is accessible for binding to a CAR is suitable for targeting the CAR expressing cell to the cancer cell. Exemplary cancer antigens and exemplary cancers are provided below in Table 3.

TABLE 3

Targeted Cancer Antigens and Corresponding Cancer Targets.

| Antigen targeted | Tumors investigated | References |
| --- | --- | --- |
| B7-H3<br>CD276 | Sarcoma and Neuroblastoma | (1) |
| B7-H6<br>Nkp30 | Ovarian and several solid cancers | (2-4) |
| CAIX<br>Carbonic Anhydrase IX | Renal cell carcinoma | (5) |
| CEA<br>Carcinoembryonic Antigen | Liver metastasis from Colon cancer, Colon, Pancreas, Gastric and Lung cancers | (6-20) |
| CSPG4<br>Chondroitin sulfate proteoglycan-4 | Melanoma, Mesothelioma, Glioblastoma, Osteosarcoma, Breast, Head and Neck cancers | (21-24) |
| DNAM-1<br>DNAX Accessory Molecule | Melanoma | (25) |
| EpHA2<br>Ephrin type A Receptor 2 | Glioblastoma and Lung cancer | (26, 27) |
| EpCAM<br>Epithelial Cell Adhesion Molecule | Prostate cancer | (28, 29) |
| ERBB family | Head and Neck and Breast cancers | (30, 31) |
| ERBB2 | Prostate, Breast, Ovarian and Pancreatic cancers, Glioblastoma, Meduloblastoma, Osteosarcoma, Ewing sarcoma, Neuroectodermal tumor, Desmoplastic small round cell tumor and Fibrosarcoma | (32-48) |
| EGFRvIII<br>Epidermal Growth Factor Receptor vIII | Glioma/Glioblastoma | (49-56) |
| FAP<br>Fibroblast Associated Protein | Tumor associated fibroblast in Lung cancer, Mesothelioma, Breast and Pancreatic cancers | (27, 57-59) |
| FRα and β<br>Folate Receptor | Ovarian cancer | (60-64) |
| GD2<br>Disialoganglioside | Neuroblastoma, Edwing sarcoma, Melanoma | (65-71) |
| GD3 | Melanoma and other Neuroectodermal tumors | (72, 73) |
| Gp100/HLA-A2 | Melanoma | (74, 75) |
| GPC3<br>Glypican 3 | Hepatocellular carcinoma | (76) |
| HERK-V | Melanoma | (77) |
| MAGE-1/HLA-A1<br>Melanoma Antigen E | Melanoma | (78, 79) |
| IL-11Rα | Osteosarcoma | (80) |
| IL-13Rα2 | Glioma/Glioblastoma Medullobastoma | (81-87) |
| Lewis-Y | Ovarian | (88) (89, 90) |
| LMP1<br>Latent Membrane Protein 1 | Nasopharyngeal cancer | (91) |
| L1-CAM<br>CD271 L1-Cellular Adhesion Molecule | Glioblastoma, Neuroblastoma, Ovarian, Lung and Renal carcinoma | (92, 93) |
| Muc-1<br>Mucin-1 | Prostate and Breast cancers | (43, 94-96) |
| Muc-16<br>Mucin-16 | Ovarian cancer | (97, 98) |
| MSLN<br>Mesothelin | Ovarian, Mesothelioma, Lung cancers | (99-107) |
| N-cam<br>CD56 Neural cell-adhesion moleculel | Neuroblastoma | (108) |
| NKG2DL<br>NKG2D Ligands | Ovarian | (109, 110) |
| PSCA<br>Prostate Stem cell Antigen | Prostate cancer | (111-113) |
| PSMA<br>Prostate Specific Membrane Antigen | Prostate | (114-117) |
| ROR1<br>Receptor tyrosine kinase-like Orphan Receptor | Epithelial solid tumors | (117, 118) |
| TAG72<br>Tumor Associated Glycoprotein 72 | Gastrointestinal, Colon and Breast cancers | (119-122) |
| TRAIL R<br>Trail Receptor | Various type of cancer | (123) |

TABLE 3-continued

Targeted Cancer Antigens and Corresponding Cancer Targets.

| Antigen targeted | Tumors investigated | References |
| --- | --- | --- |
| VEGFR2<br>Vascular Endothelial Growth Factor Receptor-2 | Tumor associated vasculature | (124-127) |
| CD166<br>CCR4<br>Lewis A<br>NYESO<br>CD19 | Lung cancer (Teicher, Biochemical Pharmacology, 2014); T regs (Sugiyama et al. PNAS 2014); Pancreatic cancer (Tempero et al. Cancer Research, 1987); Multiple cancer (Nicholaou et al. Imm & Cell Biol 2006); Leukemia<br>CD166 (Teicher B. A., Biochemical Pharmacology, 87(2): 211-9 (2014)); CCR (Sugiyama D., Proc Natl Acad Sci U.S.A., 110(44): 17945-50 (2013)); Lewis A (Tempero M. A., Cancer Res, 47(20): 5501-3 (1987)); NY-ESO-1 (Nicholaou et al., Immunol Cell Biol., 84: 303-17 (2006)); CD19 (Sadelain M., J Clin Invest., 125: 3392-400 (2015)) | |

1. Cheung et al., *Hybrid Hybridomics*, 22: 209-18 (2003);
2. Zhang et al., *J Immunol.*, 189: 2290-9 (2012);
3. Wu et al., *Gene Ther.*, 22: 675-684 (2015);
4. Wu et al., *J Immunol.*, 194: 5305-11 (2015);
5. Lamers et al., *Mol Ther.*, 21: 904-12 (2013);
6. Darcy et al., *Eur J Immunol.*, 28: 1663-72 (1998);
7. Nolan et al., *Clin Cancer Res.*, 5: 3928-41 (1999);
8. Darcy et al., *J Immunol.*, 164: 3705-12 (2000);
9. Hombach et al., *Gene Ther.*, 6: 300-4 (1999);
10. Haynes et al., *J Immunol.*, 166: 182-7 (2001);
11. Haynes et al., *J Immunol.*, 169: 5780-6 (2002);
12. Schirrmann et al., *Cancer Gene Ther.*, 9: 390-8 (2002);
13. Arakawa et al., *Anticancer Res.* 2002; 22: 4285-9.
14. Gyobu et al., *Cancer Res.*, 64: 1490-5 (2004);
15. Shibaguchi et al., *Anticancer Res.*, 26: 4067-72 (2006);
16. Emtage et al., *Clin Cancer Res.* 14: 8112-22 (2008);
17. Chmielewski et al., *Gastroenterology*, 143: 1095-107 e2 (2012);
18. Chmielewski et al., *Gene Ther.*, 20: 177-86 (2013);
19. Burga et al., *Cancer Immunol Immunother.*, 64: 817-29 (2015);
20. Katz et al. *Clin Cancer Res.*, 21: 3149-59 (2015);
21. Beard et al., *J Immunother Cancer*, 2: 25 (2014);
22. Burns et al., *Cancer Res.*, 70: 3027-33 (2010);
23. Geldres et al., *Clin Cancer Res.*, 20: 962-71 (2014);
24. Schmidt et al., *Proc Natl Acad Sci USA*, 108: 2474-9(2011);
25. Wu et al., *Cancer Immunol Immunother.*, 64: 409-18 (2015);
26. Chow et al., *Mol Ther.*, 21: 629-37 (2013);
27. Kakarla et al., *Mol Ther.*, 21: 1611-20 (2013);
28. Shirasu et al., *J Biomed Biotechnol.*, 2012: 853879 (2012);
29. Deng et al., *BMC Immunol.*, 16: 1 (2015);
30. Davies et al., *Mol Med.*, 18: 565-76 (2012);
31. Papa et al., *Methods Mol Biol.*, 1317: 365-82 (2015);
32. Stancovski et al., *J Immunol.*, 151: 6577-82 (1993);
33. Moritz et al., *Proc Natl Acad Sci USA*, 91: 4318-22 (1994);
34. Haynes et al., *Cancer Immunol Immunother.*, 47: 278-86 (1999);
35. Pinthus et al., *Cancer Res.*, 63: 2470-6 (2003);
36. Ahmed et al., *Cancer Res.*, 67: 5957-64 (2007);
37. Li et al., *Cancer Gene Ther.* 15: 382-92 (2008);
38. Wang et al., *Clin Cancer Res.*, 15: 943-50 (2009);
39. Ahmed et al., *Mol Ther.*, 17: 1779-87 (2009);
40. Zhao et al., *J Immunol.*, 183: 5563-74 (2009);
41. Ahmed et al., *Clin Cancer Res.*, 16: 474-85 (2010);
42. Duong et al., *Immunotherapy*, 3: 33-48 (2011);
43. Wilkie et al., *J Clin Immunol.*, 32: 1059-70 (2012);
44. Lanitis et al., *PLoS One*, 7: e49829 (2012);
45. Maliar et al., *Gastroenterology*, 143: 1375-84 e1-5 (2012);
46. Rainusso et al., *Cancer Gene Ther.*, 19: 212-7 (2012);
47. Sun et al., *Breast Cancer Res.*, 16: R61 (2014);
48. Ahmed et al., *J Clin Oncol.*, 33: 1688-96 (2015);
49. Ohno et al., *Cancer Sci.*, 101: 2518-24 (2010);
50. Morgan et al., *Hum Gene Ther.*, 23: 1043-53 (2012);
51. Choi et al., *J Clin Neurosci.*, 21: 189-90 (2014);
52. Ohno et al., *J Immunother Cancer*, 1: 21 (2013);
53. Shen et al., *J Hematol Oncol.*, 6: 33 (2013);
54. Sampson et al., *Clin Cancer Res.*, 20: 972-84 (2014);
55. Miao et al., *PLoS One*, 9: e94281 (2014);
56. Johnson et al., *Sci Transl Med.*, 7: 275ra22 (2015);
57. Petrausch et al., *BMC Cancer*, 12: 615 (2012);
58. Schuberth et al., *J Transl Med.*, 11: 187 (2013);
59. Wang et al., *Cancer Immunol Res.*, 2: 154-66 (2014);
60. Parker et al., *Hum Gene Ther.*, 11: 2377-87 (2000);

TABLE 3-continued

Targeted Cancer Antigens and Corresponding Cancer Targets.

| Antigen targeted | Tumors investigated | References |
| --- | --- | --- |

61. Kershaw et al., *Clin Cancer Res.*, 12: 6106-15 (2006);
62. Song et al., *Cancer Res.*, 71: 4617-27 (2011);
63. Kandalaft et al., *J Transl Med.*, 10: 157 (2012);
64. Song et al., *Oncotarget*, (2015);
65. Krause et al., *J Exp Med.*, 188: 619-26 (1998);
66. Rossig et al., *Int J Cancer*, 94: 228-36 (2001);
67. Pule et al., *Nat Med.*, 14: 1264-70 (2008);
68. Yvon et al., *Clin Cancer Res.*, 15: 5852-60 (2009);
69. Louis et al., *Blood*, 118: 6050-6 (2011);
70. Kailayangiri et al., *Br J Cancer*, 106: 1123-33 (2012);
71. Singh et al., *Cancer Immunol Res.*, 2: 1059-70 (2014);
72. Yun et al., *Neoplasia*, 2: 449-59 (2000);
73. Lo et al., *Clin Cancer Res.*, 16: 2769-80 (2010);
74. Zhang et al., *Immunol Cell Biol.*, 91: 615-24 (2013);
75. Zhang et al., *Sci Rep.*, 4: 3571 (2014);
76. Gao et al., *Clin Cancer Res.*, 20: 6418-28 (2014);
77. Krishnamurthy et al., *Clin Cancer Res.*, 21: 3241-51 (2015);
78. Willemsen et al., *Gene Ther.*, 8: 1601-8 (2001);
79. Willemsen et al., *J Immunol.*, 174: 7853-8 (2005);
80. Huang et al., *Cancer Res.*, 72: 271-81 (2012);
81. Stastny et al., *J Pediatr Hematol Oncol.*, 29: 669-77 (2007);
82. Chang et al., *Cytotherapy*, 9: 771-84 (2007);
83. Lazovic et al., *Clin Cancer Res.*, 14: 3832-9 (2008);
84. Kong et al., *Clin Cancer Res.*, 18: 5949-60 (2012);
85. Hegde et al., *Mol Ther.*, 21: 2087-101 (2013);
86. Krebs et al., *Cytotherapy*, 16: 1121-31 (2014);
87. Brown et al., *Clin Cancer Res.*, (2015);
88. Westwood et al., *Proc Natl Acad Sci USA*, 102: 19051-6 (2005);
89. Westwood et al., *J Immunother.*, 32: 292-301 (2009);
90. Neeson et al., *Gene Ther.*, 17: 1105-16 (2010);
91. Tang et al., *J Biomed Res.*, 28: 468-75 (2014);
92. Park et al., *Mol Ther.*, 15: 825-33 (2007);
93. Hong et al., *J Immunother.*, 37: 93-104 (2014);
94. Wilkie et al., *J Immunol.*, 180: 4901-9 (2008);
95. Bakhtiari et al., *Hybridoma (Larchmt).*, 28: 85-92 (2009);
96. Sanchez et al., *Prostate Cancer Prostatic Dis.*, 16: 123-31, S1 (2013);
97. Chekmasova et al., *Discov Med.*, 9: 62-70 (2010);
98. Koneru et al., *Oncoimmunology*, 4: e994446 (2015);
99. Carpenito et al., *Proc Natl Acad Sci USA*, 106: 3360-5 (2009);
100. Zhao et al., *Cancer Res.*, 70: 9053-61 (2010);
101. Lanitis et al., *Mol Ther.*, 20: 633-43 (2012);
102. Riese et al., *Cancer Res.*, 73: 3566-77 (2013);
103. Moon et al., *Clin Cancer Res.*, 20: 4262-73 (2014);
104. Guedan et al., *Blood*, 124: 1070-80 (2014);
105. Beatty, *Oncoimmunology*, 3: e28327 (2014);
106. Adusumilli et al., *Sci Transl Med.*, 6: 261ra151 (2014);
107. Wang et al., *Cancer Immunol Res.*, 3: 815-26 (2015);
108. Gilham et al., *J Immunother.*, 25: 139-51 (2002);
109. Barber et al., *J Immunol.*, 183: 6939-47 (2009);
110. Song et al., *Hum Gene Ther.*, 24: 295-305 (2013);
111. Morgenroth et al., *Prostate*, 67: 1121-31 (2007);
112. Hillerdal et al., *BMC Cancer*, 14: 30 (2014);
113. Abate-Daga et al., *Hum Gene Ther.*, 25: 1003-12 (2014);
114. Maher et al., *Nat Biotechnol.*, 20: 70-5 (2002);
115. Ma et al., *Prostate*, 61: 12-25 (2004);
116. Gade et al., *Cancer Res.*, 65: 9080-8 (2005);
117. Hudecek et al., *Clin Cancer Res.*, 19: 3153-64 (2013);
118. Deniger et al., *PLoS One*, 10: e0128151 (2015);
119. Hombach et al., *Gastroenterology*, 113: 1163-70 (1997);
120. McGuinness et al., *Hum Gene Ther.*, 10: 165-73 (1999);
121. Patel et al., *Cancer Gene Ther.* 7: 1127-34 (2000);
122. Sharifzadeh et al., *Cancer Lett.*, 334: 237-44 (2013);
123. Kobayashi et al., *Biochem Biophys Res Commun.* 453: 798-803 (2014);
124. Chinnasamy et al., *Clin Cancer Res.*, 18: 1672-83 (2012);
125. Kanagawa et al., *Cancer Gene Ther.*, 20: 57-64 (2013);
126. Chinnasamy et al., *Cancer Res.*, 73: 3371-80 (2013);
127. Wang et al., *Gene Ther.*, 20: 970-8 (2013);
128. Ordonez, *Am J Surg Pathol.*, 27: 1418-28 (2003);
129. Dennis et al., *Clin Cancer Res.*, 11: 3766-72 (2005);
130. Alvarez et al., *Nanomedicine*, 4: 295-301 (2008);
131. Rizk et al., *Cancer Epidemiol Biomarkers Prev.*, 21: 482-6 (2012);
132. Ordonez, *Mod Pathol.*, 16: 192-7 (2003);
133. Frierson et al., *Hum Pathol.*, 34: 605-9 (2003);
134. Tchou et al., *Breast Cancer Res Treat.*, 33: 799-804 (2012);
135. Parinyanitikul et al., *Clin Breast Cancer*, 13: 378-84 (2013);
136. Wang et al., *J Int Med Res.*, 40: 909-16 (2012);

TABLE 3-continued

Targeted Cancer Antigens and Corresponding Cancer Targets.

| Antigen targeted | Tumors investigated | References |
| --- | --- | --- |

137. Li et al., *Breast Cancer Res Treat.*, 147: 675-84 (2014);
138. Ordonez et al., *Hum Pathol.*, 45: 1529-40 (2014);
139. Tozbikian et al., *PLoS One*, 9: e114900 (2014);
140. Bayoglu et al., *Biomed Pharmacother.*, 70: 190-5 (2015);
141. Einama et al., *Br J Cancer*, 107: 137-42 (2012);
142. Baba et al., *J Surg Oncol.*, 105: 195-9 (2012);
143. Ito et al., *Oncol Rep.*, 31: 27-33 (2014);
144. Hassan et al., *Am J Clin Pathol.*, 124: 838-45 (2005);
145. Yu et al., *J Cancer*, 1: 141-9 (2010);
146. Kawamata et al., *Int J Oncol.*, 41: 2109-18 (2012);
147. Nomura et al., *Int Surg.*, 98: 164-9 (2013);
148. Argani Pedram et al., *Clin Cancer Res.*, 7: 3862-8 (2001);
149. Swierczynski et al., *Hum Pathol.* 35: 357-66 (2004);
150. Inami et al., *Oncol Rep.*, 20: 1375-80 (2008);
151. Frank et al., *Am J Clin Pathol.*, 142: 313-9 (2014);
152. Scales et al., *Mol Cancer Ther.*, 13: 2630-40 (2014);
153. Liebig et al., *Cancer Lett.*, 223: 159-67 (2005);
154. Kawamata et al., *J Gastroenterol.*, 49: 81-92 (2014);
155. Miettinen et al., *Am J Surg Pathol.*, 27: 150-8 (2003);
156. Ordonez, *Am J Surg Pathol.*, 27: 1031-51 (2003);
157. Ordonez, *Mod Pathol.* 19: 417-28 (2006);
158. Kushitani et al., *Pathol Int.*, 57: 190-9 (2007);
159. Pu et al., *Diagn Cytopathol.*, 36: 20-5 (2008);
160. Kachala et al., *Clin Cancer Res.*, 20: 1020-8 (2014);
161. Anish et al., *Oncotarget*, (2015);
162. Pan et al., *Hum Pathol.*, 34: 1155-62 (2003);
163. Yuanbin et al., *2014 ASCO Annual Meeting*, (2014);
164. Ordonez, *Hum Pathol.*, 35: 697-710 (2004);
165. Galloway et al., *Histopathology*, 48: 767-9 (2006);
166. Roe et al., *Lung Cancer*, 61: 235-43 (2008);
167. Tan et al., *Hum Pathol.*, 41: 1330-8 (2010);
168. Servais et al., *Clin Cancer Res.*, 18: 2478-89 (2012);
169. Drapkin et al., *Hum Pathol.*, 35: 1014-21 (2004);
170. Rosen et al., *Gynecol Oncol.* 99: 267-77 (2005);
171. Hassan et al., *Appl Immunohistochem Mol Morphol.* 13: 243-7 (2005);
172. Cao et al., *Int J Gynecol Pathol.*, 24: 67-72 (2005);
173. Yen et al., *Clin Cancer Res.*, 12: 827-31 (2006);
174. Dainty et al., *Gynecol Oncol.*, 105: 563-70 (2007);
175. Obulhasim et al., *Eur J Gynaecol Oncol.*, 31: 63-71 (2010).

Suitable cancer antigens include, but are not limited to, mesothelin (MSLN), prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (Ep-CAM), folate-binding protein (FBP), fetal acetylcholine receptor (AChR), folate receptor-α and β (FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R). It is understood that these or other cancer antigens can be utilized for targeting by a cancer antigen CAR.

As described above, a CAR also contains a signaling domain that functions in the T cell expressing the CAR. Such a signaling domain can be, for example, derived from CDζ or Fc receptor γ (see Sadelain et al., *Cancer Discov.* 3:288-298 (2013). In general, the signaling domain will induce persistence, trafficking and/or effector functions in the transduced T cells, or precursor cells thereof (Sharpe et al., *Dis. Model Mech.* 8:337-350 (2015); Finney et al., *J. Immunol.* 161:2791-2797 (1998); Krause et al., *J. Exp. Med.* 188:619-626 (1998)). In the case of CDζ or Fc receptor γ, the signaling domain corresponds to the intracellular domain of the respective polypeptides, or a fragment of the intracellular domain that is sufficient for signaling. Exemplary signaling domains are described below in more detail.

Exemplary polypeptides are described herein with reference to GenBank numbers, GI numbers and/or SEQ ID NOS. It is understood that one skilled in the art can readily identify homologous sequences by reference to sequence sources, including but not limited to GenBank (ncbi.nlm.nih.gov/genbank/) and EMBL (embl.org/).

CD3ζ. In a non-limiting embodiment, a CAR can comprise a signaling domain derived from a CD3ζ polypeptide, for example, a signaling domain derived from the intracellular domain of CD3ζ, which can activate or stimulate a T cell. CD3ζ comprises 3 Immune-receptor-Tyrosine-based- Activation-Motifs (ITAMs), and transmits an activation signal to the cell, for example, a cell of the lymphoid lineage such as a T cell, after antigen is bound. A CD3ζ polypeptide can have an amino acid sequence corresponding to the sequence having GenBank No. NP_932170 (GI:37595565; see below), or fragments thereof. In one embodiment, the CD3ζ polypeptide has an amino acid sequence of amino acids 52 to 164 of the CD3ζ polypeptide sequence provided below, or a fragment thereof that is sufficient for signaling activity. See GenBank NP_932170 for reference to domains within CD3ζ, for example, signal peptide, amino acids 1 to 21; extracellular domain, amino acids 22 to 30; transmembrane domain, amino acids 31 to 51; intracellular domain, amino acids 52 to 164. It is understood that a "CD3ζ nucleic acid molecule" refers to a polynucleotide encoding a CD3ζ polypeptide.

signaling domain (see FIG. 1B). A CD28 polypeptide can have an amino acid sequence corresponding to the sequence having GenBank No. P10747 or NP_006130 (GI:5453611), as provided below, or fragments thereof. If desired, CD28 sequences additional to the intracellular domain can be included in a CAR of the invention. For example, a CAR can comprise the transmembrane of a CD28 polypeptide. In one embodiment, a CAR can have an amino acid sequence comprising the intracellular domain of CD28 corresponding to amino acids 180 to 220 of CD28, or a fragment thereof. In another embodiment, a CAR can have an amino acid sequence comprising the transmembrane domain of CD28 corresponding to amino acids 153 to 179, or a fragment thereof. See GenBank NP_006130 for reference to domains within CD28, for example, signal peptide, amino acids 1 to

```
                                                           (NP_932170; SEQ ID NO: 16)
  1    MKWKALFTAA ILQAQLPITE AQSFGLLDPK LCYLLDGILF IYGVILTALF LRVKFSRSAD

61    APAYQQGQNQ LYNELNLGRR EEYDVLDKRR GRDPEMGGKP QRRKNPQEGL YNELQKDKMA

121    EAYSEIGMKG ERRRGKGHDG LYQGLSTATK DTYDALHMQA LPPR
```

In certain non-limiting embodiments, an intracellular domain of a CAR can further comprise at least one co-stimulatory signaling domain. Such a co-stimulatory signaling domain can provide increased activation of a T cell. A co-stimulatory signaling domain can be derived from a CD28 polypeptide, a 4-1BB polypeptide, an OX40 polypeptide, an ICOS polypeptide, a DAP10 polypeptide, a 2B4 polypeptide, and the like. CARs comprising an intracellular domain that comprises a co-stimulatory signaling region 18; extracellular domain, amino acids 19 to 152; transmembrane domain, amino acids 153 to 179; intracellular domain, amino acids 180 to 220. It is understood that sequences of CD28 that are shorter or longer than a specific delineated domain can be included in a CAR, if desired. It is understood that a "CD28 nucleic acid molecule" refers to a polynucleotide encoding a CD28 polypeptide.

```
                                                           (NP_006130; SEQ ID NO: 17)
  1    MLRLLLALNL FPSIQVTGNK ILVKQSPMLV AYDNAVNLSC KYSYNLFSRE FRASLHKGLD

61    SAVEVCVVYG NYSQQLQVYS KTGFNCDGKL GNESVTFYLQ NLYVNQTDIY FCKIEVMYPP

121    PYLDNEKSNG TIIHVKGKHL CPSPLFPGPS KPFWVLVVVG GVLACYSLLV TVAFIIFWVR

181    SKRSRLLHSD YMNMTPRRPG PTRKHYQPYA PPRDFAAYRS
``` comprising 4-1BB, ICOS or DAP-10 have been described previously (see U.S. Pat. No. 7,446,190, which is incorporated herein by reference, which also describes representative sequences for 4-1BB, ICOS and DAP-10). In some embodiments, the intracellular domain of a CAR can comprise a co-stimulatory signaling region that comprises two co-stimulatory molecules, such as CD28 and 4-1BB (see Sadelain et al., *Cancer Discov.* 3(4):388-398 (2013)), or CD28 and OX40, or other combinations of co-stimulatory ligands, as disclosed herein.

CD28. Cluster of Differentiation 28 (CD28) is a protein expressed on T cells that provides co-stimulatory signals for T cell activation and survival. CD28 is the receptor for CD80 (B7.1) and CD86 (B7.2) proteins. In one embodiment, a CAR can comprise a co-stimulatory signaling domain derived from CD28. For example, as disclosed herein, a CAR can include at least a portion of an intracellular/cytoplasmic domain of CD28, for example an intracellular/cytoplasmic domain that can function as a co-stimulatory 4-1BB. 4-1BB, also referred to as tumor necrosis factor receptor superfamily member 9, can act as a tumor necrosis factor (TNF) ligand and have stimulatory activity. In one embodiment, a CAR can comprise a co-stimulatory signaling domain derived from 4-1BB. A 4-1BB polypeptide can have an amino acid sequence corresponding to the sequence having GenBank No. P41273 or NP_001552 (GI:5730095) or fragments thereof. In one embodiment, a CAR can have a co-stimulatory domain comprising the intracellular domain of 4-1BB corresponding to amino acids 214 to 255, or a fragment thereof. In another embodiment, a CAR can have a transmembrane domain of 4-1BB corresponding to amino acids 187 to 213, or a fragment thereof. See GenBank NP_001552 for reference to domains within 4-1BB, for example, signal peptide, amino acids 1 to 17; extracellular domain, amino acids 18 to 186; transmembrane domain, amino acids 187 to 213; intracellular domain, amino acids 214 to 255. It is understood that sequences of 4-1BB that are shorter or longer than a specific delineated domain can be included in a CAR, if desired. It is also understood that a "4-1BB nucleic acid molecule" refers to a polynucleotide encoding a 4-1BB polypeptide.

```
                                              (NP_001552; SEQ ID NO: 18)
  1    MGNSCYNIVA  TLLLVLNFER  TRSLQDPCSN  CPAGTFCDNN  RNQICSPCPP  NSFSSAGGQR

61    TCDICRQCKG  VFRTRKECSS  TSNAECDCTP  GFHCLGAGCS  MCEQDCKQGQ  ELTKKGCKDC

121    CFGTFNDQKR  GICRPWTNCS  LDGKSVLVNG  TKERDVVCGP  SPADLSPGAS  SVTPPAPARE

181    PGHSPQIISF  FLALTSTALL  FLLFFLTLRF  SVVKRGRKKL  LYIFKQPFMR  PVQTTQEEDG

241    CSCRFPEEEE  GGCEL
```

OX40. OX40, also referred to as tumor necrosis factor receptor superfamily member 4 precursor or CD134, is a member of the TNFR-superfamily of receptors. In one embodiment, a CAR can comprise a co-stimulatory signaling domain derived from OX40. An OX40 polypeptide can have an amino acid sequence corresponding to the sequence having GenBank No. P43489 or NP_003318 (GI:4507579), provided below, or fragments thereof. In one embodiment, a CAR can have a co-stimulatory domain comprising the intracellular domain of OX40 corresponding to amino acids 236 to 277, or a fragment thereof. In another embodiment, a CAR can have an amino acid sequence comprising the transmembrane domain of OX40 corresponding to amino acids 215 to 235 of OX40, or a fragment thereof. See GenBank NP_003318 for reference to domains within OX40, for example, signal peptide, amino acids 1 to 28; extracellular domain, amino acids 29 to 214; transmembrane domain, amino acids 215 to 235; intracellular domain, amino acids 236 to 277. It is understood that sequences of OX40 that are shorter or longer than a specific delineated domain can be included in a CAR, if desired. It is also understood that an "OX40 nucleic acid molecule" refers to a polynucleotide encoding an OX40 polypeptide.

```
                                              (NP_003318; SEQ ID NO: 19)
  1    MCVGARRLGR  GPCAALLLLG  LGLSTVTGLH  CVGDTYPSND  RCCHECRPGN  GMVSRCSRSQ

61    NTVCRPCGPG  FYNDVVSSKP  CKPCTWCNLR  SGSERKQLCT  ATQDTVCRCR  AGTQPLDSYK

121    PGVDCAPCPP  GHFSPGDNQA  CKPWTNCTLA  GKHTLQPASN  SSDAICEDRD  PPATQPQETQ

181    GPPARPITVQ  PTEAWPRTSQ  GPSTRPVEVP  GGRAVAAILG  LGLVLGLLGP  LAILLALYLL

241    RRDQRLPPDA  HKPPGGGSFR  TPIQEEQADA  HSTLAKI
```

ICOS. Inducible T-cell costimulator precursor (ICOS), also referred to as CD278, is a CD28-superfamily costimulatory molecule that is expressed on activated T cells. In one embodiment, a CAR can comprise a co-stimulatory signaling domain derived from ICOS. An ICOS polypeptide can have an amino acid sequence corresponding to the sequence having GenBank No. NP_036224 (GI:15029518), provided below, or fragments thereof. In one embodiment, a CAR can have a co-stimulatory domain comprising the intracellular domain of ICOS corresponding to amino acids 162 to 199 of ICOS. In another embodiment, a CAR can have an amino acid sequence comprising the transmembrane domain of ICOS corresponding to amino acids 141 to 161 of ICOS, or a fragment thereof. See GenBank NP_036224 for reference to domains within ICOS, for example, signal peptide, amino acids 1 to 20; extracellular domain, amino acids 21 to 140; transmembrane domain, amino acids 141 to 161; intracellular domain, amino acids 162 to 199. It is understood that sequences of ICOS that are shorter or longer than a specific delineated domain can be included in a CAR, if desired. It is also understood that an "ICOS nucleic acid molecule" refers to a polynucleotide encoding an ICOS polypeptide.

```
                                              (NP_036224; SEQ ID NO: 20)
  1    MKSGLWYFFL  FCLRIKVLTG  EINGSANYEM  FIFHNGGVQI  LCKYPDIVQQ  FKMQLLKGGQ

61    ILCDLTKTKG  SGNTVSIKSL  KFCHSQLSNN  SVSFFLYNLD  HSHANYYFCN  LSIFDPPPFK

121    VTLTGGYLHI  YESQLCCQLK  FWLPIGCAAF  VVVCILGCIL  ICWLTKKKYS  SSVHDPNGEY

181    MFMRAVNTAK  KSRLTDVTL
```

DAP10. DAP10, also referred to as hematopoietic cell signal transducer, is a signaling subunit that associates with a large family of receptors in hematopoietic cells. In one embodiment, a CAR can comprise a co-stimulatory domain derived from DAP10. A DAP10 polypeptide can have an amino acid sequence corresponding to the sequence having GenBank No. NP_055081.1 (GI:15826850), provided below, or fragments thereof. In one embodiment, a CAR can have a co-stimulatory domain comprising the intracellular domain of DAP10 corresponding to amino acids 70 to 93, or a fragment thereof. In another embodiment, a CAR can have a transmembrane domain of DAP10 corresponding to amino acids 49 to 69, or a fragment thereof. See GenBank NP_055081.1 for reference to domains within DAP10, for example, signal peptide, amino acids 1 to 19; extracellular domain, amino acids 20 to 48; transmembrane domain, amino acids 49 to 69; intracellular domain, amino acids 70 to 93. It is understood that sequences of DAP10 that are shorter or longer than a specific delineated domain can be included in a CAR, if desired. It is also understood that a "DAP10 nucleic acid molecule" refers to a polynucleotide encoding an DAP10 polypeptide.

(NP_055081.1; SEQ ID NO: 21)
```
  1    MIHLGHILFL LLLPVAAAQT TPGERSSLPA FYPGTSGSCS GCGSLSLPLL AGLVAADAVA
 61    SLLIVGAVFL CARPRRSPAQ EDGKVYINMP GRG
```

The extracellular domain of a CAR can be fused to a leader or a signal peptide that directs the nascent protein into the endoplasmic reticulum and subsequent translocation to the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a CAR is generally expressed at the cell surface as a mature protein lacking the signal peptide, whereas the precursor form of the polypeptide includes the signal peptide. A signal peptide or leader can be essential if a CAR is to be glycosylated and/or anchored in the cell membrane. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. Any suitable signal peptide, as are well known in the art, can be applied to a CAR to provide cell surface expression in a T cell (see Gierasch *Biochem.* 28:923-930 (1989); von Heijne, *J. Mol. Biol.* 184 (1):99-105 (1985)). Particularly useful signal peptides can be derived from cell surface proteins naturally expressed in the T cell thereof, including any of the signal peptides of the polypeptides disclosed herein. Thus, any suitable signal peptide can be utilized to direct a CAR to be expressed at the cell surface of a T cell.

In certain non-limiting embodiments, an extracellular antigen-binding domain of a CAR can comprise a linker sequence or peptide linker connecting the heavy chain variable region and light chain variable region of the extracellular antigen-binding domain. In certain non-limiting embodiments, a CAR can also comprise a spacer region or sequence that links the domains of the CAR to each other. For example, a spacer can be included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains with other polypeptides, for example, to allow the antigen binding domain to have flexibility in orientation in order to facilitate antigen recognition. The spacer region can be, for example, the hinge region from an IgG, the $CH_2CH_3$ (constant) region of an immunoglobulin, and/or portions of CD3 (cluster of differentiation 3) or some other sequence suitable as a spacer.

The transmembrane domain of a CAR generally comprises a hydrophobic alpha helix that spans at least a portion of the membrane. Different transmembrane domains result in different receptor stability. After antigen recognition, receptors cluster and a signal is transmitted to the cell. In an embodiment, the transmembrane domain of a CAR can be derived from another polypeptide that is naturally expressed in the T cell. In one embodiment, a CAR can have a transmembrane domain derived from CD8, CD28, CD3, CD4, 4-1BB, OX40, ICOS, CTLA-4, PD-1, LAG-3, 2B4, BTLA, or other polypeptides expressed in the T cell having a transmembrane domain, including others as disclosed herein or that are well known in the art. Optionally, the transmembrane domain can be derived from a polypeptide that is not naturally expressed in the T cell, so long as the transmembrane domain can function in transducing signal from antigen bound to the CAR to the intracellular signaling and/or co-stimulatory domains. It is understood that the portion of the polypeptide that comprises a transmembrane domain of the polypeptide can include additional sequences from the polypeptide, for example, additional sequences adjacent on the N-terminal or C-terminal end of the transmembrane domain, or other regions of the polypeptide, as desired.

CD8. Cluster of differentiation 8 (CD8) is a transmembrane glycoprotein that serves as a co-receptor for the T cell receptor (TCR). CD8 binds to a major histocompatibility complex (MHC) molecule and is specific for the class I MHC protein. In one embodiment, a CAR can comprise a transmembrane domain derived from CD8. A CD8 polypeptide can have an amino acid sequence corresponding to the sequence having GenBank No. NP_001139345.1 (GI: 225007536), as provided below, or fragments thereof. In one embodiment, a CAR can have an amino acid sequence comprising the transmembrane domain of CD8 corresponding to amino acids 183 to 203, or fragments thereof. See GenBank NP_001139345.1 for reference to domains within CD8, for example, signal peptide, amino acids 1 to 21; extracellular domain, amino acids 22 to 182; transmembrane domain amino acids, 183 to 203; intracellular domain, amino acids 204 to 235. It is understood that additional sequence of CD8 beyond the transmembrane domain of amino acids 183 to 203 can be included in a CAR, if desired. It is further understood that sequences of CD8 that are shorter or longer than a specific dilineated domain can be included in a CAR, if desired. It also is understood that a "CD8 nucleic acid molecule" refers to a polynucleotide encoding a CD8 polypeptide.

(NP_001139345.1; SEQ ID NO: 22)
```
  1    MALPVTALLL PLALLLHAAR PSQFRVSPLD RTWNLGETVE LKCQVLLSNP TSGCSWLFQP
 61    RGAAASPTFL LYLSQNKPKA AEGLDTQRFS GKRLGDTFVL TLSDFRRENE GYYFCSALSN
121    SIMYFSHFVP VFLPAKPTTT PAPRPPTPAP TIASQPLSLR PEACRPAAGG AVHTRGLDFA
181    CDIYIWAPLA GTCGVLLLSL VITLYCNHRN RRRVCKCPRP VVKSGDKPSL SARYV
```

CD4. Cluster of differentiation 4 (CD4), also referred to as T-cell surface glycoprotein CD4, is a glycoprotein found on the surface of immune cells such as T helper cells, monocytes, macrophages, and dendritic cells. In one embodiment, a CAR can comprise a transmembrane domain derived from CD4. CD4 exists in various isoforms. It is understood that any isoform can be selected to achieve a desired function. Exemplary isoforms include isoform 1 (NP_000607.1, GI:10835167), isoform 2 (NP_001181943.1, GI:303522479), isoform 3 (NP_001181944.1, GI:303522485; or NP_001181945.1, GI:303522491; or NP_001181946.1, GI:303522569), and the like. One exemplary isoform sequence, isoform 1, is provided below. In one embodiment, a CAR can have an amino acid sequence comprising the transmembrane domain of CD4 corresponding to amino acids 397 to 418, or fragments thereof. See GenBank NP_000607.1 for reference to domains within CD4, for example, signal peptide, amino acids 1 to 25; extracellular domain, amino acids 26 to 396; transmembrane domain amino acids, 397 to 418; intracellular domain, amino acids 419 to 458. It is understood that additional sequence of CD4 beyond the transmembrane domain of amino acids 397 to 418 can be included in a CAR, if desired. It is further understood that sequences of CD4 that are shorter or longer than a specific dilineated domain can be included in a CAR, if desired. It also is understood that a "CD4 nucleic acid molecule" refers to a polynucleotide encoding a CD4 polypeptide.

antigen-specific co-stimulatory receptor, which mimics the affects 4-1BB, OX40, ICOS or CD70 (depending on the co-stimulatory domain of the CCR) upon binding to its binding partner, i.e., a target antigen.

Exemplary Costimulatory Ligands (CLs) useful as a product that can be encoded by a therapeutic transgene include, but are not limited to, costimulatory ligands 4-1BBL; OX40L; ICOSL; CD70, and the like. Exemplary Chimeric Costimulatory Receptors (CCRs) that can be encoded by a therapeutic transgene include, but are not limited to, an antigen-specific costimulatory receptor, mimicking the effects of 4-1BB, OX40, ICOS or CD70 upon binding to a target antigen.

Cytokines. A cytokine is an exemplary product encoded by a therapeutic transgene of the invention. Cytokines that are particularly useful when encoded by a therapeutic transgene include those that stimulate or sustain activation of a T cell of the invention. Exemplary cytokines useful as a product encoded by a therapeutic transgene for stimulating an immune response include, but are not limited to, IL2, IL12, IL15, IL18, and the like. Exemplary cytokines useful as a product encoded by a therapeutic transgene for inhibiting an immune response include, but are not limited to, TGFBeta, IL10, and the like.

```
                                    (NP_000607.1; SEQ ID NO: 23)
  1    MNRGVPFRHL  LLVLQLALLP  AATQGKKVVL  GKKGDTVELT  CTASQKKSIQ  FHWKNSNQIK

61    ILGNQGSFLT  KGPSKLNDRA  DSRRSLWDQG  NFPLIIKNLK  IEDSDTYICE  VEDQKEEVQL

121    LVFGLTANSD  THLLQGQSLT  LTLESPPGSS  PSVQCRSPRG  KNIQGGKTLS  VSQLELQDSG

181    TWTCTVLQNQ  KKVEFKIDIV  VLAFQKASSI  VYKKEGEQVE  FSFPLAFTVE  KLTGSGELWW

241    QAERASSSKS  WITFDLKNKE  VSVKRVTQDP  KLQMGKKLPL  HLTLPQALPQ  YAGSGNLTLA

301    LEAKTGKLHQ  EVNLVVMRAT  QLQKNLTCEV  WGPTSPKLML  SLKLENKEAK  VSKREKAVWV

361    LNPEAGMWQC  LLSDSGQVLL  ESNIKVLPTW  STPVQPMALI  VLGGVAGLLL  FIGLGIFFCV

421    RCRHRRRQAE  RMSQIKRLLS  EKKTCQCPHR  FQKTCSPI
```

It is understood that domains of the polypeptides described herein can be used in a cancer antigen CAR, as useful to provide a desired function such as a signal peptide, antigen binding domain, transmembrane domain, intracellular signaling domain and/or co-stimulatory domain. For example, a domain can be selected such as a signal peptide, a transmembrane domain, an intracellular signaling domain, or other domain, as desired, to provide a particular function to a CAR of the invention. Possible desirable functions can include, but are not limited to, providing a signal peptide and/or transmembrane domain.

Chimeric Co-stimulatory Receptors (CCRs). A chimeric co-stimulatory receptor (CCR) is an exemplary product encoded by a therapeutic transgene of the invention. Chimeric co-stimulatory receptors (CCRs) are chimeric receptors that, similar to a CAR, comprise an antigen-binding extracellular domain, a transmembrane domain and an intracellular signaling domain (Sadelain et al., Cancer Discov. 3(4):388-398 (2013)). CCRs do not have a T cell activation domain, but do comprise a co-stimulatory domain, such as one of the co-stimulatory domains described above for a CAR, for example, CD28, 4-1BB, OX40, ICOS, DAP10, 2B4, CD70, or the like. CCRs can be used in conjunction with a T cell receptor or a CAR to enhance T cell reactivity against dual-antigen expressing T cells (Sadelain et al., supra, 2013). CCRs can also be used to enhance selective tumor targeting (Sadelain et al., supra, 2013). A CCR is an Dominant negatives. A dominant negative is an exemplary product of encoded by a therapeutic transgene of the invention. Dominant negatives that are particularly useful when encoded by a therapeutic transgene include those that stimulate or sustain activation of a T cell of the invention. Exemplary dominant negatives include, but are not limited to, an inhibitory chimeric antigen receptor (iCAR), a secretable soluble cytokine receptor (e.g., for TGFBeta, IL10), a secretable soluble T-cell inhibitory receptor (e.g., derived from PD1, CTLA4, LAG3, or TIM-3), and the like. Inhibitory chimeric antigen receptors are cell-surface receptors composed of an extracellular scFV domain (binds a cell-surface molecule in the target cell) fused to an intracellular signaling domain derived from inhibitory T-cell receptors (such as PD1, CTL4). Engineered T cells are inhibited upon interaction with a target cell.

Microenvironment Modulators. Microenvironment modulators are exemplary products encoded by therapeutic transgenes of the invention. A microenvironment modulator refers to a molecule that modulates the activity of cells in the vicinity of the therapeutic engineered T cell. Microenvironment modulators that are particularly useful when encoded by a therapeutic transgene include those that stimulate or sustain activation of a T cell of the invention. Exemplary microenvironment modulators include, but are not limited to, heparanase, Herpes Virus Entry Mediator (HVEM), also referred to as TNFRSF14, and the like.

Antibodies. An antibody is an exemplary product encoded by a therapeutic transgene of the invention. Exemplary antibodies include, but are not limited to, an antibody against a T-cell inhibitory ligand, such as PD1L, CD80, CD86, Galectin-9, Fas ligand, and the like.

The antibody can be expressed as an immunoglobulin, for example, an IgG, or as a Bi-specific T-cell engager (BiTE), a diabody, a duel affinity re-targeting antibody (DART), a Fab, a F(ab'), a single chain variable fragment (scFv), a nanobody, a bi-specific antibody, or the like (see, for example, Harlow and Lane, *Antibodies: A Laboratory Manual*, Cold Spring Harbor Laboratory (1988); Chames et al., *Br. J. Pharmacol.* 157:220-233 (2009); Rader, *Blood*, 117:4403-4404 (2011)).

Biosensors. A biosensor is an exemplary product encoded by a therapeutic transgene of the invention. A biosensor is a biological molecule (protein, DNA, or RNA) that, upon ligand binding, signals to the cell to produce a specific effect. The biosensor can be, for example, a biosensor for protein, DNA, RNA, microRNA, metabolite, ion, or the like. Exemplary biosensors include, but are not limited to, toll-like receptor (TLR), which is a biosensor for DNA, RNA, toxin, and a biosensor for an ion, for example, Calcium-sensing Calmodulin (CaM)-calmodulin-binding peptide. The expression of specific TLRs allows the engineered T cell to respond to the presence of target molecules (such as RNA, toxin) in the cytoplasm, thus triggering a determined signal that the cell can use to activate the expression of a therapeutic molecule. A similar strategy applies to CaM-calmodulin binding protein (which senses intracellular calcium). These biosensors can act as an intermediate during the production of a therapeutic molecule, and they do so only when it is required to have such an effect. For example, the biosensor can be used to sense a state of the cell and then activate expression of another transgene. In a particular embodiment, or example, a biosensor can be used that specifically detect a specific HIV RNA sequence. Upon binding, the biosensor undergoes a conformational change that causes the release of a chimeric transcription repressor which then translocates to the nucleus and specifically inhibits HIV genome transcription.

Chimeric Receptor Ligands (CRLs). A chimeric receptor ligand (CRL) is an exemplary product encoded by a therapeutic transgene of the invention. A CRL is a cell-surface ligand that is recognized by a target-cell receptor (such as a cytokine receptor) and that, upon interaction with its specific receptor, will trigger a T-cell response. A CRL contains an intracellular domain that will initiate a T-cell response upon interaction with its specific receptor in the target cell.

Chimeric Immune Receptor Ligands (CIRLs). A chimeric immune receptor (CIRL) is an exemplary product encoded by a therapeutic transgene of the invention. A CIRL is a cell-surface ligand that is recognized by an immune-cell receptor (such as a TCR or Immunoglobulin) and that, upon interaction with its specific receptor, will trigger a T-cell response. A CIRL contains an intracellular domain that will initiate a T-cell response upon interaction with its specific receptor in the target cell.

Soluble Receptors. A soluble receptor is an exemplary product encoded by a therapeutic transgene of the invention. Such soluble receptors can be intracellular or extracellular. Exemplary soluble receptors include, but are not limited to, IL4R, IL10R, PD1, CTL4, TIM-3, LAG3, and the like. Such soluble receptors generally have a stimulatory effect on an immune response.

Solute Transporters. A solute transporter is an exemplary product encoded by a therapeutic transgene of the invention. Exemplary solute transporters include, but are not limited to, a glucose transporter, such as Glut1 or Glut3. Effector T cells are known to require increased uptake of glucose to generate energy. Engineered T cells expressing glucose transporters can benefit from an increased number of glucose transporters when T cells are in a competitive environment where tumor cells (usually in larger numbers) are consuming glucose.

Enzymes. An enzyme is an exemplary product encoded by a therapeutic transgene of the invention. An exemplary therapeutic enzyme includes, but is not limited to, PKM2. Pyruvate Kinase Muscle isozyme 2 (PKM2) is an enzyme that is needed in dividing cells, such as effector T cells, with high glycolysis rate and high demand of biosynthetic precursors. Overexpression of PKM2 helps to increase biosynthetic precursors, thus improving proliferation of engineered T cells.

Ribozymes. A ribozyme is an exemplary product encoded by a therapeutic transgene of the invention. An exemplary ribozyme that is the product of a therapeutic transgene includes, but is not limited to, a pathogen-specific or viral-specific ribozyme that cleaves pathogen or viral genome, respectively. In the case of a viral pathogen, the ribozyme can thus inhibit both virus RNA reverse transcription during virus entrance and virus RNA genome packaging during virus assembly. It is readily apparent that ribozymes to various pathogens, including targeting viral genomes, can be expressed as the product of a therapeutic transgene. In a specific embodiment, the transgene encodes a HIV-specific ribozyme that cleaves HIV RNA genome, thus inhibiting both virus RNA reverse transcription during virus entrance and virus RNA genome packaging during virus assembly.

Genetic Circuits. A genetic circuit is an exemplary product encoded by a therapeutic transgene of the invention. A genetic circuit is a set of gene expression units that are functionally connected.

One embodiment of a genetic circuit is a constitutive transcription unit that expresses a cell-surface ligand-specific synthetic transcription factor (TF) where upon ligand binding the TF moiety is released and translocates to the nucleus. Then, the TF binds its cognate DNA sequence in the second transcription unit (inducible by definition), which activates the expression of an inhibitory ligand-specific soluble receptor that is secreted into the microenvironment to trap such an inhibitory ligand. In another embodiment, a constitutive transcription unit that expresses a chimeric antigen receptor (CAR) that, upon target-cell recognition, induces the expression of a secretable tumor suppressor (such as the lymphoma-specific soIHEVM) via a NFAT-responsive element; in such an embodiment, the CAR is encoded by a first transgene under the control of a constitutive endogenous promoter, which CAR, upon target-cell recognition, induces the expression of a secretable tumor suppressor (such as the lymphoma-specific soIHEVM) from a transgene under the control of a NFAT-responsive inducible endogenous promoter. In a particular embodiment, a synthetic TF is expressed from one transcription unit (a single transgene integrated at one location); the soluble receptor is expressed from a second transcription unit (a single transgenic expression cassette, integrated at the same or different location) and that expression occurs when TF bind to this second transcription unit.

In a particular embodiment of a genetic circuit, a CAR-expressing T cell contains a genetic circuit composed of HIF1a-dependent and TALE-VP64-dependent transcription units. When the CART cell is in a tumor microenvironment with low oxygen levels, HIF1alpha transcription factor is activated in the T cells, binds the HIF1a-dependent transcription unit and induces the expression of a chimeric transcription factor TALE-VP64, which then binds to the TALE-VP64-dependent transcription unit and stimulates the expression of secretable scFvs that targets an inhibitory molecule in the microenvironment such as PD1L or CD80. From this second transcription unit, a recombinant HIF1a is also expressed which will result in a positive feedback to the first transcription unit. In the foregoing specific embodiment, expression of a first transgene is under the control of an endogenous inducible promoter induced by HIF1 alpha transcription factor, expression of a second transgene is under the control of an endogenous inducible promoter induced by TALE-VP64, and the first transgene encodes TALE-VP64, and the second transgene encodes the secretable scFv. Optionally, the expression of a third transgene, which third transgene encodes HIF1a, is under the control of a different endogenous inducible promoter that also is induced by TALE-VP64. In one embodiment, a transcription factor can drive expression of one or multiple gene products, the latter occurring in the case of a polycistronic message. Examples of bicistronic transcription units: the alpha and beta chains to assemble a TCR; two scFvs in tandem, and the like. In one embodiment, a single TALE-VP64-responsive transcription unit will contain both the scFv and HIF1a; this is a bicistronic construct: two genes will be expressed from a single promoter.

In another particular embodiment, a constitutive transcription unit that expresses a cell-surface CD19-specific scFV-NFAT fusion protein that upon binding to B cells the NFAT moiety is released, it translocates to the nucleus, and binds to its cognate DNA sequence in the second transcription unit, from which a chimeric immune receptor ligand is expressed. This second gene encodes a fusion protein composed on an extracellular antigen (that is recognized by a specific immunoglobulin receptor on the target B cell) and intracellular signaling domain(s) that activates the engineered T cell, resulting in target B-cell death. Thus, in this particular embodiment, expression of a first transgene is under the control of an endogenous constitutive promoter, which first transgene encodes the cell-surface CD19-specific scFv-NFAT fusion protein, and expression of a second transgene is under the control of an endogenous inducible promoter that is induced by binding of the cell-surface CD19-specific scFv-NFAT fusion protein to B cells, and the second transgene encodes a fusion protein comprising (i) an extracellular antigen (that is recognized by an immunoglobulin receptor on the target B cell), and (ii) at least one intracellular signaling domain that activates the engineered T cell, resulting in target B-cell death (for example, due to cytolytic activity of the activated T cell).

Epigenetic Modifiers. An epigenetic modifier is an exemplary product encoded by a therapeutic transgene of the invention. An epigenetic modifier is a protein/enzyme that catalyzes specific modifications of the chromatin, either the histone proteins or DNA, at a particular genomic location. These modifications result in specific changes of gene expression, either activation or repression. Exemplary epigenetic modifiers include, but are not limited to, chimeric programmable sequence-specific DNA binding domain fused to p300 acetyltransferase domain (a histone H3 acetylase), which activates target gene expression; and chimeric programmable sequence-specific DNA binding domain fused to KRAB repressor domain (a protein that recruits heterochromatin-forming complexes), which represses target gene expression.

Transcriptional Activators or Repressors. A transcriptional activator or repressor (transcription factor) is an exemplary product encoded by a therapeutic transgene of the invention. The transcriptional activator or repressor can be naturally occurring or chimeric. In some cases, an activator for one gene can be a repressor for another gene, or vice versa. Exemplary transcription factors that can be expressed by a therapeutic transgene include, but are not limited to, Foxp3, NFAT, HIF-1alpha, and the like.

Exemplary chimeric transcriptional activators include, but are not limited to, fusion proteins composed of a DNA binding domain (such TAL, zinc-finger, CRISPR/deactivatedCas9) and a transactivation domain (such VP16, VP64, p65, Rta, or combinations of them), which can be designed to specifically activate one or more genes. Thus, in a specific embodiment, a therapeutic transgene encodes a fusion protein comprising a DNA binding domain and a transactivation domain.

Exemplary chimeric transcriptional repressors include, but are not limited to, fusion proteins composed of a DNA binding domain (such TAL, zinc-finger, CRISPR/deactivatedCas9) and a repressor domain (such as KRAB), which can be designed to specifically repress one or more genes. Thus, in a specific embodiment, a therapeutic transgene encodes a fusion protein comprising a DNA binding domain and a repressor domain.

Non-coding RNA. Non-coding RNA is an exemplary product encoded by a therapeutic transgene of the invention. Exemplary non-coding RNAs (microRNAs or small interfering RNAs) include those that target inhibitory receptor gene messenger RNAs such as PD1, TIM-3, LAG3, CTLA-4, and the like. Thus, in a specific embodiment, a therapeutic transgene encodes a non-coding RNA such as a microRNA (miRNA), small interfering RNA (siRNA), antisense RNA, etc. In a specific embodiment wherein stimulation of the activity of the engineered T cell is desired, the non-coding RNA can target, for example, target inhibitory receptor gene messenger RNAs such as messenger RNAs of PD1, TIM-3, LAG3, CTLA-4, or the like.

In the case where stimulating an immune response is desired, a therapeutic transgene is selected preferably to encode a product that stimulates an immune response. Such a product that stimulates an immune response can be, but is not limited to, IL12, IL15, IL18, or a functional domains derived from any of these factors. In the case wherein inhibiting an an inhibitor of an immune response is desired, a therapeutic transgene is selected preferably to encode a product that inhibits an inhibitor of an immune response. Such a product that inhibits an inhibitor of an immune response, can be, but is not limited to, an antibody specific to a ligand (e.g., PD1L, CD80, CD86, or Galectin-9) that binds a T-cell inhibitory receptor (e.g., PD1, CTLA4, LAG3, or TIM3); a soluble receptor that binds a factor such TGFbeta, TNFalpha, IL4, IL6, or IL10, thus preventing the activation of the factor's cell-surface receptor; an antigen or functional derivative thereof that binds a specific autoimmune immune receptor on a B or T cell to induce immunological tolerance or cell death, etc. In one embodiment, for example, PD1L, CD80, CD86, Galectin-9 ligands are known to inhibit T-cell activity by binding to specific receptors on T cells. The therapeutic antibodies bind the ligands—not the T-cell inhibitory receptors; the antibody will block the interaction between the ligand and its corresponding T-cell inhibitory receptor. Therefore, engineered T cells that secrete these antibodies will not be inhibited by these ligands. In one embodiment, for example, TGFbeta is a cytokine that also inhibits T-cell activity. A therapeutic soluble receptor specific for this cytokine will block its activity by preventing its binding to the receptor expressed on T cells. Therefore, engineered T cells that secrete a TGFbeta soluble receptor will not be inhibited by this cytokine.

In another embodiment, the T cell can optionally express a transgene that produces a reporter. A reporter is an exemplary transgene of the invention that can be co-expressed in a T cell with a therapeutic transgene. An example of such a transgene is truncated EGF receptor (EGFRt), which allows for both detection and elimination (i.e., can function as a cell suicide switch), if needed, of the therapeutic T cell. There are specific antibodies (e.g., cetuximab) that recognize this reporter and trigger antibody-mediated target-cell death in vivo (see U.S. Pat. No. 8,802,374)). Thus, in a specific embodiment, the engineered T cell (in which expression of a therapeutic transgene is under the control of an endogenous promoter) further comprises a reporter transgene, the reporter transgene being a transgene encoding a detectable marker (preferably cell-surface) protein, wherein expression of the reporter transgene is under the control of an endogenous promoter of the T cell (e.g., any of the endogenous promoters described hereinabove). In a specific embodiment, the reporter transgene does not encode IL4 or a membrane-bound form of IL4. In another specific embodiment, the reporter transgene encodes a cell suicide switch. In a specific embodiment, the cell suicide switch is EGFRt; in such an embodiment, after administration of the engineered T cell to the subject for therapeutic purpose, the subject can be administered an antibody that recognizes EGFRt and triggers cell death of the engineered T cell, to shut down the T cell activity when desired post-treatment.

7.6. Methods of Treatment

The invention also relates to methods of treating a subject with T cell therapy, wherein the subject is in need of such therapy. In embodiments wherein the T cell therapy is to promote an immune response (i.e., treating a subject in need of a stimulated immune response), by way of example, the subject being treated may have cancer or an infectious disease, and administration of the recombinant T cells of the invention is to treat the cancer or infectious disease, respectively. The T cells may be targeted to the cancer or infectious disease by virtue of recombinantly expressing a binding partner (e.g., a CAR or antibody or receptor) (which may be encoded by the therapeutic transgene) to a target antigen associated with the cancer or infectious disease, or by virtue of being sensitized to a target antigen associated with the cancer or infectious disease. In a specific embodiment using sensitized T cells, the T cells are sensitized to an antigen of the cancer or infectious disease, respectively. In a preferred embodiment, the invention also relates to methods of treating a subject with CAR therapy, wherein the subject is in need of such therapy. In embodiments wherein the CAR therapy is to promote an immune response, by way of example, the subject being treated may have cancer or an infectious disease, administration of the recombinant T cells of the invention is to treat the cancer or infectious disease, and the CAR binds to an antigen of the cancer or infectious disease pathogen, respectively. In such embodiments, the T cell can be CD8+, CD4+, a TSCM, a TCM, effector memory T cell, effector T cell, Th1 cell, Th2 cell, Th9 cell, Th17 cell, Th22 cell, Tfh (follicular helper) cell, or other T cell as disclosed herein.

In embodiments wherein the T cell therapy is to suppress an immune response (i.e., treating a subject in need of an inhibited immune response), by way of example, the subject being treated may have an autoimmune disease or is at risk of transplant rejection, and administration of the recombinant T cells of the invention is to treat the autoimmune disease or to promote transplant tolerance, respectively. As another example, wherein the T cell therapy is to suppress an immune response, the subject being treated may be at risk for or have graft versus host disease, and administration of the recombinant (used interchangeably herein with "engineered") T cells of the invention is to prevent or reduce the graft versus host disease. The T cells may be targeted to the autoimmune disease, transplant, or graft by virtue of recombinantly expressing a binding partner (e.g., a CAR or antibody or receptor) (which may be encoded by the therapeutic transgene) to a target antigen associated with the autoimmune disease (e.g., the autoantigen), transplant, or graft, or by virtue of being sensitized to a target antigen associated with the autoimmune disease, transplant, or graft. In a specific embodiment using sensitized T cells, the T cells are sensitized to an antigen at the site of the autoimmune reaction or the transplanted cells or graft (or cells derived therefrom), respectively. In such embodiments, the T cell can be a T regulatory cell (Treg). In preferred embodiments wherein CAR therapy is to suppress an immune response, by way of example, the subject being treated may have an autoimmune disease or is at risk of transplant rejection, administration of the recombinant T cells of the invention is to treat the autoimmune disease or to promote transplant tolerance, and the CAR binds to an antigen at the site of the autoimmune reaction or the transplanted cells, respectively. As another example, the subject being treated may have or be at risk of graft versus host disease (GVHD), administration of the recombinant T cells of the invention is to treat or prevent or reduce the risk of GVHD, and the CAR binds to an antigen associated with the GVHD. In such embodiments, the T cell can be a T regulatory cell (Treg). Such autoimmune disorders include, but are not limited to, rheumatoid arthritis, systemic lupus erythematosus, celiac sprue disease, pernicious anemia, vitiligo, scleroderma, psoriasis, inflammatory bowel disease, Hashimoto's disease, Addison's disease, Graves' disease, reactive arthritis, Sjögren's syndrome, and type 1 diabetes. Transplants can be organ or tissue transplants, e.g. transplants of lung, kidney, heart, intestine, liver, and pancreas, etc. Treating or preventing GVHD can be following a hematopoietic stem cell transplant of the subject.

In one embodiment, the subject has cancer. In such an embodiment, the T cell therapy targets the cancer. In a particular embodiment, the T cell expresses a CAR. (Thus the therapeutic transgene encodes a CAR). In a preferred embodiment, the CAR binds to a cancer antigen. The cancer antigen is chosen to target a cancer of the subject.

The invention relates to various methods of using the T cells expressing a transgene. In a specific embodiment, the cells are administered as a population of cells expressing a transgene. In a preferred embodiment, the invention relates to various methods of using the T cells expressing a CAR (wherein the transgene encodes a CAR). In a specific embodiment the cells are administered as a population of cells expressing a CAR. Optionally, the cells to be administered can be purified or enriched for the cells of the invention.

In one embodiment, the methods of the invention are used to treat cancer. In one embodiment, the T cells express a CAR. Thus, the transgene encodes a CAR. In one embodiment, the CAR is a cancer antigen-specific CAR.

It is understood that a method of treating cancer can include any effect that ameliorates a sign or symptom associated with cancer. Such signs or symptoms include, but are not limited to, reducing the number of leukemia cells, reducing tumor burden, including inhibiting growth of a tumor, slowing the growth rate of a tumor, reducing the size of a tumor, reducing the number of tumors, eliminating a tumor, all of which can be measured using routine tumor imaging techniques well known in the art. Other signs or symptoms associated with cancer include, but are not limited to, fatigue, pain, weight loss, and other signs or symptoms associated with various cancers. Thus, administration of the cells of the invention can reduce the number of tumor cells, reduce tumor size, and/or eradicate the tumor in the subject. The tumor can be a blood cancer or a solid tumor. The methods of the invention can also provide for increased or lengthened survival of a subject having cancer. Additionally, methods of the invention can provide for an increased immune response in the subject, for example, an increased immune response against the cancer.

In the methods of the invention, the T cells are administered to a subject in need of T cell therapy, for example, a subject in need of treatment, for example, treatment of cancer, an infectious disease, an autoimmune disorder, transplant rejection, and the like as disclosed herein. In a preferred embodiment of the methods of the invention, the T cells are administered to a subject in need of CAR therapy, for example, a subject in need of treatment, for example, treatment of cancer, an infectious disease, an autoimmune disorder, transplant rejection, and the like as disclosed herein. The subject can be a mammal, in particular a human. Preferably, the subject is a human. A pharmaceutical composition comprising a cell of the invention is administered to a subject to elicit an immune response, with the objective of palliating the subject's condition. Clinical improvement comprises decreased risk or rate of progression or reduction in pathological consequences of the disorder being treated with T cell therapy, for example, cancer. In a preferred embodiment, clinical improvement comprises decreased risk or rate of progression or reduction in pathological consequences of the disorder being treated with CAR therapy, for example, cancer.

The subject can have an advanced form of disease, in which case the treatment objective can include mitigation or reversal of disease progression, and/or amelioration of side effects. The subjects can have a history of the condition, for which they have already been treated, in which case the therapeutic objective can be to decrease or delay the risk of recurrence. In the case of cancer treatment, refractory or recurrent malignancies can be treated using the cells of the invention. Optionally, a cell of the invention can be administered for treatment prophylactically to prevent the occurrence of a disease or condition in a subject suspected of having a predisposition to a disease or condition, for example, based on family history and/or genetic testing.

The cells of the invention are administered to a subject, such as a human subject, in need of T cell therapy, for example, treatment of cancer, an infectious disease, an autoimmune disease, transplant rejection, and the like. In a preferred embodiment, the cells of the invention are administered to a subject, such as a human subject, in need of CAR therapy, for example, treatment of cancer, an infectious disease, an autoimmune disease, transplant rejection, and the like. In the case of cancer, the cancer can involve a solid tumor or a blood cancer not involving a solid tumor. Cancers to be treated using the cells of the invention comprise cancers typically responsive to immunotherapy. Exemplary types of cancers include, but are not limited to, carcinomas, sarcoma, leukemia, lymphoma, multiple myeloma, melanoma, brain and spinal cord tumors, germ cell tumors, neuroendocrine tumors, carcinoid tumors, and the like. The cancer can be a solid tumor or a blood cancer that does not form a solid tumor. In the case of a solid tumor, the tumor can be a primary tumor or a metastatic tumor.

Examples of other neoplasias or cancers that can be treated using the methods of the invention include bone cancer, intestinal cancer, liver cancer, skin cancer, cancer of the head or neck, melanoma (cutaneous or intraocular malignant melanoma), renal cancer (for example, clear cell carcinoma), throat cancer, prostate cancer (for example, hormone refractory prostate adenocarcinoma), blood cancers (for example, leukemias, lymphomas, and myelomas), uterine cancer, rectal cancer, cancer of the anal region, bladder cancer, brain cancer, stomach cancer, testicular cancer, carcinoma of the fallopian tubes, carcinoma of the endometrium, carcinoma of the cervix, carcinoma of the vagina, carcinoma of the vulva, leukemias (for example, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease, Waldenstrom's macroglobulinemia), cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, heavy chain disease, and solid tumors such as sarcomas and carcinomas, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilm's tumor, cervical cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, retinoblastoma, malignant pleural disease, mesothelioma, lung cancer (for example, non-small cell lung cancer), pancreatic cancer, ovarian cancer, breast cancer (for example, metastatic breast cancer, metastatic triple-negative breast cancer), colon cancer, pleural tumor, glioblastoma, esophageal cancer, gastric cancer, and synovial sarcoma. Solid tumors can be primary tumors or tumors in a metastatic state.

In a specific embodiment, the cells recombinantly expressing a transgene that are administered to the subject comprise both $CD4^+$ and $CD8^+$ T cells, with the aim of generating both helper and cytotoxic T lymphocyte (CTL) responses in the subject. In a preferred embodiment wherein a CAR is encoded by the transgene, the cells recombinantly expressing a CAR that are administered to the subject comprise both CD4+ and CD8+ T cells, with the aim of generating both helper and cytotoxic T lymphocyte (CTL) responses in the subject.

In one embodiment, the invention provides a method of treating a subject with T cell therapy in need thereof, wherein the subject is in need of an inhibited immune response, comprising administering T cells of the invention that are immunoinhibitory cells. In one embodiment, the subject has an autoimmune disease. In a particular embodiment in the case where the T cell expresses a CAR (encoded by the transgene), the CAR binds to an autoimmune antigen of the autoimmune disorder. Autoimmune disorders include, but are not limited to, rheumatoid arthritis, systemic lupus erythematosus, celiac sprue disease, pernicious anemia, vitiligo, scleroderma, psoriasis, inflammatory bowel disease, Hashimoto's disease, Addison's disease, Graves' disease, reactive arthritis, Sjögren's syndrome, and type 1 diabetes.

In another embodiment, the subject in need of treatment with an immunoinhibitory cell has an organ transplant. In such a method, the T cells of the invention that are immunoinhibitory are administered to the subject to enhance immune tolerance for the transplanted organ. In a particular embodiment in the case where the T cell expresses a CAR (encoded by the transgene), the CAR binds to an antigen of the transplanted organ. Transplants can be transplants of lung, kidney, heart, intestine, liver, and pancreas, etc.

In another embodiment, the subject in need of treatment with an immunoinhibitory cell is in need of reducing or preventing GVHD, for example, where the subject has had a hematopoietic stem cell transplant. In such a method, the T cells of the invention that are immunoinhibitory are administered to the subject to enhance immune tolerance by the stem cell transplant or cells derived therefrom of antigens of the subject. In a particular embodiment in the case where the T cell expresses a CAR (encoded by the transgene), the CAR binds to an antigen of the transplanted cells.

For treatment, the amount administered is an amount effective for producing the desired effect. An effective amount or therapeutically effective amount is an amount sufficient to provide a beneficial or desired clinical result upon treatment. An effective amount can be provided in a single administration or a series of administrations (one or more doses). An effective amount can be provided in a bolus or by continuous perfusion. In terms of treatment, an effective amount is an amount that is sufficient to palliate, ameliorate, stabilize, reverse or slow the progression of the disease, or otherwise reduce the pathological consequences of the disease. The effective amount can be determined by the physician for a particular subject. Several factors are typically taken into account when determining an appropriate dosage to achieve an effective amount. These factors include age, sex and weight of the subject, the condition being treated, the severity of the condition and the form and effective concentration of the cells of the invention being administered.

The cells of the invention are generally administered as a dose based on cells per kilogram (cells/kg) of body weight. Generally the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$, depending on the mode and location of administration. In general, in the case of systemic administration, a higher dose is used than in regional administration, where the T cells of the invention are administered in the region, an organ or a tumor. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $1\times10^8$, $6\times10^4$, to $1\times10^8$, $7\times10^4$ to $1\times10^8$, $8\times10^4$ to $1\times10^8$, $9\times10^4$ to $1\times10^8$, $1\times10^5$ to $1\times10^8$, for example, $1\times10^5$ to $5\times10^7$, $1\times10^5$ to $4\times10^7$, $1\times10^5$ to $3\times10^7$, $1\times10^5$ to $2\times10^7$, $1\times10^5$ to $1\times10^7$, $1\times10^5$ to $9\times10^6$, $1\times10^5$ to $8\times10^6$, $1\times10^5$ to $7\times10^6$, $1\times10^5$ to $6\times10^6$, $1\times10^5$ to $5\times10^6$, $1\times10^5$ to $4\times10^6$, $1\times10^5$ to $3\times10^6$, $1\times10^5$ to $2\times10^6$, $2\times10^5$ to $7\times10^6$, $2\times10^5$ to $6\times10^6$, $2\times10^5$ to $5\times10^6$, $2\times10^5$ to $4\times10^6$, $3\times10^5$ to $3\times10^6$, and the like. Such dose ranges can be particularly useful for regional administration. In a particular embodiment, cells are provided in a dose of $1\times10^5$ to $5\times10^6$, in particular $1\times10^5$ to $3\times10^6$ or $3\times10^5$ to $3\times10^6$ cells/kg for regional administration, for example, intrapleural administration. Exemplary dose ranges also can include, but are not limited to, $5\times10^5$ to $1\times10^8$, for example, $6\times10^5$ to $1\times10^8$, $7\times10^5$ to $1\times10^8$, $8\times10^5$ to $1\times10^8$, $9\times10^5$ to $1\times10^8$, $1\times10^6$ to $1\times10^8$, $1\times10^6$ to $9\times10^7$, $1\times10^6$ to $8\times10^7$, $1\times10^6$ to $7\times10^7$, $1\times10^6$ to $6\times10^7$, $1\times10^6$ to $5\times10^7$, $1\times10^6$ to $4\times10^7$, $1\times10^6$ to $3\times10^7$, and the like. Such does can be particularly useful for systemic administration. In a particular embodiment, cells are provided in a dose of $1\times10^6$ to $3\times10^7$ cells/kg for systemic administration. Exemplary cell doses include, but are not limited to, a dose of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ and so forth in the range of about $10^4$ to about $10^{10}$. In addition, the dose can also be adjusted to account for whether a single dose is being administered or whether multiple doses are being administered. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

The cells of the invention can be administered by any methods known in the art, including, but not limited to, pleural administration, intravenous administration, subcutaneous administration, intranodal administration, intratumoral administration, intrathecal administration, intrapleural administration, intraperitoneal administration, intracranial administration, and direct administration to the thymus. In one embodiment, the cells of the invention can be delivered regionally to an organ, a tumor or site of an autoimmune disease or site of an infectious disease using well known methods, including but not limited to, hepatic or aortic pump; limb, lung or liver perfusion; in the portal vein; through a venous shunt; in a cavity or in a vein that is nearby a tumor, and the like. In another embodiment, the cells of the invention can be administered systemically. In still another embodiment, the cells are administered regionally at the site of a desired therapy, for example, at the site of a tumor. In the case of a tumor, the cells can also be administered intratumorally, for example, by direct injection of the cells at the site of a tumor and/or into the tumor vasculature. One skilled in the art can select a suitable mode of administration based on the type of target tissue or target region and/or location of a target tissue or target region to be treated. The cells can be introduced by injection or catheter. Optionally, expansion and/or differentiation agents can be administered to the subject prior to, during or after administration of cells to increase production of the cells of the invention in vivo.

Proliferation of the cells of the invention is generally done ex vivo, prior to administration to a subject, and can be desirable in vivo after administration to a subject (see Kaiser et al., *Cancer Gene Therapy* 22:72-78 (2015)). Cell proliferation should be accompanied by cell survival to permit cell expansion and persistence, such as with T cells. Thus, the T cells can proliferate ex vivo or in vivo, as desired.

The methods of the invention can further comprise adjuvant therapy in combination with, either prior to, during, or after treatment with the cells of the invention. Thus, the cell therapy methods of the invention can be used with other standard care and/or therapies that are compatible with administration of the cells of the invention.

7.7. Pharmaceutical Compositions

The invention additionally provides pharmaceutical compositions comprising the cells of the invention. The pharmaceutical composition comprises an effective amount of a cell of the invention and a pharmaceutically acceptable carrier. The cells of the invention and compositions comprising the cells can be conveniently provided in sterile liquid preparations, for example, typically isotonic aqueous solutions with cell suspensions, or optionally as emulsions, dispersions, or the like, which are typically buffered to a selected pH. The compositions can comprise carriers, for example, water, saline, phosphate buffered saline, and the like, suitable for the integrity and viability of the cells, and for administration of a cell composition.

Sterile injectable solutions can be prepared by incorporating cells of the invention in a suitable amount of the appropriate solvent with various amounts of the other ingredients, as desired. Such compositions can include a pharmaceutically acceptable carrier, diluent, or excipient such as sterile water, physiological saline, glucose, dextrose, or the like, that are suitable for use with a cell composition and for administration to a subject such as a human. Suitable buffers for providing a cell composition are well known in the art. Any vehicle, diluent, or additive used is compatible with preserving the integrity and viability of the cells of the invention.

The compositions will generally be isotonic, that is, they have the same osmotic pressure as blood and lacrimal fluid. The desired isotonicity of the cell compositions of the invention can be accomplished using sodium chloride, or other pharmaceutically acceptable agents such as dextrose, boric acid, sodium tartrate, or other inorganic or organic solutes. Sodium chloride is preferred particularly for buffers containing sodium ions. One particularly useful buffer is saline, for example, normal saline. Those skilled in the art will recognize that the components of the compositions should be selected to be chemically inert and will not affect the viability or efficacy of the cells of the invention and will be compatible for administration to a subject, such as a human. The skilled artisan can readily determine the amount of cells and optional additives, vehicles, and/or carrier in compositions to be administered in methods of the invention.

The cells of the invention can be administered in any physiologically acceptable vehicle. Suitable doses for administration are described herein. A cell population comprising cells of the invention can comprise a purified population of cells. Those skilled in the art can readily determine the percentage of cells in a cell population using various well-known methods, as described herein. The ranges of purity in cell populations comprising genetically modified cells of the invention can be from about 25% to about 50%, from about 30% to about 50%, from about 30% to about 40%, from about 40% to 50%, from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. It is understood that such a population can be generated efficiently with the methods of the invention, as disclosed herein, or optionally enriched for the genetically modified cells expressing a transgene, as disclosed herein. In a preferred embodiment wherein the transgene encodes a CAR, it is understood that such a population can be generated efficiently with the methods of the invention, as disclosed herein, or optionally enriched for the genetically modified cells expressing a CAR, as disclosed herein. Dosages can be readily adjusted by those skilled in the art; for example, a decrease in purity may require an increase in dosage.

The invention also provides kits for preparation of cells of the invention. In one embodiment, the kit comprises in one or more containers: one or more vectors for generating a genetically engineered T cell that contains a transgene integrated within its genome such that expression of the transgene is under control of an endogenous promoter of the T cell. In a preferred embodiment, the transgene is a CAR, and in a particular embodiment, the kit comprises one or more vectors for generating a genetically engineered T cell that expresses a CAR. In a particular embodiment, the kit comprises in a container a recombinant non-integrating gamma retrovirus, as disclosed herein. The kit can also contain a suitable homologous recombination system, such as a zinc-finger nuclease (ZFN), a transcription activator-like effector nuclease (TALEN), a clustered regularly-interspersed short palindromic repeats (CRISPR) associated protein 9 (Cas9), Cpf1, Meganuclease or a Mega-Tal, preferably in a separate container. The kits can be used to generate genetically engineered T cells from autologous cells derived from a subject or from non-autologous cells to be administered to a compatible subject. In another embodiment, the kits can comprise cells of the invention for autologous or non-autologous administration to a subject. In specific embodiments, the kit comprises the T cells of the invention in one or more containers.

In another embodiment, the invention provides a kit comprising a recombinant non-integrating gamma retrovirus, as disclosed herein. In specific embodiments, the kit comprises the non-integrating gamma retrovirus of the invention in one or more containers.

7.8. Alternative Embodiment Relating to Reporter Transgenes

In an alternative specific embodiment of the invention, a T cell has integrated into its genome a reporter transgene (optionally instead of a therapeutic transgene), wherein the expression of the reporter transgene is under the control of an endogenous promoter, which can be any of the promoters described hereinabove. The reporter transgene is a transgene encoding a detectable marker (preferably cell-surface) protein. In a specific embodiment, the reporter transgene does not encode IL4 or a membrane-bound form of IL4. In another specific embodiment, the reporter transgene encodes a cell suicide switch. In a specific embodiment, the cell suicide switch is a truncated EGF receptor (EGFRt), which allows for both detection and elimination, if needed, of the therapeutic T cell. There are specific antibodies (e.g., cetuximab) that recognize this reporter and trigger antibody-mediated target-cell death in vivo (see U.S. Pat. No. 8,802,374). Thus, for example, the transgene encoding the EGFRt can under the control of an endogenous constitutive or inducible promoter, and after administration of the engineered T cell to the subject for therapeutic purpose, the subject can be administered an antibody that recognizes EGFRt and triggers cell death of the engineered T cell, to shut down the T cell activity when desired post-treatment.

7.9. Exemplary Embodiments

The invention provides the following exemplary embodiments.

Embodiment 1. A T cell wherein a transgene is integrated at a first site within the genome of the T cell such that expression of the transgene is under control of an endogenous promoter of the T cell, wherein the transgene encodes a therapeutic protein or therapeutic nucleic acid.

Embodiment 2. The T cell of embodiment 1, wherein the transgene encodes a therapeutic protein.

Embodiment 3. The T cell of embodiment 1, wherein the transgene encodes a therapeutic nucleic acid.

Embodiment 4. The T cell of any one of embodiments 1-3, wherein the transgene is integrated at a single site within the genome.

Embodiment 5. The T cell of any one of embodiments 1-3, wherein the transgene is integrated at two sites within the genome of the cell.

Embodiment 6. The T cell of any one of embodiments 1-5, wherein the first site is an exon of the endogenous gene under control of the endogenous promoter.

Embodiment 7. The T cell of embodiment 6, wherein the first site is within the first exon of the endogenous gene.

Embodiment 8. The T cell of any one of embodiments 1-7, wherein the endogenous promoter is constitutive.

Embodiment 9. The T cell of embodiment 8, wherein the promoter is selected from the group consisting of CD4 promoter, CD8a promoter, CD8b promoter, TCRa promoter, TCRb promoter, CD3d promoter, CD3g promoter, CD3e promoter, and CD3z promoter.

Embodiment 10. The T cell of any one of embodiments 1-7, wherein the endogenous promoter is active in a subset of T cells.

Embodiment 11. The T cell of embodiment 10, wherein the endogenous promoter is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

Embodiment 12. The T cell of any one of embodiments 1-7, wherein the endogenous promoter is inducible.

Embodiment 13. The T cell of embodiment 12, wherein the endogenous promoter is induced by activation of the T cell.

Embodiment 14. The T cell of embodiment 12, wherein the promoter is induced by binding of a chimeric antigen receptor (CAR), a chimeric co-stimulatory receptor (CCR), T cell receptor (TCR), CD28, CD27, or 4-1BB expressed by the T cell to its respective binding partner.

Embodiment 15. The T cell of embodiment 14, wherein the promoter is induced by binding of a CAR, CCR or TCR expressed by the T cell to its respective binding partner.

Embodiment 16. The T cell of embodiment 15, wherein the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

Embodiment 17. The T cell of embodiment 12, wherein the promoter is induced by binding of a ligand to an inhibitory receptor expressed by the T cell.

Embodiment 18. The T cell of embodiment 17, wherein the inhibitory receptor is selected from the group consisting of PD-1, CTLA4, TRAIL, LAG-3, BTLA, TIM-3, Fas, TIGIT, and 2B4.

Embodiment 19. The T cell of embodiment 17, wherein the promoter is selected from the group consisting of CPT1a promoter and ATGL promoter.

Embodiment 20. The T cell of embodiment 12, wherein the promoter is induced by binding of a cytokine to a cytokine receptor expressed by the T cell.

Embodiment 21. The T cell of embodiment 20, wherein the cytokine is selected from the group consisting of interleukin 2 (IL2), interleukin 7 (IL7), interleukin 15 (IL15), and interleukin 21 (IL21).

Embodiment 22. The T cell of embodiment 20, wherein the cytokine is selected from the group consisting of interleukin 10 (IL10) and transforming growth factor β (TGFβ).

Embodiment 23. The T cell of embodiment 20, wherein the promoter is selected from the group consisting of T-bet promoter, Eomes promoter, GATA3 promoter, and CD45RA promoter.

Embodiment 24. The T cell of embodiment 12, wherein the promoter is induced by contact of the cell with a nucleic acid.

Embodiment 25. The T cell of embodiment 24, wherein the nucleic acid is selected from the group consisting of viral DNA, viral RNA, and intracellular microRNA.

Embodiment 26. The T cell of embodiment 25, wherein the promoter is selected from the group consisting of Type I interferon (IFN) alpha, Type I IFN beta, IRF3, IRF7, NF1d3, AP-1, TNF-alpha, IL1, and IL6.

Embodiment 27. The T cell of embodiment 12, wherein the promoter is induced by contact of the cell with a metabolite.

Embodiment 28. The T cell of embodiment 27, wherein the metabolite is selected from the group consisting of pyruvate, glutamine, and beta-hydroxybutyrate.

Embodiment 29. The T cell of embodiment 12, wherein the promoter is induced by a metabolic change in the cell or contact of the cell with a substance that causes a metabolic change in the cell.

Embodiment 30. The T cell of embodiment 29, wherein the promoter is PKM2 promoter.

Embodiment 31. The T cell of embodiment 12, wherein the promoter is induced by a particular ion concentration in the cell or contact of the cell with a particular ion concentration.

Embodiment 32. The T cell of embodiment 31, wherein the ion is potassium or calcium.

Embodiment 33. The T cell of embodiment 31, wherein the promoter is selected from the group consisting of IL2 promoter, TNFalpha promoter, and IFNgamma promoter.

Embodiment 34. The T cell of any one of embodiments 1-33, wherein the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

Embodiment 35. The T cell of embodiment 34, wherein the transgene encodes a cytokine, and optionally the cytokine is immunostimulatory.

Embodiment 36. The T cell of embodiment 35, wherein the cytokine is immunostimulatory, and the cytokine is selected from the group consisting of IL2, IL12, IL15, and IL18.

Embodiment 37. The T cell of embodiment 34, wherein the transgene encodes a cytokine, and optionally the cytokine is immunoinhibitory.

Embodiment 38. The T cell of embodiment 37, wherein the cytokine is immunoinhibitory, and the cytokine is selected from the group consisting of TGFBeta and IL10.

Embodiment 39. The T cell of embodiment 34, wherein the transgene encodes an antibody, and optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

Embodiment 40. The T cell of embodiment 34, wherein the transgene encodes a CAR.

Embodiment 41. The T cell of embodiment 40, wherein the CAR binds to a cancer antigen.

Embodiment 42. The T cell of any one of embodiments 1-39, wherein the T cell is sensitized to a target antigen.

Embodiment 43. The T cell of any one of embodiments 1-42, wherein a transgene (hereinafter "reporter transgene") encoding a reporter molecule is integrated within the genome of the T cell such that expression of the reporter transgene is under control of a promoter, preferably an endogenous promoter of the T cell.

Embodiment 44. The T cell of any one of embodiments 1-43 which is derived from a human.

Embodiment 45. The T cell of embodiment 44, wherein the T cell is a primary human T cell, a T cell derived from a CD34 hematopoietic stem cell, a T cell derived from an embryonic stem cell, or a T cell derived from an induced pluripotent stem cell.

Embodiment 46. The T cell of any one of embodiments 1-45, wherein the transgene is integrated into the first site by targeted homologous recombination.

Embodiment 47. The T cell of embodiment 46, wherein the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, *Aureus*, Meganuclease or a Mega-Tal.

Embodiment 48. The T cell of any one of embodiments 1-47, wherein the transgene is integrated at a plurality of sites within the genome of the T cell, and such that expression of the transgene at said plurality of sites is under the control of different endogenous promoters.

Embodiment 49. A T cell wherein a first transgene is integrated at a first site within the genome of the cell such that expression of the first transgene is under control of a first endogenous promoter of the T cell, and wherein a second transgene is integrated at a second site within the genome of the cell, such that expression of the second transgene is under the control of a second endogenous promoter, wherein said first and second endogenous promoters are different promoters, and wherein the first transgene encodes a first therapeutic protein or first therapeutic nucleic acid, and the second transgene encodes a second therapeutic protein or second therapeutic nucleic acid, preferably wherein the first therapeutic protein or first therapeutic nucleic acid is different from said second therapeutic protein or second therapeutic nucleic nucleic, respectively.

Embodiment 50. The T cell of embodiment 49, wherein the first transgene encodes a first therapeutic protein.

Embodiment 51. The T cell of embodiment 49, wherein the first transgene encodes a first therapeutic nucleic acid.

Embodiment 52. The T cell of embodiment 49, wherein the second transgene encodes a second therapeutic protein.

Embodiment 53. The T cell of embodiment 49, wherein the second transgene encodes a second therapeutic nucleic acid.

Embodiment 54. The T cell of any one of embodiments 49-53, wherein the first endogenous promoter is constitutive, and the second endogenous promoter is inducible.

Embodiment 55. The T cell of embodiment 54, wherein the constitutive promoter is selected from the group consisting of CD4 promoter, CD8a promoter, CD8b promoter, TCRa promoter, TCRb promoter, CD3d promoter, CD3g promoter, CD3e promoter, and CD3z promoter.

Embodiment 56. The T cell of embodiment 54, wherein the first endogenous promoter and/or the second endogenous promoter is active in a subset of T cells.

Embodiment 57. The T cell of embodiment 56, wherein the first endogenous promoter and/or the second endogenous promoter is independently selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

Embodiment 58. The T cell of embodiment 54, wherein the inducible promoter is induced by activation of the T cell.

Embodiment 59. The T cell of embodiment 54, wherein the inducible promoter is induced by binding of a chimeric antigen receptor (CAR), a chimeric co-stimulatory receptor (CCR), T cell receptor (TCR), CD28, CD27, and 4-1BB expressed by the T cell to its respective binding partner.

Embodiment 60. The T cell of embodiment 59, wherein the inducible promoter is induced by binding of a CAR, CCR or TCR expressed by the T cell to its respective binding partner.

Embodiment 61. The T cell of embodiment 60, wherein the inducible promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

Embodiment 62. The T cell of embodiment 54, wherein the inducible promoter is induced by binding of a ligand to an inhibitory receptor expressed by the T cell.

Embodiment 63. The T cell of embodiment 62, wherein the inhibitory receptor is selected from the group consisting of PD-1, CTLA4, TRAIL, LAG-3, BTLA, TIM-3, Fas, TIGIT, and 2B4.

Embodiment 64. The T cell of embodiment 62, wherein the inducible promoter is selected from the group consisting of CPT1a promoter and ATGL promoter.

Embodiment 65. The T cell of embodiment 54, wherein the inducible promoter is induced by binding of a cytokine to a cytokine receptor expressed by the T cell.

Embodiment 66. The T cell of embodiment 65, wherein the cytokine is selected from the group consisting of interleukin 2 (IL2), interleukin 7 (IL7), interleukin 15 (IL15), and interleukin 21 (IL21).

Embodiment 67. The T cell of embodiment 65, wherein the cytokine is selected from the group consisting of interleukin 10 (IL10) and transforming growth factor β (TGFβ).

Embodiment 68. The T cell of embodiment 65, wherein the inducible promoter is selected from the group consisting of T-bet promoter, Eomes promoter, GATA3 promoter, and CD45RA promoter.

Embodiment 69. The T cell of embodiment 54, wherein the inducible promoter is induced by contact of the cell with a nucleic acid.

Embodiment 70. The T cell of embodiment 69, wherein the nucleic acid is selected from the group consisting of viral DNA, viral, RNA, and intracellular microRNA.

Embodiment 71. The T cell of embodiment 70, wherein the inducible promoter is selected from the group consisting of Type I interferon (IFN) alpha, Type I IFN beta, IRF3, IRF7, NFkB, AP-1, TNF-alpha, IL1, and IL6.

Embodiment 72. The T cell of embodiment 54, wherein the inducible promoter is induced by contact of the cell with a metabolite.

Embodiment 73. The T cell of embodiment 72, wherein the metabolite is selected from the group consisting of pyruvate, glutamine, and beta-hydroxybutyrate.

Embodiment 74. The T cell of embodiment 54, wherein the inducible promoter is induced by a metabolic change in the cell or contact of the cell with a substance that causes a metabolic change in the cell.

Embodiment 75. The T cell of embodiment 74, wherein the inducible promoter is PKM2 promoter.

Embodiment 76. The T cell of embodiment 54, wherein the inducible promoter is induced by a particular ion concentration in the cell or contact of the cell with a particular ion concentration.

Embodiment 77. The T cell of embodiment 76, wherein the ion is potassium or calcium.

Embodiment 78. The T cell of embodiment 76, wherein the inducible promoter is selected from the group consisting of IL2 promoter, TNFalpha promoter, and IFNgamma promoter.

Embodiment 79. The T cell of any one of embodiments 49-78, wherein the first transgene and/or second transgene each encodes a molecule independently selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

Embodiment 80. The T cell of embodiment 79, wherein the first transgene and/or second transgene encodes a cytokine, preferably wherein the cytokine is immunostimulatory.

Embodiment 81. The T cell of embodiment 80, wherein the cytokine is immunostimulatory, and is selected from the group consisting of IL2, IL12, IL15, and IL18.

Embodiment 82. The T cell of embodiment 79, wherein wherein the first transgene and/or second transgene encodes a cytokine, preferably wherein the cytokine is immunoinhibitory.

Embodiment 83. The T cell of embodiment 82, wherein the cytokine is immunoinhibitory, and is selected from the group consisting of TGFBeta and IL10.

Embodiment 84. The T cell of embodiment 79, wherein the first transgene and/or second transgene encodes an antibody, and the antibody is an immunoglobulin, a Bi-specific T-cell engager (BiTE), a diabody, a dual affinity re-targeting (DART), a Fab, a F(ab'), a single chain variable fragment (scFv), and a nanobody.

Embodiment 85. The T cell of embodiment 79, wherein the first transgene and/or second transgene encodes a CAR.

Embodiment 86. The T cell of embodiment 85, wherein the CAR binds to a cancer antigen.

Embodiment 87. The T cell of any one of embodiments 49-84, wherein the T cell is sensitized to a target antigen.

Embodiment 88. The T cell of any one of embodiments 49-87, wherein a transgene (hereinafter "reporter transgene") encoding a reporter molecule is integrated within the genome of the T cell such that expression of the reporter transgene is under control of a promoter, preferably an endogenous promoter of the T cell.

Embodiment 89. The T cell of any one of embodiments 49-88 which is derived from a human.

Embodiment 90. The T cell of embodiment 89, wherein the T cell is a primary human T cell, a T cell derived from a CD34 hematopoietic stem cell, a T cell derived from an embryonic stem cell, or a T cell derived from an induced pluripotent stem cell.

Embodiment 91. The T cell of any one of embodiments 49-90, wherein the first transgene and/or second transgene is integrated into the first site by targeted homologous recombination.

Embodiment 92. The T cell of embodiment 91, wherein the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, *Aureus*, Meganuclease or a Mega-Tal.

Embodiment 93. The T cell of any one of embodiments 49-92, wherein the first therapeutic protein or first therapeutic nucleic acid is different from said second therapeutic protein or second therapeutic nucleic nucleic, respectively.

Embodiment 94. The T cell of embodiment 54, wherein the second endogenous promoter is induced by activation of the T cell.

Embodiment 95. The T cell of embodiment 54, wherein the first transgene encodes a CAR.

Embodiment 96. The T cell of embodiment 95, wherein the first endogenous promoter is a T cell receptor promoter.

Embodiment 97. The T cell of embodiment 96, wherein the promoter is selected from the group consisting of T cell receptor alpha chain promoter, T cell receptor beta chain promoter, CD3 gamma chain promoter, CD3 delta chain promoter, CD3 epsilon chain promoter, and CD3 zeta chain promoter.

Embodiment 98. The T cell of embodiment 97, wherein the promoter is T cell receptor alpha chain promoter.

Embodiment 99. The T cell of any one of embodiments 1-36, 39-81 or 84-98 (except insofar as the foregoing embodiments depend directly or indirectly on embodiments 37-38), wherein the T cell is an immunostimulatory T cell.

Embodiment 100. The T cell of embodiment 99, wherein the T cell is selected from the group consisting of cytotoxic T lymphocyte (CTL), CD4+ subtype, CD8+ subtype, central memory T cell (TCM), stem memory T cell (TSCM), effector memory T cell, effector T cell, Th1 cell, Th2 cell, Th9 cell, Th17 cell, Th22 cell, and Tfh (follicular helper) cell.

Embodiment 101. The T cell of embodiment 100, wherein the T cell is CD4+.

Embodiment 102. The T cell of embodiment 100, wherein the T cell is CD8+.

Embodiment 103. The T cell of any one of embodiments 1-34, 37-79 or 82-98 (except insofar as the foregoing embodiments depend directly or indirectly on embodiments 35-36), wherein the T cell is an immunoinhibitory T cell.

Embodiment 104. The T cell of embodiment 103, wherein the T cell is a regulatory T cell.

Embodiment 105. An isolated population of T cells, which comprises a plurality of the T cell of any one of embodiments 1-98.

Embodiment 106. An isolated population of T cells, which comprises a plurality of the T cell of any one of embodiments 99-102.

Embodiment 107. An isolated population of T cells, which comprises a plurality of the T cell of embodiment 103 or 104.

Embodiment 108. A pharmaceutical composition comprising a therapeutically effective amount of the T cell of any one of embodiments 1-98; and a pharmaceutically acceptable carrier.

Embodiment 109. A pharmaceutical composition comprising a therapeutically effective amount of a population of T cells, which population comprises a plurality of the T cell of any one of embodiments 1-98; and a pharmaceutically acceptable carrier.

Embodiment 110. A pharmaceutical composition comprising a therapeutically effective amount of the T cell of any one of embodiments 99-102; and a pharmaceutically acceptable carrier.

Embodiment 111. A pharmaceutical composition comprising a therapeutically effective amount of a population of T cells, which population comprises a plurality of the T cell of any one of embodiments 99-102 and a pharmaceutically acceptable carrier.

Embodiment 112. A pharmaceutical composition comprising a therapeutically effective amount of the T cell of embodiment 103 or 104; and a pharmaceutically acceptable carrier.

Embodiment 113. A pharmaceutical composition comprising a therapeutically effective amount of a population of T cells, which population comprises a plurality of the T cell of embodiment 103 or 104; and a pharmaceutically acceptable carrier.

Embodiment 114. A method of treating a subject with T cell therapy in need thereof, comprising administering to the subject a therapeutically effective amount of the T cell of any one of embodiments 1-98.

Embodiment 115. A method of treating a subject with T cell therapy in need thereof, comprising administering to the subject a therapeutically effective amount of the T cell population of embodiment 105.

Embodiment 116. A method of treating a subject with T cell therapy in need thereof, comprising administering to the subject the pharmaceutical composition of embodiment 108 or 109.

Embodiment 117. The method of any one of embodiments 114-116, wherein the subject is a human, and wherein the cell is derived from a human.

Embodiment 118. The method of any one of embodiments 114-117, wherein the T cell is autologous to the subject.

Embodiment 119. The method of any one of embodiments 114-117, wherein the T cell is non-autologous to the subject.

Embodiment 120. A method of treating a subject with T cell therapy in need thereof, wherein the subject is in need of a stimulated immune response, comprising administering to the subject a therapeutically effective amount of a T cell, wherein a transgene is integrated at a first site within the genome of the T cell such that expression of the transgene is under control of an endogenous promoter of the T cell, wherein the transgene encodes a therapeutic protein or therapeutic nucleic acid.

Embodiment 121. The method of embodiment 116, wherein the cell or cell population is administered to the subject as a pharmaceutical composition.

Embodiment 122. The method of embodiment 120, wherein the transgene encodes a therapeutic protein.

Embodiment 123. The method of embodiment 120, wherein the transgene encodes a therapeutic nucleic acid.

Embodiment 124. The method of any one of embodiments 116-123, wherein the transgene is integrated at a single site within the genome.

Embodiment 125. The method of any one of embodiments 116-123, wherein the transgene is integrated at two sites within the genome of the cell.

Embodiment 126. The method of any one of embodiments 116-125, wherein the first site is an an exon of the endogenous gene under control of the endogenous promoter.

Embodiment 127. The method of embodiment 126, wherein the first site is within the first exon of the endogenous gene.

Embodiment 128. The method of any one of embodiments 116-127, wherein the endogenous promoter is constitutive.

Embodiment 129. The method of embodiment 128, wherein the promoter is selected from the group consisting of CD4 promoter, CD8a promoter, CD8b promoter, TCRa promoter, TCRb promoter, CD3d promoter, CD3g promoter, CD3e promoter, and CD3z promoter.

Embodiment 130. The method of any one of embodiments 116-127, wherein the endogenous promoter is active in a subset of T cells.

Embodiment 131. The method of embodiment 130, wherein the endogenous promoter is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

Embodiment 132. The method of any one of embodiments 116-127, wherein the endogenous promoter is inducible.

Embodiment 133. The method of embodiment 132, wherein the endogenous promoter is induced by activation of the T cell.

Embodiment 134. The method of embodiment 132, wherein the promoter is induced by binding of a chimeric antigen receptor (CAR), a chimeric co-stimulatory receptor (CCR), T cell receptor (TCR), CD28, CD27, or 4-1BB expressed by the T cell to its respective binding partner.

Embodiment 135. The method of embodiment 134, wherein the promoter is induced by binding of a CAR, CCR or TCR expressed by the T cell to its respective binding partner.

Embodiment 136. The method of embodiment 135, wherein the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

Embodiment 137. The method of embodiment 132, wherein the promoter is induced by binding of a ligand to an inhibitory receptor expressed by the T cell.

Embodiment 138. The method of embodiment 137, wherein the inhibitory receptor is selected from the group consisting of PD-1, CTLA4, TRAIL, LAG-3, BTLA, TIM-3, Fas, TIGIT, and 2B4.

Embodiment 139. The method of embodiment 137, wherein the promoter is selected from the group consisting of CPT1a promoter and ATGL promoter.

Embodiment 140. The method of embodiment 132, wherein the promoter is induced by binding of a cytokine to a cytokine receptor expressed by the T cell.

Embodiment 141. The method of embodiment 140, wherein the cytokine is selected from the group consisting of interleukin 2 (IL2), interleukin 7 (IL7), interleukin 15 (IL15), and interleukin 21 (IL21).

Embodiment 142. The method of embodiment 140, wherein the promoter is selected from the group consisting of T-bet promoter, Eomes promoter, GATA3 promoter, and CD45RA promoter.

Embodiment 143. The method of embodiment 132, wherein the promoter is induced by contact of the cell with a nucleic acid.

Embodiment 144. The method of embodiment 143, wherein the nucleic acid is selected from the group consisting of viral DNA, viral, RNA, and intracellular microRNA.

Embodiment 145. The method of embodiment 144, wherein the promoter is selected from the group consisting of Type I interferon (IFN) alpha, Type I IFN beta, IRF3, IRF7, NFkB, AP-1, TNF-alpha, IL1, and IL6.

Embodiment 146. The method of embodiment 132, wherein the promoter is induced by contact of the cell with a metabolite.

Embodiment 147. The method of embodiment 146, wherein the metabolite is selected from the group consisting of pyruvate, glutamine, and beta-hydroxybutyrate.

Embodiment 148. The method of embodiment 132, wherein the promoter is induced by a metabolic change in the cell or contact of the cell with a substance that causes a metabolic change in the cell.

Embodiment 149. The method of embodiment 148, wherein the promoter is PKM2 promoter.

Embodiment 150. The method of embodiment 132, wherein the promoter is induced by a particular ion concentration in the cell or contact of the cell with a particular ion concentration.

Embodiment 151. The method of embodiment 150, wherein the ion is potassium or calcium.

Embodiment 152. The method of embodiment 150, wherein the promoter is selected from the group consisting of IL2 promoter, TNFalpha promoter, and IFNgamma promoter.

Embodiment 153. The method of any one of embodiments 120-152, wherein the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

Embodiment 154. The method of embodiment 153, wherein the transgene encodes a cytokine, and optionally the cytokine is immunostimulatory.

Embodiment 155. The method of embodiment 154, wherein the cytokine is immunostimulatory, and the cytokine is selected from the group consisting of IL2, IL12, IL15, and IL18.

Embodiment 156. The method of embodiment 153, wherein the transgene encodes an antibody, and optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

Embodiment 157. The method of embodiment 153, wherein the transgene encodes a CAR.

Embodiment 158. The method of embodiment 157, wherein the CAR binds to a cancer antigen.

Embodiment 159. The method of any one of embodiments 120-156, wherein the T cell is sensitized to a target antigen.

Embodiment 160. The method of any one of embodiments 120-159, wherein a transgene (hereinafter "reporter transgene") encoding a reporter molecule is integrated within the genome of the T cell such that expression of the reporter transgene is under control of a promoter, preferably an endogenous promoter of the T cell.

Embodiment 161. The method of any one of embodiments 120-160 which is derived from a human.

Embodiment 162. The method of embodiment 161, wherein the T cell is a primary human T cell, a T cell derived from a CD34 hematopoietic stem cell, a T cell derived from an embryonic stem cell, or a T cell derived from an induced pluripotent stem cell.

Embodiment 163. The method of any one of embodiments 120-162, wherein the transgene is integrated into the first site by targeted homologous recombination.

Embodiment 164. The method of embodiment 163, wherein the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, Aureus, Meganuclease or a Mega-Tal.

Embodiment 165. The T cell of any one of embodiments 120-164, wherein the transgene is integrated at a plurality of sites within the genome of the T cell, and such that expression of the transgene at said plurality of sites is under the control of different endogenous promoters.

Embodiment 166. The T cell of any one of embodiments 120-165, wherein the T cell is an immunostimulatory T cell.

Embodiment 167. The T cell of embodiment 166, wherein the T cell is selected from the group consisting of cytotoxic T lymphocyte (CTL), CD4+ subtype, CD8+ subtype, central memory T cell (TCM), stem memory T cell (TSCM), effector memory T cell, effector T cell, Th1 cell, Th2 cell, Th9 cell, Th17 cell, Th22 cell, and Tfh (follicular helper) cell.

Embodiment 168. The T cell of embodiment 167, wherein the T cell is CD4+.

Embodiment 169. The T cell of embodiment 167, wherein the T cell is CD8+.

Embodiment 170. The method of any one of embodiments 120-169, wherein the subject has cancer.

Embodiment 171. The method of embodiment 170, wherein the cancer is leukemia.

Embodiment 172. The method of any one of embodiments 120-170, wherein the subject has a tumor.

Embodiment 173. The method of any one of embodiments 120-172, wherein the subject is a human, and wherein the cell is derived from a human.

Embodiment 174. The method of any one of embodiments 120-173, wherein the cell is autologous to the subject.

Embodiment 175. The method of any one of embodiments 120-173, wherein the cell is non-autologous to the subject.

Embodiment 176. A method of treating a subject with T cell therapy in need thereof, wherein the subject is in need of an inhibited immune response, comprising administering to the subject a therapeutically effective amount of a cell or population of cells, wherein the cell is a T cell wherein a transgene is integrated at a first site within the genome of the cell such that expression of the transgene is under control of an endogenous promoter of the T cell, wherein the transgene encodes a therapeutic protein or therapeutic nucleic acid.

Embodiment 177. The method of embodiment 176, wherein the cell or cell population is administered as a pharmaceutical composition.

Embodiment 178. The method of embodiment 176, wherein the transgene encodes a therapeutic protein.

Embodiment 179. The method of embodiment 176, wherein the transgene encodes a therapeutic nucleic acid.

Embodiment 180. The method of any one of embodiments 176-179, wherein the transgene is integrated at a single site within the genome.

Embodiment 181. The method of any one of embodiments 176-179, wherein the transgene is integrated at two sites within the genome of the cell.

Embodiment 182. The method of any one of embodiments 176-181, wherein the first site is an an exon of the endogenous gene under control of the endogenous promoter.

Embodiment 183. The method of embodiment 182, wherein the first site is within the first exon of the endogenous gene.

Embodiment 184. The method of any one of embodiments 176-183, wherein the endogenous promoter is constitutive.

Embodiment 185. The method of embodiment 184, wherein the promoter is selected from the group consisting of CD4 promoter, CD8a promoter, CD8b promoter, TCRa promoter, TCRb promoter, CD3d promoter, CD3g promoter, CD3e promoter, and CD3z promoter.

Embodiment 186. The method of any one of embodiments 176-183, wherein the endogenous promoter is active in a subset of T cells.

Embodiment 187. The method of embodiment 186, wherein the endogenous promoter is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

Embodiment 188. The method of any one of embodiments 176-183, wherein the endogenous promoter is inducible.

Embodiment 189. The method of embodiment 188, wherein the endogenous promoter is induced by activation of the T cell.

Embodiment 190. The method of embodiment 188, wherein the promoter is induced by binding of a chimeric antigen receptor (CAR), a chimeric co-stimulatory receptor (CCR), T cell receptor (TCR), CD28, CD27, or 4-1BB expressed by the T cell to its respective binding partner.

Embodiment 191. The method of embodiment 190, wherein the promoter is induced by binding of a CAR, CCR or TCR expressed by the T cell to its respective binding partner.

Embodiment 192. The method of embodiment 191, wherein the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

Embodiment 193. The method of embodiment 188, wherein the promoter is induced by binding of a ligand to an inhibitory receptor expressed by the T cell.

Embodiment 194. The method of embodiment 193, wherein the inhibitory receptor is selected from the group consisting of PD-1, CTLA4, TRAIL, LAG-3, BTLA, TIM-3, Fas, TIGIT, and 2B4.

Embodiment 195. The method of embodiment 193, wherein the promoter is selected from the group consisting of CPT1a promoter and ATGL promoter.

Embodiment 196. The method of embodiment 188, wherein the promoter is induced by binding of a cytokine to a cytokine receptor expressed by the T cell.

Embodiment 197. The method of embodiment 196, wherein the cytokine is selected from the group consisting of interleukin 10 (IL10) and transforming growth factor β (TGFβ).

Embodiment 198. The method of embodiment 196, wherein the promoter is selected from the group consisting of T-bet promoter, Eomes promoter, GATA3 promoter, and CD45RA promoter.

Embodiment 199. The method of embodiment 188, wherein the promoter is induced by contact of the cell with a nucleic acid.

Embodiment 200. The method of embodiment 199, wherein the nucleic acid is selected from the group consisting of viral DNA, viral, RNA, and intracellular microRNA.

Embodiment 201. The method of embodiment 200, wherein the promoter is selected from the group consisting of Type I interferon (IFN) alpha, Type I IFN beta, IRF3, IRF7, NFkB, AP-1, TNF-alpha, IL1, and IL6.

Embodiment 202. The method of embodiment 188, wherein the promoter is induced by contact of the cell with a metabolite.

Embodiment 203. The method of embodiment 202, wherein the metabolite is selected from the group consisting of pyruvate, glutamine, and beta-hydroxybutyrate.

Embodiment 204. The method of embodiment 188, wherein the promoter is induced by a metabolic change in the cell or contact of the cell with a substance that causes a metabolic change in the cell.

Embodiment 205. The method of embodiment 204, wherein the promoter is PKM2 promoter.

Embodiment 206. The method of embodiment 188, wherein the promoter is induced by a particular ion concentration in the cell or contact of the cell with a particular ion concentration.

Embodiment 207. The method of embodiment 206, wherein the ion is potassium or calcium.

Embodiment 208. The method of embodiment 206, wherein the promoter is selected from the group consisting of IL2 promoter, TNFalpha promoter, and IFNgamma promoter.

Embodiment 209. The method of any one of embodiments 176-208, wherein the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

Embodiment 210. The method of embodiment 209, wherein the transgene encodes a cytokine, and optionally the cytokine is immunoinhibitory.

Embodiment 211. The method of embodiment 210, wherein the cytokine is immunoinhibitory, and the cytokine is selected from the group consisting of TGFBeta and IL10.

Embodiment 212. The method of embodiment 209, wherein the transgene encodes an antibody, and optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

Embodiment 213. The method of embodiment 209, wherein the transgene encodes a CAR.

Embodiment 214. The method of embodiment 213, wherein the CAR binds to a cancer antigen.

Embodiment 215. The method of any one of embodiments 176-212, wherein the T cell is sensitized to a target antigen.

Embodiment 216. The method of any one of embodiments 176-215, wherein a transgene (hereinafter "reporter transgene") encoding a reporter molecule is integrated within the genome of the T cell such that expression of the reporter transgene is under control of a promoter, preferably an endogenous promoter of the T cell.

Embodiment 217. The method of any one of embodiments 176-216 which is derived from a human.

Embodiment 218. The method of embodiment 217, wherein the T cell is a primary human T cell, a T cell derived from a CD34 hematopoietic stem cell, a T cell derived from an embryonic stem cell, or a T cell derived from an induced pluripotent stem cell.

Embodiment 219. The method of any one of embodiments 176-218, wherein the transgene is integrated into the first site by targeted homologous recombination.

Embodiment 220. The method of embodiment 219, wherein the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, *Aureus*, Meganuclease or a Mega-Tal.

Embodiment 221. The method of any one of embodiments 176-220, wherein the transgene is integrated at a plurality of sites within the genome of the T cell, and such that expression of the transgene at said plurality of sites is under the control of different endogenous promoters.

Embodiment 222. The method of any one of embodiments 176-221, wherein the T cell is an immunoinhibitory T cell.

Embodiment 223. The method of embodiment 222, wherein the T cell is a regulatory T cell.

Embodiment 224. The method of any one of embodiments 176-223, wherein the subject is a human, and wherein the cell is derived from a human.

Embodiment 225. The method of any one of embodiments 176-224, wherein the cell is autologous to the subject.

Embodiment 226. The method of any one of embodiments 176-224, wherein the cell is non-autologous to the subject.

Embodiment 227. A method of generating a T cell that expresses a therapeutic transgene, comprising:
introducing into a T cell:
(i) a transgene, and
(ii) a homologous recombination system suitable for targeted integration of the transgene at a site within the genome of the cell, whereby the homologous recombination system integrates the transgene at said site within the genome of the cell, and wherein expression of the transgene is under the control of an endogenous promoter, wherein the transgene encodes a therapeutic protein or a therapeutic nucleic acid.

Embodiment 228. The method of embodiment 227, wherein the transgene encodes a therapeutic protein.

Embodiment 229. The method of embodiment 227, wherein the transgene encodes a therapeutic nucleic acid.

Embodiment 230. The method of embodiment 227, wherein the endogenous promoter is constitutive.

Embodiment 231. The method of embodiment 230, wherein the promoter is selected from the group consisting of CD4 promoter, CD8a promoter, CD8b promoter, TCRa promoter, TCRb promoter, CD3d promoter, CD3g promoter, CD3e promoter, and CD3z promoter.

Embodiment 232. The method of embodiment 227, wherein the endogenous promoter is active in a subset of T cells.

Embodiment 233. The method of embodiment 232, wherein the endogenous promoter is selected from the group consisting of CD4 promoter, CD8a promoter, CD8b promoter, TCRa promoter, TCRb promoter, CD3d promoter, CD3g promoter, CD3e promoter, CD3z promoter, actin promoter, CD25 promoter, IL2 promoter, CD69 promoter, GzmB promoter, T-bet promoter, IFNgamma promoter, TIM3 promoter, IL4 promoter, GATA3 promoter, IL5 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, c-Kit promoter, and CD130 promoter.

Embodiment 234. The method of embodiment 227, wherein the endogenous promoter is inducible.

Embodiment 235. The method of embodiment 234, wherein the endogenous promoter is induced by activation of the T cell.

Embodiment 236. The method of embodiment 234, wherein the promoter is induced by binding of a chimeric antigen receptor (CAR), a chimeric co-stimulatory receptor (CCR), T cell receptor (TCR), CD28, CD27, and 4-1BB expressed by the T cell to its respective binding partner.

Embodiment 237. The method of embodiment 236, wherein the promoter is induced by binding of a CAR, CCR or TCR expressed by the T cell to its respective binding partner.

Embodiment 238. The method of embodiment 237, wherein the promoter is selected from the group consisting of nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, and 2B4 promoter.

Embodiment 239. The method of embodiment 234, wherein the promoter is induced by binding of a ligand to an inhibitory receptor expressed by the T cell.

Embodiment 240. The method of embodiment 239, wherein the inhibitory receptor is selected from the group consisting of PD-1, CTLA4, TRAIL, LAG-3, BTLA, TIM-3, Fas, TIGIT, and 2B4.

Embodiment 241. The method of embodiment 239, wherein the promoter is selected from the group consisting of CPT1a promoter and ATGL promoter.

Embodiment 242. The method of embodiment 234, wherein the promoter is induced by binding of a cytokine to a cytokine receptor expressed by the T cell.

Embodiment 243. The method of embodiment 242, wherein the cytokine is selected from the group consisting of interleukin 2 (IL2), interleukin 7 (IL7), interleukin 15 (IL15), and interleukin 21 (IL21).

Embodiment 244. The method of embodiment 242, wherein the cytokine is selected from the group consisting of interleukin 10 (IL10) and transforming growth factor β (TGFβ).

Embodiment 245. The method of embodiment 242, wherein the promoter is selected from the group consisting of T-bet promoter, Eomes promoter, GATA3 promoter, and CD45RA promoter.

Embodiment 246. The method of embodiment 234, wherein the promoter is induced by contact of the cell with a nucleic acid.

Embodiment 247. The method of embodiment 246, wherein the nucleic acid is selected from the group consisting of viral DNA, viral, RNA, and intracellular microRNA.

Embodiment 248. The method of embodiment 247, wherein the promoter is selected from the group consisting of Type I interferon (IFN) alpha, Type I IFN beta, IRF3, IRF7, NFkB, AP-1, TNF-alpha, IL1, and IL6.

Embodiment 249. The method of embodiment 234, wherein the promoter is induced by contact of the cell with a metabolite.

Embodiment 250. The method of embodiment 249, wherein the metabolite is selected from the group consisting of pyruvate, glutamine, and beta-hydroxybutyrate.

Embodiment 251. The method of embodiment 234, wherein the promoter is induced by a metabolic change in the cell or contact of the cell with a substance that causes a metabolic change in the cell.

Embodiment 252. The method of embodiment 251, wherein the promoter is PKM2 promoter.

Embodiment 253. The method of embodiment 234, wherein the promoter is induced by a particular ion concentration in the cell or contact of the cell with a particular ion concentration.

Embodiment 254. The method of embodiment 253, wherein the ion is potassium or calcium.

Embodiment 255. The method of embodiment 253, wherein the promoter is selected from the group consisting of IL2 promoter, TNFalpha promoter, and IFNgamma promoter.

Embodiment 256. The method of any one of embodiments 227-255, wherein the transgene encodes a molecule selected from the group consisting of a CAR, a CCR, a cytokine, a dominant negative, a microenvironment modulator, an antibody, a biosensor, a chimeric receptor ligand (CRL), a chimeric immune receptor ligand (CIRL), a soluble receptor, a solute transporter, an enzyme, a ribozyme, a genetic circuit, an epigenetic modifier, a transcriptional activator, a transcriptional repressor, and non-coding RNA.

Embodiment 257. The method of embodiment 256, wherein the transgene encodes a cytokine, and optionally the cytokine is immunostimulatory.

Embodiment 258. The method of embodiment 257, wherein the cytokine is immunostimulatory, and the cytokine is selected from the group consisting of IL2, IL12, IL15, and IL18.

Embodiment 259. The method of embodiment 256, wherein the transgene encodes a cytokine, and optionally the cytokine is immunoinhibitory.

Embodiment 260. The method of embodiment 259, wherein the cytokine is immunoinhibitory, and the cytokine is selected from the group consisting of TGFBeta and IL10.

Embodiment 261. The method of embodiment 256, wherein the transgene encodes an antibody, and optionally the antibody is selected from the group consisting of an immunoglobulin, a Bi-specific T-cell engager (BiTE), a diabody, a dual affinity re-targeting (DART), a Fab, a F(ab'), a single chain variable fragment (scFv), and a nanobody.

Embodiment 262. The method of embodiment 256, wherein the transgene encodes a CAR.

Embodiment 263. The method of embodiment 262, wherein the CAR binds to a cancer antigen.

Embodiment 264. The method of any one of embodiments 227-263, wherein the T cell is sensitized to a target antigen.

Embodiment 265. The method of any one of embodiments 227-264, wherein a transgene (hereinafter "reporter transgene") encoding a reporter molecule is integrated within the genome of the T cell such that expression of the reporter transgene is under control of a promoter, preferably an endogenous promoter of the T cell.

Embodiment 266. The method of any one of embodiments 227-265 which is derived from a human.

Embodiment 267. The method of embodiment 266, wherein the T cell is a primary human T cell, a T cell derived from a CD34 hematopoietic stem cell, a T cell derived from an embryonic stem cell, or a T cell derived from an induced pluripotent stem cell.

Embodiment 268. The method of any one of embodiments 227-267, wherein the transgene is integrated into the first site by targeted homologous recombination.

Embodiment 269. The method of embodiment 268, wherein the targeted homologous recombination is carried out by a method comprising using a zinc-finger nuclease (ZFN), a transcription activator-like effector nuclease (TALEN), a clustered regularly-interspersed short palindromic repeats (CRISPR) associated protein 9 (Cas9), Cpf1, pyrogen, *Aureus*, Meganuclease or a Mega-Tal.

Embodiment 270. The method of any one of embodiments 227-269, wherein the transgene is integrated at a plurality of sites within the genome of the T cell, and such that expression of the transgene at said plurality of sites is under the control of different endogenous promoters.

Embodiment 271. The method of any one of embodiments 227-270, wherein the transgene that is introduced into the cell is contained in a targeting construct.

Embodiment 272. The method of embodiment 271, wherein the targeting construct comprises viral nucleic acid sequences.

Embodiment 273. The method of embodiment 271 or 272, wherein the targeting construct is packaged into a natural or recombinant adeno-associated virus (AVV) viral particle.

Embodiment 274. The method of embodiment 273, wherein the AAV particle comprises AAV6 sequences.

Embodiment 275. The method of embodiment 271 or 272, wherein the targeting construct is packaged into a non-integrating gamma-retrovirus.

Embodiment 276. The method of any one of embodiments 227-275, wherein the transgene in the targeting construct are not operably linked to a promoter.

Embodiment 277. The method of any one of embodiments 227-276, further comprising introducing a second transgene into the T cell.

Embodiment 278. The method of embodiment 277, wherein the first transgene is under control of an endogenous constitutive promoter and the second transgene is under control of an endogenous inducible promoter.

Embodiment 279. The method of embodiment 278, wherein the first transgene is a CAR.

Embodiment 280. The method of embodiment 279, wherein the endogenous constitutive promoter is a T cell receptor promoter.

Embodiment 281. The method of embodiment 280, wherein the promoter is selected from the group consisting of T cell receptor alpha chain promoter, T cell receptor beta chain promoter, CD3 gamma chain promoter, CD3 delta chain promoter, CD3 epsilon chain promoter, and CD3 zeta chain promoter.

Embodiment 282. The method of embodiment 281, wherein the promoter is T cell receptor alpha chain promoter.

Embodiment 283. A vector comprising a non-integrating gamma-retrovirus.

Embodiment 284. The vector of embodiment 283, wherein the non-integrating gamma-retrovirus comprises a mutated integrase.

Embodiment 285. The vector of embodiment 284, wherein the mutated integrase is mutated at a DDE motif.

Embodiment 286. The vector of embodiment 285, wherein the mutated integrase has a mutation selected from the group consisting of D124A, D124E, D124N, D124V, D183A, D183N, D124A and D183A, D124A and D183N, D124E and D183A, D124E and D183N, D124N and D183A, D124N and D183N, D124V and D183A, and D124V and D183N.

Embodiment 287. A T cell wherein a recombinant nucleic acid sequence encoding a chimeric antigen receptor (CAR) is integrated at a first site within the genome of the cell such that the CAR is expressed by the cell at the surface of the cell, and wherein integration of the nucleic acid encoding the CAR at said first site reduces or prevents expression of a functional T cell receptor (TCR) complex at the surface of the cell.

Embodiment 288. The T cell of embodiment 287, wherein the nucleic acid sequence encoding the CAR is integrated at a single site within the genome.

Embodiment 289. The T cell of embodiment 287, wherein the nucleic acid sequence encoding the CAR is integrated at two sites within the genome of the cell.

Embodiment 290. The T cell of embodiment 289, wherein the first site is an an exon of the gene encoding a protein of the TCR complex.

Embodiment 291. The T cell of any one of embodiments 287-290, wherein integration of the nucleic acid sequence encoding the CAR at the first site reduces or prevents expression of a protein selected from the group consisting of T cell receptor alpha chain, T cell receptor beta chain, CD3 gamma chain, CD3 delta chain, CD3 epsilon chain, and CD3 zeta chain.

Embodiment 292. The T cell of any one of embodiments 287-291, wherein expression of the integrated nucleic acid sequence in the T cell is under the control of an endogenous promoter.

Embodiment 293. The T cell of embodiment 292, wherein the endogenous promoter is a T cell receptor complex promoter.

Embodiment 294. The T cell of embodiment 292, wherein the endogenous promoter is a promoter of a gene encoding a T cell receptor alpha chain, T cell receptor beta chain, CD3 gamma chain, CD3 delta chain, CD3 epsilon chain, or CD3 zeta chain.

Embodiment 295. The T cell of any one of embodiments 287-294, wherein the CAR binds to a cancer antigen.

Embodiment 296. The T cell of any one of embodiments 287-295, wherein the T cell is selected from the group consisting of cytotoxic T lymphocyte (CTL), CD4+ subtype, CD8+ subtype, central memory T cell (TCM), stem memory T cell (TSCM), effector memory T cell, effector T cell, Th1 cell, Th2 cell, Th9 cell, Th17 cell, Th22 cell, Tfh (follicular helper) cell, and T regulatory cell.

Embodiment 297. The T cell of any one of embodiments 287-296 which is derived from a human.

Embodiment 298. The T cell of embodiment 297, wherein the T cell is a primary human T cell, a T cell derived from a CD34 hematopoietic stem cell, a T cell derived from an embryonic stem cell, or a T cell derived from an induced pluripotent stem cell.

Embodiment 299. The T cell of any one of embodiments 287-298, wherein the nucleic acid sequence encoding the CAR is integrated into the first site by targeted homologous recombination.

Embodiment 300. The T cell of embodiment 299, wherein the targeted homologous recombination is carried out using a zinc-finger nuclease (ZFN), a transcription activator-like effector nuclease (TALEN), a clustered regularly-interspersed short palindromic repeats (CRISPR) associated protein 9 (Cas9), Cpf1, Meganuclease or a Mega-Tal.

Embodiment 301. The T cell of embodiment 287, wherein the nucleic acid sequence encoding the CAR is integrated at a plurality of sites within the genome of the cell, and such that expression of the nucleic acid sequence encoding the CAR at said plurality of sites is under the control of a different endogenous promoter.

Embodiment 302. The T cell of any one of embodiments 287-301, wherein said nucleic acid sequence encoding a CAR is also integrated at a second site within the genome of the cell such that the CAR is expressed by the cell at the surface of the cell.

Embodiment 303. The T cell of embodiment 302, wherein integration of the nucleic acid encoding the CAR at said second site also reduces or prevents expression of a functional TCR complex at the surface of the cell, wherein said first site and said second site are in different genes.

Embodiment 304. The T cell of any one of embodiments 287-303, wherein a second nucleic acid sequence encoding a second CAR is integrated at a second site within the genome of the cell such that the second CAR is expressed by the cell at the surface of the cell, and such that expression of the second nucleic acid sequence is under the control of an endogenous promoter at said second site, wherein said first site and said second site are in different genes.

Embodiment 305. A human T cell wherein a promoterless recombinant nucleic acid sequence encoding a CAR is integrated at a site in the genome of the cell, said site being the first exon of the TCR alpha chain, such that the CAR is expressed under control of the endogenous TCR alpha chain promoter, to produce said CAR at the surface of the cell, and wherein integration of the CAR at said site reduces or prevents expression of a functional TCR alpha chain.

Embodiment 306. The human T cell of embodiment 305, wherein the CAR binds to CD19.

Embodiment 307. An isolated population of T cells, which comprises a plurality of the cell of any one of embodiments 287-306.

Embodiment 308. A pharmaceutical composition comprising a therapeutically effective amount of the cell of any one of embodiments 287-306; and a pharmaceutically acceptable carrier.

Embodiment 309. A pharmaceutical composition comprising a therapeutically effective amount of a population of T cells, which population comprises a plurality of the cell of any one of embodiments 287-306; and a pharmaceutically acceptable carrier.

Embodiment 310. A method of treating a subject with CAR therapy in need thereof, comprising administering to the subject a therapeutically effective amount of the cell of any one of embodiments 287-306.

Embodiment 311. A method of treating a subject with CAR therapy in need thereof, comprising administering to the subject the pharmaceutical composition of embodiment 308.

Embodiment 312. A method of treating a subject with CAR therapy in need thereof, comprising administering to the subject a therapeutically effective amount of the cell population of embodiment 307.

Embodiment 313. A method of treating a subject with CAR therapy in need thereof, comprising administering to the subject the pharmaceutical composition of embodiment 309.

Embodiment 314. The method of any one of embodiments 310-313, wherein the subject has cancer, and wherein the CAR binds to a cancer antigen of the cancer.

Embodiment 315. The method of embodiment 314, wherein the cancer is leukemia.

Embodiment 316. The method of any one of embodiments 310-314, wherein the subject has a tumor.

Embodiment 317. The method of any one of embodiments 310-316, wherein the subject is a human, and wherein the cell is derived from a human.

Embodiment 318. The method of any one of embodiments 310-317, wherein the cell is autologous to the subject.

Embodiment 319. The method of any one of embodiments 310-317, wherein the cell is non-autologous to the subject.

Embodiment 320. A method of generating a T cell that expresses a chimeric antigen receptor (CAR) and lacks a functional T cell receptor (TCR) complex, comprising:
introducing into a T cell:
(i) a nucleic acid sequence encoding a CAR, and
(ii) a homologous recombination system suitable for targeted integration of the nucleic acid sequence at a site within the genome of the cell, whereby the homologous recombination system integrates the nucleic acid sequence encoding the CAR at said site within the genome of the cell such that integration of the CAR at said site reduces or prevents expression of a functional T cell receptor complex at the surface of the cell, thereby generating a T cell that expresses the CAR and lacks a functional TCR complex.

Embodiment 321. The method of embodiment 320, wherein expression of the CAR is under the control of an endogenous promoter.

Embodiment 322. The method of embodiment 321, wherein the endogenous promoter is a promoter of a gene encoding a T cell receptor alpha chain, T cell receptor beta chain, CD3 gamma chain, CD3 delta chain, CD3 epsilon chain, or CD3 zeta chain.

Embodiment 323. The method of any one of embodiments 320-322, wherein the homologous recombination system comprises a zinc-finger nuclease (ZFN), a transcription activator-like effector nuclease (TALEN), or clustered regularly-interspersed short palindromic repeats (CRISPR) associated protein 9 (Cas9), Cpf1, Meganuclease or a Mega-Tal.

Embodiment 324. The method of any one of embodiments 320-323, wherein the nucleic acid sequence encoding the CAR that is introduced into the cell is contained in a targeting construct.

Embodiment 325. The method of embodiment 324, wherein the targeting construct comprises adeno-associated virus 2 (AAV2) sequences.

Embodiment 326. The method of embodiment 324 or 325, wherein the targeting construct is packaged into a natural or recombinant adeno-associated virus (AVV) viral particle.

Embodiment 327. The method of embodiment 326, wherein the AAV particle comprises AAV6 sequences.

Embodiment 328. The method of any one of embodiments 320-327, wherein the nucleic acid sequences encoding the CAR in the targeting construct are not operably linked to a promoter.

Embodiment 329. The method of any one of embodiments 320-328, wherein the targeting construct comprises in 5' to 3' order: a first viral sequence, a left homology arm, a nucleic acid sequence encoding a self-cleaving porcine teschovirus 2A, the nucleic acid sequence encoding the CAR, a polyadenylation sequence, a right homology arm, and a second viral sequence.

Embodiment 330. The method of embodiment 329, wherein the first or the second viral sequence is from an adeno-associated virus (AAV).

Embodiment 331. The method of embodiment 330, wherein the AAV is AAV2, AAV5 or AAV6.

Embodiment 332. An induced pluripotent stem cell, wherein a recombinant nucleic acid sequence encoding a chimeric antigen receptor (CAR) is integrated at a first site within the genome of the cell such that the CAR is expressed by the cell at the surface of the cell, and wherein integration of the nucleic acid encoding the CAR at said first site reduces or prevents expression of a functional T cell receptor (TCR) complex at the surface of the cell.

It is understood that modifications which do not substantially affect the activity of the various embodiments of this invention are also provided within the definition of the invention provided herein. Accordingly, the following examples are intended to illustrate but not limit the present invention.

8. EXAMPLES

8.1 Example 1: One-Step Generation of Universal CART Cells

Described below is a strategy for one-step generation of universal CAR T cells.

The method involves a two-in-one genome editing strategy to generate universal CAR T cells with the CAR under the control of the TCR alpha promoter. To do so, the TCR expression was disrupted by targeting a CAR into the TCR alpha constant chain gene and the endogenous promoter was used to express the CAR. Tailored nucleases (TALEN and CRISPR/cas9) were designed targeting the first exon of the TRAC gene, and an AAV vector was used to promote integration of the CAR in frame with the TRAC gene by homologous directed repair (HDR).

Tailored Nucleases: TALEN and a gRNA were designed to target the first exon on the TRAC gene. The sequence targeted is located upstream of the transmembrane domain of the TCR alpha. This domain is required for the TCR alpha and beta assembly and addressing to the cell surface. Non-homologous end joining (NHEJ) or integration of the CAR by HDR at this locus efficiently disrupts the TCR complex.

```
TRAC-gRNA sequence:
                                          (SEQ ID NO: 24)
C*A*G*GGUUCUG GAUAUCUGUG UUUUAGAGCU AGAAAUAGCA

AGUUAAAAUA AGGCUAGUCC GUUAUCAACU UGAAAAAGUG

GCACCGAGUC GGUGCU*U*U*U

*2'-O-methyl 3' phosphorothioate

TALEN target sequence (spacer underlined):
                                          (SEQ ID NO: 25)
TTGTCCCACAGATATCC AGAACCCTGACCCTG

CCGTGTACCAGCTGAGA
```

Messenger RNA: The plasmids coding for the TALEN were synthesized by Transposagen and linearized with AgeI. TALEN mRNA were transcribed and polyadenylated in vitro using the mMessage mMachine T7 Ultra kit (Life Technologies; Carlsbad, CA). RNA was purified with RNeasy columns (Qiagen; Valencia, CA) and quantified using the Nanodrop machine. Quality of the RNA was verified on a denaturing formaldehyde/MOPS agarose gel. Modified guide RNAs (gRNAs) and Cas9 mRNA were synthesized by TriLink Biotechnologies. gRNAs were reconstituted at 1 ug/uL in cytoporation T Buffer (Harvard Apparatus; Holliston, MA).

AAV: For TRAC targeting (see FIG. 1A), based on a pAAV-GFP backbone (Cellbiolabs; San Diego, CA), the pAAV-TRAC-P2A-1928z was designed and cloned containing 1.9 kb of genomic TRAC (amplified by PCR) flanking the TALEN and gRNA targeting sequences, a self-cleaving P2A peptide in frame with the first exon of TRAC, followed by the 1928z CAR used in clinical trials (Brentjens et al., Sci. Transl. Med. 5(177):177ra38. doi: 10.1126/scitranslmed.3005930 (2013)). Briefly, the CAR comprises a single chain variable fragment 19scFV, specific for the human CD19 preceded by a CD8a leader peptide and followed by CD28 hinge-transmembrane-intracellular regions and CD3 intracellular domain. The cassette is terminated by the bovine growth hormone polyA signal (BGHpA).

Cells: Buffy coats from healthy volunteer donors were obtained from the New York Blood Center. Peripheral blood mononuclear cells were isolated by density gradient centrifugation, and T lymphocytes were then purified using the Pan T cells isolation kit (Miltenyi Biotech; San Diego, CA). Cells were activated with Dynabeads (1:1 beads:Cell) Human T-Activator CD3/CD28 (ThermoFisher; Carlsbad CA) in X-vivo 15 medium (Lonza; Basel, Switzerland) supplemented human serum (Gemini Bioproducts; West Sacramento, CA) with 200 U/ml IL-2 (Miltenyi Biotech) at a density of $10^6$ cells/ml. The medium was changed every 2 days, and cells were replated at $10^6$ cells/ml.

Gene Targeting: After a 48h-activation, the CD3/CD28 beads were magnetically removed, and the cells were cultured in the absence of beads for 12-16 hours. T lymphocytes were transfected by electrotransfer of TALEN or Cas9/gRNA RNAs using an AgilePulse MAX system (Harvard Apparatus). Briefly, cells were washed in cytoporation medium T (Harvard Apparatus). Cells were then pelleted, resuspended in cytoporation medium T at $30 \times 10^6$ cells/ml. $3 \times 10^6$ cells were mixed with the indicated dose of each mRNA encoding the tailored nucleases into a 0.2 cm cuvette. The electroporation consisted of two 0.1 ms pulses at 600 V followed by four 0.2 ms pulses at 100V. Following electroporation, cells were diluted into culture medium and incubated at 37° C., 5% $CO_2$. AAV was added to the culture 2 to 4 hours after electroporation, followed by continued 30° C. incubation for 20 additional hours. AAV donor was added at the indicated MOI (1e5 to 1e6 MOI). Subsequently, edited cells were cultured using standard conditions (37° C. and expanded in T cell growth medium, replenished as needed to maintain a density of ~1e6 cells/ml every 2 to 3 days).

These conditions are highly reproducible among donors and resulted in up to 50% of TCR−/CAR+ T cells in one single step with both TALEN and CRISPR.

To obtain TCR-negative T cells, TCR-positive T cells were removed from the culture using magnetic PE-anti-TCRab and anti-PE microbeads and LS columns (Miltenyi Biotech).

Retroviral Vector Constructs and Retroviral Production: Plasmids encoding the SFG γ-retroviral vector (Rivière et al., Proc. Natl. Acad. Sci. USA 92(15):6733-6737 (1995)) were prepared using standard molecular biology techniques. Synthesis of SFG-1928z and SFG-P28z has been previously described (Brentjens et al., Nat Med. 9(3):279-286 (2003), Brentjens et al., 2007 Clin. Cancer Res. 13(18 Pt 1):5426-5435 (2007); Maher et al., Nat. Biotechnol. 20(1):70-5 (2002)). VSV-G pseudotyped retroviral supernatants derived from transduced gpg29 fibroblasts (H29) were used to construct stable retroviral-producing cell lines as previously described (Gong et al., Neoplasia 1:123-127 (1999)).

Retroviral Transduction: T cells were transduced on two consecutive days by centrifugation on Retronectin (Takara; Mountain View, CA)-coated oncoretroviral vector-bound plates.

Cytotoxicity assays: The cytotoxicity of T cells transduced with a CAR was determined by standard luciferase-based assay. In brief, NALM6 expressing firefly luciferase-GFP served as target cells. The effector (E) and tumor target (T) cells were co-cultured in triplicates at indicated E/T ratio using black-walled 96 well plates with $1 \times 10^5$ target cells in a total volume of 100 µl/well in NALM6 Medium. Target cells alone were plated at the same cell density to determine the maximal luciferase expression (relative light units; RLUmax). 18 hr later, 100 µl luciferase substrate (Bright-Glo, Promega; Madison, WI) was directly added to each well. Emitted light was detected in a luminescence plate reader or Xenogen IVIS Imaging System (Xenogen; Alameda, CA), and quantified using Living Image software (Xenogen). Lysis was determined as [1−(RLUsample)/(RLUmax)]×100.

Mouse Systemic Tumor Model: The mouse model used was 8- to 12-week-old NOD.Cg-PrkdcscidIl2rgtm1Wjl/SzJ (NSG) mice (Jackson Laboratory; Bar Harbor, ME), under a protocol approved by the MSKCC Institutional Animal Care and Use Committee. Mice were inoculated with $0.5 \times 10^6$ FFLuc-GFP NALM6 cells by tail vein injection, followed by $2 \times 10^5$ CAR T cells injected four days later. NALM6 produce very even tumor burdens and no mice were excluded prior to treatment. No blinding method was used. Bioluminescence imaging utilized the Xenogen IVIS Imaging System (Xenogen) with Living Image software (Xenogen) for acquisition of imaging datasets. Tumor burden was assessed as previously described (Gade et al., Cancer Res. 65(19):9080-9088 (2005)).

FIG. 1A shows a schematic of tailored nuclease (TALEN or CRISPR/Cas9)-induced targeted integration into TCR alpha constant (TRAC) locus. The targeting construct (AAV6) contains the CAR gene flanked by homology sequences (left homologous arm, LHA and right homologous arm, RHA). Once integrated CAR expression is driven by the endogenous TCRa promoter while TRAC locus is disrupted (TRAV: TCR alpha variable region; TRAJ: TCR alpha joining region; 2A: the self cleaving Porcine teschovirus 2A sequence; pA: bovine growth hormone PolyA sequence). FIG. 1B shows representative TCR/CAR flow plot 5 days after transfection of T cells with TRAC TALEN mRNA and addition of AAV6 at the noted MOI. As shown in FIG. 1B, the expression of CAR increased and the expression of TCR decreased with increasing AAV MOI. FIG. 1C shows a bar-graph of the percentage of TCR disruption (KO: knockout) and targeted integration (KI: knockin) depending on the AAV6 MOI. The percentages were assessed by FACS analysis. FIG. 1 D shows average CAR expression mean fluorescence intensity (MFI) 5 days after CAR vectorization into T cells (n=6 to 8 independent experiments). The results show that targeted integration of CAR in the TRAC locus resulted in a homogenous population of T cells with similar expression levels of CAR. FIG. 1E shows coefficient of variation of the CAR+ T cells measuring the dispersion in the CAR expression (ratio of the standard deviation to the mean). TRAC-P2A-1928z: Targeted integration into TRAC. SFG-1928z: semi-random integration using the SFG retrovirus. ****P<0.0001 (unpaired T-test). These results show that targeted integration of CAR in the TRAC locus resulted in a homogeneous population of T cells with similar expression.

FIG. 2A shows flow cytometry analysis showing CAR and TCR expression. TRAC-P2A-1928z were generated as in FIG. 1. TALEN-generated TCR− cells were transduced with SFG-1928z retrovirus. TCR+ cells were transduced with either SFG-1928z or SGF-P28z retrovirus. FIG. 2B shows cumulative cell counts of indicated CAR T cells upon weekly stimulation with CD19+ target cells, showing that cells expressing 1928z exhibited in vitro proliferation. FIG. 2C shows cytotoxic activity using an 18 hr bioluminescence assay, using firefly luciferase (FFL)-expressing NALM6 as target cells. Cells expressing 1928z exhibited cytotoxic activity. FIGS. 2D and 2E show FFL-NALM6 bearing mice were treated with $2 \times 10^5$ CAR T cells. Tumor burden is shown as bioluminescent signal quantified per animal every week over a 40-day period. Quantification is the average photon count of ventral and dorsal acquisitions per animal at all given time points, and it is expressed as radiance. Each line in FIG. 2E represents one mouse. n=7 mice per group. The lower right figure is Kaplan-Meier analysis of survival of mice in FIGS. 2D and 2E. These results demonstrate that targeted integration of a CAR into TRAC resulted in survival significantly longer than with semi-random integration using the SFG retrovirus.

Taken together these results show that, at an equivalent dose of CAR T cell injected, cells with the CAR targeted into the TRAC locus are strongly more potent than the cells retrovirally transduced with CAR.

As described above, a strategy for one-step generation of universal CAR T cells was developed by targeting the integration of a promoter-less CAR gene cassette in the TCR alpha constant chain (TRAC) first exon. This results in CAR expression under the control of the endogenous TCR alpha promoter with concomitant disruption of the TCR alpha gene expression. As all components of the TCR complex are required for its localization to the cytoplasmic membrane, the TCR alpha disruption leads to TCR negative cells. This approach is suitable with the commonly used genome editing platforms (for example, TALEN, CRISPR/Cas9, ZFN) and results in homologous recombination at the TRAC target site using an AAV donor template in T cells. The efficiency of TALEN and CRISPR/Cas9 to promote homologous recombination using AAV6 donor template in T cells was compared. Conditions were established yielding up to 50% of universal CAR T cells combining target gene disruption and CAR targeted insertion in a single step. The targeted integration of the CAR transgene was molecularly confirmed, which results in highly homogeneous and stable CAR expression in human peripheral blood T cells. These T cells exhibited the same in vitro tumor lysis activity and proliferation than retrovirally transduced CAR T cells, which supports their usefulness in in vivo anti-tumor activity. The endogenous TCR alpha promoter provided unanticipated benefits. The method provided highly homogeneous and stable CAR expression in human peripheral blood T cells, and also improved T cell persistence. Most importantly, these T cells exhibited higher in vitro and in vivo tumor lysis activity, proliferation and persistence than retrovirally transduced CAR T cells, while their Graft versus host disease potential was removed by reducing or preventing expression of a functional T cell receptor complex at the surface of the cell. The process described herein, which combines the scalability of universal T cell manufacturing with the uniformity and safety of targeted CAR gene integration, is useful for the development of off-the-shelf CAR therapy that can be scaled up and readily provided to patients, as needed.

8.2 Example 2: Targeting a CAR to the TRAC Locus with CRISPR/Cas9 Enhances Tumor Rejection This example shows expression by a T cell of a CAR encoded by a transgene was carried out, wherein the expression of the transgene was under the control of an endogenous T cell promoter, specifically the human T cell receptor a chain (TRAC) promoter. Described below are experiments showing that directing a CD19-specific CAR to the human T cell receptor a chain (TRAC) locus not only result in uniform CAR expression in human peripheral blood T cells, but also enhances T cell potency, with edited cells vastly outperforming conventionally generated CAR T cells in a mouse model of acute lymphoblastic leukaemia. It is further demonstrated that targeting the CAR to the TRAC locus averts tonic CAR signalling and establishes effective internalization and re-expression of the CAR following single or repeated exposure to antigen, delaying effector T cell differentiation and exhaustion. These findings uncover facets of CAR immunobiology and underscore the vast potential of CRISPR/Cas9 genome editing to advance immunotherapies.

Methods. Guide-RNA: A guide RNA (gRNA) gRNA was designed to target the first exon of the constant chain of the TCRa gene (TRAC). The sequence targeted is located upstream of the transmembrane domain of the TCR alpha. This domain is required for the TCR alpha and beta assembly and addressing to the cell-surface. Both non-homologous end joining (NHEJ) and integration of the CAR by HDR at this locus would then efficiently disrupt the TCR complex.

For the B2M, both a gRNA and a TALEN (Transcription activator-like effector nucleases) targeting the first exon of B2M gene were designed, and a higher cutting efficiency was obtained with the TALEN. The same protocol was used, similar cytotoxicity and specificity was obtained for both methods, and the CAR T cells obtained were not discernable in term of activity and proliferation. For manufacturing reasons the B2M TALEN was mainly used in this study.

```
TRAC-gRNA sequence:
                                          (SEQ ID NO: 26)
C*A*G*GGUUCUG GAUAUCUGUG UUUUAGAGCU AGAAAUAGCA

AGUUAAAAUA AGGCUAGUCC GUUAUCAACU UGAAAAAGUG

GCACCGAGUC GGUGCU*U*U*U

B2M-gRNA sequence:
                                          (SEQ ID NO: 27)
G*G*C*CACGGAG CGAGACAUCU UUUUAGAGCU AGAAAUAGCA

AGUUAAAAUA AGGCUAGUCC GUUAUCAACU UGAAAAAGUG

GCACCGAGUC GGUGCU*U*U*U

*2'-O-methyl 3' phosphorothioate

B2M-TALEN targeting sequence:
                                          (SEQ ID NO: 28)
TTAGCTGTGCTCGCGC (TACTCTCTCTTTCTG)

GCCTGGAGGCTATCCA.

Left TAL effector (spacer) Right TAL effector.
```

Messenger RNA: Modified guide RNAs (gRNAs) and Cas9 mRNA were synthesized by TriLink Biotechnologies (San Diego, CA). Guide RNAs were reconstituted at 1 µg/µL in cytoporation T Buffer (Harvard Apparatus; Holliston, MA).

AAV: Based on a pAAV-GFP backbone (Cell Biolabs; San Diego, CA), the pAAV-TRAC-1928z was designed and cloned containing 1.9 kb of genomic TRAC (amplified by PCR) flanking the gRNA targeting sequences, a self-cleaving P2A peptide in frame with the first exon of TRAC followed by the 1928z CAR used in clinical trials (Brentjens et al., Sci. Trans. Med. 5:177ra138 (2013)). Briefly, the CAR comprises a single chain variable fragment 19scFV specific for the human CD19 preceded by a CD8a leader peptide and followed by CD28 hinge-transmembrane-intracellular regions and CD3 intracellular domain. The CAR cDNA is followed by the bovine growth hormone polyA signal (bGHpA). When targeting the B2M locus, a similar strategy was followed, except that no P2A sequence was required since the 1928z-pA sequence was placed in frame at the ATG of the B2M gene. When using exogenous promoters (EF1α, LTR, PGK, or PGK100), the promoter-1928z-pA cassette was placed in reverse orientation at the same TRAC or B2M entry points.

Cells: Buffy coats from healthy volunteer donors were obtained from the New York Blood Center. Peripheral blood mononuclear cells were isolated by density gradient centrifugation, and T lymphocytes were then purified using the Pan T cell isolation kit (Miltenyi Biotech; San Diego, CA). Cells were activated with Dynabeads (1:1 beads:cell) Human T-Activator CD3/CD28 (ThermoFisher; Carlsbad, CA) in X-vivo 15 medium (Lonza; Basel, Switzerland) supplemented with 5% human serum (Gemini Bioproducts; West Sacramento, CA) with 200 U/ml IL-2 (Miltenyi Biotech) at a density of $10^6$ cells/ml. The medium was changed every 2 days, and cells were replated at $10^6$ cells/ml.

Gene Targeting: 48 hours after initiating T cell activation, the CD3/CD28 beads were magnetically removed, and the T cells were transfected by electrotransfer of Cas9 mRNA and gRNA using an AgilePulse MAX system (Harvard Apparatus). $3\times10^6$ cells were mixed with 5 µg of Cas9 and 5 µg of gRNA into a 0.2 cm cuvette. Following electroporation, cells were diluted into culture medium and incubated at 37° C./5% $CO_2$. Recombinant AAV6 donor vector (manufactured by SignaGen; Gaithersburg, MD) was added to the culture 2 to 4 hours after electroporation, at the indicated MOI ($1\times10^5$ to $1\times10^6$ range). Subsequently, edited cells were cultured using standard conditions (37° C. and expanded in T cell growth medium, replenished as needed to maintain a density of ~$1\times10^6$ cells/ml every 2 to 3 days).

To obtain TCR-negative T cells, TCR-positive T cells were removed from the culture using magnetic biotin-anti-TCRαβ and anti-biotin microbeads and LS columns (Miltenyi Biotech). For details of targeting constructs and strategies, see FIGS. 7 and 14.

Retroviral vector constructs, retroviral production and transduction: Plasmids encoding the SFG γ-retroviral (RV) vector (Rivière et al., *Proc. Natl. Acad. Sci. USA* 92:6733-6737 (1995)) were prepared as previously described (Brentjens et al., *Nat. Med.* 9, 279-286, (2003); Maher et al., *Nat. Biotechnol.* 20:70-75 (2002)). VSV-G pseudotyped retroviral supernatants derived from transduced gpg29 fibroblasts (H29) were used to construct stable retroviral-producing cell lines as previously described (Gong et al., Cancer patient T cells genetically targeted to prostate-specific membrane antigen specifically lyse prostate cancer cells and release cytokines in response to prostate-specific membrane antigen. *Neoplasia* 1:123-127 (1999)). T cells were transduced by centrifugation on Retronectin (Takara)-coated plates.

Cell lines: NALM-6 and NIH/3T3 were obtained from ATCC and were regularly tested for mycoplasma contamination using the MycoAlert Mycoplasma Detection Kit (Lonza). NALM-6 cells were transduced to express firefly luciferase-GFP and NIH/3T3 cells transduced to express human CD19 (Brentjens et al., *Nat. Med.* 9, 279-286, (2003); Zhao et al., *Cancer Cell* 28:415-428 (2015)).

Cytotoxicity assays: The cytotoxicity of T cells transduced with a CAR was determined by standard luciferase-based assay. In brief, NALM-6 expressing firefly luciferase-GFP served as target cells. The effector (E) and tumour target (T) cells were co-cultured in triplicates at the indicated E/T ratio using black-walled 96 well plates with $1\times10^5$ target cells in a total volume of 100 µl/well in NALM-6 Medium. Target cells alone were plated at the same cell density to determine the maximal luciferase expression (relative light units; RLUmax). 18 hr later, 100 µl luciferase substrate (Bright-Glo, Promega; Madison, WI) was directly added to each well. Emitted light was detected in a luminescence plate reader or Xenogen IVIS Imaging System (Xenogen; Alameda, CA), and quantified using Living Image software (Xenogen). Lysis was determined as $[1-(RLUsample)/(RLUmax)]\times100$.

Antigen stimulation and proliferation assays: NIH/3T3 expressing human CD19 were used as artificial antigen-presenting cells (Brentjens et al., *Nat. Med.* 9, 279-286, (2003)). For weekly stimulations, $3\times10^5$ Irradiated CD19+ AAPCs were plated in 24 well plates 12 hours before the addition of $5\times10^5$ CART cells in X-vivo 15+ human serum+ 50U IL-2/mL. Every 2 days, cells were counted and media was added to reach a concentration of $1\times10^6$ T cells/mL. For repeated proximal stimulations (FIG. 6D), cells were transferred to a new well plated with 3T3-CD19 after 24 h (2 stimulations) or every 12 h (4 stimulations). For each condition, T cells were counted and analysed by FACS for CAR, phenotypic and exhaustion markers expression every 12 h.

Antibodies and intracellular staining: CAR was labelled with a goat anti-mouse Fab (Jackson ImmunoResearch, 115-606-003; West Grove, PA). For T cell phenotyping, the following antibodies were used: mouse anti-human BUV-395CD4 (563552), APC-cy7-CD8 (557834), BV-421-CD62L (563862), BV-510-CD279 (PD1, 563076) from BD biosciences (San Jose, CA); mouse anti-human APC-CD25 (17-0259-42), FITC-CD45RA (11-0458-42), PerCP-eFluor710 CD223 (LAG-3, 46-2239-42) form eBiosciences (Carslbad, CA), and FITC mouse anti-human CD366 (TIM-3, 345032) from Biolegend (San Diego, CA). For intracellular staining, T cells were fixed and permeabilized using BD Cytofix/Cytoperm Plus kit (BD Biosciences) as per the recommendation of the manufacturer. Anti-CD8-FITC (clone HIT8a, ebiosciencce) and anti-CD4-BUV-395 (clone SK3, BD Horizon; BD Biosciences) were used for extracellular staining. Anti TNF-Alexa Fluor 700 (clone MAb 11, BD pharmingen; BD Biosciences), anti-IL2-BV421 (clone 5344.111, BD Horizon) and anti-IFNg-BV510 (clone B27, BD Horizon) were used for intracellular staining.

Mouse Systemic Tumour Model: 8- to 12-week-old NOD/SCID/IL-2Rγ-null (NSG) male mice (Jackson Laboratory) were used, under a protocol approved by the MSKCC Institutional Animal Care and Use Committee. Mice were inoculated with $0.5\times10^6$ FFLuc-GFP NALM-6 cells by tail vein injection, followed by $2\times10^5$, $1\times10^5$ or $5\times10^4$, CART cells injected four days later. NALM-6 produce very even tumour burdens and no mice were excluded prior to treatment. No randomization or blinding methods were used. Bioluminescence imaging utilized the Xenogen IVIS Imaging System (Xenogen) with Living Image software (Xenogen) for acquisition of imaging datasets. Tumour burden was assessed as previously described (Gade et al., *Cancer Res.* 65:9080-9088 (2005)).

RNA extraction and real-time quantitative PCR: Total RNA was extracted from T cells by using the RNeasy kit (QIAGEN; Hilden, Germany) combined with QIAshredder (QIAGEN), following the manufacturer's instructions. RNA concentration and quality were assessed by UV spectroscopy using the NanoDrop spectrophotometer (Thermo Fisher Scientific; Carlsbad, CA). One hundred to 200 ng total RNA were used to prepare cDNA using the SuperScript III First-Strand Synthesis SuperMix (Invitrogen; Carlsbad, CA), with a 1:1 volume ratio of random hexamers and oligo dT. Completed cDNA synthesis reactions were treated with 2U RNase H for 20 min at 37° C. Quantitative PCR was performed using the ABsolute Blue qPCR SYBR Green Low ROX Mix (Thermo Fisher Scientific), and the following primer sets: Ribosomal 18S: forward 5'-aacccgttgaaccc-catt (SEQ ID NO:29), reverse 5'-ccatccaatcggtagtagcg (SEQ ID NO:30); 1928z: forward 5'-cgtgcagtctaaagacttgg (SEQ ID NO:31), reverse 5'-ataggggacttggacaaagg (SEQ ID NO:32); T-bet: forward 5'-gaaacccagttcattgccgt (SEQ ID NO:33), reverse 5'-ccccaaggaattgacagttg (SEQ ID NO:34); EOMES: forward 5'-actggttcccactggatgag (SEQ ID NO:35), reverse 5'-ccacgccatcctctgtaact (SEQ ID NO:36); GATA3: forward 5'-cacaaccacactctggagga (SEQ ID NO:37), reverse 5'-ggtttctggtctggatgcct (SEQ ID NO:38). PCR assays were run on the QuantStudio™ 7 Flex System (Thermo Fisher Scientific), and Ct values were obtained with the QuantStudio Real-Time PCR software. Relative changes in gene expression were analysed with the $2^{\Delta\Delta Ct}$ method. RNA expression levels were normalized to the percentage of CAR+ T cells for each group of T cells analysed.

Statistics: All experimental data are presented as mean±s.e.m. No statistical methods were used to predetermine sample size. Groups were compared using the Welch's two-sample t-test for parametric data (sample size >10) or the Mann-Whitney Test for non-parametric data (sample size <10). Welch's correction was used, as the variances were not equal. For the comparison of CAR MFI and RNA level upon CAR stimulation, ANOVA F-tests were used.

Statistical analysis was performed on GraphPad Prism 7 software (GraphPad Software; La Jolla, CA).

To disrupt the TRAC locus and place the 1928z CAR (Brentjens et al., *Sci. Transl.* Med. 5, 177ra138 (2013)) under its transcriptional control (TRAC-CAR), a guide RNA was designed targeting the 5' end of TRAC's first exon and an adeno-associated virus (AAV) vector repair matrix encoding a self-cleaving P2A peptide followed by the CAR cDNA (FIG. 3A and FIG. 7A). T cell electroporation of Cas9 mRNA and gRNA yielded a high knock-out (KO) frequency (~70%, FIG. 3B and FIG. 7D) without limited cell death. The knock-in (KI) was proportional to AAV dosage, exceeding 40% at a multiplicity of infection (MOI) of $10^6$ (FIG. 3B and FIGS. 7C and 7E). This efficient targeting, reported here for the first time at the TRAC locus, is comparable to levels reached in T cells at the AAVS1, CCR5 or CD40L loci (Sather et al., *Sci. Transl. Med.* 7:307ra156 (2015); Wang et al., *Nucleic Acids Res.* 44:e30 (2016); Hubbard et al., *Blood* 127:2513-2522 (2016)). Approximately 95% of CAR+ cells were T-cell receptor (TCR)—negative (FIG. 7G), validating the 2-in-1 TCR-knockout and CAR-knock-in strategy. The observed 5% of CAR+/TCR+ cells is consistent with the typical frequency of dual-TCRα-expressing T cells (Corthay et al., *J. Autoimmun.* 16:423-429 (2001)). The targeting specificity was confirmed by mapping AAV vector integration over the whole genome (de Vree et al., Nat. Biotechnol. 32:1019-1025 (2014)), which confirmed the high selectivity for TRAC integration and absence of off-target hotspots (FIG. 8). These results demonstrate the high efficiency and precision of gene targeting offered by CRISPR/Cas9 and our ability to reproducibly generate up to $50 \times 10^6$ of TRAC-CAR T cells. Homogenous and consistent expression of TRAC-CAR was found in multiple donors, in contrast to retrovirally encoded CAR (RV-CAR), which showed variegated expression with a twofold higher mean expression (FIGS. 3C and 3D).

In vitro functional studies did not reveal any notable differences between TRAC-encoded and randomly integrated 1928z, in terms of either cytotoxicity or T cell proliferation in response to weekly stimulation with CD19+ antigen-presenting cells (Brentjens et al., *Nat. Med.* 9:279-286 (2003)) (FIGS. 9A and 9C). These experiments included a control group where TCR-disrupted T cells expressing retrovirally transduced CAR (RV-CAR-TCR—) responded similarly to RV-CAR TCR+ T cells (FIG. 9A). In vivo, however, in the pre-B acute lymphoblastic leukaemia NALM-6 mouse model using the "CAR stress test", in which CAR T-cell dosage is gradually lowered to reveal the functional limits of different T-cell populations (Brentjens et al., *Nat. Med.* 9:279-286 (2003); Zhao et al., *Cancer Cell* 28:415-428 (2015)), TRAC-CAR, RV-CAR and RV-CAR-TCR–T cells differed markedly in their anti-tumour activity. TRAC-CAR T cells induced far greater responses and markedly prolonged median survival at every T-cell dose (FIG. 3E and FIG. 10A). TCR disruption had no discernable effect on the potency of RV-CAR T cells. Bone marrow studies in mice injected with $1 \times 10^5$ CAR T cells showed similar T-cell accumulation at the tumour site after 10 days (FIG. 3F). However, only the TRAC-CAR T cells achieved tumour control (FIGS. 3G and 3H). By day 17, TRAC-CAR T cells exceeded RV-CAR T cells in number, as the latter diminished relative to day 10, despite the continued presence of CD19+ tumour cells (FIG. 3F-3G and FIG. 10B). Furthermore, the CAR T-cell groups differed in their degree of T-cell differentiation and exhaustion, as reflected in the proportion of terminal effector cells (CD45RA+CD62L–) and accumulation of co-expressed PD1, LAG3 and TIM3 (Blackburn et al., *Nat. Immunol.* 10:29-37 (2009)), respectively. Thus, conventional CAR T cells showed up to 50% positive expression of the markers of exhaustion by day 17, in contrast to less than 2% of the TRAC-CAR T cells, which also retained a larger effector memory composition (FIGS. 3I-3J and FIGS. 10C-10D). Terminal differentiation and acquisition of this exhaustion phenotype is consistent with diminished anti-tumour activity (Gattinoni et al., *Nat. Med.* 17:1290-1297 (2011)). Intriguingly, CAR expression in bone marrow T cells was similar to pre-infusion levels for TRAC-CAR T cells but diminished in both RV-CAR groups (FIG. 10E). Importantly, cell-surface expression of the mutant LNGFR reporter (Gallardo et al., *Gene Ther.* 4:1115-1119 (1997)) (co-expressed via a self-cleaving 2A element) was undiminished, ruling out vector silencing as the explanation for diminished CAR expression (FIGS. 10G-10H). The CAR expression level measured in RV-CAR T cells negatively correlated with tumour burden (FIG. 10I), suggesting that cell-surface CAR was down-regulated in proportion to tumour antigen. These in vivo findings thus not only demonstrated the superior anti-tumour activity of TRAC-CAR T cells, but also forged a link between tumour control, T cell differentiation and exhaustion, and CAR expression levels. These same patterns were observed with another CAR, 19BBz, which utilizes the 4-1BB cytoplasmic domain as its costimulatory moiety (FIG. 11).

To further analyse the impact of CAR expression levels on T-cell function, we first examined T-cell phenotype when cultured in the absence or presence of antigen (FIG. 4). Five days after transduction, RV-CAR T cells already showed evidence of activation, exhaustion and differentiation (FIG. 4A and FIG. 12A), similar to results obtained with a previously described retrovirally delivered CAR22. By contrast, TRAC–CAR T cells maintained a phenotype analogous to untransduced T cells (FIG. 4A), mainly composed of naive and central memory cells (CD62L+ cells), a phenotype associated with greater in vivo anti-tumour activity (Gattinoni et al., *Nat. Med.* 17:1290-1297 (2011); Sommermeyer et al., *Leukemia* 30:492-500 (2016)). Consistent with constitutive activating signalling, we found that RV-CARs, but not TRAC-CARs, had phosphorylated immune-based tyrosine activation motifs (Long et al., *Nat. Med.* 21:581-590 (2015)) (FIGS. 4B and 4C). Further differences were noted upon exposure to antigen. In contrast to TRAC-CAR T cells, RV-CAR T cells stimulated 1, 2 or 4 times in a 48h period differentiate into effector T cells, identified on the basis of phenotype (loss of CD62L), cytokine secretion (increased IFNγ, IL2 and TNFα) and expression of master transcription factors (increased T-bet, EOMES and GATA3) (FIGS. 4D-4E and FIGS. 12B-12D). These results indicated that the improved efficacy of TRAC-CAR T cells is related to its CAR expression level by reducing tonic signalling and delaying T cell differentiation upon stimulation.

To control CAR expression, it was first attempted to vary the retroviral vector copy number. Lowered gene transfer efficiency only modestly affected the CAR expression level (FIG. 13). Interestingly, even when mean RV-CAR expression matched that of TRAC-CAR, the former still displayed accelerated differentiation upon multiple stimulations, suggesting that dynamic regulation of CAR expression, and not just baseline expression, promotes distinct functional characteristics.

To further define the importance of CAR expression levels, T cells that expressed CAR from different genomic loci and promoters were generated. To examine the specific contribution of the TRAC locus and its promoter, a further seven constructs were designed targeting the 1928z CAR to the TRAC or the B2-microglobulin (B2M) locus (MHC-I related gene known to be expressed in all T cells), using either endogenous or exogenous promoters (FIGS. 5A-5B and FIGS. 14A-14E). Engineered CAR T cells were successfully engineered at both loci, achieving homogenous CAR expression with mean levels ranging from seven times lower (B2M-PGK100) to more than double (TRAC-EF1α) of TRAC-CAR endogenous promoter (FIGS. 5C-5E and FIG. 14).

All of the combinations that conferred higher CAR expression than TRAC-CAR displayed the tonic signalling signature, in stark contrast to those providing lower expression, consistent with a previous study linking expression level to antigen-independent signalling (Frigault et al., *Cancer Immunol Res.* 3:356-367 (2015)) (FIG. 5E and FIG. 14F). Three of these were selected for in depth analysis: high-expressing TRAC-EF1a and low-expressing B2M-CAR and TRAC-LTR (RV enhancer-promoter), comparing their in vitro and in vivo potency against TRAC-CAR. In vitro, following repeated antigenic stimulations, TRAC-EF1a CAR T cells rapidly acquired effector profiles while B2M and TRAC-CAR T cells retained a central memory phenotype (FIG. 5F and FIG. 15A). Interestingly, although TRAC-LTR directed lower baseline CAR expression than RV-CAR and averted the tonic signalling, the LTR still promoted from within the TRAC locus the same differentiation pattern as RV-CAR. In the NALM-6 stress test model, none of the 3 locus-promoter combination displayed the same anti-tumour efficacy as TRAC-CAR (FIGS. 5G-5H). 10 and 17 days after infusion of 1×10$^5$ CAR T cells, the number of CAR T cells accumulated in bone marrow was similar or higher than for TRAC-CAR T cells; however, only TRAC-CAR T cells could efficiently control tumour progression (FIGS. 15C-15E). Although B2M-CAR T cells seemed to preserve an effector/effector-memory ratio similar to TRAC-CAR T cells, they too acquired a preponderant exhaustion signature (FIGS. 15F-15G), suggesting that delayed differentiation may be independent from exhaustion. Together these results underscored the effect of CAR targeting and further suggested regulation of CAR expression extending beyond baseline transcriptional control.

CAR expression was closely analyzed upon encounter with antigen. To this end, CAR T cells were admixed with CD19+ antigen-presenting cells and cell-surface CAR expression was examined at regular time intervals (FIG. 6A). CAR expression decreased within hours of exposure to CD19 in both targeted and randomly integrated CAR T cells, accompanied by a deeper drop and longer recovery lag when the initial level was lower. The subsequent return to baseline expression most notably distinguished the different T-cell populations.

To better study the mechanism behind the drop in the CAR cell-surface expression, we designed a CAR-GFP fusion protein to analyse both cell-surface and intra-cellular CAR expression, and compare it to cells expressing a CAR with a co-translated but cleaved LNGFR reporter (FIGS. 6B-6C). We observed that CAR expression was downregulated independently of LNGFR, suggesting a physical internalization rather than a transcriptional process. The co-reduction of CAR and GFP signal following antigen encounter indicated that CAR internalization was followed by its degradation. The occurrence of CAR degradation following exposure to antigen suggested that de novo CAR synthesis from CAR mRNA would be needed to precisely and timely restore CAR expression and support effective T-cell function. Careful analysis of CAR cell-surface expression following repeated antigen stimulation (FIG. 6D and FIG. 16A) identified two main patterns in the recovery phase (12-48h hours after antigen exposure). In TRAC-EF1α, TRAC-LTR and RV-CAR T cells, CAR cell-surface expression increased after each stimulation, two- to fourfold above baseline within 24h. In both TRAC- and B2M-CAR T cells, CAR expression decreased upon repeated stimulations and remained below baseline after 48 hours (FIG. 6D). Steady-state mRNA analysis showed a linear correlation between cell-surface protein level (FIG. 6E and FIG. 16B) and the transcriptional response to CAR T cell activation (FIG. 6F), pointing to the essential role of promoter strength and regulation to enable optimal post-stimulation replenishment of cell-surface CAR expression.

This CAR protein/RNA downregulation and subsequent re-expression is reminiscent of TCR regulation upon stimulation of human T cells (Schrum et al., *Immunol Rev.* 196:7-24, (2003)) and antigen-induced TCR recirculation in mouse T cells (Liu et al., *Immunity* 13, 665-675, (2000); Call et al., *Annu. Rev. Immunol.* 23, 101-125, (2005); Allison et al., *Elife.* 5, (2016)). Similarly, accelerated differentiation and exhaustion have been reported in the context of excessive and continuous activation of the TCR (Schietinger et al., *Trends Immunol.* 35, 51-60, (2014); Wherry et al., *Nat. Rev. Immunol.* 15, 486-499, (2015)). Altogether, these converging findings support the conclusion that TRAC has a role in control of CAR expression in two critical ways. One is to promote optimal baseline expression, which prevented tonic signalling in the absence of antigen and allowed effective CAR internalization upon single or multiple contacts with antigen. The other is to direct a balanced transcriptional response resulting in a kinetically optimal recovery of baseline CAR expression after antigen engagement. In contrast to T cells with higher CAR expression, the TRAC-CAR profile correlated with decreased T-cell differentiation and exhaustion, resulting in superior tumour eradication. Our studies, which compared randomly integrating CARs versus CARs targeted to two loci in 8 different transcriptional configurations, illustrate the exquisite sensitivity of CAR regulation. Thus, although the endogenous B2M promoter responded similarly to TRAC upon CAR stimulation, B2M-CAR did not perform as well as TRAC-CAR in vivo, indicating that the lower basal expression level it offered is insufficient for effective CAR activity. TRAC-LTR likewise provided baseline expression comparable to TRAC, but its prompt rebound after activation was associated with poor T-cell performance and accelerated differentiation. We therefore conclude that both the basal and dynamic CAR expression levels contribute to sustaining T-cell function.

In summary, the results demonstrate that targeting a CAR coding sequence to the TCR locus, placing it under the control of endogenous regulatory elements, reduces tonic signalling, averts accelerated T-cell differentiation and exhaustion, and increases the therapeutic potency of engineered T cells. The kinetic measurements of antigen-induced CAR internalization and degradation revealed differential recovery of cell-surface CAR depending on the enhancer/promoter elements driving CAR expression. These findings demonstrate that tight transcriptional regulation of CAR expression is critical for effective tumour eradication. The targeting of CARs to a TCR locus may thus provide a safer therapeutic T cell (by minimizing the risks of insertional oncogenesis and TCR-induced autoimmunity and alloreactivity), a better defined T-cell product (by yielding constant CAR expression and avoiding position-effect variegation and vector copy number variation) and a more potent T cell (by reducing constitutive signalling and delaying T-cell exhaustion). Finally, the results demonstrate the relevance of studying CAR immunobiology and the vast potential of genome editing to advance T-cell therapies.

8.3 Example 3. Expression of Therapeutic Transgenes Under Control of Endogenous Promoters In one example, a therapeutic chimeric antigen receptor (CAR) is integrated at the TRAC locus (under the control of endogenous promoter/enhancer elements); an NFAT-responsive transcription unit is integrated at the T cell receptor beta chain constant (TRBC) locus, from which two therapeutic PD1L-specific and-CTLA4 scFvs are expressed. With this setup, engineered T cells are activated through the CAR, which leads to NFAT activation followed by the expression of the therapeutic scFvs. Alternatively, these transgenes can be integrated at the NFAT-responsive CD69 locus. In a particular embodiment, a chimeric cell surface ligand—transcription factor is CD19-NFAT. Accordingly, in one embodiment, the CAR is encoded by a first transgene, and the PD1L scFv and the CTLA4 scFV are encoded by a second transgene that is bicistronic, wherein the expression of the second transgene is under the control of the endogenous TRBC promoter that is induced by NFAT. In an alternative embodiment, the PD1L and CTLA4 scFvs are expressed from separate transgenes (i.e., second and third transgenes). In a specific embodiment, the PD1L and CTLA4 scFvs are expressed from a single, polycistronic transgene. Such a construct can optionally include a cleavable sequence, such as a P2A sequence, to provide for expression of the PD1L and CTLA4 scFvs as separate molecules.

In another example, a chimeric cell-surface ligand (extracellular)-transcription factor (TF; intracellular) fusion gene is integrated at the TRAC locus (under the control of endogenous promoter/enhancer elements) that specifically interacts with the CD19 molecule in B cells; a TF-responsive transcription unit integrated at the TRBC locus, from which a therapeutic chimeric immune receptor ligand (CIRL) is expressed. This design allows engineered T cells to respond to the interaction with B cells by releasing the TF, which then activates the expression of the CIRL, which interacts with a specific autoimmune B-cell immunoglobulin receptor (IgR). The latter interaction signals/activates a cytotoxic T-cell response leading to autoimmune B-cell death. In one embodiment, a chimeric cell-surface ligand (extracellular)-transcription factor (TF; intracellular) fusion gene is encoded by a first transgene. In one embodiment, the CIRL is encoded by a second transgene.

In another example, a DNA sequence encoding a HIV-specific ribozyme is integrated at CD4 locus; an interferon-responsive transcription unit integrated at the CCR5 locus that expresses an intracellular scFv that interacts with HIV Rev protein. This therapeutic T cell will inhibit HIV replication threefold: by cleaving the HIV genome through the ribozyme, preventing HIV infection by eliminating CCR5 expression, and inhibiting HIV packaging by blocking HIV Rev activity. In one embodiment, an HIV-specific ribozyme is encoded by a first transgene. In one embodiment, an intracellular scFv is encoded by a second transgene, for example, a scFv that interacts with HIV rev protein.

8.4 Example 4. Generation of Non-Integrating Gamma-Retrovirus

Recombinant non-integrating (or integration-deficient) gamma-retrovirus (rNIgRV or IDgRV) is a retroviral vector that contains a mutant integrase protein, which cannot catalyze viral DNA integration into the host cell genome. To make this mutant retroviral vector, a plasmid DNA encoding a mutant integrase protein (with mutations as indicated previously) is used in combination with the envelope-encoding and the retroviral genome-encoding plasmid DNAs. These three plasmids are transfected into producer mammalian cells, and the recombinant mutant viral vector is released into the medium, which is later collected and used to transduce human peripheral blood T cells.

As shown in FIG. 18, mutant integrases were generated by mutating amino acids in the DDE motif (see Andrake and Skalka (2015). Retroviral Integrase: Then and Now. Ann. Rev. Virol. 2:241-264. The DDE amino acids positions are: D124, D183, E 219 (residue numbering based on GenBank accession number NP 955592 (NP 955592.1). The mutants generated were D124A, D124E, D124N, D124V, D183A, D183N, D124A and D183A, D124A and D183N, D124E and D183A, D124E and D183N, D124N and D183A, D124N and D183N, D124V and D183A, and D124V and D183N. Mutants were generated using standard molecular biology techniques. A plasmid containing the Moloney Murine Leukemia Virus (MLV) Gag-Pol sequences was modified using standard molecular techniques. Mutants were generated by replacing the DNA sequence region containing the DDE motif with a new DNA sequence where the specific codon(s) is mutated to generate the each specific mutant. The resulting plasmids were used to produce NIgRVs.

Taking advantage of its transient nature inside the target cells, rNIgRVs can be used for different applications. For example, to transiently express genes that maintain a certain cell phenotype-like memory T cells; to transiently expresses chimeric nucleases or CRISPR/Cas components to disrupt specific DNA sequences; to deliver exogenous DNA flanked with DNA sequences homologous to specific genomic locations, thus enabling integration of the flanked DNA sequence into the T cell genome via homologous recombination; to deliver and integrate the transgenic retroviral DNA at specific DNA breaks in an integrase-independent NHEJ-dependent manner.

9. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating a human subject with CAR therapy in need thereof, comprising administering to the subject a therapeutically effective amount of a human T cell wherein a promoter-less recombinant nucleic acid sequence encoding a CAR is integrated at a site in the genome of the cell, said site being the first exon of the T cell receptor (TCR) alpha chain gene, such that the CAR is expressed under control of the endogenous TCR alpha chain gene promoter, to produce said CAR at the surface of the cell, and wherein integration of the nucleic acid sequence encoding the CAR at said site prevents expression of a functional TCR alpha chain.

2. The method of claim 1, which comprises administering to the subject an isolated population of T cells comprising a plurality of the human T cell.

3. The method of claim 1, which comprises administering to the subject a pharmaceutical composition comprising a therapeutically effective amount of the human T cell; and a pharmaceutically acceptable carrier.

4. The method of claim 1, wherein the CAR therapy is to promote an immune response, the subject has cancer, and the CAR binds to a cancer antigen of a cancer in the subject.

5. The method of claim 4 wherein the CAR binds to CD19.

6. The method of claim 1, wherein the CAR therapy is to promote an immune response, the subject has an infectious disease, and the CAR binds to an antigen of a pathogen of the infectious disease.

7. The method of claim 1, wherein the CAR therapy is to suppress an immune response, the human T cell is a T regulatory cell, the subject has an autoimmune disorder, and the CAR binds to an autoimmune antigen of the autoimmune disorder.

8. The method of claim 1, wherein the nucleic acid sequence encoding the CAR is integrated into the site by targeted homologous recombination.

9. A method of treating cancer in a human subject in need thereof comprising administering to the subject a therapeutically effective amount of a human T cell wherein a promoter-less recombinant nucleic acid sequence encoding a CAR is integrated at a site in the genome of the cell, said site being the first exon of the T cell receptor (TCR) alpha chain gene, such that the CAR is expressed under control of the endogenous TCR alpha chain gene promoter, to produce said CAR at the surface of the cell, wherein integration of the nucleic acid sequence encoding the CAR at said site prevents expression of a functional TCR, and wherein the CAR binds to a cancer antigen of the cancer in the subject.

10. The method of claim 9 wherein the CAR binds to CD19.

11. The method of claim 9, which comprises administering to the subject an isolated population of T cells comprising a plurality of the human T cell.

12. The method of claim 9, which comprises administering to the subject a pharmaceutical composition comprising a therapeutically effective amount of the human T cell; and a pharmaceutically acceptable carrier.

13. The method of claim 9, wherein the cancer is selected from the group consisting of a carcinoma, sarcoma, leukemia, lymphoma, multiple myeloma, melanoma, brain tumor, spinal cord tumor, germ cell tumor, neuroendocrine tumor, and carcinoid tumor.

14. The method of claim 9, wherein the cancer is a blood cancer.

15. The method of claim 14, wherein the cancer is a lymphoma or leukemia.

\* \* \* \* \*

SEQUENCE LISTING

<160> NUMBER OF SEQ ID NOS: 41

<210> SEQ ID NO 1

```
<211> LENGTH: 407
<212> TYPE: PRT
<213> ORGANISM: Moloney murine leukemia virus

<400> SEQUENCE: 1

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Asp Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asp Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Gly Pro Ser
    370                 375                 380

Ser Arg Leu Thr Trp Arg Val Gln Arg Ser Gln Asn Pro Leu Lys Ile
```

```
                385                 390                 395                 400
Arg Leu Thr Arg Glu Ala Pro
                    405

<210> SEQ ID NO 2
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Ala Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asp Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335
```

His Gln Thr Lys Asn Leu Glu Pro Arg Trp Lys Gly Pro Tyr Thr Val
          340                 345                 350

Leu Leu Thr Thr Pro Thr Ala Leu Lys Val Asp Gly Ile Ala Ala Trp
          355                 360                 365

Ile His Ala Ala His Val Lys Ala Ala Asp Pro Gly Gly Gly Pro Ser
370                 375                 380

Ser Arg Leu Thr Trp Arg Val Gln Arg Ser Gln Asn Pro Leu Lys Ile
385                 390                 395                 400

Arg Leu Thr Arg Glu Ala Pro
              405

<210> SEQ ID NO 3
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Glu Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asp Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

```
Pro Leu Val Asn Phe Pro Asp Pro Asp Met Thr Arg Val Thr Asn Ser
            275                 280                 285

Pro Ser Leu Gln Ala His Leu Gln Ala Leu Tyr Leu Val Gln His Glu
        290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Pro Ser
370                 375                 380

Ser Arg Leu Thr Trp Arg Val Gln Arg Ser Gln Asn Pro Leu Lys Ile
385                 390                 395                 400

Arg Leu Thr Arg Glu Ala Pro
            405
```

<210> SEQ ID NO 4
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Asn Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asp Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
```

```
                        210                 215                 220
Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
                275                 280                 285

Pro Ser Leu Gln Ala His Leu Gln Ala Leu Tyr Leu Val Gln His Glu
            290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
                340                 345                 350

Leu Leu Thr Thr Pro Thr Ala Leu Lys Val Asp Gly Ile Ala Ala Trp
            355                 360                 365

Ile His Ala Ala His Val Lys Ala Ala Asp Pro Gly Gly Gly Pro Ser
            370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 5
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
                20                  25                  30

Lys Tyr Trp Val Tyr Gln Gly Lys Pro Val Met Pro Asp Gln Phe Thr
            35                  40                  45

Phe Glu Leu Leu Asp Phe Leu His Gln Leu Thr His Leu Ser Phe Ser
50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
                100                 105                 110

Arg Gly His Arg Pro Gly Thr His Trp Glu Ile Val Phe Thr Glu Ile
            115                 120                 125

Lys Pro Gly Leu Tyr Gly Tyr Lys Tyr Leu Leu Val Phe Ile Asp Thr
            130                 135                 140

Phe Ser Gly Trp Ile Glu Ala Phe Pro Thr Lys Lys Glu Thr Ala Lys
145                 150                 155                 160
```

-continued

```
Val Val Thr Lys Lys Leu Leu Glu Glu Ile Phe Pro Arg Phe Gly Met
                165                 170                 175

Pro Gln Val Leu Gly Thr Asp Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Gly Pro Ser
    370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405
```

<210> SEQ ID NO 6
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95
```

Ala Gln Val Asn Ala Ser Lys Ser Ala Val Lys Gln Gly Thr Arg Val
                100                 105                 110

Arg Gly His Arg Pro Gly Thr His Trp Glu Ile Asp Phe Thr Glu Ile
            115                 120                 125

Lys Pro Gly Leu Tyr Gly Tyr Lys Tyr Leu Leu Val Phe Ile Asp Thr
        130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Ala Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
                210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
        290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Pro Ser
                370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 7
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr

```
            35                  40                  45
Phe Glu Leu Leu Asp Phe Leu His Gln Leu Thr His Leu Ser Phe Ser
 50                  55                  60

Lys Met Lys Ala Leu Leu Glu Arg Ser His Ser Pro Tyr Tyr Met Leu
 65                  70                  75                  80

Asn Arg Asp Arg Thr Leu Lys Asn Ile Thr Glu Cys Lys Ala Cys
                 85                  90                  95

Ala Gln Val Asn Ala Ser Lys Ser Ala Val Lys Gln Gly Thr Arg Val
                100                 105                 110

Arg Gly His Arg Pro Gly Thr His Trp Glu Ile Asp Phe Thr Glu Ile
                115                 120                 125

Lys Pro Gly Leu Tyr Gly Tyr Lys Tyr Leu Leu Val Phe Ile Asp Thr
                130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asn Asn Gly Pro Ala Phe Val Ser Lys Val
                180                 185                 190

Ser Gln Thr Val Ala Asp Leu Leu Gly Ile Asp Trp Lys Leu His Cys
                195                 200                 205

Ala Tyr Arg Pro Gln Ser Ser Gly Gln Val Glu Arg Met Asn Arg Thr
                210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
                260                 265                 270

Pro Leu Val Asn Phe Pro Asp Pro Asp Met Thr Arg Val Thr Asn Ser
                275                 280                 285

Pro Ser Leu Gln Ala His Leu Gln Ala Leu Tyr Leu Val Gln His Glu
                290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
                340                 345                 350

Leu Leu Thr Thr Pro Thr Ala Leu Lys Val Asp Gly Ile Ala Ala Trp
                355                 360                 365

Ile His Ala Ala His Val Lys Ala Ala Asp Pro Gly Gly Gly Pro Ser
                370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 8
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 8

```
Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Ala Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Ala Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Gly Pro Ser
    370                 375                 380

Ser Arg Leu Thr Trp Arg Val Gln Arg Ser Gln Asn Pro Leu Lys Ile
385                 390                 395                 400
```

```
Arg Leu Thr Arg Glu Ala Pro
                405

<210> SEQ ID NO 9
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Ala Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asn Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
```

```
                    340                 345                 350
Leu Leu Thr Thr Pro Thr Ala Leu Lys Val Asp Gly Ile Ala Ala Trp
            355                 360                 365

Ile His Ala Ala His Val Lys Ala Ala Asp Pro Gly Gly Pro Ser
    370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 10
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Glu Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Ala Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285
```

```
Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
            355                 360                 365

Ile His Ala Ala His Val Lys Ala Asp Pro Gly Gly Gly Pro Ser
    370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 11
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Glu Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asn Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220
```

```
Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
            355                 360                 365

Ile His Ala Ala His Val Lys Ala Ala Asp Pro Gly Gly Gly Pro Ser
370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 12
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65              70                  75                  80

Asn Arg Asp Arg Thr Leu Lys Asn Ile Thr Glu Thr Cys Lys Ala Cys
            85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Asn Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
```

```
                165                 170                 175
Pro Gln Val Leu Gly Thr Ala Asn Gly Pro Ala Phe Val Ser Lys Val
            180                 185                 190

Ser Gln Thr Val Ala Asp Leu Leu Gly Ile Asp Trp Lys Leu His Cys
            195                 200                 205

Ala Tyr Arg Pro Gln Ser Ser Gly Gln Val Glu Arg Met Asn Arg Thr
            210                 215                 220

Ile Lys Glu Thr Leu Thr Lys Leu Thr Leu Ala Thr Gly Ser Arg Asp
225                 230                 235                 240

Trp Val Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
            275                 280                 285

Pro Ser Leu Gln Ala His Leu Gln Ala Leu Tyr Leu Val Gln His Glu
            290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
            355                 360                 365

Ile His Ala Ala His Val Lys Ala Asp Pro Gly Gly Pro Ser
            370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 13
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110
```

-continued

Arg Gly His Arg Pro Gly Thr His Trp Glu Ile Asn Phe Thr Glu Ile
            115                 120                 125

Lys Pro Gly Leu Tyr Gly Tyr Lys Tyr Leu Leu Val Phe Ile Asp Thr
        130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asn Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
                275                 280                 285

Pro Ser Leu Gln Ala His Leu Gln Ala Leu Tyr Leu Val Gln His Glu
        290                 295                 300

Val Trp Arg Pro Leu Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Gly Pro Ser
    370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 14
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
                20                  25                  30

Lys Tyr Trp Val Tyr Gln Gly Lys Pro Val Met Pro Asp Gln Phe Thr
            35                  40                  45

```
Phe Glu Leu Leu Asp Phe Leu His Gln Leu Thr His Leu Ser Phe Ser
         50                  55                  60

Lys Met Lys Ala Leu Leu Glu Arg Ser His Ser Pro Tyr Tyr Met Leu
 65                  70                  75                  80

Asn Arg Asp Arg Thr Leu Lys Asn Ile Thr Glu Thr Cys Lys Ala Cys
                 85                  90                  95

Ala Gln Val Asn Ala Ser Lys Ser Ala Val Lys Gln Gly Thr Arg Val
                100                 105                 110

Arg Gly His Arg Pro Gly Thr His Trp Glu Ile Val Phe Thr Glu Ile
            115                 120                 125

Lys Pro Gly Leu Tyr Gly Tyr Lys Tyr Leu Leu Val Phe Ile Asp Thr
130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Ala Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Gly Pro Ser
    370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405

<210> SEQ ID NO 15
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 15

Glu Asn Ser Ser Pro Tyr Thr Ser Glu His Phe His Tyr Thr Val Thr
1               5                   10                  15

Asp Ile Lys Asp Leu Thr Lys Leu Gly Ala Ile Tyr Asp Lys Thr Lys
            20                  25                  30

Lys Tyr Trp Val Tyr Gln Gly Lys Pro Val Met Pro Asp Gln Phe Thr
        35                  40                  45

Phe Glu Leu Leu Asp Phe Leu His Gln Leu Thr His Leu Ser Phe Ser
    50                  55                  60

Lys Met Lys Ala Leu Leu Glu Arg Ser His Ser Pro Tyr Tyr Met Leu
65                  70                  75                  80

Asn Arg Asp Arg Thr Leu Lys Asn Ile Thr Glu Thr Cys Lys Ala Cys
                85                  90                  95

Ala Gln Val Asn Ala Ser Lys Ser Ala Val Lys Gln Gly Thr Arg Val
            100                 105                 110

Arg Gly His Arg Pro Gly Thr His Trp Glu Ile Val Phe Thr Glu Ile
        115                 120                 125

Lys Pro Gly Leu Tyr Gly Tyr Lys Tyr Leu Leu Val Phe Ile Asp Thr
    130                 135                 140

Phe Ser Gly Trp Ile Glu Ala Phe Pro Thr Lys Lys Glu Thr Ala Lys
145                 150                 155                 160

Val Val Thr Lys Lys Leu Leu Glu Glu Ile Phe Pro Arg Phe Gly Met
                165                 170                 175

Pro Gln Val Leu Gly Thr Asn Asn Gly Pro Ala Phe Val Ser Lys Val
            180                 185                 190

Ser Gln Thr Val Ala Asp Leu Leu Gly Ile Asp Trp Lys Leu His Cys
        195                 200                 205

Ala Tyr Arg Pro Gln Ser Ser Gly Gln Val Glu Arg Met Asn Arg Thr
    210                 215                 220

Ile Lys Glu Thr Leu Thr Lys Leu Thr Leu Ala Thr Gly Ser Arg Asp
225                 230                 235                 240

Trp Val Leu Leu Leu Pro Leu Ala Leu Tyr Arg Ala Arg Asn Thr Pro
                245                 250                 255

Gly Pro His Gly Leu Thr Pro Tyr Glu Ile Leu Tyr Gly Ala Pro Pro
            260                 265                 270

Pro Leu Val Asn Phe Pro Asp Pro Asp Met Thr Arg Val Thr Asn Ser
        275                 280                 285

Pro Ser Leu Gln Ala His Leu Gln Ala Leu Tyr Leu Val Gln His Glu
    290                 295                 300

Val Trp Arg Pro Leu Ala Ala Ala Tyr Gln Glu Gln Leu Asp Arg Pro
305                 310                 315                 320

Val Val Pro His Pro Tyr Arg Val Gly Asp Thr Val Trp Val Arg Arg
                325                 330                 335

His Gln Thr Lys Asn Leu Glu Pro Arg Trp Lys Gly Pro Tyr Thr Val
            340                 345                 350

Leu Leu Thr Thr Pro Thr Ala Leu Lys Val Asp Gly Ile Ala Ala Trp
        355                 360                 365

Ile His Ala Ala His Val Lys Ala Ala Asp Pro Gly Gly Gly Pro Ser
    370                 375                 380

Ser Arg Leu Thr Trp Arg Val Gln Arg Ser Gln Asn Pro Leu Lys Ile
385                 390                 395                 400

Arg Leu Thr Arg Glu Ala Pro
                405
```

<210> SEQ ID NO 16
<211> LENGTH: 164
<212> TYPE: PRT
<213> ORGANISM: Homo sapiens

<400> SEQUENCE: 16

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 17
<211> LENGTH: 220
<212> TYPE: PRT
<213> ORGANISM: Homo sapiens

<400> SEQUENCE: 17

```
Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160
```

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
            210                 215                 220

<210> SEQ ID NO 18
<211> LENGTH: 255
<212> TYPE: PRT
<213> ORGANISM: Homo sapiens

<400> SEQUENCE: 18

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 19
<211> LENGTH: 277
<212> TYPE: PRT
<213> ORGANISM: Homo sapiens

<400> SEQUENCE: 19

Met Cys Val Gly Ala Arg Arg Leu Gly Arg Gly Pro Cys Ala Ala Leu
1               5                   10                  15

```
Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
50                      55                  60

Arg Pro Cys Gly Pro Gly Phe Tyr Asn Asp Val Val Ser Ser Lys Pro
65                      70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
            130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                    165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
            210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                    245                 250                 255

Gly Ser Phe Arg Thr Pro Ile Gln Glu Glu Gln Ala Asp Ala His Ser
                260                 265                 270

Thr Leu Ala Lys Ile
            275

<210> SEQ ID NO 20
<211> LENGTH: 199
<212> TYPE: PRT
<213> ORGANISM: Homo sapiens

<400> SEQUENCE: 20

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
            35                  40                  45

Gln Gln Phe Lys Met Gln Leu Leu Lys Gly Gly Gln Ile Leu Cys Asp
        50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110
```

-continued

```
Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Leu
                195

<210> SEQ ID NO 21
<211> LENGTH: 93
<212> TYPE: PRT
<213> ORGANISM: Homo sapiens

<400> SEQUENCE: 21

Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80

Glu Asp Gly Lys Val Tyr Ile Asn Met Pro Gly Arg Gly
                85                  90

<210> SEQ ID NO 22
<211> LENGTH: 235
<212> TYPE: PRT
<213> ORGANISM: Homo sapiens

<400> SEQUENCE: 22

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140
```

```
Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 23
<211> LENGTH: 458
<212> TYPE: PRT
<213> ORGANISM: Homo sapiens

<400> SEQUENCE: 23

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
```

```
              275                 280                 285
Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Gln Ala Glu Arg Met
                420                 425                 430

Ser Gln Ile Lys Arg Leu Leu Ser Glu Lys Lys Thr Cys Gln Cys Pro
            435                 440                 445

His Arg Phe Gln Lys Thr Cys Ser Pro Ile
    450                 455
```

<210> SEQ ID NO 24
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
caggguucug gauaucugug uuuuagagcu agaaauagca aguuaaaaua aggcuagucc    60
guuaucaacu ugaaaaagug gcaccgaguc ggugcuuuu                          99

<210> SEQ ID NO 25
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
ttgtcccaca gatatccaga accctgaccc tgccgtgtac cagctgaga               49

<210> SEQ ID NO 26
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
caggguucug gauaucugug uuuuagagcu agaaauagca aguuaaaaua aggcuagucc    60
guuaucaacu ugaaaaagug gcaccgaguc ggugcuuuu                    99

<210> SEQ ID NO 27
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ggccacggag cgagacaucu uuuuagagcu agaaauagca aguuaaaaua aggcuagucc    60
guuaucaacu ugaaaaagug gcaccgaguc ggugcuuuu                          99

<210> SEQ ID NO 28
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ttagctgtgc tcgcgctact ctctctttct ggcctggagg ctatcca                 47

<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
aacccgttga accccatt                                                 18

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
ccatccaatc ggtagtagcg                                               20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
cgtgcagtct aaagacttgg                                               20

<210> SEQ ID NO 32
<211> LENGTH: 20
<212> TYPE: DNA
<213> ORGANISM: Artificial Sequence

```
-continued

<220> FEATURE:
<221> NAME/KEY: source
<223> OTHER INFORMATION: /note="Description of Artificial Sequence:
      Synthetic primer"

<400> SEQUENCE: 32 atagggact tggacaaagg                                                    20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gaaacccagt tcattgccgt                                                   20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ccccaaggaa ttgacagttg                                                   20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
actggttccc actggatgag                                                   20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
ccacgccatc ctctgtaact                                                   20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
cacaaccaca ctctggagga                                                   20
```

```
<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
ggtttctggt ctggatgcct                                                   20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
acaatgagaa gagcaatgga                                                   20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
gagattgtcc tggtttctgt                                                   20

<210> SEQ ID NO 41
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
tcctaaccct gatcctcttg tcccacagat atccagaacc ctgaccctgc cgtgtaccag       60
ctgagagact ctaaatccag                                                   80
```